(12) United States Patent
Apte et al.

(10) Patent No.: US 10,381,112 B2
(45) Date of Patent: *Aug. 13, 2019

(54) METHOD AND SYSTEM FOR CHARACTERIZING ALLERGY-RELATED CONDITIONS ASSOCIATED WITH MICROORGANISMS

(71) Applicant: uBiome, Inc., San Francisco, CA (US)

(72) Inventors: Zachary Apte, San Francisco, CA (US); Jessica Richman, San Francisco, CA (US); Daniel Almonacid, San Francisco, CA (US); Catalina Valdivia, San Francisco, CA (US); Rodrigo Ortiz, San Francisco, CA (US); Inti Pedroso, San Francisco, CA (US); Victoria Dumas, San Francisco, CA (US); Paz Tapia, San Francisco, CA (US); Eduardo Morales, San Francisco, CA (US)

(73) Assignee: uBiome, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,360

(22) Filed: Dec. 15, 2017

(65) Prior Publication Data

US 2018/0114592 A1    Apr. 26, 2018

Related U.S. Application Data

(63) Continuation-in-part of application No. 15/606,743, filed on May 26, 2017, which is a continuation of application No. 14/919,614, filed on Oct. 21, 2015, now Pat. No. 9,703,929.

(60) Provisional application No. 62/066,369, filed on Oct. 21, 2014, provisional application No. 62/087,551, filed on Dec. 4, 2014, provisional application No. 62/092,999, filed on Dec. 17, 2014, provisional application No. 62/147,376, filed on Apr. 14, 2015, provisional application No. 62/147,212, filed on Apr. 14, 2015, provisional application No. 62/147,362, filed on Apr. 14, 2015, provisional application No. 62/146,855, filed on Apr. 13, 2015, provisional application No. 62/206,654, filed on Aug. 18, 2015, provisional application No. 62/434,881, filed on Dec. 15, 2016, provisional application No. 62/434,894, filed on Dec. 15, 2016, provisional application No. 62/434,902, filed on Dec. 15, 2016, provisional application No. 62/434,912, filed on Dec. 15, 2016, provisional application No. 62/434,917, filed on Dec. 15, 2016, provisional application No. 62/434,923, filed on Dec. 15, 2016, provisional application No. 62/557,423, filed on Sep. 12, 2017, provisional application No. 62/564,777, filed on Sep. 28, 2017, provisional application No. 62/522,293, filed on Jun. 20, 2017, provisional application No. 62/555,782, filed on Sep. 8, 2017, provisional application No. 62/558,489, filed on Sep. 14, 2017, provisional application No. 62/582,172, filed on Nov. 6, 2017, provisional application No. 62/582,191, filed on Nov. 6, 2017, provisional application No. 62/582,162, filed on Nov. 6, 2017.

(51) Int. Cl.
| | |
|---|---|
| *G01N 33/48* | (2006.01) |
| *G16H 10/40* | (2018.01) |
| *G16B 50/00* | (2019.01) |
| *G06G 7/58* | (2006.01) |
| *G16H 20/60* | (2018.01) |
| *G16H 50/20* | (2018.01) |

(52) U.S. Cl.
CPC ............ *G16H 10/40* (2018.01); *G16B 50/00* (2019.02); *G16H 20/60* (2018.01); *G16H 50/20* (2018.01); *Y02A 90/26* (2018.01)

(58) Field of Classification Search
None
See application file for complete search history.

(56) References Cited

U.S. PATENT DOCUMENTS

| | | |
|---|---|---|
| 6,033,864 A | 3/2000 | Braun et al. |
| 6,309,643 B1 | 10/2001 | Braun et al. |
| 6,632,641 B1 | 10/2003 | Brennan et al. |

(Continued)

FOREIGN PATENT DOCUMENTS

| | | |
|---|---|---|
| CN | 105407728 | 3/2015 |
| EP | 2631240 | 8/2013 |

(Continued)

OTHER PUBLICATIONS

"K03100: IepB: signal peptidase I," KEGG, Aug. 7, 2012 (Aug. 7, 2012), p. 1 Of 1. Retrieved from the Internet: on Jun. 12, 2016 (Jun. 12, 2016).

(Continued)

*Primary Examiner* — Eric S Dejong
(74) *Attorney, Agent, or Firm* — Kilpatrick Townsend & Stockton LLP

(57) ABSTRACT

Embodiments of a method and/or system for characterizing an allergy-related condition for a user can include one or more of: generating a microbiome dataset for each of an aggregate set of biological samples associated with a population of subjects, based on sample processing of the biological samples; processing a supplementary dataset associated with one or more allergy-related conditions for the set of users; and performing an allergy-related characterization process for the one or more allergy-related conditions, based on the supplementary dataset and/or microbiome features extracted from the microbiome dataset.

22 Claims, 11 Drawing Sheets

(56) References Cited

U.S. PATENT DOCUMENTS

| | | |
|---|---|---|
| 6,861,053 B1 | 3/2005 | Lin et al. |
| D521,843 S | 5/2006 | Hung |
| 7,048,906 B2 | 5/2006 | Lin et al. |
| 7,176,002 B2 | 2/2007 | Lao et al. |
| 8,478,544 B2 | 7/2013 | Colwell et al. |
| 8,598,203 B2 | 12/2013 | Tarcic et al. |
| 8,883,264 B2 | 11/2014 | Yang et al. |
| 9,028,841 B2 | 5/2015 | Henn et al. |
| 9,149,473 B2 | 10/2015 | Ecker et al. |
| 9,433,651 B2 | 9/2016 | Jones et al. |
| 9,447,195 B2 | 9/2016 | Cordova et al. |
| 9,506,109 B2 | 11/2016 | Savelkoul et al. |
| 9,663,831 B2 | 5/2017 | Apte et al. |
| 9,710,606 B2 | 7/2017 | Apte et al. |
| 10,242,160 B2 | 3/2019 | Apte et al. |
| 2002/0012926 A1 | 1/2002 | Quake et al. |
| 2003/0190314 A1 | 10/2003 | Campbell et al. |
| 2005/0196785 A1 | 9/2005 | Quake et al. |
| 2006/0073501 A1 | 4/2006 | Van Den Boom et al. |
| 2006/0089310 A1 | 4/2006 | Goldstein et al. |
| 2007/0134652 A1 | 6/2007 | Slepnev et al. |
| 2007/0259337 A1 | 11/2007 | Hully et al. |
| 2008/0131556 A1 | 6/2008 | De Simone et al. |
| 2010/0035232 A1 | 2/2010 | Ecker et al. |
| 2010/0129816 A1 | 5/2010 | Savelkoul et al. |
| 2010/0172874 A1 | 7/2010 | Turnbaugh et al. |
| 2011/0027219 A1 | 2/2011 | Tarcic et al. |
| 2011/0177976 A1 | 7/2011 | Gordon et al. |
| 2012/0045771 A1 | 2/2012 | Beier et al. |
| 2012/0129794 A1 | 5/2012 | Dowd et al. |
| 2012/0149584 A1 | 6/2012 | Olle et al. |
| 2012/0252775 A1 | 10/2012 | Finegold et al. |
| 2013/0017999 A1 | 1/2013 | Fremont et al. |
| 2013/0045874 A1 | 2/2013 | Ehrlich |
| 2013/0108598 A1 | 5/2013 | Oresic et al. |
| 2013/0121968 A1 | 5/2013 | Quay |
| 2013/0184302 A1 | 7/2013 | Bortey et al. |
| 2014/0093478 A1 | 4/2014 | Turnbaugh et al. |
| 2014/0136120 A1 | 5/2014 | Colwell et al. |
| 2014/0179726 A1 | 6/2014 | Bajaj et al. |
| 2014/0199281 A1 | 7/2014 | Henn et al. |
| 2014/0315929 A1 | 10/2014 | Chiosis |
| 2014/0341853 A1 | 11/2014 | Hovanky |
| 2014/0363399 A1 | 12/2014 | Jones et al. |
| 2015/0050245 A1 | 2/2015 | Herman et al. |
| 2015/0211055 A1 | 7/2015 | Apte et al. |
| 2015/0211078 A1 | 7/2015 | Apte et al. |
| 2015/0213193 A1 | 7/2015 | Apte et al. |
| 2015/0259728 A1 | 9/2015 | Cutliffe et al. |
| 2015/0374761 A1 | 12/2015 | Sadowsky et al. |
| 2016/0032363 A1 | 2/2016 | Stintzi et al. |
| 2016/0040216 A1 | 2/2016 | Akins et al. |
| 2016/0110515 A1 | 4/2016 | Apte et al. |
| 2016/0138089 A1 | 5/2016 | Harris et al. |
| 2016/0199424 A1 | 7/2016 | Berry et al. |
| 2016/0228003 A1 | 8/2016 | Apte et al. |
| 2016/0232313 A1 | 8/2016 | Apte et al. |
| 2017/0039347 A1 | 2/2017 | Apte et al. |
| 2017/0262608 A1 | 9/2017 | Apte et al. |
| 2017/0268045 A1 | 9/2017 | Apte et al. |
| 2017/0268046 A1 | 9/2017 | Apte et al. |
| 2017/0270268 A1 | 9/2017 | Apte et al. |
| 2017/0270269 A1 | 9/2017 | Apte et al. |
| 2017/0270270 A1 | 9/2017 | Apte et al. |
| 2017/0270271 A1 | 9/2017 | Apte et al. |
| 2017/0270272 A1 | 9/2017 | Apte et al. |
| 2017/0286619 A1 | 10/2017 | Apte et al. |
| 2017/0286620 A1 | 10/2017 | Apte et al. |
| 2017/0327864 A1 | 11/2017 | Apte et al. |
| 2017/0344719 A1 | 11/2017 | Apte et al. |
| 2018/0070827 A1 | 3/2018 | Apte et al. |
| 2019/0085396 A1 | 3/2019 | Apte et al. |

FOREIGN PATENT DOCUMENTS

| | | |
|---|---|---|
| EP | 2994756 | 3/2016 |
| WO | 050513 | 4/2012 |
| WO | 121298 | 8/2014 |
| WO | 138999 | 9/2014 |
| WO | 144092 | 9/2014 |
| WO | 145958 | 9/2014 |
| WO | 013214 | 1/2015 |
| WO | 085326 | 6/2015 |
| WO | 095241 | 6/2015 |
| WO | 103165 | 7/2015 |
| WO | 112352 | 7/2015 |
| WO | 170979 | 11/2015 |
| WO | 2015/095241 A4 | 12/2015 |
| WO | 2016/065075 A1 | 4/2016 |
| WO | 138337 | 9/2016 |
| WO | 172643 | 10/2016 |
| WO | 044902 | 3/2017 |

OTHER PUBLICATIONS

"KEGG: Aminoacyl-tRNA biosynthesis—Reference pathway," Jul. 20, 2013 (Jul. 20, 2013). Retrieved from the internet: <http://web:archive.org/web/20130720015616/http:www.genome.jp/kegg-bin/show_pathway?map=map00970&show_description=show. on Jun. 20, 2016 (Jun. 20, 2016).

Avila, Maria et al., The Oral Microbiota: Living with a Permanent Guest, DNA and Cell Biology, Nov. 8, 2009, vol. 28, No. 8.

Carroll et al. "Alterations in composition and diversity of the intestinal microbiota in patients with diarrhea-predominant irritable bowel syndrome," Feb. 20, 2012 (Feb. 29, 2012), vol. 24, pp. 1-19 [Original pp. 5215-5230] entire document.

Cho et al. "The Human Microbiome: at the Interface of Health and Disease," Nature Reviews Genetics, Apr. 1, 2012 (Apr. 1, 2012), vol. 13, pp. 260-270.

Dewhirst, Floyd et al., The Human Oral Microbiome, Journal of Bacteriology, Oct. 2010, vol. 192, No. 19, pp. 5002-5017.

Evans, Morgan, Prosthetic valve endocarditis due to *Neisseria elongata* subsp. *elongata* in a patient with Klinefelter's syndrome, Journal of Medical Microbiology, Jun. 1, 2007, vol. 56, No. 6, pp. 860-862.

Greenblum et al. "Metagenomic Systems Biology of the Human Gut Microbiome Reveals Topological Shifts Associated with Obesity and Inflammatory Bowel Disease," Proceeding of the National Academy of Sciences, Dec. 19, 2011 (Dec. 19, 2011), vol. 109, pp. 594-599.

Kanehisa et al. "KEGG: Kyoto encyclopedia of genes and genomes," Nucleic Acids Research, Jan. 1, 2000 (Jan. 1, 2000), vol. 28, No. 1, pp. 27-30.

Mak et al. "MetaboLyzer: A Novel Statistical Workflow for Analyzing Post Processed LC/MS Metabolomics Data," Anal Chem, Jan. 7, 2014 (Jan. 7, 2014), vol. 86, pp. 506-513.

Morgan et al. "Dysfunction of the intestinal microbiome in inflammatory bowel disease and treatment," Genome Biol. Apr. 16, 2012 (Apr. 16, 2012), vol. 13(9):R79, pp. 1-18. entire document.

Mutlu et al. "A Compositional Look at the Human Gastrointestinal Microbiome and Immune Activation Parameters in HIV Infected Subjects," PLoS Pathogens, Feb. 20, 2014 (Feb. 20, 2014), vol. 10, pp. 1-18.

Nakayama et al. "Aberrant Structures of Fecal Bacterial Community in Allergic Infants Profiled by 16S rRNA Gene Pyrosequencing," FEMS Immunology & Medical Microbiology, Dec. 1, 2011 (Dec. 1, 2011), vol. 63, pp. 397-406.

Ponnusamy et al. "Microbial community and metabolomic comparison of irritable bowel syndrome faeces," Feb. 17, 2011 (Feb. 17, 2011), vol. 60, pp. 817-827. entire document.

Canadian Application No. 2,962,466, Examination Report dated Mar. 23, 2018, 4 pages.

Chua, et al., "Intestinal Dysbiosis Featuring Abundance of Ruminococcus Gnavus Associates with Allergic Diseases in Infants", Gastroenterology, vol. 154, No. 1, Jan. 2018, pp. 154-167.

(56) References Cited

OTHER PUBLICATIONS

European Application No. 15852829.9, Extended European Search Report dated May 14, 2018, 8 pages.
International Application No. PCT/US2015/056767, International Preliminary Report on Patentability dated May 4, 2017, 9 pages.
International Application No. PCT/US2015/056767, International Search Report and Written Opinion dated Jan. 11, 2016, 10 pages.
International Application No. PCT/US2017/066866, International Search Report and Written Opinion dated Mar. 9, 2018, 12 pages.
Kinross, et al., "Gut Microbiome-host Interactions in Health and Disease", Genome Medicine, vol. 3, No. 14, 2011, pp. 1-12.
Morgan, et al., "Biodiversity and Functional Genomics in the Human Microbiome", Trends Genet., vol. 29, No. 1, Jan. 2013, pp. 51-58.
U.S. Appl. No. 14/919,614, Non-Final Office Action dated Jul. 14, 2016, 10 pages.
U.S. Appl. No. 14/919,614, Notice of Allowance dated May 19, 2017, 10 pages.
U.S. Appl. No. 15/606,743, Non-Final Office Action dated Dec. 19, 2017, 10 pages.
U.S. Appl. No. 15/606,743, Notice of Allowance dated Sep. 20, 2018, 5 pages.
U.S. Appl. No. 15/606,824, Final Office Action dated Sep. 20, 2018. 8 pages.
U.S. Appl. No. 15/606,824, Non-Final Office Action dated Jan. 16, 2018, 10 pages.
U.S. Appl. No. 15/606,874, Final Office Action dated Aug. 31, 2018, 8 pages.
U.S. Appl. No. 15/606,874, Non-Final Office Action dated Feb. 9, 2018, 10 pages.
U.S. Appl. No. 15/606,874, Notice of Allowance dated Jan. 17, 2019, 5 pages.
U.S. Appl. No. 15/606,909, Final Office Action dated Sep. 20, 2018, 8 pages.
U.S. Appl. No. 15/606,909, Non-Final Office Action dated Mar. 9, 2018, 10 pages.
U.S. Appl. No. 15/606,909, Notice of Allowance dated Feb. 20, 2019, 5 pages.
U.S. Appl. No. 15/606,943, Final Office Action dated Nov. 1, 2018, 7 pages.
U.S. Appl. No. 15/606,943, Non-Final Office Action dated Apr. 10, 2018, 10 pages.
U.S. Appl. No. 15/606,943, Notice of Allowance dated Mar. 8, 2019, 5 pages.
U.S. Appl. No. 15/606,975, Final Office Action dated Jun. 14, 2018, 8 pages.
U.S. Appl. No. 15/606,975, Non-Final Office Action dated Sep. 25, 2017, 10 pages.
U.S. Appl. No. 15/606,975, Notice of Allowance dated Oct. 19, 2018, 5 pages.
U.S. Appl. No. 15/621,144, Final Office Action dated Nov. 1, 2018. 7 pages.
U.S. Appl. No. 15/621,144, Non-Final Office Action dated Apr. 10, 2018, 10 pages.
U.S. Appl. No. 15/621,144, Notice of Allowance dated Mar. 8, 2019, 6 pages.
U.S. Appl. No. 15/621,152, Final Office Action dated Nov. 1, 2018, 7 pages.
U.S. Appl. No. 15/621,152, Non-Final Office Action dated Apr. 10, 2018, 10 pages.
U.S. Appl. No. 15/621,152, Notice of Allowance dated Mar. 8, 2019, 6 pages.
U.S. Appl. No. 15/606,824, "Notice of Allowance", dated Mar. 26, 2019, 5 pages.
U.S. Appl. No. 15/606,975, "Notice of Allowance", dated Apr. 3, 2019, 5 pages.

METHOD AND SYSTEM FOR CHARACTERIZING ALLERGY-RELATED CONDITIONS ASSOCIATED WITH MICROORGANISMS

CROSS-REFERENCE TO RELATED APPLICATIONS

This application is a continuation-in-part of U.S. application Ser. No. 15/606,743, filed 26 May 2017, which is a continuation of U.S. application Ser. No. 14/919,614, filed 21 Oct. 2015, which claims the benefit of U.S. Provisional Application Ser. No. 62/066,369 filed 21 Oct. 2014, U.S. Provisional Application Ser. No. 62/087,551 filed 4 Dec. 2014, U.S. Provisional Application Ser. No. 62/092,999 filed 17 Dec. 2014, U.S. Provisional Application Ser. No. 62/147,376 filed 14 Apr. 2015, U.S. Provisional Application Ser. No. 62/147,212 filed 14 Apr. 2015, U.S. Provisional Application Ser. No. 62/147,362 filed 14 Apr. 2015, U.S. Provisional Application Ser. No. 62/146,855 filed 13 Apr. 2015, and U.S. Provisional Application Ser. No. 62/206,654 filed 18 Aug. 2015, which are each incorporated in its entirety herein by this reference.

This application additionally claims the benefit of U.S. Provisional Application Ser. No. 62/434,881 filed 15 Dec. 2016, U.S. Provisional Application Ser. No. 62/434,894 filed 15 Dec. 2016, U.S. Provisional Application Ser. No. 62/434,902 filed 15 Dec. 2016, U.S. Provisional Application Ser. No. 62/434,912 filed 15 Dec. 2016, U.S. Provisional Application Ser. No. 62/434,917 filed 15 Dec. 2016, U.S. Provisional Application Ser. No. 62/434,923 filed 15 Dec. 2016, U.S. Provisional Application Ser. No. 62/557,423 filed 12 Sep. 2017, U.S. Provisional Application Ser. No. 62/564,777 filed 28 Sep. 2017, each of which are incorporated in its entirety by this reference.

This application also claims the benefit of U.S. Provisional Application Ser. No. 62/522,293 filed 20 Jun. 2017, U.S. Provisional Application Ser. No. 62/555,782 filed 8 Sep. 2017, U.S. Provisional Application Ser. No. 62/558,489 filed 14 Sep. 2017, U.S. Provisional Application Ser. No. 62/582,172 filed 6 Nov. 2017, U.S. Provisional Application Ser. No. 62/582,191 filed 6 Nov. 2017, and U.S. Provisional Application Ser. No. 62/582,162 filed 6 Nov. 2017, which are each herein incorporated in their entireties by this reference.

TECHNICAL FIELD

This invention relates generally to the field of microbiology and more specifically to a new and useful method and system for characterizing and/or treating allergy-related conditions associated with microorganisms.

BACKGROUND

A microbiome is an ecological community of commensal, symbiotic, and pathogenic microorganisms that are associated with an organism. The human microbiome includes over 10 times more microbial cells than human cells, but characterization of the human microbiome is still in nascent stages due to limitations in sample processing techniques, genetic analysis techniques, and resources for processing large amounts of data. Nonetheless, the microbiome is suspected to play at least a partial role in a number of health/disease-related states (e.g., preparation for childbirth, diabetes, auto-immune disorders, gastrointestinal disorders, rheumatoid disorders, neurological disorders, etc.). Given the profound implications of the microbiome in affecting a subject's health, efforts related to the characterization of the microbiome, the generation of insights from the characterization, and the generation of therapeutics configured to rectify states of dysbiosis should be pursued. Current methods and systems for analyzing the microbiomes of humans and providing therapeutic measures based on gained insights have, however, left many questions unanswered. In particular, methods for characterizing certain health conditions and therapies (e.g., probiotic therapies) tailored to specific subjects based upon microbiome composition and/or functional features have not been viable due to limitations in current technologies.

As such, there is a need in the field of microbiology for a new and useful method and system for characterizing health conditions in an individualized and population-wide manner.

DESCRIPTION OF THE EMBODIMENTS

The following description of the embodiments of the invention is not intended to limit the invention to these embodiments, but rather to enable any person skilled in the art to make and use this invention.

1. Overview

Figure 1A:
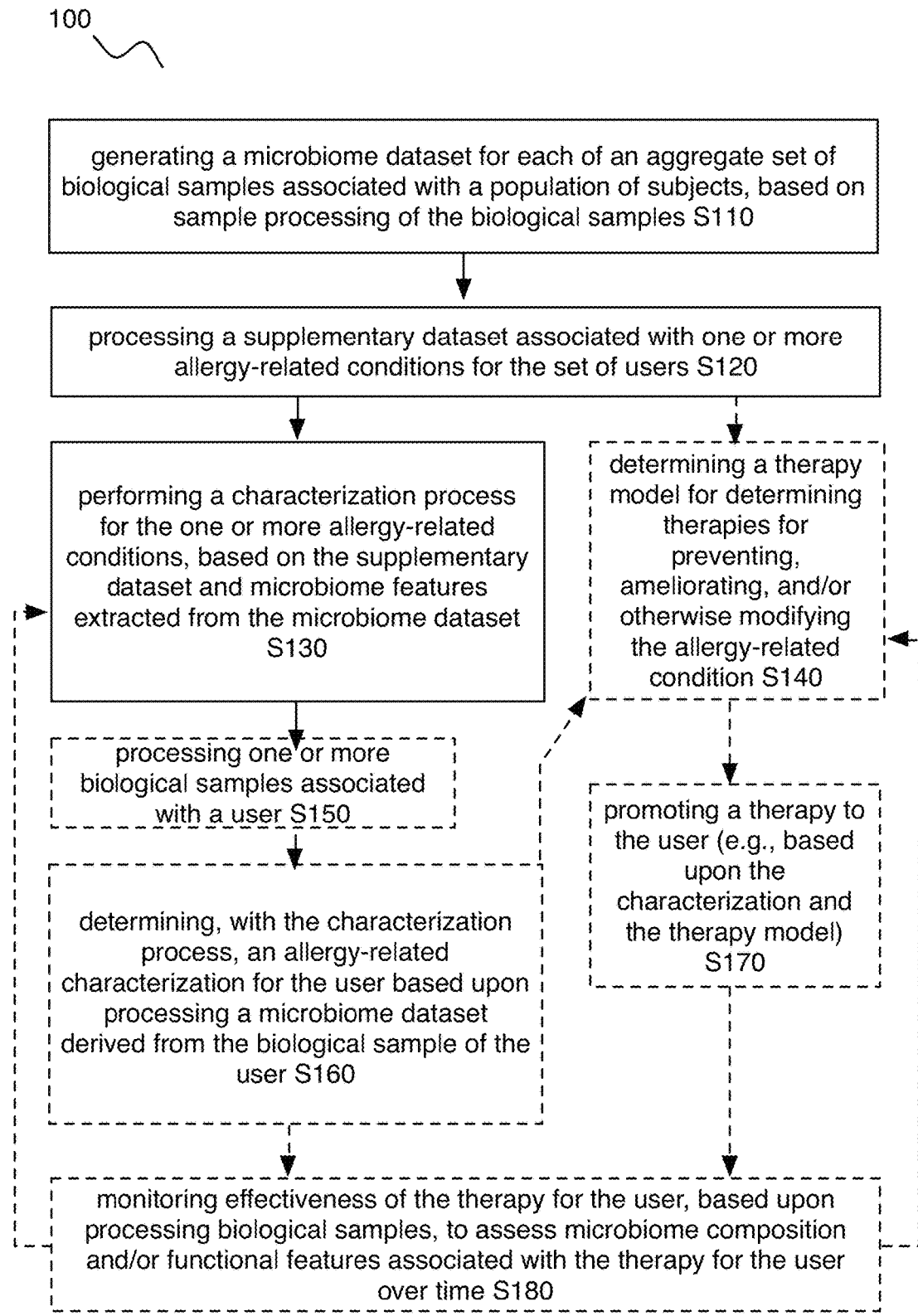
FIGS. 1A-1B are flowchart representations of variations of an embodiment of a method.
Figure 1B:
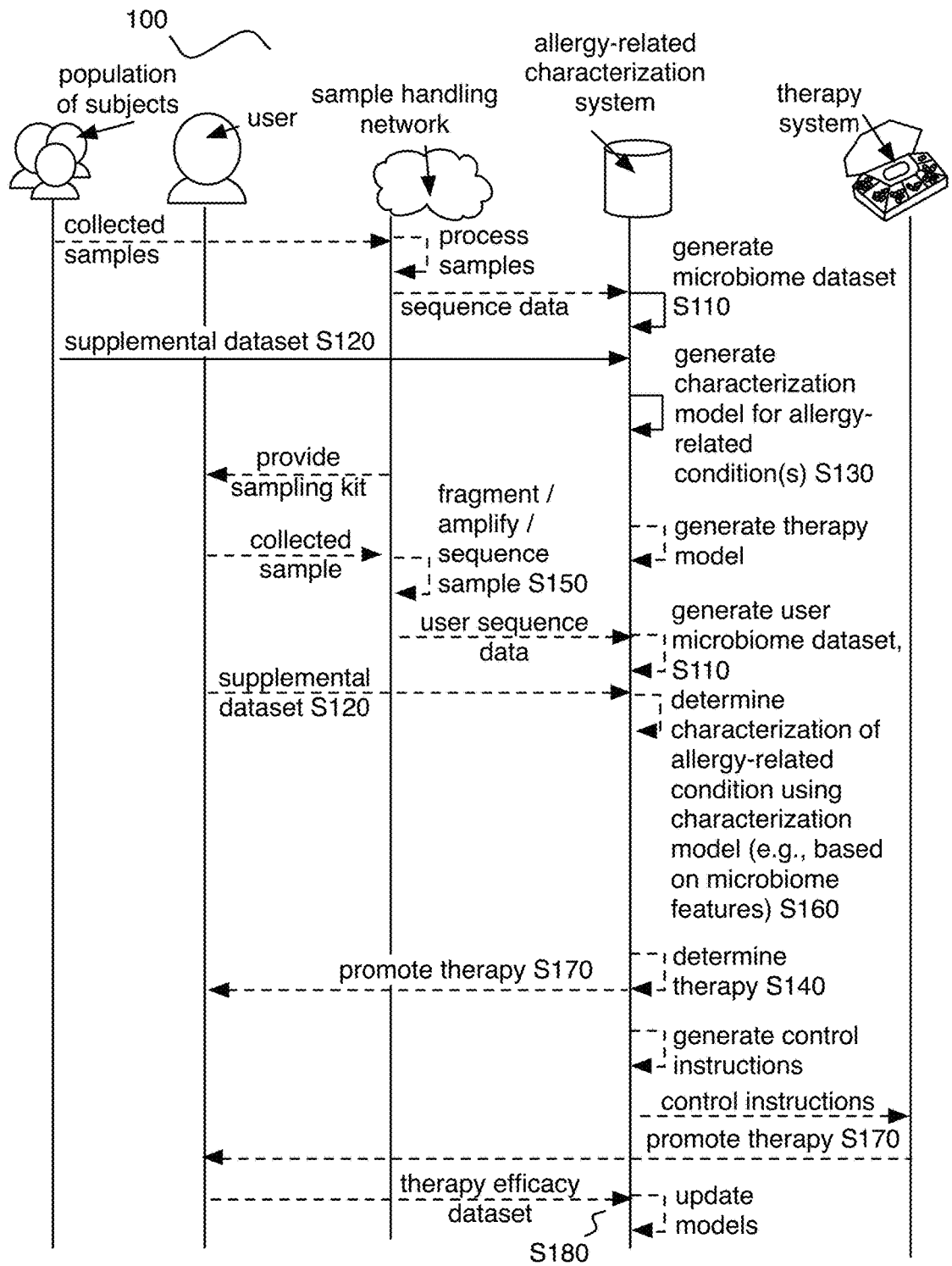

As shown in FIGS. 1A-1B, embodiments of a method 100 for characterizing one or more allergy-related conditions associated with microorganisms can include: generating a microbiome dataset (e.g., microorganism sequence dataset, microbiome composition diversity dataset, microbiome functional diversity dataset, etc.) for each of an aggregate set of biological samples associated with a population of subjects, based on sample processing of the biological samples S110; processing a supplementary dataset associated with (e.g., informative of; describing; indicative of; etc.) one or more allergy-related conditions for the set of users S120; and performing a characterization process for the one or more allergy-related conditions, based on the supplementary dataset and microbiome features (e.g., microbiome composition diversity features; microbiome functional diversity features; etc.) extracted from the microbiome dataset S130.

Embodiments of the method 100 can additionally or alternatively include one or more of: determining a therapy model for determining therapies for preventing, ameliorating, and/or otherwise modifying one or more allergy-related conditions S140; processing one or more biological samples associated with a user (e.g., subject, human, animal, patient, etc.) S150; determining, with the characterization process, an allergy-related characterization for the user based upon processing a microbiome dataset (e.g., user microorganism sequence dataset, microbiome composition dataset, microbiome functional diversity dataset, etc.) derived from the biological sample of the user S160; promoting a therapy for the allergy-related condition to the user (e.g., based upon the allergy-related characterization and/or a therapy model) S170; monitoring effectiveness of the therapy for the user, based upon processing biological samples, to assess microbiome composition and/or functional features associated with the therapy for the user over time S180; and/or any other suitable operations.

Embodiments of the method 100 and/or system 200 can function to characterize (e.g., assess, evaluate, diagnose, etc.) and/or treat users in relation to one or more allergy-related conditions, based on at least one of user microbiome composition, microbiome function, and/or other suitable microbiome-related aspects. Additionally or alternatively, embodiments can function to determine allergy-related characterizations and/or promote associated therapies in relation to specific physiological sites (e.g., gut, healthy gut, skin, nose, mouth, genitals, other suitable physiological sites, other sample collection sites, etc.). Additionally or alternatively, embodiments can function to generate models (e.g., allergy-related characterization models; therapy models; etc.) that can be used to characterize and/or diagnose subjects according to at least one of their microbiome composition and functional features (e.g., as a clinical diagnostic, as a companion diagnostic, etc.), and/or provide therapeutic measures (e.g., probiotic-based therapeutic measures, phage-based therapeutic measures, small-molecule-based therapeutic measures, clinical measures, etc.) to subjects in relation to one or more allergy-related conditions. Additionally or alternatively, embodiments can perform any suitable functionality described herein.

As such, data from a population of subjects can be used to characterize subjects according to their microbiome composition and/or functional features, indicate states of health and areas of improvement based upon the characterization(s), and promote one or more therapies that can modulate the composition of a subject's microbiome toward one or more of a set of desired equilibrium states (e.g., correlated with improved health states associated with one or more allergy-related conditions; etc.). Variations of the method 100 can further facilitate monitoring and/or adjusting of therapies provided to a subject, for instance, through reception, processing, and analysis of additional samples from a subject over time (e.g., throughout the course of a therapy regimen, through the extent of a user's experiences with allergy-relation conditions; etc.), which can facilitate therapy efficacy monitoring and/or therapy adjustment, microbiome characterization and/or related therapies over time, and/or performance of any suitable portion of the method 100 (e.g., over time, etc.).

Embodiments of the method 100 and/or system 200 can preferably generate and/or promote (e.g., provide) characterizations and/or therapies for one or more allergy-related conditions, which can include one or more of allergy-related: symptoms, causes (e.g., triggers, etc.), diseases, disorders, associated risk, associated severity, and/or any other suitable aspects associated with allergy-related conditions. Allergy-related conditions preferably include one or more food-related allergy conditions, which can include any one or more: a wheat allergy, a treenut allergy (e.g., allergies associated with almonds, cashews, chestnuts, pecans, pistachios, pine nuts, walnuts, macadamia nuts, etc.), a shellfish allergy, a soy allergy, a peanut allergy, an egg allergy, a fruit allergy, a milk allergy, a garlic allergy, a corn allergy, an alpha-gal allergy, a fish allergy, a meat allergy, a spices-related allergy, chemical additive-related allergy, food coloring-related allergy, food protein-induced enterocolitis syndrome (FPIES), and/or any other suitable allergies related to food items (e.g., ingredients, natural food items, combinations of food items such as meals, etc.).

Additionally or alternatively, allergy-related conditions can include any one or more of: a drug-related allergy (e.g., antibiotic medication-related allergies; etc.), a latex allergy, a seasonal allergy, an animal allergy (e.g., pet allergy, insect-related allergy such as a insect venom allergy, etc.), a mold allergy, a dust allergy, a skin allergy, a genetic-related allergy, a stress-related allergy, a hygiene-related allergy, respiratory allergies, and/or any other suitable types of allergies. Allergy-related conditions can include symptoms including one or more of: dizziness, nausea, vomiting, swelling (e.g., of tongue, throat, lips, etc.), hives, sneezing, runny nose, stuffy nose, itchiness (e.g., eye itchiness, etc.), rash, cramps (e.g., stomach cramps), diarrhea, breathing-related symptoms (e.g., difficulty breathing), throat symptoms (e.g., scratchy throat, sore throat, cough, etc.), and/or any other suitable allergy-related symptoms.

Embodiments of the method 100 and/or system 200 can be implemented for a single user for whom microbiome characterization and/or microbiome modulation with therapeutics is of interest, and/or can additionally or alternatively be implemented for a population of users (e.g., including the subject, excluding the subject), where the population of user can include other users dissimilar to and/or similar to the user (e.g., in health condition, in dietary needs, in demographic features, in behavior, in microbiome composition and/or function, etc.); for a subgroup of users (e.g., sharing characteristics, such as characteristics affecting microbiome characterization and/or therapy determination; etc.). Thus, information derived from a set of users (e.g., population of users, subgroup of users, etc.) can be used to provide additional insight into connections between behaviors of a subject and effects on the subject's microbiome, due to aggregation of data from the set of users. In a variation, an aggregate set of biological samples is preferably received from a wide variety of users, collectively including users of one or more of: different demographics (e.g., genders, ages, marital statuses, ethnicities, nationalities, socioeconomic statuses, sexual orientations, etc.), different health conditions (e.g., health and disease states; different allergy-related conditions; different genetic dispositions; etc.), different living situations (e.g., living alone, living with pets, living with a significant other, living with children, etc.), different dietary habits (e.g., omnivorous, vegetarian, vegan, sugar consumption, acid consumption, caffeine consumption, etc.), different behavioral tendencies (e.g., levels of physical activity, drug use, alcohol use, etc.), different levels of mobility (e.g., related to distance traveled within a given time period), and/or any other suitable trait associated with (e.g., has an effect on, etc.) microbiome composition and/or functional features. As such, as the number of users increases, the predictive power of processes implemented in portions of the method 100 can increase, such as in relation to characterizing a variety of users based upon their microbiomes. However, the method 100 can involve generation of characterization and therapies derived from biological sample data from any other suitable group of users.

Data described herein (e.g., sequence data, microbiome composition features, microbiome functional features, allergy-related characterizations, therapy determinations, etc.) can be associated with any suitable temporal indicators (e.g., seconds, minutes, hours, days, weeks, etc.) including one or more: temporal indicators indicating when the data was collected (e.g., temporal indicators indicating when a sample was collected; etc.), determined, transmitted, received, and/or otherwise processed; temporal indicators providing context to content described by the data (e.g., temporal indicators associated with allergy-related characterizations, such as where the allergy-related characterization describes the allergy-related conditions and/or user microbiome status at a particular time; etc.); changes in temporal indicators (e.g., changes in allergy-related characterizations over time, such as in response to receiving a therapy; latency between sample collection, sample analysis, provision of an allergy-related characterization or therapy to a user, and/or other suitable portions of the method 100; etc.); and/or any other suitable indicators related to time.

Additionally or alternatively, parameters, metrics, inputs, outputs, and/or other suitable data can be associated with value types including: scores (e.g., microbiome diversity scores; risk scores for allergy-related conditions; severity scores for allergy-related conditions; microbiome composition diversity scores; microbiome functional diversity scores; etc.), binary values (e.g., presence or absence of a microbiome feature; presence or absence of an allergy-related condition; etc.), classifications (e.g., allergy-related condition classifications for different types of allergies; behavioral classifications; demographic classifications; etc.), confidence levels (e.g., associated with microorganism sequence datasets; with microbiome diversity scores; with other allergy-related characterizations; etc.), values along a spectrum, and/or any other suitable types of values. Any suitable types of data described herein can be used as inputs (e.g., for different models described herein), generated as outputs (e.g., of different models), and/or manipulated in any suitable manner for any suitable components associated with the method 100 and/or system 200.

One or more instances and/or portions of the method 100 and/or processes described herein can be performed asynchronously (e.g., sequentially), concurrently (e.g., multiplex sample processing, such as multiplex amplification of microorganism nucleic acid fragments corresponding to target sequences associated with allergy-related conditions; performing sample processing and analysis for substantially concurrently evaluating a panel of allergy-related conditions; computationally determining microbiome datasets, microbiome features, and/or allergy-related conditions in parallel for a plurality of users, such as concurrently on different threads for parallel computing to improve system processing ability; etc.), in temporal relation (e.g., substantially concurrently with, in response to, serially, prior to, subsequent to, etc.) to a trigger event (e.g., performance of a portion of the method 100), and/or in any other suitable order at any suitable time and frequency by and/or using one or more instances of the system 200, components, and/or entities described herein. For example, the method 100 can include generating a microorganism sequence dataset based on processing microorganism nucleic acids of a biological sample with a bridge amplification substrate of a next generation sequencing platform of a sample handling system, and determining microbiome composition diversity features and microbiome functional diversity features at computing devices operable to communicate with the next generation sequencing platform.

Figure 2:
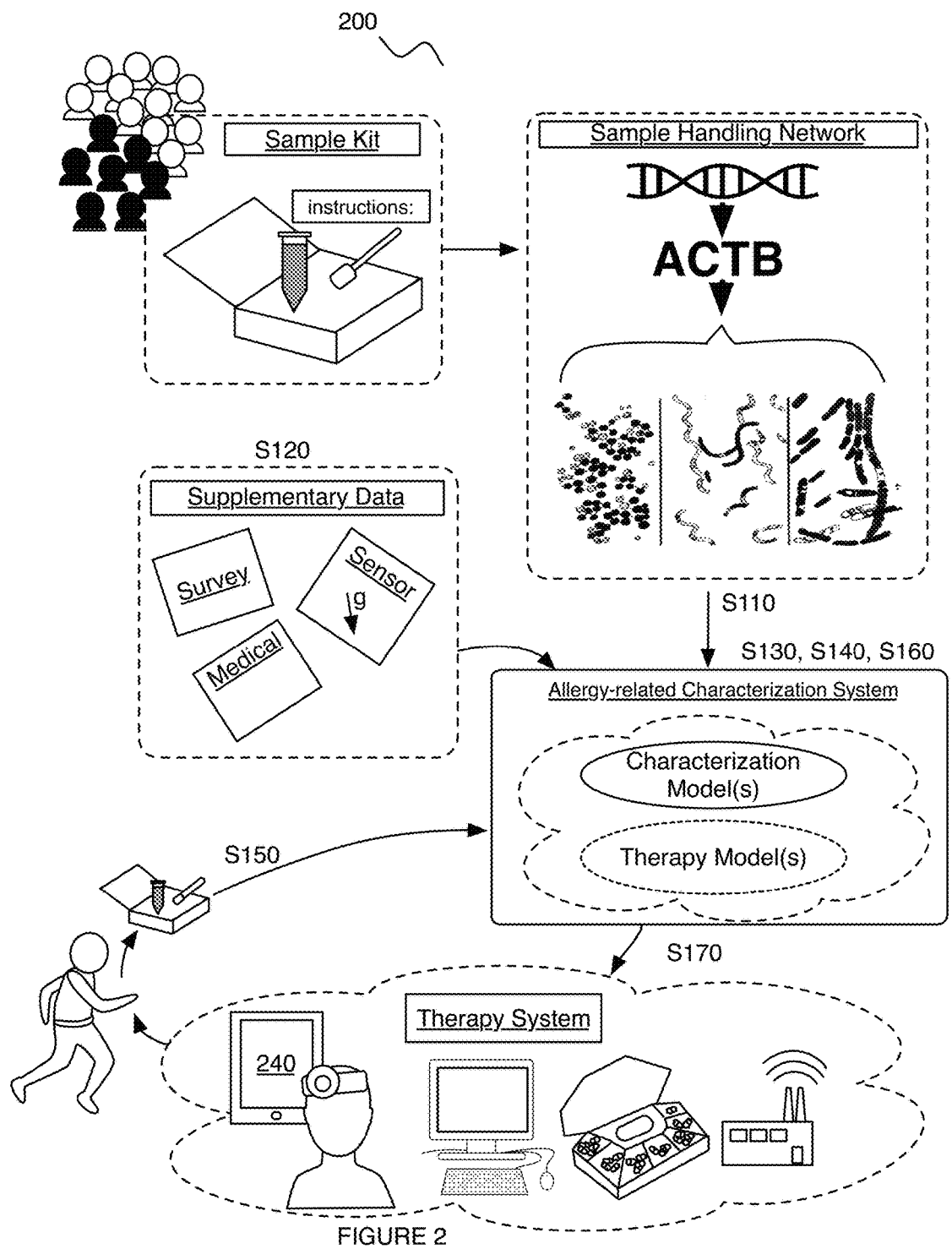
FIG. 2 depicts embodiments of a method and system.

As shown in FIG. 2, embodiments of the system 200 can include any one or more of: a handling system (e.g., a sample handling system, etc.) operable to collect biological samples (e.g., collected by users and included in containers including pre-processing reagents; etc.) from one or more users (e.g., a human subject, patient, animal subject, environmental ecosystem, care provider, etc.), the handling system including a sequencing platform (e.g., next-generation sequencing platform) operable to determine a microorganism sequence dataset for the one or more users from the biological samples; an allergy-related characterization system operable to: determine user microbiome features (e.g., microbiome composition features; microbiome functional features; diversity features; relative abundance ranges; etc.) based on the microorganism sequence dataset (and/or other suitable data described herein), and determine allergy-related characterizations based on the user microbiome features; and/or a treatment system operable to promote a therapy for one or more allergy-related conditions based on the allergy-related characterization. However, the method 100 and/or system 200 can be configured in any suitable manner.

2. Benefits.

Microbiome analysis can enable accurate and/or efficient characterization and/or therapy provision (e.g., according to portions of the method 100, etc.) for allergy-related conditions caused by and/or otherwise associated with microorganisms. The technology can overcome several challenges faced by conventional approaches in characterizing a user condition and/or promoting associated therapies. First, conventional approaches can require patients to visit one or more care providers to receive a characterization and/or a therapy recommendation for an allergy-related condition (e.g., through diagnostic medical procedures such as skin prick testing; etc.), which can amount to inefficiencies and/or health-risks associated with the amount of time elapsed before diagnosis and/or treatment, with inconsistency in healthcare quality, and/or with other aspects of care provider visitation. Second, conventional genetic sequencing and analysis technologies for human genome sequencing can be incompatible and/or inefficient when applied to the microbiome (e.g., where the human microbiome can include over 10 times more microbial cells than human cells; where optimal sample processing techniques can differ, such as for reducing amplification bias; where different approaches to allergy-related characterizations can be employed; where the types of conditions and correlations can differ; where sequence reference databases can differ; where the microbiome can vary across different body regions of the user; etc.). Third, the onset of sequencing technologies (e.g., next-generation sequencing) has given rise to technological issues (e.g., data processing and analysis issues for the plethora of generated sequence data; issues with processing a plurality of biological samples in a multiplex manner; information display issues; therapy prediction issues, therapy provision issues, etc.) that would not exist but for the unprecedented advances in speed and data generation associated with sequencing genetic material. Specific examples of the method 100 and/or system 200 can confer technologically-rooted solutions to at least the challenges described above.

First, the technology can transform entities (e.g., users, biological samples, treatment systems including medical devices, etc.) into different states or things. For example, the technology can transform a biological sample into components able to be sequenced and analyzed for characterizing users in relation to allergy-related conditions (e.g., using next-generation sequencing systems; multiplex amplification operations; etc.). In another example, the technology can identify therapies (e.g., personalized therapies based on a microbiome characterization; etc.) to promote to a user to modify a microbiome composition (e.g., composition diversity), microbiome function (e.g., functional diversity) and/or other microbiome-related aspects to prevent and/or ameliorate one or more allergy-related conditions, thereby transforming the microbiome and/or health of the patient (e.g., improving a health state associated with an allergy-related condition; etc.). In another example, the technology can transform microbiome composition and/or function at different physiological sites of a user, such as targeting and/or transforming a gut, nose, skin, mouth, and/or gentials microbiome. In another example, the technology can control treatment-related systems (e.g., automated medication dispensers; allergen detection systems; etc.) to promote therapies (e.g., by generating control instructions for the treatment system to execute; etc.)), thereby transforming the treatment system.

Second, the technology can confer improvements in computer-related technology (e.g., modeling associated with characterizing and/or promoting therapies for allergy-related conditions; improving computational efficiency in storing, retrieving, and/or processing microorganism-related data for allergy-related conditions; computational processing associated with biological sample processing; etc.) by facilitating computer performance of functions not previously performable. For example, the technology can computationally generate allergy-related characterizations and/or recommended therapies associated with microbiome analysis based on techniques (e.g., leveraging microorganism taxonomic databases, etc.) that are recently viable due to advances in sample processing techniques and/or sequencing technology.

Third, the technology can confer improvements in processing speed, allergy-related characterization accuracy, microbiome-related therapy determination and promotion, and/or other suitable aspects in relation to allergy-related conditions. For example, the technology can generate and apply feature-selection rules (e.g., microbiome diversity feature-selection rules for composition, function, etc.) to select an optimized subset of features (e.g., microbiome composition diversity features such as reference relative abundance features indicative of healthy ranges of taxonomic groups associated with allergy-related conditions; user relative abundance features that can be compared to reference relative abundance features correlated with allergy-related conditions and/or therapy responses; etc.) out of a vast potential pool of features (e.g., extractable from the plethora of microbiome data such as sequence data) for generating and/or applying characterization models and/or therapy models. The potential size of microbiomes (e.g., human microbiomes, animal microbiomes, etc.) can translate into a plethora of data, giving rise to questions of how to process and analyze the vast array of data to generate actionable microbiome insights in relation to allergy-related conditions. However, the feature-selection rules and/or other suitable computer-implementable rules can enable one or more of: shorter generation and execution times (e.g., for generating and/or applying models; for determining allergy-related characterizations and/or associated therapies; etc.); optimized sample processing techniques (e.g., improving transformation of microorganism nucleic acids from biological samples through using primer types, other biomolecules, and/or other sample processing components identified through computational analysis of taxonomic groups, sequences, and/or other suitable data associated with allergy-related conditions, such as while optimizing for improving specificity, reducing amplification bias, and/or other suitable parameters; etc.); model simplification facilitating efficient interpretation of results; reduction in overfitting; network effects associated with generating, storing, and applying microbiome characterizations for a plurality of users over time in relation to allergy-related conditions (e.g., through collecting and processing an increasing amount of microbiome-related data associated with an increasing number of users to improve predictive power of the allergy-related characterizations and/or therapy determinations; etc.), improvements in data storage and retrieval (e.g., storing specific models such as in association with different users and/or sets of users; microbiome datasets in association with user accounts; therapy monitoring data in association with one or more therapies and/or user receiving the therapies; features, allergy-related characterizations, and/or other suitable data in association with a user and/or set of users to improve delivery of personalized characterizations and/or treatments for the allergy-related conditions, etc.), and/or other suitable improvements to technological areas.

Fourth, the technology can amount to an inventive distribution of functionality across a network including a sample handling system, an allergy-related characterization system, and a plurality of users, where the sample handling system can handle substantially concurrent processing of biological samples (e.g., in a multiplex manner) from the plurality of users, which can be leveraged by the allergy-related characterization system in generating personalized characterizations and/or therapies (e.g., customized to the user's microbiome such as in relation to the user's dietary behavior, probiotics-associated behavior, medical history, demographics, other behaviors, preferences, etc.) for allergy-related conditions.

Fifth, the technology can improve the technical fields of at least microbiome-related digital medicine, digital medicine generally, genetic sequencing, modeling (e.g., of allergy-related conditions associated with microbiomes; etc.) and/or other relevant fields. Sixth, the technology can leverage specialized computing devices (e.g., devices associated with the sample handling system, such as next-generation sequencing platforms; allergy-related characterization systems; treatment systems; etc.) in determining and processing microbiome datasets in relation to allergy-related characterization and/or therapy provision. The technology can, however, provide any other suitable benefit(s) in the context of using non-generalized computer systems for allergy-related characterization, microbiome modulation, and/or for performing other suitable portions of the method 100.

3.1 Generating a Microbiome Dataset.

Block S110 recites: generating a microbiome dataset (e.g., microorganism sequence dataset, microbiome composition diversity dataset, microbiome functional diversity dataset, etc.) for each of an aggregate set of biological samples associated with a population of users (e.g., subjects), based on sample processing of the biological samples. Block S110 functions to process each of an aggregate set of biological samples (e.g., associated with a population of subjects, a subpopulation of subjects, a subgroup of subjects sharing a demographic characteristic and/or other suitable characteristics, etc.), in order to determine compositional, functional, pharmacogenomics, and/or other suitable aspects associated with the microbiomes of the users, such as in relation to one or more allergy-related conditions. Compositional and/or functional aspects can include one or more aspects at the microorganism level, including parameters related to distribution of microorganisms across different groups of kingdoms, phyla, classes, orders, families, genera, species, subspecies, strains, and/or any other suitable infraspecies taxon (e.g., as measured in total abundance of each group, relative abundance of each group, total number of groups represented, etc.). Compositional and/or functional aspects can also be represented in terms of operational taxonomic units (OTUs). Compositional and/or functional aspects can additionally or alternatively include compositional aspects at the genetic level (e.g., regions determined by multilocus sequence typing, 16S sequences, 18S sequences, ITS sequences, other genetic markers, other phylogenetic markers, etc.). Compositional and functional aspects can include the presence or absence or the quantity of genes associated with specific functions (e.g. enzyme activities, transport functions, immune activities, etc.). Outputs of Block S110 can thus be used to provide features of interest for the characterization process of Block S130 and/or other suitable portions of the method 100 (e.g., where Block S110 can lead to outputs of microbiome composition datasets, microbiome functional datasets, and/or other suitable microbiome datasets from which microbiome features can be extracted, etc.), where the features can be microorganism-based (e.g., presence of a genus of bacteria), genetic-based (e.g., based upon representation of specific genetic regions and/or sequences) and/or functional-based (e.g., presence of a specific catalytic activity).

In one variation, Block S110 can include assessment and/or processing based upon phylogenetic markers derived from bacteria and/or archaea in relation to gene families associated with one or more of: ribosomal protein S2, ribosomal protein S3, ribosomal protein S5, ribosomal protein S7, ribosomal protein S8, ribosomal protein S9, ribosomal protein S10, ribosomal protein S11, ribosomal protein S12/S23, ribosomal protein S13, ribosomal protein S15P/S13e, ribosomal protein S17, ribosomal protein S19, ribosomal protein L1, ribosomal protein L2, ribosomal protein L3, ribosomal protein L4/L1e, ribosomal protein L5, ribosomal protein L6, ribosomal protein L10, ribosomal protein L11, ribosomal protein L14b/L23e, ribosomal protein L15, ribosomal protein L16/L10E, ribosomal protein L18P/L5E, ribosomal protein L22, ribosomal protein L24, ribosomal protein L25/L23, ribosomal protein L29, translation elongation factor EF-2, translation initiation factor IF-2, metalloendopeptidase, ffh signal recognition particle protein, phenylalanyl-tRNA synthetase beta subunit, phenylalanyl-tRNA synthetase alpha subunit, tRNA pseudouridine synthase B, Porphobilinogen deaminase, ribosomal protein L13, phosphoribosylformylglycinamidine cyclo-ligase, and ribonuclease HII. Additionally or alternatively, markers can include target sequences (e.g., sequences associated with a microorganism taxonomic group; sequences associated with functional aspects; sequences correlated with allergy-related conditions; sequences indicative of user responsiveness to different therapies; sequences that are invariant across a population and/or any suitable set of subjects, such as to facilitate multiplex amplification using a primer type sharing a primer sequence; conserved sequences; sequences including mutations, polymorphisms; nucleotide sequences; amino acid sequences; etc.), proteins (e.g., serum proteins, antibodies, etc.), peptides, carbohydrates, lipids, other nucleic acids, whole cells, metabolites, natural products, genetic predisposition biomarkers, diagnostic biomarkers, prognostic biomarkers, predictive biomarkers, other molecular biomarkers, gene expression markers, imaging biomarkers, and/or other suitable markers. However, markers can include any other suitable marker(s) associated with microbiome composition, microbiome functionality, and/or allergy-related conditions.

Characterizing the microbiome composition and/or functional aspects for each of the aggregate set of biological samples thus preferably includes a combination of sample processing techniques (e.g., wet laboratory techniques), including, but not limited to, amplicon sequencing (e.g., 16S, 18S, ITS), unique molecule identifiers (UMIs), 3 step PCR, CRISPR, metagenomic approaches, metatranscriptomics, use of random primers, and computational techniques (e.g., utilizing tools of bioinformatics) to quantitatively and/or qualitatively characterize the microbiome and functional aspects associated with each biological sample from a subject or population of subjects.

In variations, sample processing in Block S110 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification of nucleic acids from the biological sample, further purification of amplified nucleic acids of the biological sample, and sequencing of amplified nucleic acids of the biological sample. In an example, Block S110 can include: collecting biological samples from a set of users (e.g., biological samples collected by the user with a sampling kit including a sample container, etc.), where the biological samples include microorganism nucleic acids associated with the allergy-related condition (e.g., microorganism nucleic acids including target sequences correlated with an allergy-related condition; etc.). In another example, Block S110 can include providing a set of sampling kits to a set of users, each sampling kit of the set of sampling kits including a sample container (e.g., including pre-processing reagents, such as lysing reagents; etc.) operable to receive a biological sample from a user of the set of users.

In variations, lysing a biological sample and/or disrupting membranes in cells of a biological sample preferably includes physical methods (e.g., bead beating, nitrogen decompression, homogenization, sonication), which omit certain reagents that produce bias in representation of certain bacterial groups upon sequencing. Additionally or alternatively, lysing or disrupting in Block S110 can involve chemical methods (e.g., using a detergent, using a solvent, using a surfactant, etc.). Additionally or alternatively, lysing or disrupting in Block S110 can involve biological methods. In variations, separation of undesired elements can include removal of RNA using RNases and/or removal of proteins using proteases. In variations, purification of nucleic acids can include one or more of: precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and any other suitable purification techniques.

In variations, amplification of purified nucleic acids can include one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically, phylogenetically, for diagnostics, for formulations (e.g., for probiotic formulations), and/or for any other suitable purpose. Thus, universal primers (e.g., a F27-R338 primer set for 16S RNA, a F515-R806 primer set for 16S RNA, etc.) configured to avoid amplification bias can be used in amplification. Additionally or alternatively include incorporated barcode sequences and/or UMIs specific to biological samples, to users, to allergy-related conditions, to taxa, to target sequences, and/or to any other suitable components, which can facilitate a post-sequencing identification process (e.g., for mapping sequence reads to microbiome composition and/or microbiome function aspects; etc.). Primers used in variations of Block S110 can additionally or alternatively include adaptor regions configured to cooperate with sequencing techniques involving complementary adaptors (e.g., Illumina Sequencing). Additionally or alternatively, Block S110 can implement any other step configured to facilitate processing (e.g., using a Nextera kit). In a specific example, performing amplification and/or sample processing operations can be in a multiplex manner (e.g., for a single biological sample, for a plurality of biological samples across multiple users; etc.). In another specific example, performing amplification can include normalization steps to balance libraries and detect all amplicons in a mixture independent of the amount of starting material, such as 3 step PCR, bead based normalization, etc.

In variations, sequencing of purified nucleic acids can include methods involving targeted amplicon sequencing, metatranscriptomic sequencing and/or metagenomic sequencing, implementing techniques including one or more of: sequencing-by-synthesis techniques (e.g., Illumina sequencing), capillary sequencing techniques (e.g., Sanger sequencing), pyrosequencing techniques, and nanopore sequencing techniques (e.g., using an Oxford Nanopore technique).

In a specific example, amplification and sequencing of nucleic acids from biological samples of the set of biological samples includes: solid-phase PCR involving bridge amplification of DNA fragments of the biological samples on a substrate with oligo adapters, where amplification involves primers having a forward index sequence (e.g., corresponding to an Illumina forward index for MiSeq/NextSeq/HiSeq platforms), a forward barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, UMIs, a sequence for targeting a specific target region (e.g., 16S region, 18S region, ITS region), a reverse index sequence (e.g., corresponding to an Illumina reverse index for MiSeq/HiSeq platforms), and a reverse barcode sequence. In the specific example, sequencing can include Illumina sequencing (e.g., with a HiSeq platform, with a MiSeq platform, with a NextSeq platform, etc.) using a sequencing-by-synthesis technique. In another specific example, the method 100 can include identifying a primer type compatible with a genetic target associated with an allergy-related condition; fragmenting microorganism nucleic acids from a biological sample; performing multiplex amplification with the fragmented microorganism nucleic acids based on the fragmented microorganism nucleic acids and the identified primer type; and/or generating the microorganism sequence dataset based on the amplified microorganism nucleic acids.

In variations, primers (e.g., of a primer type corresponding to a primer sequence; etc.) used in Block S110 and/or other suitable portions of the method 100 can include primers associated with protein genes (e.g., coding for conserved protein gene sequences across a plurality of taxa, such as to enable multiplex amplification for a plurality of targets and/or taxa; etc.). Primers can additionally or alternatively be associated with allergy-related conditions (e.g., primers compatible with genetic targets including microorganism sequence biomarkers for microorganisms correlated with allergy-related conditions; etc.), microbiome composition features (e.g., identified primers compatible with a genetic target corresponding to microbiome composition features associated with a group of taxa correlated with an allergy-related condition; genetic sequences from which relative abundance features are derived etc.), functional diversity features, supplementary features, and/or other suitable features and/or data. Primers (and/or other suitable molecules, markers, and/or biological material described herein) can possess any suitable size (e.g., sequence length, number of base pairs, conserved sequence length, variable region length, etc.). Additionally or alternatively, any suitable number of primers can be used in sample processing for performing characterizations (e.g., allergy-related characterizations; etc.), improving sample processing (e.g., through reducing amplification bias, etc.), and/or for any suitable purposes. The primers can be associated with any suitable number of targets, sequences, taxa, conditions, and/or other suitable aspects. Primers used in Block S110 and/or other suitable portions of the method 100 can be selected through processes described in Block S110 (e.g., primer selection based on parameters used in generating the taxonomic database) and/or any other suitable portions of the method 100. In an example, Block S110 can include: identifying a primer type for a microorganism nucleic acid sequence associated with the allergy-related condition (e.g., a primer type for a primer operable to amplify microorganism nucleic acid sequences correlated with an allergy-related condition; etc.); and generating the microorganism sequence dataset based on the primer type and the microorganism nucleic acids (e.g., using primers of the primer type for amplification of microorganism nucleic acids; and sequencing the amplified nucleic acids to generate the microorganism sequence dataset; etc.). In a specific example, Block S110 can include: fragmenting the microorganism nucleic acids; and performing multiplex amplification with the fragmented microorganism nucleic acids based on the fragmented microorganism nucleic acids and the identified primer type associated with the allergy-related condition. Additionally or alternatively, primers (and/or processes associated with primers) can include and/or be analogous to that described in U.S. application Ser. No. 14/919,614, filed 21 Oct. 2015, which is herein incorporated in its entirety by this reference. However, identification and/or usage of primers can be configured in any suitable manner.

Some variations of sample processing can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and/or any other suitable purification technique.

In variations, computational processing in Block S110 can include any one or more of: identification of microbiome-derived sequences (e.g., as opposed to subject sequences and contaminants), alignment and mapping of microbiome-derived sequences (e.g., alignment of fragmented sequences using one or more of single-ended alignment, ungapped alignment, gapped alignment, pairing), and generating features derived from compositional and/or functional aspects of the microbiome associated with a biological sample.

Identification of microbiome-derived sequences can include mapping of sequence data from sample processing to a subject reference genome (e.g., provided by the Genome Reference Consortium), in order to remove subject genome-derived sequences. Unidentified sequences remaining after mapping of sequence data to the subject reference genome can then be further clustered into operational taxonomic units (OTUs) based upon sequence similarity and/or reference-based approaches (e.g., using VAMPS, using MG-RAST, using QIIME databases), aligned (e.g., using a genome hashing approach, using a Needleman-Wunsch algorithm, using a Smith-Waterman algorithm), and mapped to reference bacterial genomes (e.g., provided by the National Center for Biotechnology Information), using an alignment algorithm (e.g., Basic Local Alignment Search Tool, FPGA accelerated alignment tool, BWT-indexing with BWA, BWT-indexing with SOAP, BWT-indexing with Bowtie, etc.). Mapping of unidentified sequences can additionally or alternatively include mapping to reference archaeal genomes, viral genomes and/or eukaryotic genomes. Furthermore, mapping of taxons can be performed in relation to existing databases, and/or in relation to custom-generated databases.

Upon identification of represented groups of microorganisms of the microbiome associated with a biological sample, generating features derived from compositional and functional aspects of the microbiome associated with a biological sample can be performed. In one variation, generating features can include generating features based upon multilocus sequence typing (MSLT), in order to identify markers useful for characterization in subsequent blocks of the method 100. Additionally or alternatively, generated features can include generating features that describe the presence or absence of certain taxonomic groups of microorganisms, and/or ratios between exhibited taxonomic groups of microorganisms. Additionally or alternatively, generating features can include generating features describing one or more of: quantities of represented taxonomic groups, networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional aspect(s). In examples, generating the allergy-related characterization can be based on a set of user microbiome features associated with at least one of: presence of a microbiome feature from a set of microbiome features, absence of a microbiome feature from a set of microbiome features, relative abundance of different taxonomic groups associated with the allergy-related condition, a ratio between at least two microbiome features associated with the different taxonomic groups, interactions between the different taxonomic groups, and phylogenetic distance between the different taxonomic groups.

Additionally or alternatively, generating features can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features derived from relative abundance factors (e.g., in relation to changes in abundance of a taxon, which affects abundance of other taxons). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon. Block S120 can, however, include generation of any other suitable feature(s) derived from sequencing and mapping of nucleic acids of a biological sample. For instance, the feature(s) can be combinatory (e.g. involving pairs, triplets), correlative (e.g., related to correlations between different features), and/or related to changes in features (e.g., temporal changes, changes across sample sites, etc., spatial changes, etc.). However, processing biological samples, generating a microbiome dataset, and/or other aspects associated with Block S110 can be performed in any suitable manner.

3.2 Processing a Supplementary Dataset.

Block S120 recites: processing (e.g., receiving, collecting, transforming, etc.) a supplementary dataset associated with (e.g., informative of; describing; indicative of; etc.) one or more allergy-related conditions for the set of users. Block S120 can function to acquire data associated with one or more subjects of the set of subjects, which can be used to train, validate, apply, and/or otherwise inform the allergy-related characterization process (e.g., in Block S130). In Block S120, the supplementary dataset preferably includes survey-derived data, but can additionally or alternatively include any one or more of: contextual data derived from sensors, medical data (e.g., current and historical medical data; medical device-derived data; data associated with medical tests; etc.), and any other suitable type of data. In variations of Block S120 including reception of survey-derived data, the survey-derived data preferably provides physiological, demographic, and behavioral information in association with a subject. Physiological information can include information related to physiological features (e.g., height, weight, body mass index, body fat percent, body hair level, etc.). Demographic information can include information related to demographic features (e.g., gender, age, ethnicity, marital status, number of siblings, socioeconomic status, sexual orientation, etc.). Behavioral information can include information related to one or more of: health conditions (e.g., health and disease states), living situations (e.g., living alone, living with pets, living with a significant other, living with children, etc.), dietary habits (e.g., omnivorous, vegetarian, vegan, sugar consumption, acid consumption, consumption of wheat, egg, soy, treenut, peanut, shellfish, and/or other suitable allergy-related foods, etc.), behavioral tendencies (e.g., levels of physical activity, drug use, alcohol use, etc.), different levels of mobility (e.g., related to distance traveled within a given time period), different levels of sexual activity (e.g., related to numbers of partners and sexual orientation), and any other suitable behavioral information. Survey-derived data can include quantitative data and/or qualitative data that can be converted to quantitative data (e.g., using scales of severity, mapping of qualitative responses to quantified scores, etc.).

In facilitating reception of survey-derived data, Block S130 can include providing one or more surveys to a subject of the population of subjects, or to an entity associated with a subject of the population of subjects. Surveys can be provided in person (e.g., in coordination with sample provision and reception from a subject), electronically (e.g., during account setup by a subject, at an application executing at an electronic device of a subject, at a web application accessible through an internet connection, etc.), and/or in any other suitable manner.

Additionally or alternatively, portions of the supplementary dataset can be derived from sensors associated with the subject(s) (e.g., sensors of wearable computing devices, sensors of mobile devices, biometric sensors associated with the user, etc.). As such, Block S130 can include receiving one or more of: physical activity- or physical action-related data (e.g., accelerometer and gyroscope data from a mobile device or wearable electronic device of a subject), environmental data (e.g., temperature data, elevation data, climate data, light parameter data, etc.), patient nutrition or diet-related data (e.g., data from food establishment check-ins, data from spectrophotometric analysis, user-inputted data, nutrition data associated with probiotic and/or prebiotic food items, types of food consumed, amount of food consumed, diets, etc.), biometric data (e.g., data recorded through sensors within the patient's mobile computing device, data recorded through a wearable or other peripheral device in communication with the patient's mobile computing device), location data (e.g., using GPS elements), and any other suitable data. In variations, sensor data can include data sampled at one or more: optical sensors (e.g., image sensors, light sensors, etc.), audio sensors, temperature sensors, volatile compound sensors, weight sensors, humidity sensors, depth sensors, location sensors (GPS receivers; etc.), inertial sensors (e.g., accelerators, gyroscope, magnetometer, etc.), biometric sensors (e.g., heart rate sensors, fingerprint sensors, bio-impedance sensors, etc.), pressure sensors, flow sensors, power sensors (e.g., Hall effect sensors), and/or or any other suitable sensor.

Additionally or alternatively, portions of the supplementary dataset can be derived from medical record data and/or clinical data of the subject(s). As such, portions of the supplementary dataset can be derived from one or more electronic health records (EHRs) of the subject(s).

Additionally or alternatively, the supplementary dataset of Block S120 can include any other suitable diagnostic information (e.g., clinical diagnosis information), which can be combined with analyses derived from features to support characterization of subjects in subsequent blocks of the method 100. For instance, information derived from a colonoscopy, biopsy, blood test, diagnostic imaging, survey-related information, and any other suitable test can be used to supplement.

Additionally or alternatively, the supplementary dataset can include therapy-related data including one or more of: therapy regimens, types of therapies, recommended therapies, therapies used by the user, therapy adherence, etc. For example, the supplementary dataset can include user adherence (e.g., medication adherence, probiotic adherence, physical exercise adherence, dietary adherence, etc.) to a recommended therapy. However, processing supplementary datasets can be performed in any suitable manner.

3.3 Performing a Characterization Process.

Block S130 recites: performing a characterization process for the one or more allergy-related conditions, based on the supplementary dataset and/or microbiome features (e.g., microbiome composition diversity features; microbiome functional diversity features; etc.) extracted from the microbiome dataset. Block S130 can function to identify, extract, and/or otherwise process features and/or feature combinations that can be used to characterize subjects or groups based upon their microbiome composition features, functional features, and/or other suitable microbiome features (e.g., such as through the generation and application of a characterization model for determining allergy-related characterizations, etc.). As such, the characterization process can be used as a diagnostic tool that can characterize a subject (e.g., in terms of behavioral traits, in terms of medical conditions, in terms of demographic traits, etc.) based upon their microbiome composition and/or functional features, in relation to one or more of their health condition states (e.g., allergy-related condition states), behavioral traits, medical conditions, demographic traits, and/or any other suitable traits. Such characterization can then be used to suggest or provide personalized therapies by way of the therapy model of Block S140.

In performing the characterization process, Block S130 can use computational methods (e.g., statistical methods, machine learning methods, artificial intelligence methods, bioinformatics methods, etc.) to characterize a subject as exhibiting features characteristic of a group of subjects with a health condition.

In one variation, characterization can be based upon features derived from a statistical analysis (e.g., an analysis of probability distributions) of similarities and/or differences between a first group of subjects exhibiting a target state (e.g., a health condition state) and a second group of subjects not exhibiting the target state (e.g., a "normal" state). In implementing this variation, one or more of a Kolmogorov-Smirnov (KS) test, a permutation test, a Cramér-von Mises test, and any other statistical test (e.g., t-test, z-test, chi-squared test, test associated with distributions, etc.) can be used. In particular, one or more such statistical hypothesis tests can be used to assess a set of features having varying degrees of abundance in a first group of subjects exhibiting a target state (e.g., a sick state) and a second group of subjects not exhibiting the target state (e.g., having a normal state). In more detail, the set of features assessed can be constrained based upon percent abundance and/or any other suitable parameter pertaining to diversity in association with the first group of subjects and the second group of subjects, in order to increase or decrease confidence in the characterization. In a specific implementation of this example, a feature can be derived from a taxon of bacteria that is abundant in a certain percentage of subjects of the first group and subjects of the second group, where a relative abundance of the taxon between the first group of subjects and the second group of subjects can be determined from the KS test, with an indication of significance (e.g., in terms of p-value). Thus, an output of Block S130 can include a normalized relative abundance value (e.g., 25% greater abundance of a taxon in subjects with an allergy-related condition vs. subjects without the allergy-related condition; in sick subjects vs. healthy subjects) with an indication of significance (e.g., a p-value of 0.0013). Variations of feature generation can additionally or alternatively implement or be derived from functional features or metadata features (e.g., non-bacterial markers). Additionally or alternatively, any suitable microbiome features can be derived based on statistical analyses (e.g., applied to a microorganism sequence dataset and/or other suitable microbiome dataset, etc.) including any one or more of: a prediction analysis, multi hypothesis testing, a random forest test, and principal component analysis.

In performing the characterization process, Block S130 can additionally or alternatively transform input data from at least one of the microbiome composition diversity dataset and microbiome functional diversity dataset into feature vectors that can be tested for efficacy in predicting characterizations of the population of subjects. Data from the supplementary dataset can be used to provide indication of one or more characterizations of a set of characterizations, where the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of subject features, of combinations of features) having high correlation with specific classifications of subjects.

In variations, feature vectors (and/or any suitable set of features) effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and any other suitable features derived from the microbiome diversity dataset and/or the supplementary dataset. In variations, microbiome features can be associated with (e.g., include, correspond to, typify, etc.) at least one of: presence of a microbiome feature from the microbiome features, absence of the microbiome features from the microbiome features, relative abundance of different taxonomic groups associated with the allergy-related condition; a ratio between at least two microbiome features associated with the different taxonomic groups, interactions between the different taxonomic groups, and phylogenetic distance between the different taxonomic groups. In a specific example, microbiome features can include one or more relative abundance characteristics associated with at least one of the microbiome composition diversity features (e.g., relative abundance associated with different taxa, etc.) and the microbiome functional diversity features (e.g., relative abundance of sequences corresponding to different functional features; etc.). Relative abundance characteristics and/or other suitable microbiome features (and/or other suitable data described herein) can be extracted and/or otherwise determined based on: a normalization, a feature vector derived from at least one of linear latent variable analysis and non-linear latent variable analysis, linear regression, non-linear regression, a kernel method, a feature embedding method, a machine learning method, and a statistical inference method. Additionally or alternatively, combinations of features can be used in a feature vector, where features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, the feature vectors can additionally or alternatively be determined in any other suitable manner.

Figure 3:
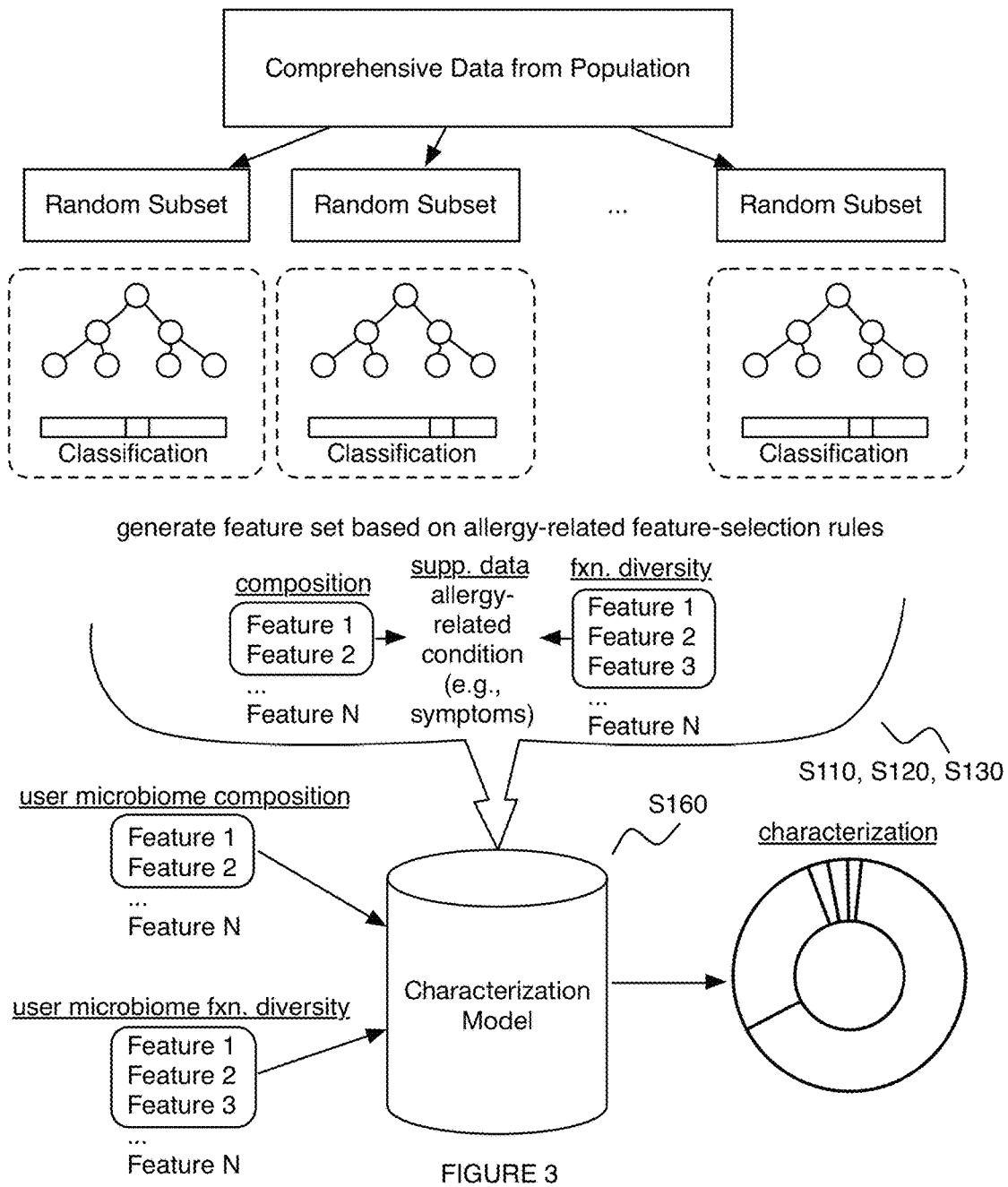
FIG. 3 depicts a variation of a process for generation of a characterization model in an embodiment of a method.

As shown in FIG. 3, in one such alternative variation of Block S130, the characterization process can be generated and trained according to a random forest predictor (RFP) algorithm that combines bagging (e.g., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this variation, measures to prevent bias (e.g., sampling bias) and/or account for an amount of bias can be included during processing to increase robustness of the model.

Additionally or alternatively, Block S130 (e.g., extracting microbiome features; generating characterization models for allergy-related conditions; etc.) and/or other suitable portions of the method 100 (e.g., determining an allergy-related characterization; determining and/or providing a therapy; etc.) can employ data processing approaches including any one or more of: performing pattern recognition on data (e.g., identifying correlations between allergy-related conditions and microbiome features; etc.), fusing data from multiple sources (e.g., generating characterization models based on microbiome data and/or supplementary data from a plurality of users associated with one or more allergy-related conditions; etc.), combination of values (e.g., averaging values, etc.), compression, conversion (e.g., digital-to-analog conversion, analog-to-digital conversion), performing statistical estimation on data (e.g. ordinary least squares regression, non-negative least squares regression, principal components analysis, ridge regression, etc.), wave modulation, normalization, updating (e.g., of characterization models and/or therapy models based on processed biological samples over time; etc.), ranking (e.g., microbiome features; therapies; etc.), weighting (e.g., microbiome features; etc.), validating, filtering (e.g., for baseline correction, data cropping, etc.), noise reduction, smoothing, filling (e.g., gap filling), aligning, model fitting, binning, windowing, clipping, transformations, mathematical operations (e.g., derivatives, moving averages, summing, subtracting, multiplying, dividing, etc.), data association, multiplexing, demultiplexing, interpolating, extrapolating, clustering, image processing techniques, other signal processing operations, other image processing operations, visualizing, and/or any other suitable processing operations. However, data processing for facilitating any suitable portions of the method 100 can be performed in any suitable manner.

In a variation, Block S130 and/or other portions of the method 100 can include applying computer-implemented rules (e.g., models, feature selection rules, etc.) to process population-level data, but can additionally or alternatively include applying computer-implemented rules to process microbiome-related data on a demographic-specific basis (e.g., subgroups sharing a demographic feature such as allergy-relation conditions therapy regiments, dietary regiments, physical activity regiments, ethnicity, age, gender, weight, sleeping behaviors, etc.), condition-specific basis (e.g., subgroups exhibiting a specific allergy-related condition, a combination of allergy-related conditions, triggers for the allergy-related conditions, associated symptoms, etc.), a sample type-specific basis (e.g., applying different computer-implemented rules to process microbiome data derived from different collection sites; etc.), a user basis (e.g., different computer-implemented rules for different users; etc.) and/or any other suitable basis. As such, Block S132 can include assigning users from the population of users to one or more subgroups; and applying different computer-implemented rules for determining features (e.g., the set of feature types used; the types of characterization models generated from the features; etc.) for the different subgroups. However, applying computer-implemented rules can be performed in any suitable manner.

In another variation, Block S130 can include processing (e.g., generating, training, updating, executing, storing, etc.) one or more characterization models (e.g., allergy-related condition characterization models, etc.) for one or more allergy-related conditions. The characterization models preferably leverage microbiome features as inputs, and preferably output allergy-related characterizations and/or any suitable components thereof; but characterization models can use and suitable inputs to generate any suitable outputs. In an example, Block S130 can include transforming the supplementary data, the microbiome composition diversity features, and the microbiome functional diversity features into a characterization model (e.g., training an allergy-related characterization model based on the supplementary data and microbiome features; etc.) for the allergy-related condition. In another example, the method 100 can include: determining a population microorganism sequence dataset (e.g., including microorganism sequence outputs for different users of the population; etc.) for a population of users associated with one or more allergy-related conditions, based on a set of samples from the population of users (e.g., and/or based on one or more primer types associated with the allergy-related condition; etc.); collecting a supplementary dataset associated with diagnosis of the one or more allergy-related conditions for the population of subjects; and generating the allergy-related condition characterization model based on the population microorganism sequence dataset and the supplementary dataset.

Figure 8A:
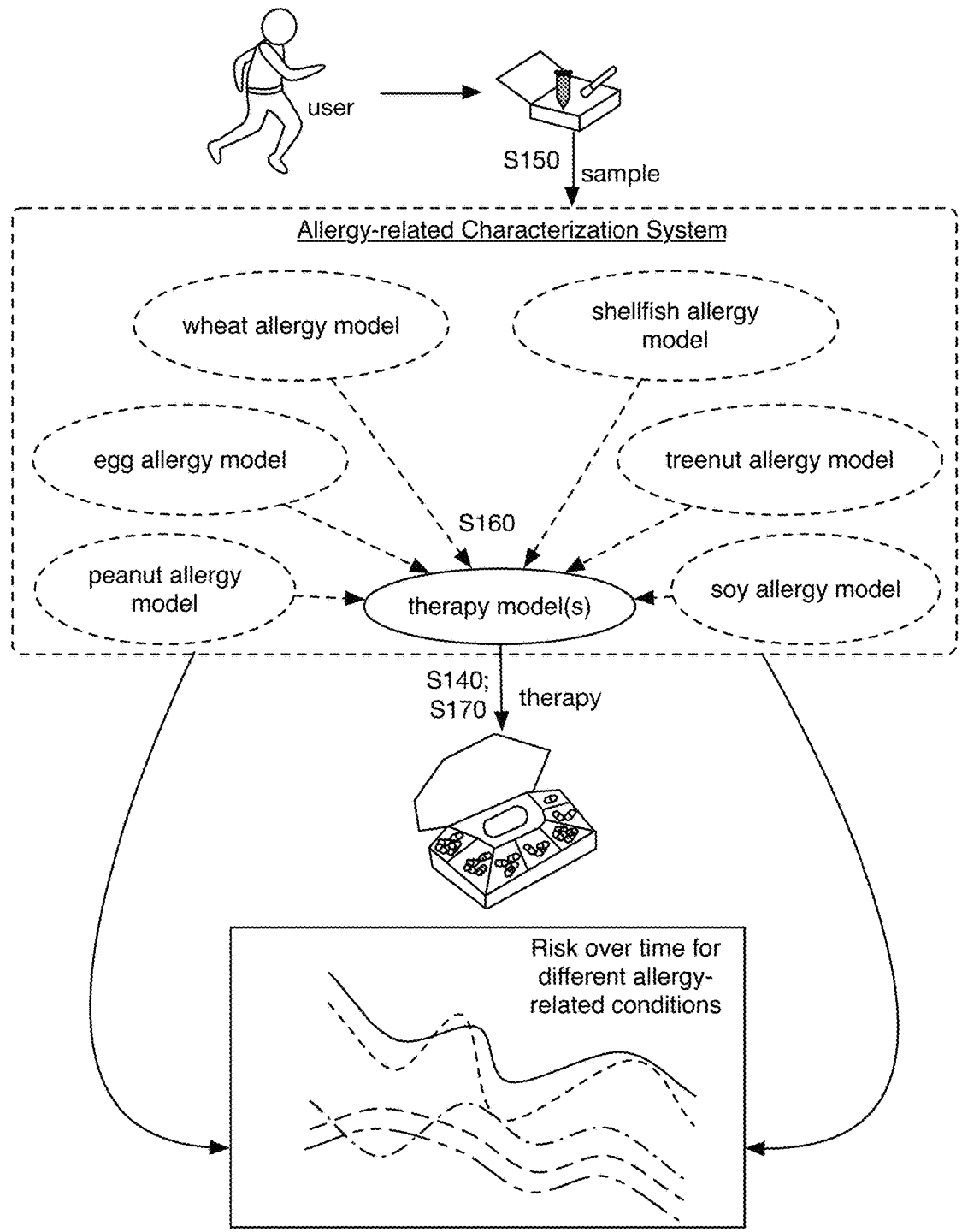
FIGS. 8A-8B depicts variations of performing characterization processes with models allergy-related models.
Figure 8B:
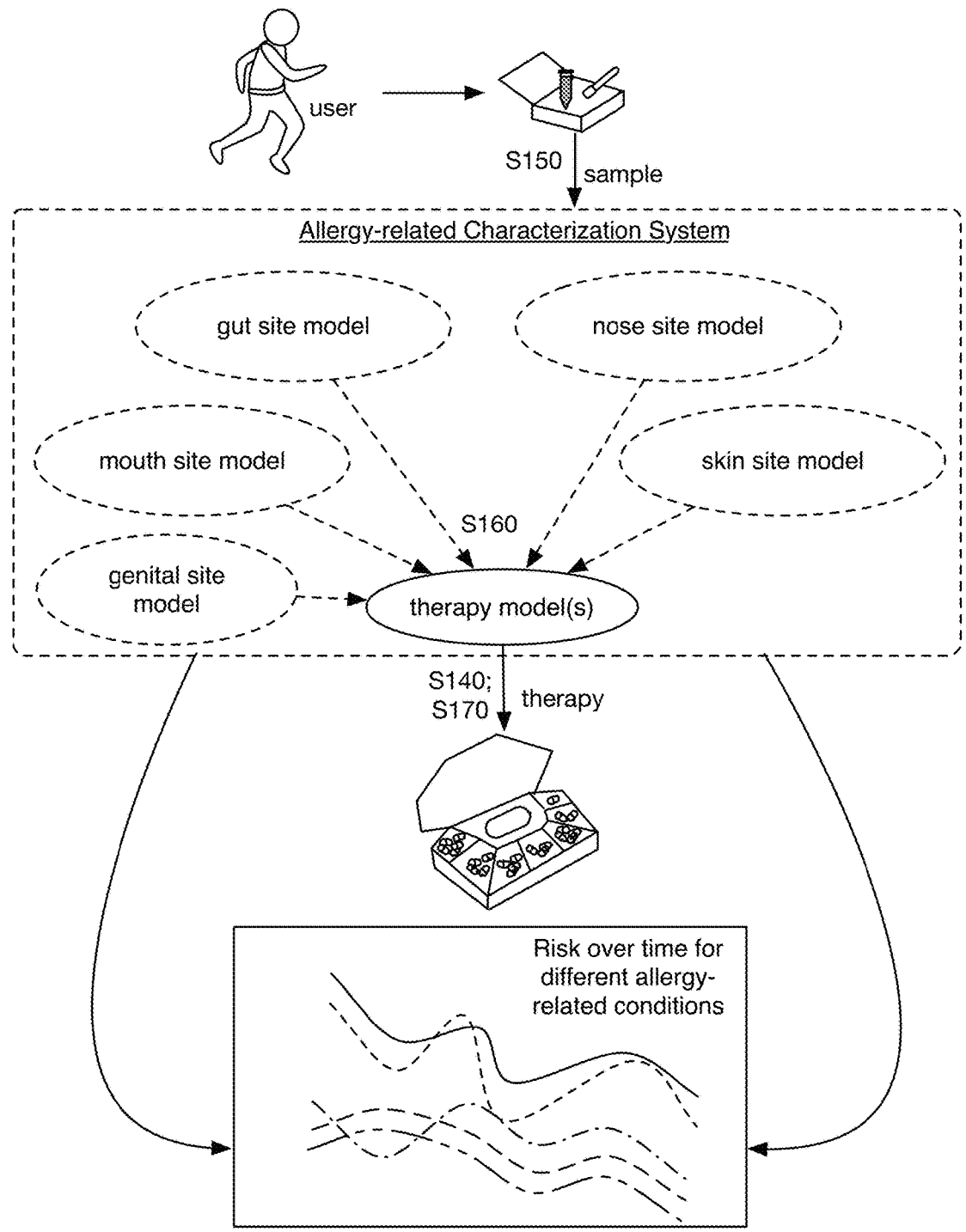

In another variation, as shown in FIGS. 8A-8B, different allergy-related characterization models and/or other suitable models (e.g., generated with different algorithms, with different sets of features, with different input and/or output types, applied in different manners such as in relation to time, frequency, component applying the model, etc.) can be generated for different demographic groups (e.g., a first characterization model for users on a dietary regimen including food items associated with the allergy-related condition, and a second characterization model for users on a dietary regimen not including the food items; different models based on physical activity level; different models based on age, gender, weight, height, ethnicity; etc.), different physiological sites (e.g., a gut site model, a nose site model, a skin site model, a mouth site model, a genitals site model, etc.) allergy-related conditions (e.g., different characterization models for users with different allergy-related conditions; etc.), individual users, supplementary data (e.g., models incorporating features derived from biometric sensor data and/or survey response data vs. models independent of supplementary data, etc.), and/or other suitable criteria.

In variations, determining allergy-related characterizations and/or any other suitable characterizations for conditions associated with microorganisms can include determining allergy-related characterizations in relation to specific physiological sites (e.g., gut, healthy gut, skin, nose, mouth, genitals, other suitable physiological sites, other sample collection sites, etc.), such as through any one or more of: determining an allergy-related characterization based on an allergy-related characterization model derived based on site-specific data (e.g., defining correlations between an allergy-related condition and microbiome features associated with one or more physiological sites); determining an allergy-related characterization based on a user biological sample collected at one or more physiological sites, and/or any other suitable site-related processes. In examples, machine learning approaches (e.g., classifiers, deep learning algorithms), statistical tests, dimension reduction approaches, and/or other suitable approaches (e.g., described herein) can be applied in determining site-related (e.g., physiological site-related, etc.) characterizations, other suitable characterizations, therapies, and/or any other suitable outputs. However, the method 100 can include determining any suitable site-related (e.g., site-specific) outputs, and/or performing any suitable portions of the method 100 (e.g., collecting samples, processing samples, determining therapies) with site-specificity and/or other site-relatedness in any suitable manner.

Characterization of the subject(s) can additionally or alternatively implement use of a high false positive test and/or a high false negative test to further analyze sensitivity of the characterization process in supporting analyses generated according to embodiments of the method 100.

However, performing a characterization process S130 can be performed in any suitable manner.

3.3.A Wheat Allergy Condition Characterization Process.

In a variation, Block S130 can include performing a wheat allergy condition characterization process (e.g., determining and/or applying a wheat allergy characterization model; etc.) for one or more users. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with a wheat allergy condition. In another example, performing a wheat allergy condition characterization process can facilitate identifications of one or more therapies operable to have a positive effect on the wheat allergy condition (e.g., based upon a random forest predictor algorithm trained with a training dataset derived from a subset of the population of subjects, and validated with a validation dataset derived from a subset of the population of subjects). In particular, a wheat allergy condition can include an immune disorder of the subject characterized by an abnormal reaction of the immune system of the subject to any suitable proteins present in wheat, and where the wheat allergy condition can be associated with diagnosis through laboratory analysis (e.g., skin-prick test, blood-samples tests, IgE tests, etc.) and/or other suitable diagnostic procedures.

Performing a wheat allergy condition characterization process (e.g., a diagnostic process) can be based on microbiome features (e.g., microbiome composition features) associated with (e.g., derived from, informative of, correlated with, etc.) one or more (e.g. in any suitable combination) of the following taxons: *Blautia luti* (species), *Collinsella aerofaciens* (species), *Flavonifractor plautii* (species), *Faecalibacterium prausnitzii* (species), *Dorea formicigenerans* (species), *Subdoligranulum variabile* (species), *Barnesiella intestinihominis* (species), *Bacteroides thetaiotaomicron* (species), *Roseburia inulinivorans* (species), *Parasutterella excrementihominis* (species), *Bifidobacterium longum* (species), *Erysipelatoclostridium ramosum* (species), *Bacteroides fragilis* (species), *Bacteroides vulgatus* (species), *Bacteroides caccae* (species), *Blautia* sp. YHC-4 (species), *Alistipes putredinis* (species), *Bifidobacterium* (genus), *Subdoligranulum* (genus), *Collinsella* (genus), *Dorea* (genus), *Sarcina* (genus), *Moryella* (genus), *Intestinibacter* (genus), *Faecalibacterium* (genus), *Oscillospira* (genus), *Terrisporobacter* (genus), *Bacteroides* (genus), *Anaerotruncus* (genus), *Marvinbryantia* (genus), *Barnesiella* (genus), *Eggerthella* (genus), *Parabacteroides* (genus), *Dialister* (genus), *Roseburia* (genus), *Akkermansia* (genus), *Sutterella* (genus), Bifidobacteriaceae (family), Ruminococcaceae (family), Coriobacteriaceae (family), Oscillospiraceae (family), Clostridiaceae (family), Bacteroidaceae (family), Peptostreptococcaceae (family), Porphyromonadaceae (family), Streptococcaceae (family), Acidaminococcaceae (family), Veillonellaceae (family), Flavobacteriaceae (family), Verrucomicrobiaceae (family), Sutterellaceae (family), Enterobacteriaceae (family), Prevotellaceae (family), Lactobacillaceae (family), Bifidobacteriales (order), Clostridiales (order), Coriobacteriales (order), Bacteroidales (order), Flavobacteriales (order), Verrucomicrobiales (order), Burkholderiales (order), Enterobacteriales (order), Rhodospirillales (order), Actinobacteria (class), Clostridia (class), Bacteroidia (class), Flavobacteriia (class), Verrucomicrobiae (class), Betaproteobacteria (class), Alphaproteobacteria (class), Actinobacteria (phylum), Firmicutes (phylum), Bacteroidetes (phylum) and Verrucomicrobia (phylum).

Additionally or alternatively, microbiome features can be associated with one or more of the following taxons in relation to a sample site (e.g., wheat allergy condition correlations with microorganisms observed at a particular sample site *Abiotrophia* (genus) (e.g., nose site); *Abiotrophia defectiva* (species) (e.g., nose site); *Acetanaerobacterium* (genus) (e.g., gut site); *Acetitomaculum* (genus) (e.g., gut site); Acetobacteraceae (family) (e.g., skin site); Acholeplasmatales (order) (e.g., gut site); Acidaminococcaceae (family) (e.g., gut site); *Acidaminococcus* (genus) (e.g., gut site); *Acidaminococcus intestini* (species) (e.g., gut site); *Acidaminococcus* sp. D21 (species) (e.g., gut site); Acidobacteria (phylum) (e.g., nose site); Acidobacteria (phylum) (e.g., skin site); Acidobacteriia (class) (e.g., nose site); Acidobacteriia (class) (e.g., skin site); *Acinetobacter* (genus) (e.g., nose site); *Actinobacillus* (genus) (e.g., gut site); *Actinobacillus porcinus* (species) (e.g., gut site); Actinobacteria (class) (e.g., gut site); Actinobacteria (phylum) (e.g., gut site); *Actinomyces* (genus) (e.g., nose site); *Actinomyces* (genus) (e.g., genital site); *Actinomyces europaeus* (species) (e.g., genital site); *Actinomyces neuii* (species) (e.g., genital site); *Actinomyces* sp. ICM41 (species) (e.g., mouth site); *Actinomyces* sp. ZSY-1 (species) (e.g., mouth site); Actinomycetaceae (family) (e.g., nose site); Actinomycetales (order) (e.g., gut site); *Adlercreutzia* (genus) (e.g., gut site); *Adlercreutzia equolifaciens* (species) (e.g., gut site); Aerococcaceae (family) (e.g., nose site); Aerococcaceae (family) (e.g., skin site); *Aerococcus* (genus) (e.g., gut site); *Aerococcus christensenii* (species) (e.g., gut site); *Aggregatibacter* (genus) (e.g., nose site); *Aggregatibacter aphrophilus* (species) (e.g., nose site); *Akkermansia* (genus) (e.g., gut site); *Akkermansia muciniphila* (species) (e.g., gut site); *Alistipes* (genus) (e.g., nose site); *Alistipes* (genus) (e.g., gut site); *Alistipes indistinctus* (species) (e.g., gut site); *Alistipes putredinis* (species) (e.g., gut site); *Alistipes* sp. EBA6-25cl2 (species) (e.g., gut site); *Alistipes* sp. HGB5 (species) (e.g., gut site); *Alistipes* sp. RMA 9912 (species) (e.g., gut site); *Alloprevotella* (genus) (e.g., mouth site); *Alloprevotella* (genus) (e.g., skin site); Alphaproteobacteria (class) (e.g., nose site); Alphaproteobacteria (class) (e.g., gut site); *Anaerobacter* (genus) (e.g., gut site); *Anaerococcus* (genus) (e.g., gut site); *Anaerococcus* (genus) (e.g., mouth site); *Anaerococcus* sp. 8404299 (species) (e.g., gut site); *Anaerococcus* sp. 9402080 (species) (e.g., gut site); *Anaerofilum* (genus) (e.g., gut site); *Anaerosporobacter* (genus) (e.g., gut site); *Anaerosporobacter mobilis* (species) (e.g., gut site); *Anaerostipes* (genus) (e.g., nose site); *Anaerostipes hadrus* (species) (e.g., gut site); *Anaerostipes* sp. 3_2_56FAA (species) (e.g., gut site); *Anaerostipes* sp. 494a (species) (e.g., gut site); *Anaerostipes* sp. 5_1_63FAA (species) (e.g., gut site); *Anaerotruncus* (genus) (e.g., gut site); *Anaerotruncus colihominis* (species) (e.g., gut site); *Anaerotruncus* sp. NML 070203 (species) (e.g., gut site); *Anaerovorax* (genus) (e.g., gut site); *Asaccharospora* (genus) (e.g., gut site); *Asaccharospora irregularis* (species) (e.g., gut site); *Atopobium* (genus) (e.g., genital site); Bacillaceae (family) (e.g., gut site); Bacillaceae (family) (e.g., nose site); Bacillales (order) (e.g., gut site); *Bacillus* (genus) (e.g., gut site); *Bacillus* (genus) (e.g., nose site); Bacteroidaceae (family) (e.g., gut site); Bacteroidaceae (family) (e.g., genital site); Bacteroidales (order) (e.g., gut site); Bacteroidales (order) (e.g., skin site); *Bacteroides* (genus) (e.g., gut site); *Bacteroides* (genus) (e.g., genital site); *Bacteroides chinchillae* (species) (e.g., gut site); *Bacteroides clarus* (species) (e.g., gut site); *Bacteroides coprocola* (species) (e.g., gut site); *Bacteroides dorei* (species) (e.g., gut site); *Bacteroides finegoldii* (species) (e.g., gut site); *Bacteroides fragilis* (species) (e.g., gut site); *Bacteroides massiliensis* (species) (e.g., gut site); *Bacteroides nordii* (species) (e.g., gut site); *Bacteroides ovatus* (species) (e.g., gut site); *Bacteroides plebeius* (species) (e.g., gut site); *Bacteroides* sp. AR20 (species) (e.g., gut site); *Bacteroides* sp. AR20 (species) (e.g., genital site); *Bacteroides* sp. AR29 (species) (e.g., gut site); *Bacteroides* sp. D22 (species) (e.g., gut site); *Bacteroides* sp. DJF_B097 (species) (e.g., gut site); *Bacteroides* sp. EBA5-17 (species) (e.g., gut site); *Bacteroides* sp. S-17 (species) (e.g., gut site); *Bacteroides* sp. SLC1-38 (species) (e.g., gut site); *Bacteroides* sp. XB12B (species) (e.g., gut site); *Bacteroides stercoris* (species) (e.g., gut site); *Bacteroides thetaiotaomicron* (species) (e.g., gut site); *Bacteroides uniformis* (species) (e.g., gut site); *Bacteroides vulgatus* (species) (e.g., nose site); *Bacteroides vulgatus* (species) (e.g., genital site); *Bacteroides vulgatus* (species) (e.g., gut site); Bacteroidetes (phylum) (e.g., gut site); Bacteroidia (class) (e.g., gut site); Bacteroidia (class) (e.g., skin site); *Barne-*

*siella* (genus) (e.g., gut site); *Barnesiella intestinihominis* (species) (e.g., gut site); *Bergeyella* (genus) (e.g., nose site); Betaproteobacteria (class) (e.g., gut site); Bifidobacteriaceae (family) (e.g., gut site); Bifidobacteriaceae (family) (e.g., nose site); Bifidobacteriales (order) (e.g., gut site); Bifidobacteriales (order) (e.g., nose site); *Bifidobacterium* (genus) (e.g., gut site); *Bifidobacterium biavatii* (species) (e.g., gut site); *Bifidobacterium choerinum* (species) (e.g., gut site); *Bifidobacterium kashiwanohense* (species) (e.g., gut site); *Bifidobacterium longum* (species) (e.g., gut site); *Bifidobacterium longum* (species) (e.g., nose site); *Bifidobacterium* sp. (species) (e.g., gut site); *Bifidobacterium stercoris* (species) (e.g., gut site); *Bilophila* (genus) (e.g., gut site); *Bilophila* sp. 4_1_30 (species) (e.g., gut site); *Blautia* (genus) (e.g., nose site); *Blautia* (genus) (e.g., gut site); *Blautia glucerasea* (species) (e.g., gut site); *Blautia hydrogenotrophica* (species) (e.g., gut site); *Blautia luti* (species) (e.g., gut site); *Blautia producta* (species) (e.g., gut site); *Blautia* sp. Ser5 (species) (e.g., gut site); *Blautia* sp. Ser8 (species) (e.g., gut site); *Blautia* sp. YHC-4 (species) (e.g., gut site); *Blautia stercoris* (species) (e.g., gut site); *Blautia wexlerae* (species) (e.g., gut site); *Brevundimonas* (genus) (e.g., nose site); Burkholderiaceae (family) (e.g., nose site); Burkholderiales (order) (e.g., genital site); Burkholderiales (order) (e.g., gut site); *Butyricimonas* (genus) (e.g., gut site); *Butyrivibrio crossotus* (species) (e.g., gut site); Caldicoprobacteraceae (family) (e.g., gut site); *Candidatus Soleaferrea* (genus) (e.g., gut site); *Capnocytophaga* (genus) (e.g., nose site); *Capnocytophaga* sp. CM59 (species) (e.g., nose site); *Capnocytophaga* sp. oral taxon 329 (species) (e.g., nose site); *Capnocytophaga sputigena* (species) (e.g., nose site); Cardiobacteriaceae (family) (e.g., mouth site); *Cardiobacterium* (genus) (e.g., mouth site); *Cardiobacterium hominis* (species) (e.g., mouth site); Carnobacteriaceae (family) (e.g., gut site); Carnobacteriaceae (family) (e.g., mouth site); Carnobacteriaceae (family) (e.g., skin site); *Catabacter* (genus) (e.g., gut site); Catabacteriaceae (family) (e.g., gut site); *Catenibacterium mitsuokai* (species) (e.g., gut site); Caulobacteraceae (family) (e.g., skin site); Caulobacterales (order) (e.g., skin site); *Centipeda* (genus) (e.g., nose site); *Centipeda periodontii* (species) (e.g., mouth site); *Citrobacter* (genus) (e.g., gut site); *Citrobacter amalonaticus* (species) (e.g., gut site); *Cloacibacillus* (genus) (e.g., gut site); *Cloacibacillus evryensis* (species) (e.g., gut site); Clostridia (class) (e.g., gut site); Clostridiaceae (family) (e.g., gut site); Clostridiales (order) (e.g., gut site); Clostridiales (family) XI. Incertae Sedis (family) (e.g., gut site); Clostridiales (family) XIII. Incertae Sedis (family) (e.g., gut site); *Collinsella* (genus) (e.g., gut site); *Collinsella aerofaciens* (species) (e.g., gut site); *Collinsella intestinalis* (species) (e.g., gut site); Comamonadaceae (family) (e.g., gut site); *Comamonas* (genus) (e.g., mouth site); *Coprobacillus* (genus) (e.g., gut site); *Coprobacillus* sp. D6 (species) (e.g., gut site); Coriobacteriaceae (family) (e.g., gut site); Coriobacteriales (order) (e.g., gut site); Corynebacteriaceae (family) (e.g., gut site); *Corynebacterium* (genus) (e.g., gut site); *Corynebacterium canis* (species) (e.g., gut site); *Corynebacterium epidermidicanis* (species) (e.g., gut site); *Corynebacterium freiburgense* (species) (e.g., gut site); *Corynebacterium glucuronolyticum* (species) (e.g., gut site); *Corynebacterium glucuronolyticum* (species) (e.g., genital site); *Corynebacterium mastitidis* (species) (e.g., genital site); *Corynebacterium* sp. NML 97-0186 (species) (e.g., nose site); *Corynebacterium spheniscorum* (species) (e.g., gut site); *Corynebacterium ulcerans* (species) (e.g., gut site); *Corynebacterium ulcerans* (species) (e.g., genital site); *Corynebacterium ulcerans* (species) (e.g., skin site); *Crono-*

*bacter* (genus) (e.g., gut site); Cyanobacteria (phylum) (e.g., nose site); Cyanobacteria (phylum) (e.g., gut site); Deinococci (class) (e.g., nose site); *Delftia* (genus) (e.g., skin site); *Delftia* sp. BN-SKY3 (species) (e.g., skin site); Deltaproteobacteria (class) (e.g., gut site); Dermabacteraceae (family) (e.g., nose site); Dermabacteraceae (family) (e.g., gut site); *Desulfovibrio piger* (species) (e.g., gut site); *Desulfovibrio* sp. (species) (e.g., gut site); Desulfovibrionaceae (family) (e.g., gut site); Desulfovibrionales (order) (e.g., gut site); *Dialister* (genus) (e.g., gut site); *Dialister* (genus) (e.g., skin site); *Dialister invisus* (species) (e.g., gut site); *Dialister propionicifaciens* (species) (e.g., gut site); *Dielma* (genus) (e.g., gut site); *Dielma fastidiosa* (species) (e.g., gut site); *Dorea* (genus) (e.g., gut site); *Dorea formicigenerans* (species) (e.g., gut site); *Dorea longicatena* (species) (e.g., gut site); *Eggerthella* (genus) (e.g., gut site); *Eggerthella sinensis* (species) (e.g., gut site); *Eggerthella* sp. HGA1 (species) (e.g., gut site); *Eisenbergiella* (genus) (e.g., gut site); *Eisenbergiella tayi* (species) (e.g., gut site); *Enterobacter* (genus) (e.g., gut site); *Enterobacter* sp. BS2-1 (species) (e.g., gut site); Enterobacteriaceae (family) (e.g., gut site); Enterobacteriales (order) (e.g., gut site); Enterococcaceae (family) (e.g., gut site); *Enterococcus* (genus) (e.g., gut site); *Enterococcus faecalis* (species) (e.g., gut site); *Enterococcus raffinosus* (species) (e.g., gut site); *Enterococcus* sp. C6I11 (species) (e.g., gut site); *Enterococcus* sp. SI-4 (species) (e.g., gut site); *Erysipelatoclostridium* (genus) (e.g., gut site); *Erysipelatoclostridium ramosum* (species) (e.g., gut site); Erysipelotrichaceae (family) (e.g., gut site); Erysipelotrichales (order) (e.g., gut site); Erysipelotrichia (class) (e.g., gut site); Eubacteriaceae (family) (e.g., gut site); *Eubacterium* (genus) (e.g., gut site); *Eubacterium callanderi* (species) (e.g., gut site); *Eubacterium* sp. SA11 (species) (e.g., gut site); Euryarchaeota (phylum) (e.g., gut site); *Faecalibacterium* (genus) (e.g., gut site); *Faecalibacterium* (genus) (e.g., mouth site); *Faecalibacterium prausnitzii* (species) (e.g., gut site); *Faecalibacterium* sp. canine oral taxon 147 (species) (e.g., gut site); *Fibrobacter* (genus) (e.g., gut site); Fibrobacteraceae (family) (e.g., gut site); Fibrobacterales (order) (e.g., gut site); Fibrobacteres (phylum) (e.g., gut site); Fibrobacteria (class) (e.g., gut site); *Finegoldia* (genus) (e.g., gut site); *Finegoldia* (genus) (e.g., genital site); *Finegoldia* (genus) (e.g., mouth site); *Finegoldia* (genus) (e.g., skin site); *Finegoldia* sp. S8 F7 (species) (e.g., gut site); *Finegoldia* sp. S8 F7 (species) (e.g., genital site); *Finegoldia* sp. S9 AA1-5 (species) (e.g., gut site); *Finegoldia* sp. S9 AA1-5 (species) (e.g., mouth site); *Finegoldia* sp. S9 AA1-5 (species) (e.g., skin site); Firmicutes (phylum) (e.g., gut site); Flavobacteriaceae (family) (e.g., gut site); Flavobacteriales (order) (e.g., skin site); Flavobacteriales (order) (e.g., gut site); Flavobacteriia (class) (e.g., gut site); *Flavobacterium* (genus) (e.g., nose site); *Flavonifractor* (genus) (e.g., gut site); *Flavonifractor plautii* (species) (e.g., gut site); *Fusicatenibacter* (genus) (e.g., gut site); *Fusicatenibacter saccharivorans* (species) (e.g., gut site); Fusobacteriaceae (family) (e.g., nose site); *Fusobacterium* (genus) (e.g., nose site); *Fusobacterium* sp. CM21 (species) (e.g., nose site); Gammaproteobacteria (class) (e.g., gut site); Gammaproteobacteria (class) (e.g., genital site); *Gelria* (genus) (e.g., gut site); *Gemella* (genus) (e.g., mouth site); *Gemella* (genus) (e.g., gut site); *Gemella* (genus) (e.g., skin site); *Gemella sanguinis* (species) (e.g., mouth site); *Gemella* sp. 933-88 (species) (e.g., gut site); *Gemella* sp. 933-88 (species) (e.g., skin site); *Gordonibacter* (genus) (e.g., gut site); *Gordonibacter pamelaeae* (species) (e.g., gut site); *Granulicatella* (genus) (e.g., gut site); *Granulicatella* (genus) (e.g., mouth site); *Granulicatella*

*adiacens* (species) (e.g., gut site); *Granulicatella adiacens* (species) (e.g., mouth site); *Granulicatella elegans* (species) (e.g., mouth site); *Haemophilus* (genus) (e.g., gut site); *Haemophilus influenzae* (species) (e.g., gut site); *Haemophilus parainfluenzae* (species) (e.g., gut site); *Herbaspirillum* (genus) (e.g., gut site); *Herbaspirillum seropedicae* (species) (e.g., gut site); *Hespellia* (genus) (e.g., gut site); *Holdemania* (genus) (e.g., gut site); *Holdemania filiformis* (species) (e.g., gut site); *Howardella* (genus) (e.g., gut site); *Howardella ureilytica* (species) (e.g., gut site); *Hydrogenoanaerobacterium* (genus) (e.g., gut site); *Intestinibacter* (genus) (e.g., gut site); *Intestinimonas* (genus) (e.g., gut site); *Intestinimonas butyriciproducens* (species) (e.g., gut site); *Kingella* (genus) (e.g., nose site); *Klebsiella* (genus) (e.g., gut site); *Klebsiella* sp. SOR89 (species) (e.g., gut site); *Kluyvera* (genus) (e.g., gut site); *Kluyvera* (genus) (e.g., mouth site); *Kluyvera georgiana* (species) (e.g., gut site); *Kluyvera georgiana* (species) (e.g., mouth site); *Kocuria* (genus) (e.g., nose site); *Lachnospira* (genus) (e.g., skin site); *Lachnospira* (genus) (e.g., gut site); *Lachnospira pectinoschiza* (species) (e.g., gut site); Lachnospiraceae (family) (e.g., nose site); Lachnospiraceae (family) (e.g., genital site); Lactobacillaceae (family) (e.g., gut site); Lactobacillaceae (family) (e.g., genital site); Lactobacillales (order) (e.g., mouth site); *Lactobacillus* (genus) (e.g., gut site); *Lactobacillus* (genus) (e.g., genital site); *Lactobacillus acidophilus* (species) (e.g., genital site); *Lactobacillus crispatus* (species) (e.g., gut site); *Lactobacillus rhamnosus* (species) (e.g., gut site); *Lactobacillus salivarius* (species) (e.g., gut site); *Lactobacillus* sp. 7_1_47FAA (species) (e.g., skin site); *Lactobacillus* sp. 7_1_47FAA (species) (e.g., gut site); *Lactobacillus* sp. 7_1_47FAA (species) (e.g., nose site); *Lactobacillus* sp. Akhmroi (species) (e.g., gut site); *Lactobacillus* sp. TAB-26 (species) (e.g., gut site); *Lactobacillus* sp. TAB-30 (species) (e.g., gut site); *Lactonifactor* (genus) (e.g., gut site); *Lactonifactor longoviformis* (species) (e.g., gut site); *Lautropia* (genus) (e.g., nose site); *Lautropia* sp. TeTO (species) (e.g., nose site); *Leptotrichia hongkongensis* (species) (e.g., mouth site); Leuconostocaceae (family) (e.g., gut site); *Marvinbryantia* (genus) (e.g., gut site); *Megasphaera* (genus) (e.g., gut site); Methanobacteria (class) (e.g., gut site); Methanobacteriaceae (family) (e.g., gut site); Methanobacteriales (order) (e.g., gut site); *Methanobrevibacter* (genus) (e.g., gut site); *Methanobrevibacter smithii* (species) (e.g., gut site); Methylobacteriaceae (family) (e.g., nose site); *Methylobacterium* (genus) (e.g., nose site); Microbacteriaceae (family) (e.g., gut site); Micrococcaceae (family) (e.g., nose site); Micrococcaceae (family) (e.g., gut site); *Micrococcus* (genus) (e.g., nose site); *Micrococcus* sp. WB18-01 (species) (e.g., nose site); Mollicutes (class) (e.g., gut site); *Moraxella* (genus) (e.g., nose site); *Moraxella* sp. WB19-16 (species) (e.g., nose site); Moraxellaceae (family) (e.g., skin site); *Moryella* (genus) (e.g., gut site); *Murdochiella* (genus) (e.g., gut site); *Murdochiella asaccharolytica* (species) (e.g., gut site); Mycobacteriaceae (family) (e.g., mouth site); *Mycobacterium* (genus) (e.g., nose site); Negativicutes (class) (e.g., gut site); *Neisseria* (genus) (e.g., skin site); *Neisseria* (genus) (e.g., gut site); *Neisseria elongata* (species) (e.g., nose site); *Neisseria macacae* (species) (e.g., skin site); *Neisseria mucosa* (species) (e.g., nose site); *Neisseria sicca* (species) (e.g., mouth site); Neisseriaceae (family) (e.g., skin site); Neisseriaceae (family) (e.g., gut site); Neisseriales (order) (e.g., skin site); Neisseriales (order) (e.g., gut site); *Odoribacter* (genus) (e.g., gut site); *Odoribacter splanchnicus* (species) (e.g., gut site); *Oscillibacter* (genus) (e.g., gut site); *Oscillospira* (genus) (e.g., gut site); Oscillospiraceae (family) (e.g., gut site); Oxalobacteraceae (family) (e.g., gut site); *Pantoea* (genus) (e.g., gut site); *Papillibacter* (genus) (e.g., gut site); *Parabacteroides* (genus) (e.g., gut site); *Parabacteroides distasonis* (species) (e.g., gut site); *Parabacteroides merdae* (species) (e.g., gut site); *Parvimonas* (genus) (e.g., mouth site); *Pasteurella* (genus) (e.g., gut site); *Pasteurella pneumotropica* (species) (e.g., gut site); Pasteurellaceae (family) (e.g., gut site); Pasteurellales (order) (e.g., gut site); *Pediococcus* (genus) (e.g., gut site); *Pediococcus* sp. MFC1 (species) (e.g., gut site); *Peptoclostridium* (genus) (e.g., gut site); Peptococcaceae (family) (e.g., gut site); *Peptococcus* (genus) (e.g., gut site); *Peptoniphilus* (genus) (e.g., gut site); *Peptoniphilus* (genus) (e.g., skin site); *Peptoniphilus lacrimalis* (species) (e.g., gut site); *Peptoniphilus* sp. 2002-2300004 (species) (e.g., skin site); *Peptoniphilus* sp. 7-2 (species) (e.g., gut site); *Peptoniphilus* sp. DNF00840 (species) (e.g., gut site); *Peptoniphilus* sp. gpac018A (species) (e.g., gut site); *Peptoniphilus* sp. oral taxon 836 (species) (e.g., gut site); Peptostreptococcaceae (family) (e.g., gut site); Peptostreptococcaceae (family) (e.g., skin site); *Peptostreptococcus* (genus) (e.g., mouth site); *Phascolarctobacterium* (genus) (e.g., gut site); *Phascolarctobacterium faecium* (species) (e.g., gut site); Porphyromonadaceae (family) (e.g., gut site); *Porphyromonas* (genus) (e.g., nose site); *Porphyromonas bennonis* (species) (e.g., genital site); *Porphyromonas catoniae* (species) (e.g., nose site); *Prevotella* (genus) (e.g., gut site); *Prevotella bivia* (species) (e.g., gut site); *Prevotella buccalis* (species) (e.g., gut site); *Prevotella oris* (species) (e.g., nose site); *Prevotella* sp. WAL 2039G (species) (e.g., nose site); Prevotellaceae (family) (e.g., gut site); Propionibacteriaceae (family) (e.g., mouth site); Propionibacteriaceae (family) (e.g., genital site); *Propionibacterium* (genus) (e.g., mouth site); *Propionibacterium acnes* (species) (e.g., nose site); *Propionibacterium* sp. MSP09A (species) (e.g., genital site); Proteobacteria (phylum) (e.g., gut site); *Proteus* (genus) (e.g., gut site); *Pseudobutyrivibrio* (genus) (e.g., nose site); *Pseudoclavibacter* (genus) (e.g., gut site); *Pseudoflavonifractor* (genus) (e.g., gut site); *Pseudoflavonifractor capillosus* (species) (e.g., gut site); Pseudomonadaceae (family) (e.g., nose site); Pseudomonadales (order) (e.g., skin site); Pseudomonadales (order) (e.g., genital site); Pseudomonadales (order) (e.g., gut site); *Pseudomonas* (genus) (e.g., nose site); *Ralstonia* (genus) (e.g., skin site); Rhizobiaceae (family) (e.g., nose site); Rhizobiales (order) (e.g., gut site); *Rhodobacter* (genus) (e.g., nose site); Rhodobacteraceae (family) (e.g., nose site); Rhodobacterales (order) (e.g., nose site); Rhodospirillaceae (family) (e.g., gut site); Rhodospirillales (order) (e.g., nose site); Rhodospirillales (order) (e.g., skin site); Rhodospirillales (order) (e.g., gut site); Rikenellaceae (family) (e.g., nose site); Rikenellaceae (family) (e.g., gut site); *Robinsoniella* (genus) (e.g., gut site); *Robinsoniella peoriensis* (species) (e.g., gut site); *Romboutsia* (genus) (e.g., gut site); *Roseburia* (genus) (e.g., gut site); *Roseburia cecicola* (species) (e.g., gut site); *Roseburia hominis* (species) (e.g., gut site); *Roseburia intestinalis* (species) (e.g., gut site); *Roseburia inulinivorans* (species) (e.g., gut site); *Roseburia* sp. 11SE39 (species) (e.g., gut site); *Roseburia* sp. 499 (species) (e.g., gut site); *Rothia* (genus) (e.g., gut site); *Rothia dentocariosa* (species) (e.g., nose site); *Rothia mucilaginosa* (species) (e.g., gut site); Ruminococcaceae (family) (e.g., gut site); *Sarcina* (genus) (e.g., nose site); *Sarcina* (genus) (e.g., gut site); Selenomonadales (order) (e.g., gut site); *Senegalimassilia* (genus) (e.g., gut site); *Shinella* (genus) (e.g., skin site); *Shinella* sp. DR33 (species) (e.g., skin site); *Shuttleworthia* (genus) (e.g., gut site); *Slackia piriformis* (species) (e.g., gut site); *Slackia* sp. NATTS (species) (e.g., gut site); Solanales (order) (e.g., nose site); Solanales (order) (e.g., gut site); Sphingomonadaceae (family) (e.g., nose site); Sphingomonadales (order) (e.g., nose site); *Sphingomonas* (genus) (e.g., nose site); *Staphylococcus* sp. C-D-MA2 (species) (e.g., skin site); *Staphylococcus* sp. C9I2 (species) (e.g., genital site); *Stenotrophomonas* sp. C-S-TSA3 (species) (e.g., skin site); Streptococcaceae (family) (e.g., mouth site); Streptococcaceae (family) (e.g., gut site); *Streptococcus* (genus) (e.g., mouth site); *Streptococcus* (genus) (e.g., gut site); *Streptococcus gordonii* (species) (e.g., nose site); *Streptococcus mitis* (species) (e.g., mouth site); *Streptococcus pasteurianus* (species) (e.g., gut site); *Streptococcus peroris* (species) (e.g., gut site); *Streptococcus* sp. BS35a (species) (e.g., mouth site); *Streptococcus* sp. oral taxon G59 (species) (e.g., gut site); *Streptococcus* sp. oral taxon G63 (species) (e.g., mouth site); *Streptococcus thermophilus* (species) (e.g., gut site); *Streptococcus thermophilus* (species) (e.g., skin site); Streptophyta (phylum) (e.g., gut site); *Subdoligranulum* (genus) (e.g., gut site); *Subdoligranulum variabile* (species) (e.g., gut site); *Sutterella* (genus) (e.g., gut site); *Sutterella* sp. YIT 12072 (species) (e.g., gut site); *Sutterella wadsworthensis* (species) (e.g., gut site); Sutterellaceae (family) (e.g., nose site); Sutterellaceae (family) (e.g., gut site); Synergistaceae (family) (e.g., gut site); Synergistales (order) (e.g., gut site); Synergistetes (phylum) (e.g., gut site); Synergistia (class) (e.g., gut site); Tenericutes (phylum) (e.g., gut site); *Terrisporobacter* (genus) (e.g., gut site); *Tessaracoccus* (genus) (e.g., mouth site); *Tessaracoccus* sp. IPBSL-7 (species) (e.g., mouth site); *Thalassospira* (genus) (e.g., gut site); Thermoanaerobacteraceae (family) (e.g., gut site); Thermoanaerobacterales (order) (e.g., gut site); *Varibaculum* sp. CCUG 45114 (species) (e.g., gut site); *Veillonella* (genus) (e.g., mouth site); *Veillonella* (genus) (e.g., gut site); *Veillonella rogosae* (species) (e.g., gut site); *Veillonella* sp. CM60 (species) (e.g., mouth site); *Veillonella* sp. CM60 (species) (e.g., gut site); *Veillonella* sp. FFA-2014 (species) (e.g., gut site); *Veillonella* sp. MSA12 (species) (e.g., gut site); Veillonellaceae (family) (e.g., gut site); Verrucomicrobia (phylum) (e.g., gut site); Verrucomicrobiaceae (family) (e.g., gut site); Verrucomicrobiae (class) (e.g., gut site); Verrucomicrobiales (order) (e.g., gut site); *Weissella* (genus) (e.g., gut site); *Weissella hellenica* (species) (e.g., gut site); Xanthomonadaceae (family) (e.g., gut site); Xanthomonadales (order) (e.g., gut site); Xanthomonadales (order) (e.g., genital site).

Additionally or alternatively, performing a wheat allergy condition characterization process can be based on microbiome features (e.g., microbiome function features) associated with one or more of (e.g., such as in relation to a corresponding sample site): Metabolism (KEGG2), Carbohydrate Metabolism (KEGG2), Translation (KEGG2), Transport and Catabolism (KEGG2), Enzyme Families (KEGG2), Biosynthesis of Other Secondary Metabolites (KEGG2), Cellular Processes and Signaling (KEGG2), Nucleotide Metabolism (KEGG2), Replication and Repair (KEGG2), Glycan Biosynthesis and Metabolism (KEGG2), Genetic Information Processing (KEGG2), Lipid Metabolism (KEGG2), Signal Transduction (KEGG2), Neurodegenerative Diseases (KEGG2), Metabolism of Other Amino Acids (KEGG2), Metabolism of Cofactors and Vitamins (KEGG2), Signaling Molecules and Interaction (KEGG2), Environmental Adaptation (KEGG2), Cell Growth and Death (KEGG2), Poorly Characterized (KEGG2), Ribosome Biogenesis (KEGG3), Ascorbate and aldarate metabolism (KEGG3), Lipoic acid metabolism (KEGG3), D-Alanine metabolism (KEGG3), Pentose and glucuronate interconversions (KEGG3), Peptidoglycan biosynthesis (KEGG3), Translation proteins (KEGG3), Huntington's disease (KEGG3), Glyoxylate and dicarboxylate metabolism (KEGG3), Others (KEGG3), Penicillin and cephalosporin biosynthesis (KEGG3), Bisphenol degradation (KEGG3), Inositol phosphate metabolism (KEGG3), Glycosaminoglycan degradation (KEGG3), Lysosome (KEGG3), MAPK signaling pathway—yeast (KEGG3), Biosynthesis and biodegradation of secondary metabolites (KEGG3), Phenylalanine metabolism (KEGG3), Other glycan degradation (KEGG3), Amino acid metabolism (KEGG3), Inorganic ion transport and metabolism (KEGG3), Ribosome biogenesis in eukaryotes (KEGG3), Nicotinate and nicotinamide metabolism (KEGG3), Sphingolipid metabolism (KEGG3), Lipopolysaccharide biosynthesis proteins (KEGG3), Cell motility and secretion (KEGG3), Phosphonate and phosphinate metabolism (KEGG3), Cysteine and methionine metabolism (KEGG3), Carbohydrate metabolism (KEGG3), Chromosome (KEGG3), Amino acid related enzymes (KEGG3), Other transporters (KEGG3), Type II diabetes mellitus (KEGG3), Taurine and hypotaurine metabolism (KEGG3), Membrane and intracellular structural molecules (KEGG3), RNA polymerase (KEGG3), Pores ion channels (KEGG3), Ion channels (KEGG3), Aminoacyl-tRNA biosynthesis (KEGG3), Biotin metabolism (KEGG3), Ribosome (KEGG3), Glycosphingolipid biosynthesis—globo series (KEGG3), Glycosphingolipid biosynthesis—ganglio series (KEGG3), Geraniol degradation (KEGG3), Sulfur metabolism (KEGG3), DNA repair and recombination proteins (KEGG3), Terpenoid backbone biosynthesis (KEGG3), Fructose and mannose metabolism (KEGG3), Phosphatidylinositol signaling system (KEGG3), Pyrimidine metabolism (KEGG3), Peroxisome (KEGG3), Other ion-coupled transporters (KEGG3), Translation factors (KEGG3), Signal transduction mechanisms (KEGG3), Galactose metabolism (KEGG3), Carbohydrate digestion and absorption (KEGG3), Nucleotide excision repair (KEGG3), Pentose phosphate pathway (KEGG3), Cyanoamino acid metabolism (KEGG3), Homologous recombination (KEGG3), Peptidases (KEGG3), Replication, recombination and repair proteins (KEGG3), Nucleotide metabolism (KEGG3), Phenylpropanoid biosynthesis (KEGG3), Plant-pathogen interaction (KEGG3), Citrate cycle (TCA cycle) (KEGG3), Purine metabolism (KEGG3), Nitrogen metabolism (KEGG3), Toluene degradation (KEGG3), Thiamine metabolism (KEGG3), Histidine metabolism (KEGG3), Type I diabetes mellitus (KEGG3), Streptomycin biosynthesis (KEGG3), Mismatch repair (KEGG3), Ubiquinone and other terpenoid-quinone biosynthesis (KEGG3), DNA replication proteins (KEGG3), Amino sugar and nucleotide sugar metabolism (KEGG3), beta-Lactam resistance (KEGG3), Aminobenzoate degradation (KEGG3), Function unknown (KEGG3), Cell cycle—*Caulobacter* (KEGG3), Butanoate metabolism (KEGG3), Caprolactam degradation (KEGG3), Pyruvate metabolism (KEGG3), Lipid metabolism (KEGG3), Valine, leucine and isoleucine degradation (KEGG3), Energy metabolism (KEGG3), Bacterial toxins (KEGG3), Polycyclic aromatic hydrocarbon degradation (KEGG3), Two-component system (KEGG3), Electron transfer carriers (KEGG3), Glycosyltransferases (KEGG3), Oxidative phosphorylation (KEGG3), One carbon pool by folate (KEGG3), Tyrosine metabolism (KEGG3), Drug metabolism—cytochrome P450 (KEGG3), Vitamin metabolism (KEGG3), Transcription factors (KEGG3), Cellular antigens (KEGG3), DNA replication (KEGG3), Drug metabolism—other enzymes (KEGG3), Protein export (KEGG3), Pantothenate and CoA biosynthesis (KEGG3), Glycerophospholipid metabolism (KEGG3), Limonene and pinene degradation (KEGG3), Carbon fixation pathways in prokaryotes (KEGG3), Epithelial cell signaling in *Helicobacter pylori* infection (KEGG3), Metabolism of xenobiotics by cytochrome P450 (KEGG3), Arginine and proline metabolism (KEGG3), Glutamatergic synapse (KEGG3), Polyketide sugar unit biosynthesis (KEGG3), 1,1,1-Trichloro-2,2-bis(4-chlorophenyl)ethane (DDT) degradation" (KEGG_Pathways_Level_3) (e.g., gut site); ABC transporters (KEGG_Pathways_Level_3) (e.g., mouth site); ABC transporters (KEGG_Pathways_Level_3) (e.g., gut site); African trypanosomiasis (KEGG_Pathways_Level_3) (e.g., gut site); alpha-Linolenic acid metabolism (KEGG_Pathways_Level_3) (e.g., gut site); Amino Acid Metabolism (KEGG_Pathways_Level_2) (e.g., genital site); Amino acid metabolism (KEGG_Pathways_Level_3) (e.g., gut site); Amino acid related enzymes (KEGG_Pathways_Level_3) (e.g., gut site); Amino sugar and nucleotide sugar metabolism (KEGG_Pathways_Level_3) (e.g., gut site); Aminoacyl-tRNA biosynthesis (KEGG_Pathways_Level_3) (e.g., gut site); Aminobenzoate degradation (KEGG_Pathways_Level_3) (e.g., gut site); Amoebiasis (KEGG_Pathways_Level_3) (e.g., skin site); Amoebiasis (KEGG_Pathways_Level_3) (e.g., gut site); Amyotrophic lateral sclerosis (ALS) (KEGG_Pathways_Level_3) (e.g., gut site); Arachidonic acid metabolism (KEGG_Pathways_Level_3) (e.g., mouth site); Ascorbate and aldarate metabolism (KEGG_Pathways_Level_3) (e.g., gut site); Bacterial chemotaxis (KEGG_Pathways_Level_3) (e.g., gut site); Bacterial toxins (KEGG_Pathways_Level_3) (e.g., gut site); Benzoate degradation (KEGG_Pathways_Level_3) (e.g., genital site); Benzoate degradation (KEGG_Pathways_Level_3) (e.g., gut site); Biosynthesis and biodegradation of secondary metabolites (KEGG_Pathways_Level_3) (e.g., gut site); Biosynthesis of Other Secondary Metabolites (KEGG_Pathways_Level_2) (e.g., skin site); Biosynthesis of Other Secondary Metabolites (KEGG_Pathways_Level_2) (e.g., gut site); Biosynthesis of vancomycin group antibiotics (KEGG_Pathways_Level_3) (e.g., mouth site); Biosynthesis of vancomycin group antibiotics (KEGG_Pathways_Level_3) (e.g., gut site); Biotin metabolism (KEGG_Pathways_Level_3) (e.g., gut site); Bisphenol degradation (KEGG_Pathways_Level_3) (e.g., gut site); Bladder cancer (KEGG_Pathways_Level_3) (e.g., nose site); Butanoate metabolism (KEGG_Pathways_Level_3) (e.g., mouth site); Butanoate metabolism (KEGG_Pathways_Level_3) (e.g., gut site); Butirosin and neomycin biosynthesis (KEGG_Pathways_Level_3) (e.g., mouth site); Cancers (KEGG_Pathways_Level_2) (e.g., nose site); Caprolactam degradation (KEGG_Pathways_Level_3) (e.g., gut site); Carbohydrate digestion and absorption (KEGG_Pathways_Level_3) (e.g., mouth site); Carbohydrate digestion and absorption (KEGG_Pathways_Level_3) (e.g., gut site); Carbohydrate Metabolism (KEGG_Pathways_Level_2) (e.g., gut site); Carbohydrate metabolism (KEGG_Pathways_Level_3) (e.g., gut site); Carbon fixation in photosynthetic organisms (KEGG_Pathways_Level_3) (e.g., gut site); Carbon fixation pathways in prokaryotes (KEGG_Pathways_Level_3) (e.g., gut site); Cardiovascular Diseases (KEGG_Pathways_Level_2) (e.g., gut site); Cell Motility (KEGG_Pathways_Level_2) (e.g., gut site); Cell motility and secretion (KEGG_Pathways_Level_3) (e.g., gut site); Cellular antigens (KEGG_Pathways_Level_3) (e.g., gut site); Cellular Processes and Signaling (KEGG_Pathways_Level_2) (e.g., gut site); Chloroalkane and chloroalkene degradation (KEGG_Pathways_Level_3) (e.g., mouth site); Chromosome (KEGG_Pathways_Level_3) (e.g., gut site); Citrate cycle (TCA cycle) (KEGG_Pathways_Level_3) (e.g., gut site); Colorectal cancer (KEGG_Pathways_Level_3) (e.g., gut site); Cysteine and methionine metabolism (KEGG_Pathways_Level_3) (e.g., gut site); Cytoskeleton proteins (KEGG_Pathways_Level_3) (e.g., gut site); D-Alanine metabolism (KEGG_Pathways_Level_3) (e.g., gut site); D-Arginine and D-ornithine metabolism (KEGG_Pathways_Level_3) (e.g., skin site); Digestive System (KEGG_Pathways_Level_2) (e.g., mouth site); DNA repair and recombination proteins (KEGG_Pathways_Level_3) (e.g., gut site); Drug metabolism—cytochrome P450 (KEGG_Pathways_Level_3) (e.g., mouth site); Electron transfer carriers (KEGG_Pathways_Level_3) (e.g., gut site); Energy Metabolism (KEGG_Pathways_Level_2) (e.g., nose site); Energy Metabolism (KEGG_Pathways_Level_2) (e.g., gut site); Energy metabolism (KEGG_Pathways_Level_3) (e.g., gut site); Environmental Adaptation (KEGG_Pathways_Level_2) (e.g., mouth site); Environmental Adaptation (KEGG_Pathways_Level_2) (e.g., gut site); Enzyme Families (KEGG_Pathways_Level_2) (e.g., gut site); Epithelial cell signaling in *Helicobacter pylori* infection (KEGG_Pathways_Level_3) (e.g., gut site); Excretory System (KEGG_Pathways_Level_2) (e.g., gut site); Fatty acid biosynthesis (KEGG_Pathways_Level_3) (e.g., gut site); Fatty acid metabolism (KEGG_Pathways_Level_3) (e.g., mouth site); Fatty acid metabolism (KEGG_Pathways_Level_3) (e.g., gut site); Flavonoid biosynthesis (KEGG_Pathways_Level_3) (e.g., gut site); "Folding, Sorting and Degradation" (KEGG_Pathways_Level_2) (e.g., mouth site); Fructose and mannose metabolism (KEGG_Pathways_Level_3) (e.g., gut site); Function unknown (KEGG_Pathways_Level_3) (e.g., gut site); Galactose metabolism (KEGG_Pathways_Level_3) (e.g., gut site); General function prediction only (KEGG_Pathways_Level_3) (e.g., mouth site); Genetic Information Processing (KEGG_Pathways_Level_2) (e.g., mouth site); Genetic Information Processing (KEGG_Pathways_Level_2) (e.g., gut site); Geraniol degradation (KEGG_Pathways_Level_3) (e.g., mouth site); Geraniol degradation (KEGG_Pathways_Level_3) (e.g., gut site); Germination (KEGG_Pathways_Level_3) (e.g., gut site); Glutamatergic synapse (KEGG_Pathways_Level_3) (e.g., gut site); Glutathione metabolism (KEGG_Pathways_Level_3) (e.g., gut site); Glycan Biosynthesis and Metabolism (KEGG_Pathways_Level_2) (e.g., gut site); Glycerophospholipid metabolism (KEGG_Pathways_Level_3) (e.g., gut site); Glycosaminoglycan degradation (KEGG_Pathways_Level_3) (e.g., gut site); Glycosphingolipid biosynthesis—ganglio series (KEGG_Pathways_Level_3) (e.g., gut site); Glycosphingolipid biosynthesis—globo series (KEGG_Pathways_Level_3) (e.g., gut site); Glycosphingolipid biosynthesis—lacto and neolacto series (KEGG_Pathways_Level_3) (e.g., gut site); Glycosyltransferases (KEGG_Pathways_Level_3) (e.g., gut site); Glyoxylate and dicarboxylate metabolism (KEGG_Pathways_Level_3) (e.g., gut site); Huntington_quote_s disease (KEGG_Pathways_Level_3) (e.g., gut site); Immune System Diseases (KEGG_Pathways_Level_2) (e.g., gut site); Infectious Diseases (KEGG_Pathways_Level_2) (e.g., gut site); Inorganic ion transport and metabolism (KEGG_Pathways_Level_3) (e.g., gut site); Inositol phosphate metabolism (KEGG_Pathways_Level_3) (e.g., gut site); Ion channels (KEGG_Pathways_Level_3) (e.g., gut site); Isoquinoline alkaloid biosynthesis (KEGG_Pathways_Level_3) (e.g., gut site); Limonene and pinene degradation (KEGG_Pathways_Level_3) (e.g., gut site); Linoleic acid metabolism (KEGG_Pathways_Level_3) (e.g., gut site); Lipid biosynthesis proteins (KEGG_Pathways_Level_3) (e.g., mouth site); Lipid metabolism (KEGG_Pathways_Level_3) (e.g., mouth site); Lipid Metabolism (KEGG_Pathways_Level_2) (e.g., gut site); Lipid metabolism (KEGG_Pathways_Level_3) (e.g., gut site); Lipoic acid metabolism (KEGG_Pathways_Level_3) (e.g., gut site); Lipopolysaccharide biosynthesis (KEGG_Pathways_Level_3) (e.g., gut site); Lipopolysaccharide biosynthesis proteins (KEGG_Pathways_Level_3) (e.g., gut site); Lysine biosynthesis (KEGG_Pathways_Level_3) (e.g., gut site); Lysine degradation (KEGG_Pathways_Level_3) (e.g., gut site); Lysosome (KEGG_Pathways_Level_3) (e.g., gut site); MAPK signaling pathway—yeast (KEGG_Pathways_Level_3) (e.g., mouth site); MAPK signaling pathway—yeast (KEGG_Pathways_Level_3) (e.g., gut site); Meiosis—yeast (KEGG_Pathways_Level_3) (e.g., gut site); Membrane and intracellular structural molecules (KEGG_Pathways_Level_3) (e.g., gut site); Membrane Transport (KEGG_Pathways_Level_2) (e.g., gut site); Metabolism (KEGG_Pathways_Level_2) (e.g., mouth site); Metabolism (KEGG_Pathways_Level_2) (e.g., gut site); Metabolism of Other Amino Acids (KEGG_Pathways_Level_2) (e.g., mouth site); Metabolism of Other Amino Acids (KEGG_Pathways_Level_2) (e.g., gut site); Metabolism of Terpenoids and Polyketides (KEGG_Pathways_Level_2) (e.g., gut site); Metabolism of xenobiotics by cytochrome P450 (KEGG_Pathways_Level_3) (e.g., mouth site); Mismatch repair (KEGG_Pathways_Level_3) (e.g., gut site); N-Glycan biosynthesis (KEGG_Pathways_Level_3) (e.g., gut site); Naphthalene degradation (KEGG_Pathways_Level_3) (e.g., genital site); Naphthalene degradation (KEGG_Pathways_Level_3) (e.g., mouth site); Nervous System (KEGG_Pathways_Level_2) (e.g., gut site); Neurodegenerative Diseases (KEGG_Pathways_Level_2) (e.g., gut site); Nicotinate and nicotinamide metabolism (KEGG_Pathways_Level_3) (e.g., gut site); Nitrogen metabolism (KEGG_Pathways_Level_3) (e.g., gut site); Nucleotide excision repair (KEGG_Pathways_Level_3) (e.g., mouth site); Nucleotide excision repair (KEGG_Pathways_Level_3) (e.g., gut site); Nucleotide Metabolism (KEGG_Pathways_Level_2) (e.g., gut site); Other glycan degradation (KEGG_Pathways_Level_3) (e.g., gut site); Other ion-coupled transporters (KEGG_Pathways_Level_3) (e.g., gut site); Others (KEGG_Pathways_Level_3) (e.g., gut site); Oxidative phosphorylation (KEGG_Pathways_Level_3) (e.g., gut site); p53 signaling pathway (KEGG_Pathways_Level_3) (e.g., gut site); Penicillin and cephalosporin biosynthesis (KEGG_Pathways_Level_3) (e.g., genital site); Penicillin and cephalosporin biosynthesis (KEGG_Pathways_Level_3) (e.g., gut site); Pentose and glucuronate interconversions (KEGG_Pathways_Level_3) (e.g., gut site); Pentose phosphate pathway (KEGG_Pathways_Level_3) (e.g., gut site); Peptidoglycan biosynthesis (KEGG_Pathways_Level_3) (e.g., gut site); Peroxisome (KEGG_Pathways_Level_3) (e.g., gut site); Pertussis (KEGG_Pathways_Level_3) (e.g., gut site); Phenylalanine metabolism (KEGG_Pathways_Level_3) (e.g., gut site); "Phenylalanine, tyrosine and tryptophan biosynthesis" (KEGG_Pathways_Level_3) (e.g., gut site); Phosphatidylinositol signaling system (KEGG_Pathways_Level_3) (e.g., gut site); Phosphonate and phosphinate metabolism (KEGG_Pathways_Level_3) (e.g., gut site); Plant-pathogen interaction (KEGG_Pathways_Level_3) (e.g., mouth site); Plant-pathogen interaction (KEGG_Pathways_Level_3) (e.g., gut site); Polycyclic aromatic hydrocarbon degradation (KEGG_Pathways_Level_3) (e.g., gut site); Polyketide sugar unit biosynthesis (KEGG_Pathways_Level_3) (e.g., mouth site); Polyketide sugar unit biosynthesis (KEGG_Pathways_Level_3) (e.g., gut site); Pores ion channels (KEGG_Pathways_Level_3) (e.g., gut site); Primary bile acid biosynthesis (KEGG_Pathways_Level_3) (e.g., gut site); Primary immunodeficiency (KEGG_Pathways_Level_3) (e.g., gut site); Prion diseases (KEGG_Pathways_Level_3) (e.g., mouth site); Prion diseases (KEGG_Pathways_Level_3) (e.g., gut site); Propanoate metabolism (KEGG_Pathways_Level_3) (e.g., gut site); Proteasome (KEGG_Pathways_Level_3) (e.g., gut site); Protein digestion and absorption (KEGG_Pathways_Level_3) (e.g., gut site); Protein export (KEGG_Pathways_Level_3) (e.g., genital site); Protein export (KEGG_Pathways_Level_3) (e.g., mouth site); Protein folding and associated processing (KEGG_Pathways_Level_3) (e.g., gut site); Protein processing in endoplasmic reticulum (KEGG_Pathways_Level_3) (e.g., nose site); Protein processing in endoplasmic reticulum (KEGG_Pathways_Level_3) (e.g., gut site); Proximal tubule bicarbonate reclamation (KEGG_Pathways_Level_3) (e.g., gut site); Pyruvate metabolism (KEGG_Pathways_Level_3) (e.g., gut site); Replication and Repair (KEGG_Pathways_Level_2) (e.g., gut site); "Replication, recombination and repair proteins" (KEGG_Pathways_Level_3) (e.g., gut site); Retinol metabolism (KEGG_Pathways_Level_3) (e.g., mouth site); Ribosome (KEGG_Pathways_Level_3) (e.g., gut site); Ribosome Biogenesis (KEGG_Pathways_Level_3) (e.g., gut site); Ribosome biogenesis in eukaryotes (KEGG_Pathways_Level_3) (e.g., gut site); RIG-I-like receptor signaling pathway (KEGG_Pathways_Level_3) (e.g., genital site); RNA degradation (KEGG_Pathways_Level_3) (e.g., gut site); RNA polymerase (KEGG_Pathways_Level_3) (e.g., gut site); RNA transport (KEGG_Pathways_Level_3) (e.g., gut site); Secondary bile acid biosynthesis (KEGG_Pathways_Level_3) (e.g., gut site); Signal transduction mechanisms (KEGG_Pathways_Level_3) (e.g., gut site); Signaling Molecules and Interaction (KEGG_Pathways_Level_2) (e.g., gut site); Small cell lung cancer (KEGG_Pathways_Level_3) (e.g., gut site); Sphingolipid metabolism (KEGG_Pathways_Level_3) (e.g., gut site); Sporulation (KEGG_Pathways_Level_3) (e.g., gut site); Starch and sucrose metabolism (KEGG_Pathways_Level_3) (e.g., gut site); Steroid hormone biosynthesis (KEGG_Pathways_Level_3) (e.g., gut site); Streptomycin biosynthesis (KEGG_Pathways_Level_3) (e.g., gut site); Styrene degradation (KEGG_Pathways_Level_3) (e.g., gut site); Sulfur metabolism (KEGG_Pathways_Level_3) (e.g., gut site); Synthesis and degradation of ketone bodies (KEGG_Pathways_Level_3) (e.g., genital site); Taurine and hypotaurine metabolism (KEGG_Pathways_Level_3) (e.g., mouth site); Taurine and hypotaurine metabolism (KEGG_Pathways_Level_3) (e.g., gut site); Terpenoid backbone biosynthesis (KEGG_Pathways_Level_3) (e.g., gut site); Thiamine metabolism (KEGG_Pathways_Level_3) (e.g., mouth site); Thiamine metabolism (KEGG_Pathways_Level_3) (e.g., gut site); Toluene degradation (KEGG_Pathways_Level_3) (e.g., gut site); Toxoplasmosis (KEGG_Pathways_Level_3) (e.g., gut site); Transcription (KEGG_Pathways_Level_2) (e.g., gut site); Transcription factors (KEGG_Pathways_Level_3) (e.g., gut site); Transcription related proteins (KEGG_Pathways_Level_3) (e.g., gut site); Translation (KEGG_Pathways_Level_2) (e.g., mouth site); Translation (KEGG_Pathways_Level_2) (e.g., gut site); Translation factors (KEGG_Pathways_Level_3) (e.g., gut site); Translation proteins (KEGG_Pathways_Level_3) (e.g., mouth site); Translation proteins (KEGG_Pathways_Level_3) (e.g., gut site); Transport and Catabolism (KEGG_Pathways_Level_2) (e.g., gut site); Transporters (KEGG_Pathways_Level_3) (e.g., gut site); Tryptophan metabolism (KEGG_Pathways_Level_3) (e.g., gut site); Tuberculosis (KEGG_Pathways_Level_3) (e.g., gut site); Type I diabetes mellitus (KEGG_Pathways_Level_3) (e.g., gut site); Type II diabetes mellitus (KEGG_Pathways_Level_3) (e.g., gut site); Tyrosine metabolism (KEGG_Pathways_Level_3) (e.g., mouth site); Ubiquinone and other terpenoid-quinone biosynthesis (KEGG_Pathways_Level_3) (e.g., gut site); Ubiquitin system (KEGG_Pathways_Level_3) (e.g., gut site); "Valine, leucine and isoleucine degradation" (KEGG_Pathways_Level_3) (e.g., gut site); Viral myocarditis (KEGG_Pathways_Level_3) (e.g., gut site); Xenobiotics Biodegradation and Metabolism (KEGG_Pathways_Level_2) (e.g., mouth site); Xenobiotics Biodegradation and Metabolism (KEGG_Pathways_Level_2) (e.g., gut site).

Determining an allergy-related characterization of a user can include diagnosing a user with a wheat allergy condition based upon one or more of the above microbiome features and/or other suitable features described herein, such as in an additional or alterative manner to typical methods of diagnosis. However, features used in the wheat allergy characterization process can include any other suitable features (e.g., features useful for diagnostics), and performing the wheat allergy characterization process can be performed in any suitable manner.

3.3.B Treenut Allergy Condition Characterization Process.

In another variation, Block S130 can include performing a treenut allergy condition characterization process (e.g., determining and/or applying a treenut allergy characterization model; etc.) for one or more users. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with a treenut allergy condition. In another example, performing a treenut allergy condition characterization process can facilitate identifications of one or more therapies operable to have a positive effect on the treenut allergy condition (e.g., based upon a random forest predictor algorithm trained with a training dataset derived from a subset of the population of subjects, and validated with a validation dataset derived from a subset of the population of subjects). In particular, a treenut allergy condition can include an immune disorder of the subject characterized by hypersensitivity to dietary substances from treenut and/or edible tree seeds causing an overreaction of the immune system, which may lead to severe physical symptoms, where diagnosis can be associated to laboratory analysis (e.g., skin-prick test, blood-samples analysis, IgE tests, etc.) and/or other suitable diagnostic procedures.

Performing a treenut allergy condition characterization process (e.g., a diagnostic process) can be based on microbiome features (e.g., microbiome composition features) associated with (e.g., derived from, informative of, correlated with, etc.) one or more: *Blautia luti* (Species), *Collinsella aerofaciens* (Species), *Parabacteroides distasonis* (Species), *Flavonifractor plautii* (Species), *Bacteroides fragilis* (Species), *Dorea formicigenerans* (Species), *Roseburia inulinivorans* (Species), *Clostridium* (Genus), *Marvinbryantia* (Genus), *Dorea* (Genus), *Eggerthella* (Genus), *Terrisporobacter* (Genus), *Sarcina* (Genus), *Bacteroides* (Genus), *Barnesiella* (Genus), Oscillospiraceae (Family), Clostridiaceae (Family), Bacteroidaceae (Family), Clostridiales (Order), Selenomonadales (Order), Bacteroidales (Order), Flavobacteriales (Order), Clostridia (Class), Negativicutes (Class), Flavobacteriia (Class), Bacteroidia (Class), Firmicutes (Phylum), Bacteroidetes (Phylum).

Additionally or alternatively, microbiome features can be associated with one or more of the following taxons in relation to a sample site (e.g., treenut allergy condition correlations with microorganisms observed at a particular sample site): *Acetitomaculum* (genus) (e.g., gut site); Acidaminococcaceae (family) (e.g., gut site); *Actinomyces* (genus) (e.g., nose site); *Actinomyces* (genus) (e.g., gut site); *Actinomyces* sp. ICM54 (species) (e.g., nose site); Actinomycetaceae (family) (e.g., nose site); Actinomycetaceae (family) (e.g., gut site); *Adlercreutzia* (genus) (e.g., gut site); *Adlercreutzia equolifaciens* (species) (e.g., gut site); Aerococcaceae (family) (e.g., nose site); *Akkermansia* (genus) (e.g., gut site); *Akkermansia muciniphila* (species) (e.g., gut site); *Alistipes putredinis* (species) (e.g., gut site); *Alistipes* sp. RMA 9912 (species) (e.g., gut site); Alphaproteobacteria (class) (e.g., mouth site); Alphaproteobacteria (class) (e.g., gut site); *Anaerostipes* (genus) (e.g., gut site); *Anaerostipes* sp. 3_2_56FAA (species) (e.g., gut site); *Anaerostipes* sp. 5_1_63FAA (species) (e.g., gut site); *Anaerotruncus colihominis* (species) (e.g., gut site); Bacteroidaceae (family) (e.g., gut site); Bacteroidales (order) (e.g., gut site); *Bacteroides* (genus) (e.g., gut site); *Bacteroides clarus* (species) (e.g., gut site); *Bacteroides fragilis* (species) (e.g., gut site); *Bacteroides massiliensis* (species) (e.g., gut site); *Bacteroides* sp. AR20 (species) (e.g., gut site); *Bacteroides* sp. AR29 (species) (e.g., gut site); *Bacteroides* sp. D22 (species) (e.g., gut site); *Bacteroides* sp. SLC1-38 (species) (e.g., gut site); *Bacteroides thetaiotaomicron* (species) (e.g., gut site); Bacteroidetes (phylum) (e.g., gut site); Bacteroidia (class) (e.g., gut site); *Barnesiella* (genus) (e.g., gut site); *Barnesiella intestinihominis* (species) (e.g., gut site); *Bifidobacterium choerinum* (species) (e.g., gut site); *Bilophila* (genus) (e.g., gut site); *Bilophila* sp. 4_1_30 (species) (e.g., gut site); *Blautia* (genus) (e.g., gut site); *Blautia luti* (species) (e.g., gut site); *Blautia* sp. Ser8 (species) (e.g., gut site); *Blautia* sp. YHC-4 (species) (e.g., gut site); *Blautia wexlerae* (species) (e.g., gut site); *Butyricicoccus* (genus) (e.g., gut site); *Campylobacter* (genus) (e.g., gut site); Campylobacteraceae (family) (e.g., gut site); Campylobacterales (order) (e.g., gut site); Cardiobacteriaceae (family) (e.g., nose site); Cardiobacteriales (order) (e.g., nose site); *Cardiobacterium* (genus) (e.g., nose site); Clostridia (class) (e.g., gut site); Clostridiaceae (family) (e.g., gut site); Clostridiales (order) (e.g., gut site); *Clostridium* (genus) (e.g., gut site); *Collinsella* (genus) (e.g., gut site); *Collinsella aerofaciens* (species) (e.g., gut site); *Corynebacterium durum* (species) (e.g., nose site); Deltaproteobacteria (class) (e.g., gut site); Desulfovibrionaceae (family) (e.g., gut site); Desulfovibrionales (order) (e.g., gut site); *Dielma* (genus) (e.g., gut site); *Dorea* (genus) (e.g., gut site); *Dorea formicigenerans* (species) (e.g., gut site); *Dorea longicatena* (species) (e.g., gut site); *Eggerthella* (genus) (e.g., gut site); *Eggerthella* sp. HGA1 (species) (e.g., gut site); *Eisenbergiella* (genus) (e.g., gut site); *Eisenbergiella tayi* (species) (e.g., gut site); *Enterobacter* (genus) (e.g., gut site); *Enterobacter* sp. BS2-1 (species) (e.g., gut site); *Enterococcus raffinosus* (species) (e.g., gut site); Epsilonproteobacteria (class) (e.g., gut site); *Erysipelatoclostridium ramosum* (species) (e.g., gut site); Erysipelotrichales (order) (e.g., gut site); *Faecalibacterium* (genus) (e.g., gut site); *Faecalibacterium prausnitzii* (species) (e.g., gut site); *Finegoldia* (genus) (e.g., skin site); *Finegoldia* sp. S9 AA1-5 (species) (e.g., skin site); Firmicutes (phylum) (e.g., gut site); Flavobacteriaceae (family) (e.g., gut site); Flavobacteriales (order) (e.g., gut site); Flavobacteriia (class) (e.g., gut site); *Flavobacterium* (genus) (e.g., gut site); *Flavonifractor plautii* (species) (e.g., gut site); *Fusicatenibacter* (genus) (e.g., gut site); *Fusicatenibacter saccharivorans* (species) (e.g., gut site); Fusobacteria (phylum) (e.g., nose site); Fusobacteria (phylum) (e.g., gut site); Fusobacteriaceae (family) (e.g., nose site); Fusobacteriales (order) (e.g., nose site); Fusobacteriales (order) (e.g., gut site); Fusobacteriia (class) (e.g., nose site); Fusobacteriia (class) (e.g., gut site); *Fusobacterium* (genus) (e.g., nose site); *Gemella* (genus) (e.g., gut site); *Gordonibacter* (genus) (e.g., gut site); *Gordonibacter pamelaeae* (species) (e.g., gut site); *Granulicatella adiacens* (species) (e.g., gut site); *Hespellia* (genus) (e.g., gut site); *Intestinimonas butyriciproducens* (species) (e.g., gut site); *Lachnospira* (genus) (e.g., gut site); *Lachnospira pectinoschiza* (species) (e.g., gut site); Lachnospiraceae (family) (e.g., gut site); *Lactobacillus crispatus* (species) (e.g., nose site); *Lactonifactor longoviformis* (species) (e.g., gut site); *Marvinbryantia* (genus) (e.g., gut site); *Megasphaera* (genus) (e.g., gut site); *Moryella* (genus) (e.g., gut site); Mycobacteriaceae (family) (e.g., nose site); *Mycobacterium* (genus) (e.g., nose site); Negativicutes (class) (e.g., gut site); *Neisseria elongata* (species) (e.g., nose site); Neisseriaceae (family) (e.g., nose site); Neisseriales (order) (e.g., nose site); *Odoribacter* (genus) (e.g., gut site); *Odoribacter splanchnicus* (species) (e.g., gut site); Oscillospiraceae (family) (e.g., gut site); *Parabacteroides distasonis* (species) (e.g., gut site); *Parabacteroides merdae* (species) (e.g., gut site); Peptococcaceae (family) (e.g., gut site); *Peptococcus* (genus) (e.g., gut site); *Peptoniphilus* (genus) (e.g., skin site); *Phascolarctobacterium* (genus) (e.g., gut site); *Phascolarctobacterium faecium* (species) (e.g., gut site); *Phascolarctobacterium* sp. 377 (species) (e.g., gut site); *Prevotella maculosa* (species) (e.g., mouth site); Rhodospirillaceae (family) (e.g., gut site); Rhodospirillales (order) (e.g., skin site); Rhodospirillales (order) (e.g., gut site); *Robinsoniella* (genus) (e.g., gut site); *Roseburia* (genus) (e.g., gut site); *Roseburia inulinivorans* (species) (e.g., gut site); *Roseburia* sp. 11SE39 (species) (e.g., gut site); *Rothia* (genus) (e.g., nose site); *Rothia dentocariosa* (species) (e.g., nose site); Ruminococcaceae (family) (e.g., gut site); *Sarcina* (genus) (e.g., gut site); Selenomonadales (order) (e.g., gut site); *Streptococcus* sp. oral taxon G59 (species) (e.g., nose site); *Subdoligranulum* (genus) (e.g., gut site); *Subdoligranulum variabile* (species) (e.g., gut site); *Terrisporobacter* (genus) (e.g., gut site); *Thalassospira* (genus) (e.g., gut site); *Veillonella* (genus) (e.g., nose site); Verrucomicrobia (phylum) (e.g., gut site); Verrucomicrobiaceae (family) (e.g., gut site); Verrucomicrobiae (class) (e.g., gut site); Verrucomicrobiales (order) (e.g., gut site).

Additionally or alternatively, performing a treenut allergy condition characterization process can be based on microbiome features (e.g., microbiome function features) associated with one or more of (e.g., such as in relation to a corresponding sample site): Transport and Catabolism (KEGG2), Glycan Biosynthesis and Metabolism (KEGG2), Biosynthesis of Other Secondary Metabolites (KEGG2), Glycosaminoglycan degradation (KEGG3), Lipoic acid metabolism (KEGG3), Lysosome (KEGG3), Inorganic ion transport and metabolism (KEGG3), Cell motility and secretion (KEGG3), Glycosphingolipid biosynthesis—ganglio series (KEGG3), Glycosphingolipid biosynthesis—globo series (KEGG3), Lipopolysaccharide biosynthesis proteins (KEGG3), Ribosome Biogenesis (KEGG3), Other glycan degradation (KEGG3), Phosphatidylinositol signaling system (KEGG3), Membrane and intracellular structural molecules (KEGG3), Sphingolipid metabolism (KEGG3), Huntington's disease (KEGG3), Peroxisome (KEGG3), Signal transduction mechanisms (KEGG3), Pores ion channels (KEGG3), Ubiquinone and other terpenoid-quinone biosynthesis (KEGG3), and/or other suitable function-related aspects.

Additionally or alternatively, microbiome features (e.g., microbiome functional features) can be associated with one or more of the following in relation to a sample site (e.g., treenut allergy condition correlations with microorganism-related function observed at a particular sample site): Metabolism (KEGG_Pathways_Level_2) (e.g., gut site); Signaling Molecules and Interaction (KEGG_Pathways_Level_2) (e.g., gut site); Glycan Biosynthesis and Metabolism (KEGG_Pathways_Level_2) (e.g., gut site); Translation (KEGG_Pathways_Level_2) (e.g., gut site); Transport and Catabolism (KEGG_Pathways_Level_2) (e.g., gut site); Cellular Processes and Signaling (KEGG_Pathways_Level_2) (e.g., gut site); Peptidoglycan biosynthesis (KEGG_Pathways_Level_3) (e.g., gut site); Aminoacyl-tRNA biosynthesis (KEGG_Pathways_Level_3) (e.g., gut site); Lipopolysaccharide biosynthesis proteins (KEGG_Pathways_Level_3) (e.g., gut site); Ribosome Biogenesis (KEGG_Pathways_Level_3) (e.g., gut site); Inorganic ion transport and metabolism (KEGG_Pathways_Level_3) (e.g., gut site); Germination (KEGG_Pathways_Level_3) (e.g., gut site); Glycosaminoglycan degradation (KEGG_Pathways_Level_3) (e.g., gut site); Aminobenzoate degradation (KEGG_Pathways_Level_3) (e.g., gut site); Lipopolysaccharide biosynthesis (KEGG_Pathways_Level_3) (e.g., gut site); Epithelial cell signaling in *Helicobacter pylori* infection (KEGG_Pathways_Level_3) (e.g., gut site); RNA transport (KEGG_Pathways_Level_3) (e.g., gut site); "Phenylalanine, tyrosine and tryptophan biosynthesis" (KEGG_Pathways_Level_3) (e.g., gut site); Chromosome (KEGG_Pathways_Level_3) (e.g., gut site); Biosynthesis of Other Secondary Metabolites (KEGG_Pathways_Level_2) (e.g., gut site); Excretory System (KEGG_Pathways_Level_2) (e.g., gut site); Cell Growth and Death (KEGG_Pathways_Level_2) (e.g., gut site); Membrane Transport (KEGG_Pathways_Level_2) (e.g., gut site); Infectious Diseases (KEGG_Pathways_Level_2) (e.g., gut site); Cell Motility (KEGG_Pathways_Level_2) (e.g., gut site); Transcription (KEGG_Pathways_Level_2) (e.g., gut site); Metabolism of Other Amino Acids (KEGG_Pathways_Level_2) (e.g., gut site); Poorly Characterized (KEGG_Pathways_Level_2) (e.g., gut site); Lipid Metabolism (KEGG_Pathways_Level_2) (e.g., gut site); Replication and Repair (KEGG_Pathways_Level_2) (e.g., gut site); Metabolism of Terpenoids and Polyketides (KEGG_Pathways_Level_2) (e.g., gut site); Carbohydrate Metabolism (KEGG_Pathways_Level_2) (e.g., gut site); Environmental Adaptation (KEGG_Pathways_Level_2) (e.g., gut site); Bacterial chemotaxis (KEGG_Pathways_Level_3) (e.g., gut site); Cell cycle—*Caulobacter* (KEGG_Pathways_Level_3) (e.g., gut site); Membrane and intracellular structural molecules (KEGG_Pathways_Level_3) (e.g., gut site); Pentose and glucuronate interconversions (KEGG_Pathways_Level_3) (e.g., gut site); RNA polymerase (KEGG_Pathways_Level_3) (e.g., gut site); N-Glycan biosynthesis (KEGG_Pathways_Level_3) (e.g., gut site); Sulfur metabolism (KEGG_Pathways_Level_3) (e.g., gut site); Xylene degradation (KEGG_Pathways_Level_3) (e.g., gut site); Huntington_quote_s disease (KEGG_Pathways_Level_3) (e.g., gut site); RNA degradation (KEGG_Pathways_Level_3) (e.g., gut site); Glycosyltransferases (KEGG_Pathways_Level_3) (e.g., gut site); Others (KEGG_Pathways_Level_3) (e.g., gut site); Phosphatidylinositol signaling system (KEGG_Pathways_Level_3) (e.g., gut site); Pores ion channels (KEGG_Pathways_Level_3) (e.g., gut site); Biosynthesis and biodegradation of secondary metabolites (KEGG_Pathways_Level_3) (e.g., gut site); Phosphonate and phosphinate metabolism (KEGG_Pathways_Level_3) (e.g., gut site); Dioxin degradation (KEGG_Pathways_Level_3) (e.g., gut site); Benzoate degradation (KEGG_Pathways_Level_3) (e.g., gut site); Translation proteins (KEGG_Pathways_Level_3) (e.g., gut site); Cell motility and secretion (KEGG_Pathways_Level_3) (e.g., gut site); Other ion-coupled transporters (KEGG_Pathways_Level_3) (e.g., gut site); D-Alanine metabolism (KEGG_Pathways_Level_3) (e.g., gut site); Bisphenol degradation (KEGG_Pathways_Level_3) (e.g., gut site); Glycosphingolipid biosynthesis—globo series (KEGG_Pathways_Level_3) (e.g., gut site); Lysosome (KEGG_Pathways_Level_3) (e.g., gut site); Proximal tubule bicarbonate reclamation (KEGG_Pathways_Level_3) (e.g., gut site); Linoleic acid metabolism (KEGG_Pathways_Level_3) (e.g., gut site); Methane metabolism (KEGG_Pathways_Level_3) (e.g., gut site); Other glycan degradation (KEGG_Pathways_Level_3) (e.g., gut site); Phenylalanine metabolism (KEGG_Pathways_Level_3) (e.g., gut site); Terpenoid backbone biosynthesis (KEGG_Pathways_Level_3) (e.g., gut site); Penicillin and cephalosporin biosynthesis (KEGG_Pathways_Level_3) (e.g., gut site); Ribosome (KEGG_Pathways_Level_3) (e.g., gut site); Glyoxylate and dicarboxylate metabolism (KEGG_Pathways_Level_3) (e.g., gut site); Lysine biosynthesis (KEGG_Pathways_Level_3) (e.g., gut site); Ion channels (KEGG_Pathways_Level_3) (e.g., gut site); Citrate cycle (TCA cycle) (KEGG_Pathways_Level_3) (e.g., gut site); Geraniol degradation (KEGG_Pathways_Level_3) (e.g., gut site); Cytoskeleton proteins (KEGG_Pathways_Level_3) (e.g., gut site); Cellular antigens (KEGG_Pathways_Level_3) (e.g., gut site); Ribosome biogenesis in eukaryotes (KEGG_Pathways_Level_3) (e.g., gut site); Protein digestion and absorption (KEGG_Pathways_Level_3) (e.g., gut site); Biosynthesis of siderophore group nonribosomal peptides (KEGG_Pathways_Level_3) (e.g., gut site); Lipoic acid metabolism (KEGG_Pathways_Level_3) (e.g., gut site); "Valine, leucine and isoleucine biosynthesis" (KEGG_Pathways_Level_3) (e.g., gut site); Glutathione metabolism (KEGG_Pathways_Level_3) (e.g., gut site); Sphingolipid metabolism (KEGG_Pathways_Level_3) (e.g., gut site); Amino sugar and nucleotide sugar metabolism (KEGG_Pathways_Level_3) (e.g., gut site); Thiamine metabolism (KEGG_Pathways_Level_3) (e.g., gut site); Signal transduction mechanisms (KEGG_Pathways_Level_3) (e.g., gut site); Bacterial toxins (KEGG_Pathways_Level_3) (e.g., gut site); Steroid hormone biosynthesis (KEGG_Pathways_Level_3) (e.g., gut site); Transcription factors (KEGG_Pathways_Level_3) (e.g., gut site); Pertussis (KEGG_Pathways_Level_3) (e.g., gut site); Sporulation (KEGG_Pathways_Level_3) (e.g., gut site); Meiosis—yeast (KEGG_Pathways_Level_3) (e.g., gut site); Amino acid related enzymes (KEGG_Pathways_Level_3) (e.g., gut site); Streptomycin biosynthesis (KEGG_Pathways_Level_3) (e.g., gut site); Transporters (KEGG_Pathways_Level_3) (e.g., gut site); Isoquinoline alkaloid biosynthesis (KEGG_Pathways_Level_3) (e.g., gut site); Function unknown (KEGG_Pathways_Level_3) (e.g., gut site); Galactose metabolism (KEGG_Pathways_Level_3) (e.g., gut site); Cyanoamino acid metabolism (KEGG_Pathways_Level_3) (e.g., gut site); Taurine and hypotaurine metabolism (KEGG_Pathways_Level_3) (e.g., gut site); Pantothenate and CoA biosynthesis (KEGG_Pathways_Level_3) (e.g., gut site); Glycosphingolipid biosynthesis—ganglio series (KEGG_Pathways_Level_3) (e.g., gut site); Toluene degradation (KEGG_Pathways_Level_3) (e.g., gut site); Nicotinate and nicotinamide metabolism (KEGG_Pathways_Level_3) (e.g., gut site); DNA repair and recombination proteins (KEGG_Pathways_Level_3) (e.g., gut site); Ubiquinone and other terpenoid-quinone biosynthesis (KEGG_Pathways_Level_3) (e.g., gut site); ABC transporters (KEGG_Pathways_Level_3) (e.g., gut site); Plant-pathogen interaction (KEGG_Pathways_Level_3) (e.g., gut site); Ubiquitin system (KEGG_Pathways_Level_3) (e.g., gut site).

Additionally or alternatively microbiome features (e.g., microbiome functional features) can be associated with one or more of the following in relation to a healthy gut sample site (and/or other suitable sites and/or healthiness levels): Biosynthesis of Other Secondary Metabolites (e.g., KEGG_Pathways_Level_2) (e.g., gut site); Excretory System (e.g., KEGG_Pathways_Level_2) (e.g., gut site); Membrane Transport (e.g., KEGG_Pathways_Level_2) (e.g., gut site); Infectious Diseases (e.g., KEGG_Pathways_Level_2) (e.g., gut site); Cell Motility (e.g., KEGG_Pathways_Level_2) (e.g., gut site); Metabolism (e.g., KEGG_Pathways_Level_2) (e.g., gut site); Signaling Molecules and Interaction (e.g., KEGG_Pathways_Level_2) (e.g., gut site); Glycan Biosynthesis and Metabolism (e.g., KEGG_Pathways_Level_2) (e.g., gut site); Transcription (e.g., KEGG_Pathways_Level_2) (e.g., gut site); Translation (e.g., KEGG_Pathways_Level_2) (e.g., gut site); Metabolism of Other Amino Acids (e.g., KEGG_Pathways_Level_2) (e.g., gut site); Poorly Characterized (e.g., KEGG_Pathways_Level_2) (e.g., gut site); Lipid Metabolism (e.g., KEGG_Pathways_Level_2) (e.g., gut site); Transport and Catabolism (e.g., KEGG_Pathways_Level_2) (e.g., gut site); Metabolism of Terpenoids and Polyketides (e.g., KEGG_Pathways_Level_2) (e.g., gut site); Cellular Processes and Signaling (e.g., KEGG_Pathways_Level_2) (e.g., gut site); Carbohydrate Metabolism (e.g., KEGG_Pathways_Level_2) (e.g., gut site); Environmental Adaptation (e.g., KEGG_Pathways_Level_2) (e.g., gut site); Bacterial chemotaxis (e.g., KEGG_Pathways_Level_3) (e.g., gut site); Membrane and intracellular structural molecules (e.g., KEGG_Pathways_Level_3) (e.g., gut site); Pentose and glucuronate interconversions (e.g., KEGG_Pathways_Level_3) (e.g., gut site); RNA polymerase (e.g., KEGG_Pathways_Level_3) (e.g., gut site); N-Glycan biosynthesis (e.g., KEGG_Pathways_Level_3) (e.g., gut site); Sulfur metabolism (e.g., KEGG_Pathways_Level_3) (e.g., gut site); Peptidoglycan biosynthesis (e.g., KEGG_Pathways_Level_3) (e.g., gut site); Xylene degradation (e.g., KEGG_Pathways_Level_3) (e.g., gut site); Aminoacyl-tRNA biosynthesis (e.g., KEGG_Pathways_Level_3) (e.g., gut site); Huntingtons disease (e.g., KEGG_Pathways_Level_3) (e.g., gut site); RNA degradation (e.g., KEGG_Pathways_Level_3) (e.g., gut site); Glycosyltransferases (e.g., KEGG_Pathways_Level_3) (e.g., gut site); Others (e.g., KEGG_Pathways_Level_3) (e.g., gut site); Lipopolysaccharide biosynthesis proteins (e.g., KEGG_Pathways_Level_3) (e.g., gut site); Phosphatidylinositol signaling system (e.g., KEGG_Pathways_Level_3) (e.g., gut site); Pores ion channels (e.g., KEGG_Pathways_Level_3) (e.g., gut site); Biosynthesis and biodegradation of secondary metabolites (e.g., KEGG_Pathways_Level_3) (e.g., gut site); Phosphonate and phosphinate metabolism (e.g., KEGG_Pathways_Level_3) (e.g., gut site); Dioxin degradation (e.g., KEGG_Pathways_Level_3) (e.g., gut site); Ribosome Biogenesis (e.g., KEGG_Pathways_Level_3) (e.g., gut site); Benzoate degradation (e.g., KEGG_Pathways_Level_3) (e.g., gut site); Translation proteins (e.g., KEGG_Pathways_Level_3) (e.g., gut site); Cell motility and secretion (e.g., KEGG_Pathways_Level_3) (e.g., gut site); Other ion-coupled transporters (e.g., KEGG_Pathways_Level_3) (e.g., gut site); Photosynthesis (e.g., KEGG_Pathways_Level_3) (e.g., gut site); D-Alanine metabolism (e.g., KEGG_Pathways_Level_3) (e.g., gut site); Bisphenol degradation (e.g., KEGG_Pathways_Level_3) (e.g., gut site); Glycosphingolipid biosynthesis—globo series (e.g., KEGG_Pathways_Level_3) (e.g., gut site); Circadian rhythm—plant (e.g., KEGG_Pathways_Level_3) (e.g., gut site); Lysosome (e.g., KEGG_Pathways_Level_3) (e.g., gut site); Proximal tubule bicarbonate reclamation (e.g., KEGG_Pathways_Level_3) (e.g., gut site); Inorganic ion transport and metabolism (e.g., KEGG_Pathways_Level_3) (e.g., gut site); Caffeine metabolism (e.g., KEGG_Pathways_Level_3) (e.g., gut site); Linoleic acid metabolism (e.g., KEGG_Pathways_Level_3) (e.g., gut site); Methane metabolism (e.g., KEGG_Pathways_Level_3) (e.g., gut site); Other glycan degradation (e.g., KEGG_Pathways_Level_3) (e.g., gut site); Germination (e.g., KEGG_Pathways_Level_3) (e.g., gut site); Phenylalanine metabolism (e.g., KEGG_Pathways_Level_3) (e.g., gut site); Glycosaminoglycan degradation (e.g., KEGG_Pathways_Level_3) (e.g., gut site); Penicillin and cephalosporin biosynthesis (e.g., KEGG_Pathways_Level_3) (e.g., gut site); Ribosome (e.g., KEGG_Pathways_Level_3) (e.g., gut site); Aminobenzoate degradation (e.g., KEGG_Pathways_Level_3) (e.g., gut site); Lysine biosynthesis (e.g., KEGG_Pathways_Level_3) (e.g., gut site); Ion channels (e.g., KEGG_Pathways_Level_3) (e.g., gut site); Citrate cycle (TCA cycle) (e.g., KEGG_Pathways_Level_3) (e.g., gut site); Lipopolysaccharide biosynthesis (e.g., KEGG_Pathways_Level_3) (e.g., gut site); Geraniol degradation (e.g., KEGG_Pathways_Level_3) (e.g., gut site); Cytoskeleton proteins (e.g., KEGG_Pathways_Level_3) (e.g., gut site); Cellular antigens (e.g., KEGG_Pathways_Level_3) (e.g., gut site); Ribosome biogenesis in eukaryotes (e.g., KEGG_Pathways_Level_3) (e.g., gut site); Protein digestion and absorption (e.g., KEGG_Pathways_Level_3) (e.g., gut site); Peroxisome (e.g., KEGG_Pathways_Level_3) (e.g., gut site); RNA transport (e.g., KEGG_Pathways_Level_3) (e.g., gut site); Biosynthesis of siderophore group nonribosomal peptides (e.g., KEGG_Pathways_Level_3) (e.g., gut site); Lipoic acid metabolism (e.g., KEGG_Pathways_Level_3) (e.g., gut site); "Valine leucine and isoleucine biosynthesis" (e.g., KEGG_Pathways_Level_3) (e.g., gut site); Sphingolipid metabolism (e.g., KEGG_Pathways_Level_3) (e.g., gut site); Amino sugar and nucleotide sugar metabolism (e.g., KEGG_Pathways_Level_3) (e.g., gut site); Steroid biosynthesis (e.g., KEGG_Pathways_Level_3) (e.g., gut site); Signal transduction mechanisms (e.g., KEGG_Pathways_Level_3) (e.g., gut site); Bacterial toxins (e.g., KEGG_Pathways_Level_3) (e.g., gut site); Steroid hormone biosynthesis (e.g., KEGG_Pathways_Level_3) (e.g., gut site); Transcription factors (e.g., KEGG_Pathways_Level_3) (e.g., gut site); Pertussis (e.g., KEGG_Pathways_Level_3) (e.g., gut site); Sporulation (e.g., KEGG_Pathways_Level_3) (e.g., gut site); Amino acid related enzymes (e.g., KEGG_Pathways_Level_3) (e.g., gut site); Streptomycin biosynthesis (e.g., KEGG_Pathways_Level_3) (e.g., gut site); Transporters (e.g., KEGG_Pathways_Level_3) (e.g., gut site); Isoquinoline alkaloid biosynthesis (e.g., KEGG_Pathways_Level_3) (e.g., gut site); Function unknown (e.g., KEGG_Pathways_Level_3) (e.g., gut site); Galactose metabolism (e.g., KEGG_Pathways_Level_3) (e.g., gut site); Cyanoamino acid metabolism (e.g., KEGG_Pathways_Level_3) (e.g., gut site); Taurine and hypotaurine metabolism (e.g., KEGG_Pathways_Level_3) (e.g., gut site); Pantothenate and CoA biosynthesis (e.g., KEGG_Pathways_Level_3) (e.g., gut site); Glycosphingolipid biosynthesis—ganglio series (e.g., KEGG_Pathways_Level_3) (e.g., gut site); Toluene degradation (e.g., KEGG_Pathways_Level_3) (e.g., gut site); Photosynthesis proteins (e.g., KEGG_Pathways_Level_3) (e.g., gut site); Ubiquinone and other terpenoid-quinone biosynthesis (e.g., KEGG_Pathways_Level_3) (e.g., gut site); ABC transporters (e.g., KEGG_Pathways_Level_3) (e.g., gut site); Plant-pathogen interaction (e.g., KEGG_Pathways_Level_3) (e.g., gut site); Ubiquitin system (e.g., KEGG_Pathways_Level_3) (e.g., gut site); Chromosome (e.g., KEGG_Pathways_Level_3) (e.g., gut site).

Determining an allergy-related characterization of a user can include diagnosing a user with a treenut allergy condition based upon one or more of the above microbiome features and/or other suitable features described herein, such as in an additional or alterative manner to typical methods of diagnosis. However, features used in the treenut allergy characterization process can include any other suitable features (e.g., features useful for diagnostics), and performing the treenut allergy characterization process can be performed in any suitable manner.

3.3.C Shellfish Allergy Condition Characterization Process.

In another variation, Block S130 can include performing a shellfish allergy condition characterization process (e.g., determining and/or applying a shellfish allergy characterization model; etc.) for one or more users. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with a shellfish allergy condition. In another example, performing a shellfish allergy condition characterization process can facilitate identifications of one or more therapies operable to have a positive effect on the shellfish allergy condition (e.g., based upon a random forest predictor algorithm trained with a training dataset derived from a subset of the population of subjects, and validated with a validation dataset derived from a subset of the population of subjects). In particular, a shellfish allergy condition can include an immune disorder characterized by an abnormal response by the immune system of the subject to proteins in certain marine animals, where diagnosis can be associated with laboratory analysis (e.g., blood-samples analysis, IgE tests, etc.) and/or other suitable diagnostic procedures.

Performing a shellfish allergy condition characterization process (e.g., a diagnostic process) can be based on microbiome features (e.g., microbiome composition features) associated with (e.g., derived from, informative of, correlated with, etc.) one or more (e.g. in any suitable combination) of the following taxons: *Parabacteroides distasonis* (Species) and/or other suitable taxa.

Additionally or alternatively, microbiome features can be associated with one or more of the following taxons in relation to a sample site (e.g., shellfish allergy condition correlations with microorganisms observed at a particular sample site): *Parabacteroides distasonis* (species) (e.g., gut site).

Additionally or alternatively microbiome features can be associated with one or more of the following taxons in relation to a healthy gut sample site (and/or other suitable sites and/or healthiness levels): Oscillospiraceae (family) (e.g., gut site); Acidaminococcaceae (family) (e.g., gut site); *Clostridium* (genus) (e.g., gut site); *Phascolarctobacterium* (genus) (e.g., gut site); *Bilophila* (genus) (e.g., gut site); *Odoribacter* (genus) (e.g., gut site); *Oscillibacter* (genus) (e.g., gut site); *Parabacteroides distasonis* (species) (e.g., gut site); *Alistipes putredinis* (species) (e.g., gut site); *Odoribacter splanchnicus* (species) (e.g., gut site); *Phascolarctobacterium faecium* (species) (e.g., gut site); *Flavonifractor plautii* (species) (e.g., gut site); *Bilophila* sp. 4_1_30 (species) (e.g., gut site); *Butyricimonas* sp. JCM 18677 (species) (e.g., gut site); *Alistipes* sp. EBA6-25cl2 (species) (e.g., gut site); *Oscillibacter* (genus) (e.g., gut site); *Intestinimonas* (genus) (e.g., gut site).

Additionally or alternatively, performing a shellfish allergy condition characterization process can be based on microbiome features (e.g., microbiome function features) associated with one or more of (e.g., such as in relation to a corresponding sample site): Signal Transduction (KEGG2), Cell Growth and Death (KEGG2), Energy Metabolism (KEGG2), Replication and Repair (KEGG2), Selenocompound metabolism (KEGG3), Cell cycle—*Caulobacter* (KEGG3), Two-component system (KEGG3), Inorganic ion transport and metabolism (KEGG3), Protein kinases (KEGG3), Fatty acid biosynthesis (KEGG3), Amino acid related enzymes (KEGG3), Translation factors (KEGG3), Mismatch repair (KEGG3), Glycerophospholipid metabolism (KEGG3), and/or other suitable function-related aspects.

Additionally or alternatively, microbiome features (e.g., microbiome functional features) can be associated with one or more of the following in relation to a sample site (e.g., shellfish allergy condition correlations with microorganism-related function observed at a particular sample site): Infectious Diseases (KEGG_Pathways_Level_2) (e.g., nose site); Metabolism of Cofactors and Vitamins (KEGG_Pathways_Level_2) (e.g., nose site); Poorly Characterized (KEGG_Pathways_Level_2) (e.g., nose site); Glyoxylate and dicarboxylate metabolism (KEGG_Pathways_Level_3) (e.g., nose site); General function prediction only (KEGG_Pathways_Level_3) (e.g., nose site); Polyketide sugar unit biosynthesis (KEGG_Pathways_Level_3) (e.g., nose site); beta-Lactam resistance (KEGG_Pathways_Level_3) (e.g., nose site); *Staphylococcus aureus* infection (KEGG_Pathways_Level_3) (e.g., nose site); Taurine and hypotaurine metabolism (KEGG_Pathways_Level_3) (e.g., nose site); Cell Growth and Death (KEGG_Pathways_Level_2) (e.g., mouth site); Metabolism (KEGG_Pathways_Level_2) (e.g., mouth site); Signal Transduction (KEGG_Pathways_Level_2) (e.g., mouth site); Digestive System (KEGG_Pathways_Level_2) (e.g., mouth site); Replication and Repair (KEGG_Pathways_Level_2) (e.g., mouth site); Cell cycle—*Caulobacter* (KEGG_Pathways_Level_3) (e.g., mouth site); Nucleotide excision repair (KEGG_Pathways_Level_3) (e.g., mouth site); Bacterial secretion system (KEGG_Pathways_Level_3) (e.g., mouth site); Ribosome (KEGG_Pathways_Level_3) (e.g., mouth site); General function prediction only (KEGG_Pathways_Level_3) (e.g., mouth site); Carbohydrate digestion and absorption (KEGG_Pathways_Level_3) (e.g., mouth site); Glutathione metabolism (KEGG_Pathways_Level_3) (e.g., mouth site); D-Glutamine and D-glutamate metabolism (KEGG_Pathways_Level_3) (e.g., mouth site); Amino acid related enzymes (KEGG_Pathways_Level_3) (e.g., mouth site); Protein export (KEGG_Pathways_Level_3) (e.g., mouth site); Restriction enzyme (KEGG_Pathways_Level_3) (e.g., mouth site); DNA repair and recombination proteins (KEGG_Pathways_Level_3) (e.g., mouth site); Biosynthesis of vancomycin group antibiotics (KEGG_Pathways_Level_3) (e.g., mouth site); Cell Growth and Death (KEGG_Pathways_Level_2) (e.g., gut site); Cell Motility (KEGG_Pathways_Level_2) (e.g., gut site); Signal Transduction (KEGG_Pathways_Level_2) (e.g., gut site); Energy Metabolism (KEGG_Pathways_Level_2) (e.g., gut site); Bacterial chemotaxis (KEGG_Pathways_Level_3) (e.g., gut site); Cell cycle—*Caulobacter* (KEGG_Pathways_Level_3) (e.g., gut site); Oxidative phosphorylation (KEGG_Pathways_Level_3) (e.g., gut site); Inorganic ion transport and metabolism (KEGG_Pathways_Level_3) (e.g., gut site); Selenocompound metabolism (KEGG_Pathways_Level_3) (e.g., gut site); Amino acid related enzymes (KEGG_Pathways_Level_3) (e.g., gut site); Two-component system (KEGG_Pathways_Level_3) (e.g., gut site); Protein kinases (KEGG_Pathways_Level_3) (e.g., gut site); Bacterial motility proteins (KEGG_Pathways_Level_3) (e.g., gut site); Flagellar assembly (KEGG_Pathways_Level_3) (e.g., gut site); Replication and Repair (KEGG_Pathways_Level_2) (e.g., gut site); Ribosome biogenesis in eukaryotes (KEGG_Pathways_Level_3) (e.g., gut site); Function unknown (KEGG_Pathways_Level_3) (e.g., gut site); DNA repair and recombination proteins (KEGG_Pathways_Level_3) (e.g., gut site).

Additionally or alternatively microbiome features (e.g., microbiome functional features) can be associated with one or more of the following in relation to a healthy gut sample site (and/or other suitable sites and/or healthiness levels): Cell Growth and Death (e.g., KEGG_Pathways_Level_2) (e.g., gut site); Cell Motility (e.g., KEGG_Pathways_Level_2) (e.g., gut site); Signal Transduction (e.g., KEGG_Pathways_Level_2) (e.g., gut site); Energy Metabolism (e.g., KEGG_Pathways_Level_2) (e.g., gut site); Bacterial chemotaxis (e.g., KEGG_Pathways_Level_3) (e.g., gut site); Cell cycle—*Caulobacter* (e.g., KEGG_Pathways_Level_3) (e.g., gut site); Basal transcription factors (e.g., KEGG_Pathways_Level_3) (e.g., gut site); Oxidative phosphorylation (e.g., KEGG_Pathways_Level_3) (e.g., gut site); Inorganic ion transport and metabolism (e.g., KEGG_Pathways_Level_3) (e.g., gut site); Secretion system (e.g., KEGG_Pathways_Level_3) (e.g., gut site); Fatty acid biosynthesis (e.g., KEGG_Pathways_Level_3) (e.g., gut site); Selenocompound metabolism (e.g., KEGG_Pathways_Level_3) (e.g., gut site); Amino acid related enzymes (e.g., KEGG_Pathways_Level_3) (e.g., gut site); Two-component system (e.g., KEGG_Pathways_Level_3) (e.g., gut site); Protein kinases (e.g., KEGG_Pathways_Level_3) (e.g., gut site); Function unknown (e.g., KEGG_Pathways_Level_3) (e.g., gut site); Bacterial motility proteins (e.g., KEGG_Pathways_Level_3) (e.g., gut site); Flagellar assembly (e.g., KEGG_Pathways_Level_3) (e.g., gut site).

Determining an allergy-related characterization of a user can include diagnosing a user with a shellfish allergy condition based upon one or more of the above microbiome features and/or other suitable features described herein, such as in an additional or alterative manner to typical methods of diagnosis. However, features used in the shellfish allergy characterization process can include any other suitable features (e.g., features useful for diagnostics), and performing the shellfish allergy characterization process can be performed in any suitable manner.

3.3.D Soy Allergy Condition Characterization Process.

In another variation, Block S130 can include performing a soy allergy condition characterization process (e.g., determining and/or applying a soy allergy characterization model; etc.) for one or more users. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with a soy allergy condition. In another example, performing a soy allergy condition characterization process can facilitate identifications of one or more therapies operable to have a positive effect on the soy allergy condition (e.g., based upon a random forest predictor algorithm trained with a training dataset derived from a subset of the population of subjects, and validated with a validation dataset derived from a subset of the population of subjects). In particular, a soy allergy condition can include an immune disorder characterized by by an abnormal reaction of the immune system of the subject to any of the proteins present in a soy bean or derivatives and food that contain soy components or derivatives; where diagnosis can be associated with laboratory analysis (e.g., skin-prick test, blood-samples analysis, IgE tests, etc.) and/or other suitable diagnostic procedures.

Performing a soy allergy condition characterization process (e.g., a diagnostic process) can be based on microbiome features (e.g., microbiome composition features) associated with (e.g., derived from, informative of, correlated with, etc.) one or more (e.g. in any suitable combination) of the following taxons: *Blautia luti* (Species), *Collinsella aerofaciens* (Species), *Dorea formicigenerans* (Species), *Flavonifractor plautii* (Species), *Subdoligranulum variabile* (Species), *Faecalibacterium prausnitzii* (Species), *Barnesiella intestinihominis* (Species), *Roseburia inulinivorans* (Species), *Blautia* sp. YHC-4 (Species), *Bacteroides caccae* (Species), *Erysipelatoclostridium ramosum* (Species), *Bacteroides thetaiotaomicron* (Species), *Odoribacter splanchnicus* (Species), *Bacteroides fragilis* (Species), *Parabacteroides distasonis* (Species), *Collinsella* (Genus), *Sarcina* (Genus), *Faecalibacterium* (Genus), *Dorea* (Genus), *Eggerthella* (Genus), *Subdoligranulum* (Genus), *Moryella* (Genus), *Marvinbryantia* (Genus), *Barnesiella* (Genus), *Terrisporobacter* (Genus), *Bacteroides* (Genus), *Anaerotruncus* (Genus), *Clostridium* (Genus), *Bifidobacterium* (Genus), *Roseburia* (Genus), *Akkermansia* (Genus), Ruminococcaceae (Family), Flavobacteriaceae (Family), Coriobacteriaceae (Family), Oscillospiraceae (Family), Clostridiaceae (Family), Bacteroidaceae (Family), Lactobacillaceae (Family), Bifidobacteriaceae (Family), Prevotellaceae (Family), Verrucomicrobiaceae (Family), Flavobacteriales (Order), Coriobacteriales (Order), Clostridiales (Order), Bifidobacteriales (Order), Bacteroidales (Order), Verrucomicrobiales (Order), Actinobacteria (Class), Flavobacteriia (Class), Clostridia (Class), Bacteroidia (Class), Verrucomicrobiae (Class), Actinobacteria (Phylum), Firmicutes (Phylum), Bacteroidetes (Phylum) and Verrucomicrobia (Phylum).

Additionally or alternatively, microbiome features can be associated with one or more of the following taxons in relation to a sample site (e.g., soy allergy condition correlations with microorganisms observed at a particular sample site): *Acetitomaculum* (genus) (e.g., gut site); Acidaminococcaceae (family) (e.g., gut site); Actinobacteria (class) (e.g., gut site); Actinobacteria (phylum) (e.g., gut site); *Actinomyces* (genus) (e.g., gut site); *Actinomyces* sp. oral taxon 175 (species) (e.g., nose site); Actinomycetaceae (family) (e.g., gut site); Actinomycetales (order) (e.g., gut site); *Adlercreutzia* (genus) (e.g., gut site); *Adlercreutzia equolifaciens* (species) (e.g., gut site); Aerococcaceae (family) (e.g., nose site); *Aggregatibacter* (genus) (e.g., gut site); *Aggregatibacter aphrophilus* (species) (e.g., nose site); *Akkermansia* (genus) (e.g., gut site); *Akkermansia muciniphila* (species) (e.g., gut site); *Alistipes* (genus) (e.g., gut site); *Alistipes putredinis* (species) (e.g., gut site); *Alistipes* sp. EBA6-25cl2 (species) (e.g., gut site); *Alistipes* sp. RMA 9912 (species) (e.g., gut site); Alphaproteobacteria (class) (e.g., gut site); *Anaerobacter* (genus) (e.g., gut site); *Anaerofilum* (genus) (e.g., gut site); *Anaerofustis* (genus) (e.g., gut site); *Anaerofustis stercorihominis* (species) (e.g., gut site); Anaeroplasmataceae (family) (e.g., gut site); *Anaerosporobacter* (genus) (e.g., gut site); *Anaerostipes* sp. 3_2_56FAA (species) (e.g., gut site); *Anaerostipes* sp. 5_1_63FAA (species) (e.g., gut site); Bacillales (order) (e.g., gut site); Bacteroidaceae (family) (e.g., gut site); Bacteroidales (order) (e.g., gut site); *Bacteroides* (genus) (e.g., gut site); *Bacteroides clarus* (species) (e.g., gut site); *Bacteroides finegoldii* (species) (e.g., gut site); *Bacteroides fragilis* (species) (e.g., gut site); *Bacteroides massiliensis* (species) (e.g., gut site); *Bacteroides nordii* (species) (e.g., gut site); *Bacteroides ovatus* (species) (e.g., gut site); *Bacteroides plebeius* (species) (e.g., gut site); *Bacteroides* sp. AR20 (species) (e.g., gut site); *Bacteroides* sp. AR29 (species) (e.g., gut site); *Bacteroides* sp. D22 (species) (e.g., gut site); *Bacteroides* sp. DJF_B097 (species) (e.g., gut site); *Bacteroides* sp. EBA5-17 (species) (e.g., gut site); *Bacteroides* sp. SLC1-38 (species) (e.g., gut site); *Bacteroides* sp. XB12B (species) (e.g., gut site); *Bacteroides thetaiotaomicron* (species) (e.g., gut site); *Bacteroides uniformis* (species) (e.g., gut site); *Bacteroides vulgatus* (species) (e.g., gut site); *Bacteroides vulgatus* (species) (e.g., genital site); Bacteroidetes (phylum) (e.g., gut site); Bacteroidia (class) (e.g., gut site); *Barnesiella* (genus) (e.g., gut site); *Barnesiella intestinihominis* (species) (e.g., gut site); *Barnesiella* sp. 177 (species) (e.g., gut site); Betaproteobacteria (class) (e.g., gut site); Bifidobacteriaceae (family) (e.g., gut site); Bifidobacteriales (order) (e.g., gut site); *Bifidobacterium* (genus) (e.g., gut site); *Bifidobacterium biavatii* (species) (e.g., gut site); *Bifidobacterium kashiwanohense* (species) (e.g., gut site); *Bifidobacterium* sp. MSX5B (species) (e.g., gut site); *Bifidobacterium stercoris* (species) (e.g., gut site); *Bilophila* (genus) (e.g., gut site); *Bilophila* sp. 4_1_30 (species) (e.g., gut site); *Blautia faecis* (species) (e.g., gut site); *Blautia glucerasea* (species) (e.g., gut site); *Blautia luti* (species) (e.g., gut site); *Blautia producta* (species) (e.g., gut site); *Blautia* sp. Ser8 (species) (e.g., gut site); *Blautia* sp. YHC-4 (species) (e.g., gut site); *Blautia wexlerae* (species) (e.g., gut site); Bradyrhizobiaceae (family) (e.g., nose site); Bradyrhizobiaceae (family) (e.g., genital site); *Bradyrhizobium* (genus) (e.g., nose site); *Bradyrhizobium* sp. 68A4SAPT (species) (e.g., nose site); Burkholderiales (order) (e.g., gut site); *Butyricicoccus* (genus) (e.g., gut site); *Butyricicoccus pullicaecorum* (species) (e.g., gut site); *Butyricimonas* (genus) (e.g., gut site); *Butyricimonas* sp. JCM 18677 (species) (e.g., gut site); *Butyricimonas virosa* (species) (e.g., gut site); *Butyrivibrio crossotus* (species) (e.g., gut site); *Campylobacter ureolyticus* (species) (e.g., gut site); Campylobacteraceae (family) (e.g., gut site); Campylobacterales (order) (e.g., gut site); *Candidatus Soleaferrea* (genus) (e.g., gut site); *Candidatus Stoquefichus* (genus) (e.g., gut site); *Capnocytophaga* sp. CM59 (species) (e.g., nose site); Carnobacteriaceae (family) (e.g., gut site); Carnobacteriaceae (family) (e.g., skin site); *Centipeda* (genus) (e.g., nose site); *Citrobacter* (genus) (e.g., gut site); *Citrobacter amalonaticus* (species) (e.g., gut site); Clostridia (class) (e.g., gut site); Clostridiaceae (family) (e.g., gut site); Clostridiales (order) (e.g., gut site); *Clostridium* (genus) (e.g., gut site); *Collin-* sella (genus) (e.g., gut site); *Collinsella aerofaciens* (species) (e.g., gut site); *Collinsella intestinalis* (species) (e.g., gut site); Coriobacteriaceae (family) (e.g., gut site); Coriobacteriales (order) (e.g., gut site); *Corynebacterium matruchotii* (species) (e.g., nose site); Cyanobacteria (phylum) (e.g., nose site); *Delftia* (genus) (e.g., nose site); *Delftia* sp. BN-SKY3 (species) (e.g., nose site); Deltaproteobacteria (class) (e.g., gut site); *Desulfovibrio piger* (species) (e.g., gut site); Desulfovibrionaceae (family) (e.g., gut site); Desulfovibrionales (order) (e.g., gut site); *Dialister* (genus) (e.g., gut site); *Dialister micraerophilus* (species) (e.g., gut site); *Dielma* (genus) (e.g., gut site); *Dielma fastidiosa* (species) (e.g., gut site); *Dorea* (genus) (e.g., gut site); *Dorea formicigenerans* (species) (e.g., gut site); *Dorea longicatena* (species) (e.g., gut site); *Eggerthella* (genus) (e.g., gut site); *Eggerthella* sp. HGA1 (species) (e.g., gut site); *Eisenbergiella* (genus) (e.g., gut site); *Eisenbergiella tayi* (species) (e.g., gut site); *Enterobacter* (genus) (e.g., gut site); *Enterobacter* sp. BS2-1 (species) (e.g., gut site); Enterobacteriaceae (family) (e.g., genital site); Enterobacteriales (order) (e.g., genital site); Enterococcaceae (family) (e.g., gut site); *Enterococcus* (genus) (e.g., gut site); *Enterococcus raffinosus* (species) (e.g., gut site); *Enterococcus* sp. C6I11 (species) (e.g., gut site); *Enterorhabdus* (genus) (e.g., gut site); Epsilonproteobacteria (class) (e.g., gut site); *Erysipelatoclostridium ramosum* (species) (e.g., gut site); Erysipelotrichaceae (family) (e.g., gut site); Erysipelotrichales (order) (e.g., gut site); Erysipelotrichia (class) (e.g., gut site); Eubacteriaceae (family) (e.g., gut site); *Eubacterium* (genus) (e.g., gut site); *Eubacterium callanderi* (species) (e.g., gut site); *Faecalibacterium* (genus) (e.g., gut site); *Faecalibacterium prausnitzii* (species) (e.g., gut site); Firmicutes (phylum) (e.g., gut site); Flavobacteriaceae (family) (e.g., gut site); Flavobacteriales (order) (e.g., gut site); Flavobacteriales (order) (e.g., skin site); Flavobacteriia (class) (e.g., gut site); Flavobacteriia (class) (e.g., skin site); *Flavonifractor* (genus) (e.g., gut site); *Flavonifractor plautii* (species) (e.g., gut site); *Fusicatenibacter* (genus) (e.g., gut site); *Fusicatenibacter saccharivorans* (species) (e.g., gut site); Gammaproteobacteria (class) (e.g., gut site); *Gemella* (genus) (e.g., gut site); *Gemella* sp. 933-88 (species) (e.g., gut site); *Gordonibacter* (genus) (e.g., gut site); *Gordonibacter pamelaeae* (species) (e.g., gut site); *Granulicatella* (genus) (e.g., gut site); *Granulicatella adiacens* (species) (e.g., gut site); *Herbaspirillum* (genus) (e.g., nose site); *Herbaspirillum seropedicae* (species) (e.g., nose site); *Hespellia* (genus) (e.g., gut site); *Holdemania* (genus) (e.g., gut site); *Holdemania filiformis* (species) (e.g., gut site); *Howardella* (genus) (e.g., gut site); *Howardella ureilytica* (species) (e.g., gut site); *Intestinibacter* (genus) (e.g., gut site); *Intestinimonas* (genus) (e.g., gut site); *Intestinimonas butyriciproducens* (species) (e.g., gut site); *Klebsiella* (genus) (e.g., gut site); *Lachnospira* (genus) (e.g., gut site); *Lachnospira pectinoschiza* (species) (e.g., gut site); Lactobacillaceae (family) (e.g., gut site); *Lactobacillus* (genus) (e.g., gut site); *Lactobacillus crispatus* (species) (e.g., gut site); *Lactobacillus* sp. 7_1_47FAA (species) (e.g., genital site); *Lactobacillus* sp. BL302 (species) (e.g., genital site); *Lactobacillus* sp. BL302 (species) (e.g., gut site); *Lactococcus* (genus) (e.g., gut site); *Lactococcus* sp. MH5-2 (species) (e.g., gut site); *Lactonifactor* (genus) (e.g., gut site); *Lactonifactor longoviformis* (species) (e.g., gut site); *Lautropia* (genus) (e.g., nose site); *Lautropia* sp. TeTO (species) (e.g., nose site); *Marvinbryantia* (genus) (e.g., gut site); *Megasphaera* (genus) (e.g., gut site); *Megasphaera genomo* sp. C1 (species) (e.g., gut site); Mollicutes (class) (e.g., gut site); *Moryella* (genus) (e.g., gut site); Mycobacteriaceae (family) (e.g., nose site); Mycobacteriaceae (family) (e.g., mouth site); *Mycobacterium* (genus) (e.g., nose site); Negativicutes (class) (e.g., gut site); *Neisseria elongata* (species) (e.g., nose site); *Neisseria mucosa* (species) (e.g., nose site); *Odoribacter* (genus) (e.g., gut site); *Odoribacter splanchnicus* (species) (e.g., gut site); *Oscillibacter* (genus) (e.g., gut site); *Oscillospira* (genus) (e.g., gut site); Oscillospiraceae (family) (e.g., gut site); Oxalobacteraceae (family) (e.g., nose site); *Parabacteroides* (genus) (e.g., gut site); *Parabacteroides distasonis* (species) (e.g., gut site); *Parabacteroides merdae* (species) (e.g., gut site); *Parasutterella* (genus) (e.g., gut site); *Parasutterella excrementihominis* (species) (e.g., gut site); Peptococcaceae (family) (e.g., gut site); *Peptococcus* (genus) (e.g., gut site); *Peptoniphilus* sp. DNF00840 (species) (e.g., genital site); *Peptoniphilus* sp. oral taxon 375 (species) (e.g., gut site); *Phascolarctobacterium* (genus) (e.g., gut site); *Phascolarctobacterium faecium* (species) (e.g., gut site); Phyllobacteriaceae (family) (e.g., gut site); *Phyllobacterium* (genus) (e.g., gut site); Porphyromonadaceae (family) (e.g., gut site); Prevotellaceae (family) (e.g., gut site); *Pseudoflavonifractor* (genus) (e.g., gut site); *Pseudoflavonifractor capillosus* (species) (e.g., gut site); Pseudomonadales (order) (e.g., gut site); Rhizobiaceae (family) (e.g., nose site); Rhizobiales (order) (e.g., gut site); Rhodospirillaceae (family) (e.g., gut site); Rhodospirillales (order) (e.g., gut site); Rikenellaceae (family) (e.g., gut site); *Robinsoniella peoriensis* (species) (e.g., gut site); *Roseburia* (genus) (e.g., gut site); *Roseburia intestinalis* (species) (e.g., gut site); *Roseburia inulinivorans* (species) (e.g., gut site); *Roseburia* sp. 11SE39 (species) (e.g., gut site); *Roseburia* sp. 499 (species) (e.g., gut site); Ruminococcaceae (family) (e.g., gut site); Ruminococcaceae (family) (e.g., genital site); *Sarcina* (genus) (e.g., gut site); Selenomonadales (order) (e.g., gut site); *Shinella* (genus) (e.g., nose site); *Shinella* sp. DR33 (species) (e.g., nose site); *Shuttleworthia* (genus) (e.g., gut site); *Slackia piriformis* (species) (e.g., gut site); *Sphingomonas* (genus) (e.g., skin site); Streptococcaceae (family) (e.g., gut site); *Streptococcus* sp. BS35a (species) (e.g., gut site); *Streptococcus* sp. BS35a (species) (e.g., mouth site); *Subdoligranulum* (genus) (e.g., gut site); *Subdoligranulum variabile* (species) (e.g., gut site); *Sutterella stercoricanis* (species) (e.g., gut site); *Sutterella wadsworthensis* (species) (e.g., gut site); Sutterellaceae (family) (e.g., gut site); Tenericutes (phylum) (e.g., gut site); *Terrisporobacter* (genus) (e.g., gut site); *Thalassospira* (genus) (e.g., gut site); *Veillonella* (genus) (e.g., gut site); Verrucomicrobia (phylum) (e.g., gut site); Verrucomicrobiaceae (family) (e.g., gut site); Verrucomicrobiae (class) (e.g., gut site); Verrucomicrobiales (order) (e.g., gut site).

Additionally or alternatively, performing a soy allergy condition characterization process can be based on microbiome features (e.g., microbiome function features) associated with one or more of (e.g., such as in relation to a corresponding sample site): Metabolism (KEGG2), Translation (KEGG2), Carbohydrate Metabolism (KEGG2), Replication and Repair (KEGG2), Cellular Processes and Signaling (KEGG2), Nucleotide Metabolism (KEGG2), Enzyme Families (KEGG2), Cell Growth and Death (KEGG2), Poorly Characterized (KEGG2), Environmental Adaptation (KEGG2), Glycan Biosynthesis and Metabolism (KEGG2), Signal Transduction (KEGG2), Metabolism of Cofactors and Vitamins (KEGG2), Signaling Molecules and Interaction (KEGG2), Transport and Catabolism (KEGG2), Xenobiotics Biodegradation and Metabolism (KEGG2), Ribosome Biogenesis (KEGG3), Ascorbate and aldarate metabolism (KEGG3), Peptidoglycan biosynthesis (KEGG3), Others (KEGG3), Amino acid related enzymes (KEGG3), RNA polymerase (KEGG3), Ribosome (KEGG3), Glyoxylate and dicarboxylate metabolism (KEGG3), Amino acid metabolism (KEGG3), Other transporters (KEGG3), Aminoacyl-tRNA biosynthesis (KEGG3), D-Alanine metabolism (KEGG3), Chromosome (KEGG3), Pentose and glucuronate interconversions (KEGG3), Translation proteins (KEGG3), Translation factors (KEGG3), Phenylalanine metabolism (KEGG3), DNA repair and recombination proteins (KEGG3), Terpenoid backbone biosynthesis (KEGG3), Pyrimidine metabolism (KEGG3), Protein export (KEGG3), Ribosome biogenesis in eukaryotes (KEGG3), Nicotinate and nicotinamide metabolism (KEGG3), Nucleotide metabolism (KEGG3), Penicillin and cephalosporin biosynthesis (KEGG3), Other ion-coupled transporters (KEGG3), Biosynthesis and biodegradation of secondary metabolites (KEGG3), Inorganic ion transport and metabolism (KEGG3), MAPK signaling pathway—yeast (KEGG3), Carbohydrate metabolism (KEGG3), Plant-pathogen interaction (KEGG3), Phosphonate and phosphinate metabolism (KEGG3), Pores ion channels (KEGG3), Homologous recombination (KEGG3), Lipoic acid metabolism (KEGG3), DNA replication proteins (KEGG3), Cell cycle—*Caulobacter* (KEGG3), Lipopolysaccharide biosynthesis proteins (KEGG3), Nucleotide excision repair (KEGG3), Function unknown (KEGG3), Cell motility and secretion (KEGG3), Glycosaminoglycan degradation (KEGG3), Photosynthesis (KEGG3), Photosynthesis proteins (KEGG3), Huntington's disease (KEGG3), Taurine and hypotaurine metabolism (KEGG3), Ion channels (KEGG3), Geraniol degradation (KEGG3), Caprolactam degradation (KEGG3), Sphingolipid metabolism (KEGG3), Lysosome (KEGG3), Biotin metabolism (KEGG3), Fructose and mannose metabolism (KEGG3), Inositol phosphate metabolism (KEGG3), Glycosphingolipid biosynthesis—globo series (KEGG3), Bacterial toxins (KEGG3), Mismatch repair (KEGG3), Vitamin metabolism (KEGG3), Membrane and intracellular structural molecules (KEGG3), Purine metabolism (KEGG3), Other glycan degradation (KEGG3), Alzheimer's disease (KEGG3), Peptidases (KEGG3), Pantothenate and CoA biosynthesis (KEGG3), Galactose metabolism (KEGG3), Glycosphingolipid biosynthesis—ganglio series (KEGG3), Thiamine metabolism (KEGG3), Glycerophospholipid metabolism (KEGG3), Lysine biosynthesis (KEGG3), Pentose phosphate pathway (KEGG3), Tuberculosis (KEGG3), Polycyclic aromatic hydrocarbon degradation (KEGG3), Sulfur metabolism (KEGG3), Aminobenzoate degradation (KEGG3), Phosphatidylinositol signaling system (KEGG3), DNA replication (KEGG3), One carbon pool by folate (KEGG3), Butanoate metabolism (KEGG3), Bisphenol degradation (KEGG3), Nitrogen metabolism (KEGG3), Amino sugar and nucleotide sugar metabolism (KEGG3), Glycan Biosynthesis and Metabolism (KEGG_Pathways_Level_2) (e.g., nose site); Excretory System (KEGG_Pathways_Level_2) (e.g., gut site); Enzyme Families (KEGG_Pathways_Level_2) (e.g., gut site); Metabolism (KEGG_Pathways_Level_2) (e.g., gut site); Signaling Molecules and Interaction (KEGG_Pathways_Level_2) (e.g., gut site); Glycan Biosynthesis and Metabolism (KEGG_Pathways_Level_2) (e.g., gut site); Translation (KEGG_Pathways_Level_2) (e.g., gut site); Xenobiotics Biodegradation and Metabolism (KEGG_Pathways_Level_2) (e.g., gut site); Transport and Catabolism (KEGG_Pathways_Level_2) (e.g., gut site); Cellular Processes and Signaling (KEGG_Pathways_Level_2) (e.g., gut site); Carbohydrate Metabolism (KEGG_Pathways_Level_2) (e.g., gut site); Genetic Information Processing (KEGG_Pathways_Level_2) (e.g., gut site); Environmental Adaptation (KEGG_Pathways_Level_2) (e.g., gut site); Pentose and glucuronate interconversions (KEGG_Pathways_Level_3) (e.g., gut site); Sulfur metabolism (KEGG_Pathways_Level_3) (e.g., gut site); Peptidoglycan biosynthesis (KEGG_Pathways_Level_3) (e.g., gut site); Aminoacyl-tRNA biosynthesis (KEGG_Pathways_Level_3) (e.g., gut site); Ascorbate and aldarate metabolism (KEGG_Pathways_Level_3) (e.g., gut site); Huntington_quote_s disease (KEGG_Pathways_Level_3) (e.g., gut site); MAPK signaling pathway—yeast (KEGG_Pathways_Level_3) (e.g., gut site); Inositol phosphate metabolism (KEGG_Pathways_Level_3) (e.g., gut site); Amino acid metabolism (KEGG_Pathways_Level_3) (e.g., gut site); Others (KEGG_Pathways_Level_3) (e.g., gut site); Pores ion channels (KEGG_Pathways_Level_3) (e.g., gut site); Biosynthesis and biodegradation of secondary metabolites (KEGG_Pathways_Level_3) (e.g., gut site); Phosphonate and phosphinate metabolism (KEGG_Pathways_Level_3) (e.g., gut site); Caprolactam degradation (KEGG_Pathways_Level_3) (e.g., gut site); Ribosome Biogenesis (KEGG_Pathways_Level_3) (e.g., gut site); Translation proteins (KEGG_Pathways_Level_3) (e.g., gut site); Other ion-coupled transporters (KEGG_Pathways_Level_3) (e.g., gut site); Bisphenol degradation (KEGG_Pathways_Level_3) (e.g., gut site); "Valine, leucine and isoleucine degradation" (KEGG_Pathways_Level_3) (e.g., gut site); Lysosome (KEGG_Pathways_Level_3) (e.g., gut site); Proximal tubule bicarbonate reclamation (KEGG_Pathways_Level_3) (e.g., gut site); Linoleic acid metabolism (KEGG_Pathways_Level_3) (e.g., gut site); Pentose phosphate pathway (KEGG_Pathways_Level_3) (e.g., gut site); Other glycan degradation (KEGG_Pathways_Level_3) (e.g., gut site); Phenylalanine metabolism (KEGG_Pathways_Level_3) (e.g., gut site); Glycosaminoglycan degradation (KEGG_Pathways_Level_3) (e.g., gut site); Terpenoid backbone biosynthesis (KEGG_Pathways_Level_3) (e.g., gut site); Polycyclic aromatic hydrocarbon degradation (KEGG_Pathways_Level_3) (e.g., gut site); Ribosome (KEGG_Pathways_Level_3) (e.g., gut site); Aminobenzoate degradation (KEGG_Pathways_Level_3) (e.g., gut site); Butanoate metabolism (KEGG_Pathways_Level_3) (e.g., gut site); Other transporters (KEGG_Pathways_Level_3) (e.g., gut site); Glyoxylate and dicarboxylate metabolism (KEGG_Pathways_Level_3) (e.g., gut site); Carbon fixation pathways in prokaryotes (KEGG_Pathways_Level_3) (e.g., gut site); Ion channels (KEGG_Pathways_Level_3) (e.g., gut site); Geraniol degradation (KEGG_Pathways_Level_3) (e.g., gut site); Cytoskeleton proteins (KEGG_Pathways_Level_3) (e.g., gut site); Epithelial cell signaling in *Helicobacter pylori* infection (KEGG_Pathways_Level_3) (e.g., gut site); Lipoic acid metabolism (KEGG_Pathways_Level_3) (e.g., gut site); Sphingolipid metabolism (KEGG_Pathways_Level_3) (e.g., gut site); Bacterial toxins (KEGG_Pathways_Level_3) (e.g., gut site); Limonene and pinene degradation (KEGG_Pathways_Level_3) (e.g., gut site); Steroid hormone biosynthesis (KEGG_Pathways_Level_3) (e.g., gut site); Pertussis (KEGG_Pathways_Level_3) (e.g., gut site); Transcription related proteins (KEGG_Pathways_Level_3) (e.g., gut site); Lipid metabolism (KEGG_Pathways_Level_3) (e.g., gut site); Meiosis—yeast (KEGG_Pathways_Level_3) (e.g., gut site); "1,1,1-Trichloro-2,2-bis(4-chlorophenyl)ethane (DDT) degradation" (KEGG_Pathways_Level_3) (e.g., gut site); Electron transfer carriers (KEGG_Pathways_Level_3) (e.g., gut site); Amyotrophic lateral sclerosis (ALS) (KEGG_Pathways_Level_3) (e.g., gut site); Tuberculosis (KEGG_Pathways_Level_3) (e.g., gut site); Homologous recombination (KEGG_Pathways_Level_3) (e.g., gut site); Prion diseases (KEGG_Pathways_Level_3) (e.g., gut site); Glycosphingolipid biosynthesis—ganglio series (KEGG_Pathways_Level_3) (e.g., gut site); Nicotinate and nicotinamide metabolism (KEGG_Pathways_Level_3) (e.g., gut site); alpha-Linolenic acid metabolism (KEGG_Pathways_Level_3) (e.g., gut site); Plant-pathogen interaction (KEGG_Pathways_Level_3) (e.g., gut site); Ubiquitin system (KEGG_Pathways_Level_3) (e.g., gut site); Chromosome (KEGG_Pathways_Level_3) (e.g., gut site); Metabolism (KEGG_Pathways_Level_2) (e.g., mouth site); Digestive System (KEGG_Pathways_Level_2) (e.g., mouth site); Xenobiotics Biodegradation and Metabolism (KEGG_Pathways_Level_2) (e.g., mouth site); Genetic Information Processing (KEGG_Pathways_Level_2) (e.g., mouth site); Butirosin and neomycin biosynthesis (KEGG_Pathways_Level_3) (e.g., mouth site); Cellular antigens (KEGG_Pathways_Level_3) (e.g., mouth site); Carbohydrate digestion and absorption (KEGG_Pathways_Level_3) (e.g., mouth site); Naphthalene degradation (KEGG_Pathways_Level_3) (e.g., mouth site); Protein export (KEGG_Pathways_Level_3) (e.g., mouth site); Cyanoamino acid metabolism (KEGG_Pathways_Level_3) (e.g., mouth site); Restriction enzyme (KEGG_Pathways_Level_3) (e.g., mouth site); Retinol metabolism (KEGG_Pathways_Level_3) (e.g., mouth site); Biosynthesis of vancomycin group antibiotics (KEGG_Pathways_Level_3) (e.g., mouth site); ABC transporters (KEGG_Pathways_Level_3) (e.g., mouth site); Biosynthesis of Other Secondary Metabolites (KEGG_Pathways_Level_2) (e.g., gut site); Cell Growth and Death (KEGG_Pathways_Level_2) (e.g., gut site); Membrane Transport (KEGG_Pathways_Level_2) (e.g., gut site); Neurodegenerative Diseases (KEGG_Pathways_Level_2) (e.g., gut site); Cell Motility (KEGG_Pathways_Level_2) (e.g., gut site); Transcription (KEGG_Pathways_Level_2) (e.g., gut site); Metabolism of Other Amino Acids (KEGG_Pathways_Level_2) (e.g., gut site); Poorly Characterized (KEGG_Pathways_Level_2) (e.g., gut site); Lipid Metabolism (KEGG_Pathways_Level_2) (e.g., gut site); Replication and Repair (KEGG_Pathways_Level_2) (e.g., gut site); Bacterial chemotaxis (KEGG_Pathways_Level_3) (e.g., gut site); Cell cycle—*Caulobacter* (KEGG_Pathways_Level_3) (e.g., gut site); Membrane and intracellular structural molecules (KEGG_Pathways_Level_3) (e.g., gut site); RNA polymerase (KEGG_Pathways_Level_3) (e.g., gut site); Nucleotide excision repair (KEGG_Pathways_Level_3) (e.g., gut site); Biotin metabolism (KEGG_Pathways_Level_3) (e.g., gut site); Primary bile acid biosynthesis (KEGG_Pathways_Level_3) (e.g., gut site); Glycosyltransferases (KEGG_Pathways_Level_3) (e.g., gut site); Lipopolysaccharide biosynthesis proteins (KEGG_Pathways_Level_3) (e.g., gut site); Phosphatidylinositol signaling system (KEGG_Pathways_Level_3) (e.g., gut site); Cell motility and secretion (KEGG_Pathways_Level_3) (e.g., gut site); Protein folding and associated processing (KEGG_Pathways_Level_3) (e.g., gut site); Photosynthesis (KEGG_Pathways_Level_3) (e.g., gut site); D-Alanine metabolism (KEGG_Pathways_Level_3) (e.g., gut site); Glycosphingolipid biosynthesis—globo series (KEGG_Pathways_Level_3) (e.g., gut site); Circadian rhythm—plant (KEGG_Pathways_Level_3) (e.g., gut site); Inorganic ion transport and metabolism (KEGG_Pathways_Level_3) (e.g., gut site); Caffeine metabolism (KEGG_Pathways_Level_3) (e.g., gut site); Alzheimer_quote_s disease (KEGG_Pathways_Level_3) (e.g., gut site); African trypanosomiasis (KEGG_Pathways_Level_3) (e.g., gut site); Fatty acid elongation in mitochondria (KEGG_Pathways_Level_3) (e.g., gut site); Germination (KEGG_Pathways_Level_3) (e.g., gut site); Type I diabetes mellitus (KEGG_Pathways_Level_3) (e.g., gut site); Secondary bile acid biosynthesis (KEGG_Pathways_Level_3) (e.g., gut site); Penicillin and cephalosporin biosynthesis (KEGG_Pathways_Level_3) (e.g., gut site); Carbohydrate metabolism (KEGG_Pathways_Level_3) (e.g., gut site); Lysine biosynthesis (KEGG_Pathways_Level_3) (e.g., gut site); Mismatch repair (KEGG_Pathways_Level_3) (e.g., gut site); Citrate cycle (TCA cycle) (KEGG_Pathways_Level_3) (e.g., gut site); Lipopolysaccharide biosynthesis (KEGG_Pathways_Level_3) (e.g., gut site); Cellular antigens (KEGG_Pathways_Level_3) (e.g., gut site); Ribosome biogenesis in eukaryotes (KEGG_Pathways_Level_3) (e.g., gut site); Protein digestion and absorption (KEGG_Pathways_Level_3) (e.g., gut site); Translation factors (KEGG_Pathways_Level_3) (e.g., gut site); Amino sugar and nucleotide sugar metabolism (KEGG_Pathways_Level_3) (e.g., gut site); Steroid biosynthesis (KEGG_Pathways_Level_3) (e.g., gut site); Thiamine metabolism (KEGG_Pathways_Level_3) (e.g., gut site); Signal transduction mechanisms (KEGG_Pathways_Level_3) (e.g., gut site); Glycerophospholipid metabolism (KEGG_Pathways_Level_3) (e.g., gut site); Transcription factors (KEGG_Pathways_Level_3) (e.g., gut site); Sporulation (KEGG_Pathways_Level_3) (e.g., gut site); Amino acid related enzymes (KEGG_Pathways_Level_3) (e.g., gut site); Streptomycin biosynthesis (KEGG_Pathways_Level_3) (e.g., gut site); Transporters (KEGG_Pathways_Level_3) (e.g., gut site); Protein export (KEGG_Pathways_Level_3) (e.g., gut site); Function unknown (KEGG_Pathways_Level_3) (e.g., gut site); Galactose metabolism (KEGG_Pathways_Level_3) (e.g., gut site); Systemic lupus erythematosus (KEGG_Pathways_Level_3) (e.g., gut site); Pyrimidine metabolism (KEGG_Pathways_Level_3) (e.g., gut site); Taurine and hypotaurine metabolism (KEGG_Pathways_Level_3) (e.g., gut site); Nitrogen metabolism (KEGG_Pathways_Level_3) (e.g., gut site); Pantothenate and CoA biosynthesis (KEGG_Pathways_Level_3) (e.g., gut site); Toluene degradation (KEGG_Pathways_Level_3) (e.g., gut site); DNA repair and recombination proteins (KEGG_Pathways_Level_3) (e.g., gut site); Glycosphingolipid biosynthesis—lacto and neolacto series (KEGG_Pathways_Level_3) (e.g., gut site); Photosynthesis proteins (KEGG_Pathways_Level_3) (e.g., gut site); Ubiquinone and other terpenoid-quinone biosynthesis (KEGG_Pathways_Level_3) (e.g., gut site); Fluorobenzoate degradation (KEGG_Pathways_Level_3) (e.g., gut site); and/or other suitable function-related aspects.

Additionally or alternatively, microbiome features (e.g., microbiome functional features) can be associated with one or more of the following in relation to a sample site (e.g., soy allergy condition correlations with microorganism-related function observed at a particular sample site): Benzoate degradation (e.g., KEGG_Pathways_Level_3) (e.g., genital site); Excretory System (e.g., KEGG_Pathways_Level_2) (e.g., gut site); Enzyme Families (e.g., KEGG_Pathways_Level_2) (e.g., gut site); Metabolism (e.g., KEGG_Pathways_Level_2) (e.g., gut site); Signaling Molecules and Interaction (e.g., KEGG_Pathways_Level_2) (e.g., gut site); Translation (e.g., KEGG_Pathways_Level_2) (e.g., gut site); Xenobiotics Biodegradation and Metabolism (e.g., KEGG_Pathways_Level_2) (e.g., gut site); Transport and Catabolism (e.g., KEGG_Pathways_Level_2) (e.g., gut site); Cellular Processes and Signaling (e.g., KEGG_Pathways_Level_2) (e.g., gut site); Carbohydrate Metabolism (e.g., KEGG_Pathways_Level_2) (e.g., gut site); Genetic Information Processing (e.g., KEGG_Pathways_Level_2) (e.g., gut site); Pentose and glucuronate interconversions (e.g., KEGG_Pathways_Level_3) (e.g., gut site); RNA polymerase (e.g., KEGG_Pathways_Level_3) (e.g., gut site); Sulfur metabolism (e.g., KEGG_Pathways_Level_3) (e.g., gut site); Peptidoglycan biosynthesis (e.g., KEGG_Pathways_Level_3) (e.g., gut site); Aminoacyl-tRNA biosynthesis (e.g., KEGG_Pathways_Level_3) (e.g., gut site); Ascorbate and aldarate metabolism (e.g., KEGG_Pathways_Level_3) (e.g., gut site); MAPK signaling pathway—yeast (e.g., KEGG_Pathways_Level_3) (e.g., gut site); Inositol phosphate metabolism (e.g., KEGG_Pathways_Level_3) (e.g., gut site); Others (e.g., KEGG_Pathways_Level_3) (e.g., gut site); Biosynthesis and biodegradation of secondary metabolites (e.g., KEGG_Pathways_Level_3) (e.g., gut site); Phosphonate and phosphinate metabolism (e.g., KEGG_Pathways_Level_3) (e.g., gut site); Caprolactam degradation (e.g., KEGG_Pathways_Level_3) (e.g., gut site); Ribosome Biogenesis (e.g., KEGG_Pathways_Level_3) (e.g., gut site); Translation proteins (e.g., KEGG_Pathways_Level_3) (e.g., gut site); Other ion-coupled transporters (e.g., KEGG_Pathways_Level_3) (e.g., gut site); Bisphenol degradation (e.g., KEGG_Pathways_Level_3) (e.g., gut site); Proximal tubule bicarbonate reclamation (e.g., KEGG_Pathways_Level_3) (e.g., gut site); Linoleic acid metabolism (e.g., KEGG_Pathways_Level_3) (e.g., gut site); Other glycan degradation (e.g., KEGG_Pathways_Level_3) (e.g., gut site); Phenylalanine metabolism (e.g., KEGG_Pathways_Level_3) (e.g., gut site); Terpenoid backbone biosynthesis (e.g., KEGG_Pathways_Level_3) (e.g., gut site); Polycyclic aromatic hydrocarbon degradation (e.g., KEGG_Pathways_Level_3) (e.g., gut site); Aminobenzoate degradation (e.g., KEGG_Pathways_Level_3) (e.g., gut site); Other transporters (e.g., KEGG_Pathways_Level_3) (e.g., gut site); Glyoxylate and dicarboxylate metabolism (e.g., KEGG_Pathways_Level_3) (e.g., gut site); Ion channels (e.g., KEGG_Pathways_Level_3) (e.g., gut site); Epithelial cell signaling in *Helicobacter pylori* infection (e.g., KEGG_Pathways_Level_3) (e.g., gut site); Lipoic acid metabolism (e.g., KEGG_Pathways_Level_3) (e.g., gut site); Sphingolipid metabolism (e.g., KEGG_Pathways_Level_3) (e.g., gut site); Pertussis (e.g., KEGG_Pathways_Level_3) (e.g., gut site); Transcription related proteins (e.g., KEGG_Pathways_Level_3) (e.g., gut site); Lipid metabolism (e.g., KEGG_Pathways_Level_3) (e.g., gut site); Tuberculosis (e.g., KEGG_Pathways_Level_3) (e.g., gut site); Prion diseases (e.g., KEGG_Pathways_Level_3) (e.g., gut site); Nicotinate and nicotinamide metabolism (e.g., KEGG_Pathways_Level_3) (e.g., gut site); alpha-Linolenic acid metabolism (e.g., KEGG_Pathways_Level_3) (e.g., gut site); Chromosome (e.g., KEGG_Pathways_Level_3) (e.g., gut site); Metabolism (e.g., KEGG_Pathways_Level_2) (e.g., mouth site); Signal Transduction (e.g., KEGG_Pathways_Level_2) (e.g., mouth site); Digestive System (e.g., KEGG_Pathways_Level_2) (e.g., mouth site); Xenobiotics Biodegradation and Metabolism (e.g., KEGG_Pathways_Level_2) (e.g., mouth site); Carbohydrate Metabolism (e.g., KEGG_Pathways_Level_2) (e.g., mouth site); Genetic Information Processing (e.g., KEGG_Pathways_Level_2) (e.g., mouth site); Environmental Adaptation (e.g., KEGG_Pathways_Level_2) (e.g., mouth site); Butirosin and neomycin biosynthesis (e.g., KEGG_Pathways_Level_3) (e.g., mouth site); Phenylpropanoid biosynthesis (e.g., KEGG_Pathways_Level_3) (e.g., mouth site); Carbohydrate digestion and absorption (e.g., KEGG_Pathways_Level_3) (e.g., mouth site); Naphthalene degradation (e.g., KEGG_Pathways_Level_3) (e.g., mouth site); Protein export (e.g., KEGG_Pathways_Level_3) (e.g., mouth site); Cyanoamino acid metabolism (e.g., KEGG_Pathways_Level_3) (e.g., mouth site); Restriction enzyme (e.g., KEGG_Pathways_Level_3) (e.g., mouth site); Biosynthesis of vancomycin group antibiotics (e.g., KEGG_Pathways_Level_3) (e.g., mouth site); ABC transporters (e.g., KEGG_Pathways_Level_3) (e.g., mouth site).

Additionally or alternatively microbiome features (e.g., microbiome functional features) can be associated with one or more of the following in relation to a healthy gut sample site (and/or other suitable sites and/or healthiness levels): Biosynthesis of Other Secondary Metabolites (e.g., KEGG_Pathways_Level_2) (e.g., gut site); Excretory System (e.g., KEGG_Pathways_Level_2) (e.g., gut site); Neurodegenerative Diseases (e.g., KEGG_Pathways_Level_2) (e.g., gut site); Metabolism (e.g., KEGG_Pathways_Level_2) (e.g., gut site); Signaling Molecules and Interaction (e.g., KEGG_Pathways_Level_2) (e.g., gut site); Glycan Biosynthesis and Metabolism (e.g., KEGG_Pathways_Level_2) (e.g., gut site); Transcription (e.g., KEGG_Pathways_Level_2) (e.g., gut site); Translation (e.g., KEGG_Pathways_Level_2) (e.g., gut site); Lipid Metabolism (e.g., KEGG_Pathways_Level_2) (e.g., gut site); Transport and Catabolism (e.g., KEGG_Pathways_Level_2) (e.g., gut site); Replication and Repair (e.g., KEGG_Pathways_Level_2) (e.g., gut site); Cellular Processes and Signaling (e.g., KEGG_Pathways_Level_2) (e.g., gut site); Carbohydrate Metabolism (e.g., KEGG_Pathways_Level_2) (e.g., gut site); Genetic Information Processing (e.g., KEGG_Pathways_Level_2) (e.g., gut site); Environmental Adaptation (e.g., KEGG_Pathways_Level_2) (e.g., gut site); Membrane and intracellular structural molecules (e.g., KEGG_Pathways_Level_3) (e.g., gut site); Pentose and glucuronate interconversions (e.g., KEGG_Pathways_Level_3) (e.g., gut site); RNA polymerase (e.g., KEGG_Pathways_Level_3) (e.g., gut site); Biosynthesis of unsaturated fatty acids (e.g., KEGG_Pathways_Level_3) (e.g., gut site); Sulfur metabolism (e.g., KEGG_Pathways_Level_3) (e.g., gut site); Biotin metabolism (e.g., KEGG_Pathways_Level_3) (e.g., gut site); Peptidoglycan biosynthesis (e.g., KEGG_Pathways_Level_3) (e.g., gut site); Aminoacyl-tRNA biosynthesis (e.g., KEGG_Pathways_Level_3) (e.g., gut site); Ascorbate and aldarate metabolism (e.g., KEGG_Pathways_Level_3) (e.g., gut site); Huntingtons disease (e.g., KEGG_Pathways_Level_3) (e.g., gut site); MAPK signaling pathway—yeast (e.g., KEGG_Pathways_Level_3) (e.g., gut site); Inositol phosphate metabolism (e.g., KEGG_Pathways_Level_3) (e.g., gut site); Amino acid metabolism (e.g., KEGG_Pathways_Level_3) (e.g., gut site); Others (e.g., KEGG_Pathways_Level_3) (e.g., gut site); Lipopolysaccharide biosynthesis proteins (e.g., KEGG_Pathways_Level_3) (e.g., gut site); Phosphatidylinositol signaling system (e.g., KEGG_Pathways_Level_3) (e.g., gut site); Pores ion channels (e.g., KEGG_Pathways_Level_3) (e.g., gut site); Biosynthesis and biodegradation of secondary metabolites (e.g., KEGG_Pathways_Level_3) (e.g., gut site); Phosphonate and phosphinate metabolism (e.g., KEGG_Pathways_Level_3) (e.g., gut site); Caprolactam degradation (e.g., KEGG_Pathways_Level_3) (e.g., gut site); Ribosome Biogenesis (e.g., KEGG_Pathways_Level_3) (e.g., gut site); Translation proteins (e.g., KEGG_Pathways_Level_3) (e.g., gut site); Cell motility and secretion (e.g., KEGG_Pathways_Level_3) (e.g., gut site); Other ion-coupled transporters (e.g., KEGG_Pathways_Level_3) (e.g., gut site); D-Alanine metabolism (e.g., KEGG_Pathways_Level_3) (e.g., gut site); Bisphenol degradation (e.g., KEGG_Pathways_Level_3) (e.g., gut site); Glycosphingolipid biosynthesis—globo series (e.g., KEGG_Pathways_Level_3) (e.g., gut site); Circadian rhythm—plant (e.g., KEGG_Pathways_Level_3) (e.g., gut site); Lysosome (e.g., KEGG_Pathways_Level_3) (e.g., gut site); Proximal tubule bicarbonate reclamation (e.g., KEGG_Pathways_Level_3) (e.g., gut site); Inorganic ion transport and metabolism (e.g., KEGG_Pathways_Level_3) (e.g., gut site); Caffeine metabolism (e.g., KEGG_Pathways_Level_3) (e.g., gut site); Linoleic acid metabolism (e.g., KEGG_Pathways_Level_3) (e.g., gut site); Other glycan degradation (e.g., KEGG_Pathways_Level_3) (e.g., gut site); Germination (e.g., KEGG_Pathways_Level_3) (e.g., gut site); Type I diabetes mellitus (e.g., KEGG_Pathways_Level_3) (e.g., gut site); Phenylalanine metabolism (e.g., KEGG_Pathways_Level_3) (e.g., gut site); Glycosaminoglycan degradation (e.g., KEGG_Pathways_Level_3) (e.g., gut site); Fructose and mannose metabolism (e.g., KEGG_Pathways_Level_3) (e.g., gut site); Terpenoid backbone biosynthesis (e.g., KEGG_Pathways_Level_3) (e.g., gut site); Penicillin and cephalosporin biosynthesis (e.g., KEGG_Pathways_Level_3) (e.g., gut site); Carbohydrate metabolism (e.g., KEGG_Pathways_Level_3) (e.g., gut site); Polycyclic aromatic hydrocarbon degradation (e.g., KEGG_Pathways_Level_3) (e.g., gut site); Ribosome (e.g., KEGG_Pathways_Level_3) (e.g., gut site); Aminobenzoate degradation (e.g., KEGG_Pathways_Level_3) (e.g., gut site); Other transporters (e.g., KEGG_Pathways_Level_3) (e.g., gut site); Glyoxylate and dicarboxylate metabolism (e.g., KEGG_Pathways_Level_3) (e.g., gut site); Carbon fixation pathways in prokaryotes (e.g., KEGG_Pathways_Level_3) (e.g., gut site); Mismatch repair (e.g., KEGG_Pathways_Level_3) (e.g., gut site); Ion channels (e.g., KEGG_Pathways_Level_3) (e.g., gut site); Geraniol degradation (e.g., KEGG_Pathways_Level_3) (e.g., gut site); Cytoskeleton proteins (e.g., KEGG_Pathways_Level_3) (e.g., gut site); Ribosome biogenesis in eukaryotes (e.g., KEGG_Pathways_Level_3) (e.g., gut site); Epithelial cell signaling in *Helicobacter pylori* infection (e.g., KEGG_Pathways_Level_3) (e.g., gut site); Protein digestion and absorption (e.g., KEGG_Pathways_Level_3) (e.g., gut site); Lipoic acid metabolism (e.g., KEGG_Pathways_Level_3) (e.g., gut site); Translation factors (e.g., KEGG_Pathways_Level_3) (e.g., gut site); Sphingolipid metabolism (e.g., KEGG_Pathways_Level_3) (e.g., gut site); Amino sugar and nucleotide sugar metabolism (e.g., KEGG_Pathways_Level_3) (e.g., gut site); Signal transduction mechanisms (e.g., KEGG_Pathways_Level_3) (e.g., gut site); Bacterial toxins (e.g., KEGG_Pathways_Level_3) (e.g., gut site); Steroid hormone biosynthesis (e.g., KEGG_Pathways_Level_3) (e.g., gut site); Glycerophospholipid metabolism (e.g., KEGG_Pathways_Level_3) (e.g., gut site); Pertussis (e.g., KEGG_Pathways_Level_3) (e.g., gut site); Transcription related proteins (e.g., KEGG_Pathways_Level_3) (e.g., gut site); Sporulation (e.g., KEGG_Pathways_Level_3) (e.g., gut site); Lipid metabolism (e.g., KEGG_Pathways_Level_3) (e.g., gut site); Meiosis—yeast (e.g., KEGG_Pathways_Level_3) (e.g., gut site); Amino acid related enzymes (e.g., KEGG_Pathways_Level_3) (e.g., gut site); Streptomycin biosynthesis (e.g., KEGG_Pathways_Level_3) (e.g., gut site); "s1 1 1-Trichloro-2 2-bis(4-chlorophenyl)ethane (DDT) degradation" (e.g., KEGG_Pathways_Level_3) (e.g., gut site); Function unknown (e.g., KEGG_Pathways_Level_3) (e.g., gut site); Galactose metabolism (e.g., KEGG_Pathways_Level_3) (e.g., gut site); Amyotrophic lateral sclerosis (ALS) (e.g., KEGG_Pathways_Level_3) (e.g., gut site); Pyrimidine metabolism (e.g., KEGG_Pathways_Level_3) (e.g., gut site); Taurine and hypotaurine metabolism (e.g., KEGG_Pathways_Level_3) (e.g., gut site); Glycosphingolipid biosynthesis—ganglio series (e.g., KEGG_Pathways_Level_3) (e.g., gut site); Toluene degradation (e.g., KEGG_Pathways_Level_3) (e.g., gut site); Nicotinate and nicotinamide metabolism (e.g., KEGG_Pathways_Level_3) (e.g., gut site); DNA repair and recombination proteins (e.g., KEGG_Pathways_Level_3) (e.g., gut site); Glycosphingolipid biosynthesis—lacto and neolacto series (e.g., KEGG_Pathways_Level_3) (e.g., gut site); Plant-pathogen interaction (e.g., KEGG_Pathways_Level_3) (e.g., gut site); Ubiquitin system (e.g., KEGG_Pathways_Level_3) (e.g., gut site); Chromosome (e.g., KEGG_Pathways_Level_3) (e.g., gut site).

Determining an allergy-related characterization of a user can include diagnosing a user with a soy allergy condition based upon one or more of the above microbiome features and/or other suitable features described herein, such as in an additional or alterative manner to typical methods of diagnosis. However, features used in the soy allergy characterization process can include any other suitable features (e.g., features useful for diagnostics), and performing the soy allergy characterization process can be performed in any suitable manner.

3.3.E Peanut Allergy Condition Characterization Process.

In another variation, Block S130 can include performing a peanut allergy condition characterization process (e.g., determining and/or applying a peanut allergy characterization model; etc.) for one or more users. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with a peanut allergy condition. In another example, performing a peanut allergy condition characterization process can facilitate identifications of one or more therapies operable to have a positive effect on the peanut allergy condition (e.g., based upon a random forest predictor algorithm trained with a training dataset derived from a subset of the population of subjects, and validated with a validation dataset derived from a subset of the population of subjects). In particular, a peanut allergy condition can include an immune disorder of the subject characterized by hypersensitivity to dietary substances from peanut, causing an overreaction of the immune system which may lead to severe physical symptoms and where diagnosis can be associated to laboratory analysis (e.g., skin-prick test, blood-samples analysis, IgE tests, etc.) and/or other suitable diagnostic procedures.

Performing a peanut allergy condition characterization process (e.g., a diagnostic process) can be based on microbiome features (e.g., microbiome composition features) associated with (e.g., derived from, informative of, correlated with, etc.) one or more (e.g. in any suitable combination) of the following taxons: *Flavonifractor plautii* (Species), *Blautia luti* (Species), *Collinsella aerofaciens* (Species), *Dorea formicigenerans* (Species), *Barnesiella intestinihominis* (Species), *Bacteroides* (Genus), *Eggerthella* (Genus), *Sarcina* (Genus), *Marvinbryantia* (Genus), *Barnesiella* (Genus), *Thalassospira* (Genus), *Dorea* (Genus), Oscillospiraceae (Family), Clostridiaceae (Family), Bacteroidaceae (Family), Flavobacteriaceae (Family), Rhodospirillaceae (Family), Flavobacteriales (Order), Bacteroidales (Order), Clostridiales (Order), Rhodospirillales (Order), Flavobacteriia (Class), Clostridia (Class), Bacteroidia (Class), Bacteroidetes (Phylum).

Additionally or alternatively, microbiome features can be associated with one or more of the following taxons in relation to a sample site (e.g., peanut allergy condition correlations with microorganisms observed at a particular sample site): *Acetitomaculum* (genus) (e.g., gut site); Acidaminococcaceae (family) (e.g., gut site); *Actinomyces* (genus) (e.g., gut site); *Actinomyces* sp. ICM54 (species) (e.g., gut site); *Actinomyces* sp. oral strain Hal-1065 (species) (e.g., mouth site); Actinomycetaceae (family) (e.g., gut site); *Adlercreutzia* (genus) (e.g., gut site); *Adlercreutzia equolifaciens* (species) (e.g., gut site); *Akkermansia* (genus) (e.g., gut site); *Alistipes* (genus) (e.g., gut site); *Alistipes* sp. EBA6-25cl2 (species) (e.g., gut site); *Alistipes* sp. NML05A004 (species) (e.g., gut site); *Alistipes* sp. RMA 9912 (species) (e.g., gut site); Alphaproteobacteria (class) (e.g., gut site); *Anaerobacter* (genus) (e.g., gut site); *Anaerofilum* (genus) (e.g., gut site); Anaeroplasmataceae (family) (e.g., gut site); Anaeroplasmatales (order) (e.g., gut site); *Anaerosporobacter* (genus) (e.g., gut site); *Anaerostipes* sp. 3_2_56FAA (species) (e.g., gut site); *Anaerostipes* sp. 5_1_63FAA (species) (e.g., gut site); *Anaerotruncus colihominis* (species) (e.g., gut site); Bacteroidaceae (family) (e.g., gut site); Bacteroidales (order) (e.g., gut site); *Bacteroides* (genus) (e.g., gut site); *Bacteroides clarus* (species) (e.g., gut site); *Bacteroides fragilis* (species) (e.g., gut site); *Bacteroides massiliensis* (species) (e.g., gut site); *Bacteroides ovatus* (species) (e.g., gut site); *Bacteroides* sp. D22 (species) (e.g., gut site); *Bacteroides thetaiotaomicron* (species) (e.g., gut site); *Bacteroides vulgatus* (species) (e.g., gut site); Bacteroidetes (phylum) (e.g., gut site); Bacteroidia (class) (e.g., gut site); *Barnesiella* (genus) (e.g., gut site); *Barnesiella intestinihominis* (species) (e.g., gut site); *Bilophila* (genus) (e.g., gut site); *Bilophila* sp. 4_1_30 (species) (e.g., gut site); *Blautia glucerasea* (species) (e.g., gut site); *Blautia luti* (species) (e.g., gut site); *Blautia* sp. Ser8 (species) (e.g., gut site); *Blautia* sp. YHC-4 (species) (e.g., gut site); *Blautia wexlerae* (species) (e.g., gut site); *Butyricimonas* (genus) (e.g., gut site); Campylobacterales (order) (e.g., gut site); *Candidatus Soleaferrea* (genus) (e.g., gut site); Carnobacteriaceae (family) (e.g., gut site); Clostridia (class) (e.g., gut site); Clostridiaceae (family) (e.g., gut site); Clostridiales (order) (e.g., gut site); Clostridiales (family) XI. Incertae Sedis (family) (e.g., nose site); *Clostridium* (genus) (e.g., gut site); *Collinsella* (genus) (e.g., gut site); *Collinsella aerofaciens* (species) (e.g., gut site); Deltaproteobacteria (class) (e.g., gut site); Desulfovibrionaceae (family) (e.g., gut site); Desulfovibrionales (order) (e.g., gut site); *Dielma* (genus) (e.g., gut site); *Dielma fastidiosa* (species) (e.g., gut site); *Dorea* (genus) (e.g., gut site); *Dorea formicigenerans* (species) (e.g., gut site); *Dorea longicatena* (species) (e.g., gut site); *Eggerthella* (genus) (e.g., gut site); *Eggerthella* sp. HGA1 (species) (e.g., gut site); *Eisenbergiella* (genus) (e.g., gut site); *Eisenbergiella tayi* (species) (e.g., gut site); Enterobacteriaceae (family) (e.g., gut site); Enterobacteriales (order) (e.g., gut site); Epsilonproteobacteria (class) (e.g., gut site); *Erysipelatoclostridium ramosum* (species) (e.g., gut site); Erysipelotrichaceae (family) (e.g., gut site); Erysipelotrichales (order) (e.g., gut site); Erysipelotrichia (class) (e.g., gut site); *Eubacterium* (genus) (e.g., gut site); *Eubacterium callanderi* (species) (e.g., gut site); *Faecalibacterium* (genus) (e.g., gut site); *Faecalibacterium prausnitzii* (species) (e.g., gut site); Firmicutes (phylum) (e.g., gut site); Flavobacteriaceae (family) (e.g., gut site); Flavobacteriales (order) (e.g., gut site); Flavobacteriia (class) (e.g., gut site); *Flavonifractor* (genus) (e.g., gut site); *Flavonifractor plautii* (species) (e.g., gut site); *Fusicatenibacter* (genus) (e.g., gut site); *Fusicatenibacter saccharivorans* (species) (e.g., gut site); Gammaproteobacteria (class) (e.g., gut site); *Gordonibacter* (genus) (e.g., gut site); *Gordonibacter pamelaeae* (species) (e.g., gut site); *Granulicatella* (genus) (e.g., gut site); *Haemophilus* (genus) (e.g., gut site); *Haemophilus parainfluenzae* (species) (e.g., gut site); *Hespellia* (genus) (e.g., gut site); *Holdemania* (genus) (e.g., gut site); *Holdemania filiformis* (species) (e.g., gut site); *Intestinimonas* (genus) (e.g., gut site); *Kluyvera* (genus) (e.g., gut site); *Kluyvera georgiana* (species) (e.g., gut site); *Lachnospira* (genus) (e.g., gut site); *Lachnospira pectinoschiza* (species) (e.g., gut site); Lactobacillaceae (family) (e.g., skin site); *Lactobacillus* (genus) (e.g., skin site); *Lactobacillus* (genus) (e.g., gut site); *Lactobacillus crispatus* (species) (e.g., gut site); *Lactobacillus* sp. BL302 (species) (e.g., gut site); *Lactonifactor* (genus) (e.g., gut site); *Lactonifactor longoviformis* (species) (e.g., gut site); *Marvinbryantia* (genus) (e.g., gut site); *Megasphaera* (genus) (e.g., gut site); Micrococcaceae (family) (e.g., gut site); Mollicutes (class) (e.g., gut site); *Moraxella* (genus) (e.g., nose site); *Moryella* (genus) (e.g., gut site); Negativicutes (class) (e.g., gut site); *Odoribacter* (genus) (e.g., gut site); *Odoribacter splanchnicus* (species) (e.g., gut site); *Oscillibacter* (genus) (e.g., gut site); Oscillospiraceae (family) (e.g., gut site); *Parabacteroides merdae* (species) (e.g., gut site); Pasteurellaceae (family) (e.g., gut site); Pasteurellales (order) (e.g., gut site); Peptococcaceae (family) (e.g., gut site); *Peptococcus* (genus) (e.g., gut site); *Phascolarctobacterium* (genus) (e.g., gut site); *Phascolarctobacterium faecium* (species) (e.g., gut site); Rhodospirillaceae (family) (e.g., gut site); Rhodospirillales (order) (e.g., gut site); Rikenellaceae (family) (e.g., gut site); *Roseburia* (genus) (e.g., gut site); *Roseburia inulinivorans* (species) (e.g., gut site); *Roseburia* sp. 11SE39 (species) (e.g., gut site); Ruminococcaceae (family) (e.g., gut site); *Sarcina* (genus) (e.g., gut site); Selenomonadales (order) (e.g., gut site); *Subdoligranulum variabile* (species) (e.g., gut site); Tenericutes (phylum) (e.g., gut site); *Terrisporobacter* (genus) (e.g., gut site); *Thalassospira* (genus) (e.g., gut site); *Veillonella* (genus) (e.g., gut site); Verrucomicrobia (phylum) (e.g., gut site); Verrucomicrobiaceae (family) (e.g., gut site); Verrucomicrobiae (class) (e.g., gut site); Verrucomicrobiales (order) (e.g., gut site).

Additionally or alternatively microbiome features can be associated with one or more of the following taxons in relation to a healthy gut sample site (and/or other suitable sites and/or healthiness levels): Clostridia (class) (e.g., gut site); Bacteroidia (class) (e.g., gut site); Negativicutes (class) (e.g., gut site); Gammaproteobacteria (class) (e.g., gut site); Alphaproteobacteria (class) (e.g., gut site); Mollicutes (class) (e.g., gut site); Flavobacteriia (class) (e.g., gut site); Clostridia (class) (e.g., gut site); Bacteroidia (class) (e.g., gut site); Erysipelotrichia (class) (e.g., gut site); Negativicutes (class) (e.g., gut site); Alphaproteobacteria (class) (e.g., gut site); Alphaproteobacteria (class) (e.g., gut site); Deltaproteobacteria (class) (e.g., gut site); Deltaproteobacteria (class) (e.g., gut site); Epsilonproteobacteria (class) (e.g., gut site); Epsilonproteobacteria (class) (e.g., gut site); Mollicutes (class) (e.g., gut site); Mollicutes (class) (e.g., gut site); Flavobacteriia (class) (e.g., gut site); Flavobacteriia (class) (e.g., gut site); Clostridia (class) (e.g., gut site); Clostridia (class) (e.g., gut site); Bacteroidia (class) (e.g., gut site); Bacteroidia (class) (e.g., gut site); Verrucomicrobiae (class) (e.g., gut site); Verrucomicrobiae (class) (e.g., gut site); Erysipelotrichia (class) (e.g., gut site); Erysipelotrichia (class) (e.g., gut site); Negativicutes (class) (e.g., gut site);

Negativicutes (class) (e.g., gut site); Bacteroidaceae (family) (e.g., gut site); Clostridiaceae (family) (e.g., gut site); Rhodospirillaceae (family) (e.g., gut site); Oscillospiraceae (family) (e.g., gut site); Ruminococcaceae (family) (e.g., gut site); Bacteroidaceae (family) (e.g., gut site); Actinomycetaceae (family) (e.g., gut site); Clostridiaceae (family) (e.g., gut site); Rhodospirillaceae (family) (e.g., gut site); Flavobacteriaceae (family) (e.g., gut site); Anaeroplasmataceae (family) (e.g., gut site); Peptococcaceae (family) (e.g., gut site); Oscillospiraceae (family) (e.g., gut site); Enterobacteriaceae (family) (e.g., gut site); Enterobacteriaceae (family) (e.g., gut site); Bacteroidaceae (family) (e.g., gut site); Bacteroidaceae (family) (e.g., gut site); Actinomycetaceae (family) (e.g., gut site); Actinomycetaceae (family) (e.g., gut site); Clostridiaceae (family) (e.g., gut site); Clostridiaceae (family) (e.g., gut site); Rhodospirillaceae (family) (e.g., gut site); Rhodospirillaceae (family) (e.g., gut site); Flavobacteriaceae (family) (e.g., gut site); Flavobacteriaceae (family) (e.g., gut site); Campylobacteraceae (family) (e.g., gut site); Campylobacteraceae (family) (e.g., gut site); Erysipelotrichaceae (family) (e.g., gut site); Erysipelotrichaceae (family) (e.g., gut site); Anaeroplasmataceae (family) (e.g., gut site); Anaeroplasmataceae (family) (e.g., gut site); Peptococcaceae (family) (e.g., gut site); Peptococcaceae (family) (e.g., gut site); Desulfovibrionaceae (family) (e.g., gut site); Desulfovibrionaceae (family) (e.g., gut site); Verrucomicrobiaceae (family) (e.g., gut site); Verrucomicrobiaceae (family) (e.g., gut site); Oscillospiraceae (family) (e.g., gut site); Oscillospiraceae (family) (e.g., gut site); Ruminococcaceae (family) (e.g., gut site); Ruminococcaceae (family) (e.g., gut site); Acidaminococcaceae (family) (e.g., gut site); Acidaminococcaceae (family) (e.g., gut site); *Bacteroides* (genus) (e.g., gut site); *Roseburia* (genus) (e.g., gut site); *Megasphaera* (genus) (e.g., gut site); *Sarcina* (genus) (e.g., gut site); *Clostridium* (genus) (e.g., gut site); *Bilophila* (genus) (e.g., gut site); *Eggerthella* (genus) (e.g., gut site); *Thalassospira* (genus) (e.g., gut site); *Hespellia* (genus) (e.g., gut site); *Eisenbergiella* (genus) (e.g., gut site); *Bacteroides* (genus) (e.g., gut site); *Megasphaera* (genus) (e.g., gut site); *Sarcina* (genus) (e.g., gut site); *Clostridium* (genus) (e.g., gut site); *Peptococcus* (genus) (e.g., gut site); *Lachnospira* (genus) (e.g., gut site); *Acetitomaculum* (genus) (e.g., gut site); *Holdemania* (genus) (e.g., gut site); *Eggerthella* (genus) (e.g., gut site); *Collinsella* (genus) (e.g., gut site); *Thalassospira* (genus) (e.g., gut site); *Dorea* (genus) (e.g., gut site); *Faecalibacterium* (genus) (e.g., gut site); *Hespellia* (genus) (e.g., gut site); *Marvinbryantia* (genus) (e.g., gut site); *Barnesiella* (genus) (e.g., gut site); *Lactonifactor* (genus) (e.g., gut site); *Moryella* (genus) (e.g., gut site); *Butyricimonas* (genus) (e.g., gut site); *Gordonibacter* (genus) (e.g., gut site); *Anaerosporobacter* (genus) (e.g., gut site); *Eisenbergiella* (genus) (e.g., gut site); *Dielma* (genus) (e.g., gut site); *Terrisporobacter* (genus) (e.g., gut site); *Kluyvera* (genus) (e.g., gut site); *Kluyvera* (genus) (e.g., gut site); *Bacteroides* (genus) (e.g., gut site); *Bacteroides* (genus) (e.g., gut site); *Roseburia* (genus) (e.g., gut site); *Roseburia* (genus) (e.g., gut site); *Megasphaera* (genus) (e.g., gut site); *Megasphaera* (genus) (e.g., gut site); *Sarcina* (genus) (e.g., gut site); *Sarcina* (genus) (e.g., gut site); *Clostridium* (genus) (e.g., gut site); *Clostridium* (genus) (e.g., gut site); *Lactobacillus* (genus) (e.g., gut site); *Lactobacillus* (genus) (e.g., gut site); *Actinomyces* (genus) (e.g., gut site); *Actinomyces* (genus) (e.g., gut site); *Peptococcus* (genus) (e.g., gut site); *Peptococcus* (genus) (e.g., gut site); *Veillonella* (genus) (e.g., gut site); *Veillonella* (genus) (e.g., gut site); *Acetitomaculum* (genus) (e.g., gut site); *Acetitomaculum* (genus) (e.g., gut site); *Phascolarctobacterium* (genus) (e.g., gut site); *Phascolarctobacterium* (genus) (e.g., gut site); *Bilophila* (genus) (e.g., gut site); *Bilophila* (genus) (e.g., gut site); *Holdemania* (genus) (e.g., gut site); *Holdemania* (genus) (e.g., gut site); *Eggerthella* (genus) (e.g., gut site); *Eggerthella* (genus) (e.g., gut site); *Eggerthella* (genus) (e.g., gut site); *Eggerthella* (genus) (e.g., gut site); *Thalassospira* (genus) (e.g., gut site); *Thalassospira* (genus) (e.g., gut site); *Dorea* (genus) (e.g., gut site); *Dorea* (genus) (e.g., gut site); *Faecalibacterium* (genus) (e.g., gut site); *Faecalibacterium* (genus) (e.g., gut site); *Akkermansia* (genus) (e.g., gut site); *Akkermansia* (genus) (e.g., gut site); *Hespellia* (genus) (e.g., gut site); *Hespellia* (genus) (e.g., gut site); *Odoribacter* (genus) (e.g., gut site); *Odoribacter* (genus) (e.g., gut site); *Barnesiella* (genus) (e.g., gut site); *Barnesiella* (genus) (e.g., gut site); *Lactonifactor* (genus) (e.g., gut site); *Lactonifactor* (genus) (e.g., gut site); *Adlercreutzia* (genus) (e.g., gut site); *Adlercreutzia* (genus) (e.g., gut site); *Oscillibacter* (genus) (e.g., gut site); *Oscillibacter* (genus) (e.g., gut site); *Butyricimonas* (genus) (e.g., gut site); *Butyricimonas* (genus) (e.g., gut site); *Gordonibacter* (genus) (e.g., gut site); *Gordonibacter* (genus) (e.g., gut site); *Flavonifractor* (genus) (e.g., gut site); *Flavonifractor* (genus) (e.g., gut site); *Intestinimonas* (genus) (e.g., gut site); *Intestinimonas* (genus) (e.g., gut site); *Fusicatenibacter* (genus) (e.g., gut site); *Fusicatenibacter* (genus) (e.g., gut site); *Eisenbergiella* (genus) (e.g., gut site); *Eisenbergiella* (genus) (e.g., gut site); *Dielma* (genus) (e.g., gut site); *Dielma* (genus) (e.g., gut site); *Terrisporobacter* (genus) (e.g., gut site); *Terrisporobacter* (genus) (e.g., gut site); Bacteroidales (order) (e.g., gut site); Clostridiales (order) (e.g., gut site); Selenomonadales (order) (e.g., gut site); Bacteroidales (order) (e.g., gut site); Anaeroplasmatales (order) (e.g., gut site); Clostridiales (order) (e.g., gut site); Flavobacteriales (order) (e.g., gut site); Rhodospirillales (order) (e.g., gut site); Erysipelotrichales (order) (e.g., gut site); Selenomonadales (order) (e.g., gut site); Verrucomicrobiales (order) (e.g., gut site); Verrucomicrobiales (order) (e.g., gut site); Enterobacteriales (order) (e.g., gut site); Enterobacteriales (order) (e.g., gut site); Bacteroidales (order) (e.g., gut site); Bacteroidales (order) (e.g., gut site); Anaeroplasmatales (order) (e.g., gut site); Anaeroplasmatales (order) (e.g., gut site); Clostridiales (order) (e.g., gut site); Clostridiales (order) (e.g., gut site); Flavobacteriales (order) (e.g., gut site); Flavobacteriales (order) (e.g., gut site); Rhodospirillales (order) (e.g., gut site); Rhodospirillales (order) (e.g., gut site); Desulfovibrionales (order) (e.g., gut site); Desulfovibrionales (order) (e.g., gut site); Campylobacterales (order) (e.g., gut site); Campylobacterales (order) (e.g., gut site); Erysipelotrichales (order) (e.g., gut site); Erysipelotrichales (order) (e.g., gut site); Selenomonadales (order) (e.g., gut site); Selenomonadales (order) (e.g., gut site); Bacteroidetes (phylum) (e.g., gut site); Firmicutes (phylum) (e.g., gut site); Bacteroidetes (phylum) (e.g., gut site); Firmicutes (phylum) (e.g., gut site); Tenericutes (phylum) (e.g., gut site); Bacteroidetes (phylum) (e.g., gut site); Bacteroidetes (phylum) (e.g., gut site); Firmicutes (phylum) (e.g., gut site); Firmicutes (phylum) (e.g., gut site); Verrucomicrobia (phylum) (e.g., gut site); Verrucomicrobia (phylum) (e.g., gut site); Tenericutes (phylum) (e.g., gut site); Tenericutes (phylum) (e.g., gut site); *Erysipelatoclostridium ramosum* (species) (e.g., gut site); *Collinsella aerofaciens* (species) (e.g., gut site); *Flavonifractor plautii* (species) (e.g., gut site); *Blautia* sp. Ser8 (species) (e.g., gut site); *Bilophila* sp. 4_1_30 (species) (e.g., gut site); *Eggerthella* sp. HGA1 (species) (e.g., gut site); *Fusicatenibacter saccharivorans* (species) (e.g., gut site); *Eisenbergiella tayi* (species) (e.g., gut site); *Faecalibacterium prausnitzii* (species) (e.g., gut site); *Erysipelatoclostridium ramosum* (species) (e.g., gut site); *Lachnospira pectinoschiza* (species) (e.g., gut site); *Dorea formicigenerans* (species) (e.g., gut site); *Holdemania filiformis* (species) (e.g., gut site); *Collinsella aerofaciens* (species) (e.g., gut site); *Dorea longicatena* (species) (e.g., gut site); *Blautia luti* (species) (e.g., gut site); *Anaerotruncus colihominis* (species) (e.g., gut site); *Flavonifractor plautii* (species) (e.g., gut site); *Lactonifactor longoviformis* (species) (e.g., gut site); *Roseburia inulinivorans* (species) (e.g., gut site); *Gordonibacter pamelaeae* (species) (e.g., gut site); *Barnesiella intestinihominis* (species) (e.g., gut site); *Blautia glucerasea* (species) (e.g., gut site); *Roseburia* sp. 11SE39 (species) (e.g., gut site); *Anaerostipes* sp. 3_2_56FAA (species) (e.g., gut site); *Blautia* sp. Ser8 (species) (e.g., gut site); *Eggerthella* sp. HGA1 (species) (e.g., gut site); *Anaerostipes* sp. 5_1_63FAA (species) (e.g., gut site); *Dielma fastidiosa* (species) (e.g., gut site); *Fusicatenibacter saccharivorans* (species) (e.g., gut site); *Blautia* sp. YHC-4 (species) (e.g., gut site); *Eisenbergiella tayi* (species) (e.g., gut site); *Bacteroides fragilis* (species) (e.g., gut site); *Bacteroides fragilis* (species) (e.g., gut site); *Bacteroides vulgatus* (species) (e.g., gut site); *Bacteroides vulgatus* (species) (e.g., gut site); *Erysipelatoclostridium ramosum* (species) (e.g., gut site); *Erysipelatoclostridium ramosum* (species) (e.g., gut site); *Lachnospira pectinoschiza* (species) (e.g., gut site); *Lachnospira pectinoschiza* (species) (e.g., gut site); *Odoribacter splanchnicus* (species) (e.g., gut site); *Odoribacter splanchnicus* (species) (e.g., gut site); *Phascolarctobacterium faecium* (species) (e.g., gut site); *Phascolarctobacterium faecium* (species) (e.g., gut site); *Dorea formicigenerans* (species) (e.g., gut site); *Dorea formicigenerans* (species) (e.g., gut site); *Lactobacillus crispatus* (species) (e.g., gut site); *Lactobacillus crispatus* (species) (e.g., gut site); *Kluyvera georgiana* (species) (e.g., gut site); *Kluyvera georgiana* (species) (e.g., gut site); *Collinsella aerofaciens* (species) (e.g., gut site); *Collinsella aerofaciens* (species) (e.g., gut site); *Dorea longicatena* (species) (e.g., gut site); *Dorea longicatena* (species) (e.g., gut site); *Blautia luti* (species) (e.g., gut site); *Blautia luti* (species) (e.g., gut site); *Anaerotruncus colihominis* (species) (e.g., gut site); *Anaerotruncus colihominis* (species) (e.g., gut site); *Flavonifractor plautii* (species) (e.g., gut site); *Flavonifractor plautii* (species) (e.g., gut site); *Lactonifactor longoviformis* (species) (e.g., gut site); *Lactonifactor longoviformis* (species) (e.g., gut site); *Roseburia inulinivorans* (species) (e.g., gut site); *Roseburia inulinivorans* (species) (e.g., gut site); *Adlercreutzia equolifaciens* (species) (e.g., gut site); *Adlercreutzia equolifaciens* (species) (e.g., gut site); *Gordonibacter pamelaeae* (species) (e.g., gut site); *Gordonibacter pamelaeae* (species) (e.g., gut site); *Barnesiella intestinihominis* (species) (e.g., gut site); *Barnesiella intestinihominis* (species) (e.g., gut site); *Roseburia* sp. 11SE39 (species) (e.g., gut site); *Roseburia* sp. 11SE39 (species) (e.g., gut site); *Bacteroides* sp. D22 (species) (e.g., gut site); *Bacteroides* sp. D22 (species) (e.g., gut site); *Bacteroides clarus* (species) (e.g., gut site); *Bacteroides clarus* (species) (e.g., gut site); *Alistipes* sp. RMA 9912 (species) (e.g., gut site); *Alistipes* sp. RMA 9912 (species) (e.g., gut site); *Lactobacillus* sp. BL302 (species) (e.g., gut site); *Lactobacillus* sp. BL302 (species) (e.g., gut site); *Anaerostipes* sp. 3_2_56FAA (species) (e.g., gut site); *Anaerostipes* sp. 3_2_56FAA (species) (e.g., gut site); *Blautia* sp. Ser8 (species) (e.g., gut site); *Blautia* sp. Ser8 (species) (e.g., gut site); *Bilophila* sp. 4_1_30 (species) (e.g., gut site); *Bilophila* sp. 4_1_30 (species) (e.g., gut site); *Eggerthella* sp. HGA1 (species) (e.g., gut site); *Eggerthella* sp. HGA1 (species) (e.g., gut site); *Anaerostipes* sp. 5_1_63FAA (species) (e.g., gut site); *Anaerostipes* sp. 5_1_63FAA (species) (e.g., gut site); *Dielma fastidiosa* (species) (e.g., gut site); *Dielma fastidiosa* (species) (e.g., gut site); *Fusicatenibacter saccharivorans* (species) (e.g., gut site); *Fusicatenibacter saccharivorans* (species) (e.g., gut site); *Fusicatenibacter saccharivorans* (species) (e.g., gut site); *Fusicatenibacter saccharivorans* (species) (e.g., gut site); *Blautia* sp. YHC-4 (species) (e.g., gut site); *Blautia* sp. YHC-4 (species) (e.g., gut site); *Eisenbergiella tayi* (species) (e.g., gut site); *Eisenbergiella tayi* (species) (e.g., gut site).

Additionally or alternatively, performing a peanut allergy condition characterization process can be based on microbiome features (e.g., microbiome function features) associated with one or more of (e.g., such as in relation to a corresponding sample site): Translation (KEGG2), Cellular Processes and Signaling (KEGG2), Carbohydrate Metabolism (KEGG2), Metabolism (KEGG2), Replication and Repair (KEGG2), Transport and Catabolism (KEGG2), Nucleotide Metabolism (KEGG2), Lipid Metabolism (KEGG2), Cell Growth and Death (KEGG2), Biosynthesis of Other Secondary Metabolites (KEGG2), Glycan Biosynthesis and Metabolism (KEGG2), and/or other suitable function-related aspects.

Additionally or alternatively, microbiome features (e.g., microbiome functional features) can be associated with one or more of the following in relation to a sample site (e.g., peanut allergy condition correlations with microorganism-related function observed at a particular sample site): Cell Motility (KEGG_Pathways_Level_2) (e.g., gut site); Metabolism (KEGG_Pathways_Level_2) (e.g., gut site); Translation (KEGG_Pathways_Level_2) (e.g., gut site); Replication and Repair (KEGG_Pathways_Level_2) (e.g., gut site); Cellular Processes and Signaling (KEGG_Pathways_Level_2) (e.g., gut site); Carbohydrate Metabolism (KEGG_Pathways_Level_2) (e.g., gut site); Environmental Adaptation (KEGG_Pathways_Level_2) (e.g., gut site); Peptidoglycan biosynthesis (KEGG_Pathways_Level_3) (e.g., gut site); Aminoacyl-tRNA biosynthesis (KEGG_Pathways_Level_3) (e.g., gut site); Ascorbate and aldarate metabolism (KEGG_Pathways_Level_3) (e.g., gut site); Others (KEGG_Pathways_Level_3) (e.g., gut site); Ribosome Biogenesis (KEGG_Pathways_Level_3) (e.g., gut site); Translation proteins (KEGG_Pathways_Level_3) (e.g., gut site); Other ion-coupled transporters (KEGG_Pathways_Level_3) (e.g., gut site); Bisphenol degradation (KEGG_Pathways_Level_3) (e.g., gut site); Inorganic ion transport and metabolism (KEGG_Pathways_Level_3) (e.g., gut site); Linoleic acid metabolism (KEGG_Pathways_Level_3) (e.g., gut site); Phenylalanine metabolism (KEGG_Pathways_Level_3) (e.g., gut site); Ribosome (KEGG_Pathways_Level_3) (e.g., gut site); Aminobenzoate degradation (KEGG_Pathways_Level_3) (e.g., gut site); Other transporters (KEGG_Pathways_Level_3) (e.g., gut site); Glyoxylate and dicarboxylate metabolism (KEGG_Pathways_Level_3) (e.g., gut site); Epithelial cell signaling in *Helicobacter pylori* infection (KEGG_Pathways_Level_3) (e.g., gut site); Translation factors (KEGG_Pathways_Level_3) (e.g., gut site); Bacterial toxins (KEGG_Pathways_Level_3) (e.g., gut site); Protein export (KEGG_Pathways_Level_3) (e.g., gut site); Prion diseases (KEGG_Pathways_Level_3) (e.g., gut site); Plant-pathogen interaction (KEGG_Pathways_Level_3) (e.g., gut site); Ubiquitin system (KEGG_Pathways_Level_3) (e.g., gut site); Chromosome (KEGG_Pathways_Level_3) (e.g., gut site); Excretory System (KEGG_Pathways_Level_2) (e.g., gut site); Cell Growth and Death (KEGG_Pathways_Level_2) (e.g., gut site); Signaling Molecules and Interaction (KEGG_Pathways_Level_2) (e.g., gut site); Glycan Biosynthesis and Metabolism (KEGG_Pathways_Level_2) (e.g., gut site); Transcription (KEGG_Pathways_Level_2) (e.g., gut site); Poorly Characterized (KEGG_Pathways_Level_2) (e.g., gut site); Lipid Metabolism (KEGG_Pathways_Level_2) (e.g., gut site); Transport and Catabolism (KEGG_Pathways_Level_2) (e.g., gut site); Bacterial chemotaxis (KEGG_Pathways_Level_3) (e.g., gut site); Cell cycle—*Caulobacter* (KEGG_Pathways_Level_3) (e.g., gut site); Membrane and intracellular structural molecules (KEGG_Pathways_Level_3) (e.g., gut site); Pentose and glucuronate interconversions (KEGG_Pathways_Level_3) (e.g., gut site); RNA polymerase (KEGG_Pathways_Level_3) (e.g., gut site); Sulfur metabolism (KEGG_Pathways_Level_3) (e.g., gut site); Nucleotide excision repair (KEGG_Pathways_Level_3) (e.g., gut site); Huntington_quote_s disease (KEGG_Pathways_Level_3) (e.g., gut site); Inositol phosphate metabolism (KEGG_Pathways_Level_3) (e.g., gut site); Lipopolysaccharide biosynthesis proteins (KEGG_Pathways_Level_3) (e.g., gut site); Phosphatidylinositol signaling system (KEGG_Pathways_Level_3) (e.g., gut site); Pores ion channels (KEGG_Pathways_Level_3) (e.g., gut site); Biosynthesis and biodegradation of secondary metabolites (KEGG_Pathways_Level_3) (e.g., gut site); Phosphonate and phosphinate metabolism (KEGG_Pathways_Level_3) (e.g., gut site); Cell motility and secretion (KEGG_Pathways_Level_3) (e.g., gut site); Glycosphingolipid biosynthesis—globo series (KEGG_Pathways_Level_3) (e.g., gut site); Lysosome (KEGG_Pathways_Level_3) (e.g., gut site); Proximal tubule bicarbonate reclamation (KEGG_Pathways_Level_3) (e.g., gut site); Alzheimer_quote_s disease (KEGG_Pathways_Level_3) (e.g., gut site); African trypanosomiasis (KEGG_Pathways_Level_3) (e.g., gut site); Other glycan degradation (KEGG_Pathways_Level_3) (e.g., gut site); Germination (KEGG_Pathways_Level_3) (e.g., gut site); Glycosaminoglycan degradation (KEGG_Pathways_Level_3) (e.g., gut site); Fructose and man (e.g., nose site) metabolism (KEGG_Pathways_Level_3) (e.g., gut site); Terpenoid backbone biosynthesis (KEGG_Pathways_Level_3) (e.g., gut site); Penicillin and cephalosporin biosynthesis (KEGG_Pathways_Level_3) (e.g., gut site); Carbohydrate metabolism (KEGG_Pathways_Level_3) (e.g., gut site); Mismatch repair (KEGG_Pathways_Level_3) (e.g., gut site); Lipopolysaccharide biosynthesis (KEGG_Pathways_Level_3) (e.g., gut site); Geraniol degradation (KEGG_Pathways_Level_3) (e.g., gut site); Cytoskeleton proteins (KEGG_Pathways_Level_3) (e.g., gut site); Cellular antigens (KEGG_Pathways_Level_3) (e.g., gut site); Ribosome biogenesis in eukaryotes (KEGG_Pathways_Level_3) (e.g., gut site); Protein digestion and absorption (KEGG_Pathways_Level_3) (e.g., gut site); Biosynthesis of siderophore group nonribosomal peptides (KEGG_Pathways_Level_3) (e.g., gut site); Lipoic acid metabolism (KEGG_Pathways_Level_3) (e.g., gut site); Sphingolipid metabolism (KEGG_Pathways_Level_3) (e.g., gut site); Amino sugar and nucleotide sugar metabolism (KEGG_Pathways_Level_3) (e.g., gut site); Signal transduction mechanisms (KEGG_Pathways_Level_3) (e.g., gut site); Steroid hormone biosynthesis (KEGG_Pathways_Level_3) (e.g., gut site); Pertussis (KEGG_Pathways_Level_3) (e.g., gut site); Transcription related proteins (KEGG_Pathways_Level_3) (e.g., gut site); Sporulation (KEGG_Pathways_Level_3) (e.g., gut site); Amino acid related enzymes (KEGG_Pathways_Level_3) (e.g., gut site); Function unknown (KEGG_Pathways_Level_3) (e.g., gut site); Galactose metabolism (KEGG_Pathways_Level_3) (e.g., gut site); Bacterial motility proteins (KEGG_Pathways_Level_3) (e.g., gut site); Flagellar assembly (KEGG_Pathways_Level_3) (e.g., gut site); Nitrogen metabolism (KEGG_Pathways_Level_3) (e.g., gut site); Homologous recombination (KEGG_Pathways_Level_3) (e.g., gut site); Pantothenate and CoA biosynthesis (KEGG_Pathways_Level_3) (e.g., gut site); Glycosphingolipid biosynthesis—ganglio series (KEGG_Pathways_Level_3) (e.g., gut site); Toluene degradation (KEGG_Pathways_Level_3) (e.g., gut site); Nicotinate and nicotinamide metabolism (KEGG_Pathways_Level_3) (e.g., gut site); DNA repair and recombination proteins (KEGG_Pathways_Level_3) (e.g., gut site); Ubiquinone and other terpenoid-quinone biosynthesis (KEGG_Pathways_Level_3) (e.g., gut site).

Additionally or alternatively microbiome features (e.g., microbiome functional features) can be associated with one or more of the following in relation to a healthy gut sample site (and/or other suitable sites and/or healthiness levels): Biosynthesis of Other Secondary Metabolites (e.g., KEGG_Pathways_Level_2) (e.g., gut site); Excretory System (e.g., KEGG_Pathways_Level_2) (e.g., gut site); Cell Growth and Death (e.g., KEGG_Pathways_Level_2) (e.g., gut site); Cell Motility (e.g., KEGG_Pathways_Level_2) (e.g., gut site); Metabolism (e.g., KEGG_Pathways_Level_2) (e.g., gut site); Signaling Molecules and Interaction (e.g., KEGG_Pathways_Level_2) (e.g., gut site); Glycan Biosynthesis and Metabolism (e.g., KEGG_Pathways_Level_2) (e.g., gut site); Translation (e.g., KEGG_Pathways_Level_2) (e.g., gut site); Poorly Characterized (e.g., KEGG_Pathways_Level_2) (e.g., gut site); Lipid Metabolism (e.g., KEGG_Pathways_Level_2) (e.g., gut site); Transport and Catabolism (e.g., KEGG_Pathways_Level_2) (e.g., gut site); Replication and Repair (e.g., KEGG_Pathways_Level_2) (e.g., gut site); Cellular Processes and Signaling (e.g., KEGG_Pathways_Level_2) (e.g., gut site); Carbohydrate Metabolism (e.g., KEGG_Pathways_Level_2) (e.g., gut site); Environmental Adaptation (e.g., KEGG_Pathways_Level_2) (e.g., gut site); Bacterial chemotaxis (e.g., KEGG_Pathways_Level_3) (e.g., gut site); Membrane and intracellular structural molecules (e.g., KEGG_Pathways_Level_3) (e.g., gut site); Pentose and glucuronate interconversions (e.g., KEGG_Pathways_Level_3) (e.g., gut site); RNA polymerase (e.g., KEGG_Pathways_Level_3) (e.g., gut site); Peptidoglycan biosynthesis (e.g., KEGG_Pathways_Level_3) (e.g., gut site); Aminoacyl-tRNA biosynthesis (e.g., KEGG_Pathways_Level_3) (e.g., gut site); Ascorbate and aldarate metabolism (e.g., KEGG_Pathways_Level_3) (e.g., gut site); Others (e.g., KEGG_Pathways_Level_3) (e.g., gut site); Lipopolysaccharide biosynthesis proteins (e.g., KEGG_Pathways_Level_3) (e.g., gut site); Phosphatidylinositol signaling system (e.g., KEGG_Pathways_Level_3) (e.g., gut site); Phosphonate and phosphinate metabolism (e.g., KEGG_Pathways_Level_3) (e.g., gut site); Ribosome Biogenesis (e.g., KEGG_Pathways_Level_3) (e.g., gut site); Translation proteins (e.g., KEGG_Pathways_Level_3) (e.g., gut site); Cell motility and secretion (e.g., KEGG_Pathways_Level_3) (e.g., gut site); Other ion-coupled transporters (e.g., KEGG_Pathways_Level_3) (e.g., gut site); Photosynthesis (e.g., KEGG_Pathways_Level_3) (e.g., gut site); D-Alanine metabolism (e.g., KEGG_Pathways_Level_3) (e.g., gut site); Bisphenol degradation (e.g., KEGG_Pathways_Level_3) (e.g., gut site); Glycosphingolipid biosynthesis—globo series (e.g., KEGG_Pathways_Level_3) (e.g., gut site); Lysosome (e.g., KEGG_Pathways_Level_3) (e.g., gut site); Inorganic ion transport and metabolism (e.g., KEGG_Pathways_Level_3) (e.g., gut site); Linoleic acid metabolism (e.g., KEGG_Pathways_Level_3) (e.g., gut site); Alzheimers disease (e.g., KEGG_Pathways_Level_3) (e.g., gut site); Other glycan degradation (e.g., KEGG_Pathways_Level_3) (e.g., gut site); Germination (e.g., KEGG_Pathways_Level_3) (e.g., gut site); Phenylalanine metabolism (e.g., KEGG_Pathways_Level_3) (e.g., gut site); Glycosaminoglycan degradation (e.g., KEGG_Pathways_Level_3) (e.g., gut site); Terpenoid backbone biosynthesis (e.g., KEGG_Pathways_Level_3) (e.g., gut site); Carbohydrate metabolism (e.g., KEGG_Pathways_Level_3) (e.g., gut site); Ribosome (e.g., KEGG_Pathways_Level_3) (e.g., gut site); Aminobenzoate degradation (e.g., KEGG_Pathways_Level_3) (e.g., gut site); Other transporters (e.g., KEGG_Pathways_Level_3) (e.g., gut site); Glyoxylate and dicarboxylate metabolism (e.g., KEGG_Pathways_Level_3) (e.g., gut site); Mismatch repair (e.g., KEGG_Pathways_Level_3) (e.g., gut site); Lipopolysaccharide biosynthesis (e.g., KEGG_Pathways_Level_3) (e.g., gut site); Ribosome biogenesis in eukaryotes (e.g., KEGG_Pathways_Level_3) (e.g., gut site); Biosynthesis of siderophore group nonribosomal peptides (e.g., KEGG_Pathways_Level_3) (e.g., gut site); Lipoic acid metabolism (e.g., KEGG_Pathways_Level_3) (e.g., gut site); Translation factors (e.g., KEGG_Pathways_Level_3) (e.g., gut site); Sphingolipid metabolism (e.g., KEGG_Pathways_Level_3) (e.g., gut site); Amino sugar and nucleotide sugar metabolism (e.g., KEGG_Pathways_Level_3) (e.g., gut site); Signal transduction mechanisms (e.g., KEGG_Pathways_Level_3) (e.g., gut site); Bacterial toxins (e.g., KEGG_Pathways_Level_3) (e.g., gut site); Steroid hormone biosynthesis (e.g., KEGG_Pathways_Level_3) (e.g., gut site); Pertussis (e.g., KEGG_Pathways_Level_3) (e.g., gut site); Sporulation (e.g., KEGG_Pathways_Level_3) (e.g., gut site); Amino acid related enzymes (e.g., KEGG_Pathways_Level_3) (e.g., gut site); Function unknown (e.g., KEGG_Pathways_Level_3) (e.g., gut site); Galactose metabolism (e.g., KEGG_Pathways_Level_3) (e.g., gut site); Pantothenate and CoA biosynthesis (e.g., KEGG_Pathways_Level_3) (e.g., gut site); Glycosphingolipid biosynthesis—ganglio series (e.g., KEGG_Pathways_Level_3) (e.g., gut site); DNA repair and recombination proteins (e.g., KEGG_Pathways_Level_3) (e.g., gut site); Photosynthesis proteins (e.g., KEGG_Pathways_Level_3) (e.g., gut site); Plant-pathogen interaction (e.g., KEGG_Pathways_Level_3) (e.g., gut site); Ubiquitin system (e.g., KEGG_Pathways_Level_3) (e.g., gut site); Chromosome (e.g., KEGG_Pathways_Level_3) (e.g., gut site).

Determining an allergy-related characterization of a user can include diagnosing a user with a peanut allergy condition based upon one or more of the above microbiome features and/or other suitable features described herein, such as in an additional or alterative manner to typical methods of diagnosis. However, features used in the peanut allergy characterization process can include any other suitable features (e.g., features useful for diagnostics), and performing the peanut allergy characterization process can be performed in any suitable manner.

3.3.F Egg Allergy Condition Characterization Process.

In another variation, Block S130 can include performing a egg allergy condition characterization process (e.g., determining and/or applying a egg allergy characterization model; etc.) for one or more users. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with a egg allergy condition. In another example, performing a egg allergy condition characterization process can facilitate identifications of one or more therapies operable to have a positive effect on the egg allergy condition (e.g., based upon a random forest predictor algorithm trained with a training dataset derived from a subset of the population of subjects, and validated with a validation dataset derived from a subset of the population of subjects). In particular, a egg allergy condition can include an immune disorder characterized by an abnormal reaction of the immune system of the subject to any food containing eggs (e.g., chicken eggs) or some of its derivatives, and diagnosis can be associated with laboratory analysis (e.g., skin-prick test, blood-samples analysis, IgE tests, etc.) and/or other suitable diagnostic procedures.

Performing a egg allergy condition characterization process (e.g., a diagnostic process) can be based on microbiome features (e.g., microbiome composition features) associated with (e.g., derived from, informative of, correlated with, etc.) one or more (e.g. in any suitable combination) of the following taxons: *Blautia luti* (Species), *Collinsella aerofaciens* (Species), *Subdoligranulum variabile* (Species), *Flavonifractor plautii* (Species), *Faecalibacterium prausnitzii* (Species), *Alistipes putredinis* (Species), *Roseburia inulinivorans* (Species), *Bacteroides caccae* (Species), *Barnesiella intestinihominis* (Species), *Parabacteroides distasonis* (Species), *Odoribacter splanchnicus* (Species), *Dorea formicigenerans* (Species), *Subdoligranulum* (Genus), *Collinsella* (Genus), *Moryella* (Genus), *Sarcina* (Genus), *Faecalibacterium* (Genus), *Terrisporobacter* (Genus), *Dorea* (Genus), *Barnesiella* (Genus), *Marvinbryantia* (Genus), *Roseburia* (Genus), *Odoribacter* (Genus), *Eggerthella* (Genus), *Sutterella* (Genus), *Anaerotruncus* (Genus), *Bacteroides* (Genus), Ruminococcaceae (Family), Coriobacteriaceae (Family), Clostridiaceae (Family), Sutterellaceae (Family), Bacteroidaceae (Family), Streptococcaceae (Family), Oscillospiraceae (Family), Coriobacteriales (Order), Clostridiales (Order), Burkholderiales (Order), Bacteroidales (Order), Actinobacteria (Class), Clostridia (Class), Betaproteobacteria (Class), Bacteroidia (Class), Actinobacteria (Phylum), Firmicutes (Phylum), Bacteroidetes (Phylum).

Additionally or alternatively, microbiome features can be associated with one or more of the following taxons in relation to a sample site (e.g., egg allergy condition correlations with microorganisms observed at a particular sample site): Acidaminococcaceae (family) (e.g., gut site); *Acidaminococcus* sp. D21 (species) (e.g., gut site); Acidobacteria (phylum) (e.g., nose site); Acidobacteriia (class) (e.g., nose site); *Acinetobacter* (genus) (e.g., nose site); *Actinobacillus* (genus) (e.g., gut site); *Actinobacillus porcinus* (species) (e.g., gut site); Actinobacteria (class) (e.g., gut site); Actinobacteria (phylum) (e.g., gut site); *Actinomyces* (genus) (e.g., nose site); *Actinomyces massiliensis* (species) (e.g., mouth site); *Actinomyces* sp. ICM54 (species) (e.g., nose site); *Actinomyces* sp. oral taxon 175 (species) (e.g., nose site); *Actinomyces* sp. ZSY-1 (species) (e.g., mouth site); Actinomycetaceae (family) (e.g., nose site); Actinomycetales (order) (e.g., gut site); *Adlercreutzia* (genus) (e.g., gut site); *Adlercreutzia equolifaciens* (species) (e.g., gut site); *Akkermansia* (genus) (e.g., gut site); *Akkermansia muciniphila* (species) (e.g., gut site); *Alistipes* (genus) (e.g., gut site); *Alistipes putredinis* (species) (e.g., gut site); *Alistipes* sp. 627 (species) (e.g., gut site); *Alistipes* sp. EBA6-25cl2 (species) (e.g., gut site); *Alistipes* sp. NML05A004

(species) (e.g., gut site); *Alistipes* sp. RMA 9912 (species) (e.g., gut site); Alphaproteobacteria (class) (e.g., nose site); Alphaproteobacteria (class) (e.g., gut site); *Anaerobacter* (genus) (e.g., gut site); *Anaerofilum* (genus) (e.g., gut site); *Anaerosporobacter* (genus) (e.g., gut site); *Anaerostipes* sp. 1y-2 (species) (e.g., gut site); *Anaerostipes* sp. 3_2_56FAA (species) (e.g., gut site); *Anaerostipes* sp. 5_1_63FAA (species) (e.g., gut site); *Anaerotruncus colihominis* (species) (e.g., gut site); *Anaerotruncus* sp. NML 070203 (species) (e.g., gut site); *Anaerovorax* (genus) (e.g., gut site); Bacteroidaceae (family) (e.g., gut site); Bacteroidaceae (family) (e.g., mouth site); Bacteroidales (order) (e.g., gut site); *Bacteroides* (genus) (e.g., gut site); *Bacteroides* (genus) (e.g., mouth site); *Bacteroides acidifaciens* (species) (e.g., gut site); *Bacteroides caccae* (species) (e.g., gut site); *Bacteroides clarus* (species) (e.g., gut site); *Bacteroides dorei* (species) (e.g., gut site); *Bacteroides eggerthii* (species) (e.g., gut site); *Bacteroides fragilis* (species) (e.g., gut site); *Bacteroides plebeius* (species) (e.g., gut site); *Bacteroides* sp. AR20 (species) (e.g., gut site); *Bacteroides* sp. AR29 (species) (e.g., gut site); *Bacteroides* sp. D22 (species) (e.g., gut site); *Bacteroides* sp. DJF_B_097 (species) (e.g., gut site); *Bacteroides* sp. EBA5-17 (species) (e.g., gut site); *Bacteroides* sp. SLC1-38 (species) (e.g., gut site); *Bacteroides* sp. XB12B (species) (e.g., gut site); *Bacteroides stercoris* (species) (e.g., gut site); *Bacteroides thetaiotaomicron* (species) (e.g., gut site); *Bacteroides uniformis* (species) (e.g., gut site); *Bacteroides vulgatus* (species) (e.g., nose site); *Bacteroides vulgatus* (species) (e.g., genital site); *Bacteroides vulgatus* (species) (e.g., gut site); Bacteroidetes (phylum) (e.g., gut site); Bacteroidia (class) (e.g., gut site); *Barnesiella* (genus) (e.g., gut site); *Barnesiella intestinihominis* (species) (e.g., gut site); *Bergeyella* (genus) (e.g., nose site); Betaproteobacteria (class) (e.g., gut site); Bifidobacteriaceae (family) (e.g., gut site); Bifidobacteriales (order) (e.g., gut site); *Bifidobacterium* (genus) (e.g., gut site); *Bifidobacterium biavatii* (species) (e.g., gut site); *Bifidobacterium choerinum* (species) (e.g., gut site); *Bifidobacterium* sp. 120 (species) (e.g., gut site); *Bifidobacterium* sp. MSX5B (species) (e.g., gut site); *Bifidobacterium stercoris* (species) (e.g., gut site); *Bilophila* (genus) (e.g., gut site); *Bilophila* sp. 4_1_30 (species) (e.g., gut site); *Blautia* (genus) (e.g., genital site); *Blautia* (genus) (e.g., gut site); *Blautia faecis* (species) (e.g., gut site); *Blautia glucerasea* (species) (e.g., gut site); *Blautia hydrogenotrophica* (species) (e.g., gut site); *Blautia luti* (species) (e.g., gut site); *Blautia producta* (species) (e.g., gut site); *Blautia* sp. Ser8 (species) (e.g., gut site); *Blautia* sp. YHC-4 (species) (e.g., gut site); *Blautia wexlerae* (species) (e.g., gut site); Burkholderiaceae (family) (e.g., nose site); Burkholderiales (order) (e.g., gut site); *Butyricimonas* (genus) (e.g., gut site); Campylobacteraceae (family) (e.g., nose site); Campylobacterales (order) (e.g., nose site); *Candidatus Soleaferrea* (genus) (e.g., gut site); *Capnocytophaga* (genus) (e.g., nose site); *Capnocytophaga* sp. AHN9576 (species) (e.g., mouth site); *Capnocytophaga* sp. CM59 (species) (e.g., nose site); Cardiobacteriaceae (family) (e.g., mouth site); *Cardiobacterium valvarum* (species) (e.g., mouth site); Carnobacteriaceae (family) (e.g., gut site); Carnobacteriaceae (family) (e.g., mouth site); *Centipeda* (genus) (e.g., nose site); *Cloacibacillus* (genus) (e.g., gut site); *Cloacibacillus evryensis* (species) (e.g., gut site); Clostridia (class) (e.g., gut site); Clostridiaceae (family) (e.g., gut site); Clostridiales (order) (e.g., gut site); Clostridiales (family) XI. Incertae Sedis (family) (e.g., gut site); Clostridiales (family) XIII. Incertae Sedis (family) (e.g., gut site); *Clostridium* (genus) (e.g., gut site); *Collinsella* (genus) (e.g., gut site); *Collinsella aerofaciens* (species) (e.g., gut site); Comamonadaceae (family) (e.g., mouth site); *Comamonas* (genus) (e.g., mouth site); *Coprobacillus* (genus) (e.g., gut site); *Coprobacillus* sp. D6 (species) (e.g., gut site); Coriobacteriaceae (family) (e.g., gut site); Coriobacteriales (order) (e.g., gut site); *Corynebacterium durum* (species) (e.g., nose site); *Corynebacterium freiburgense* (species) (e.g., genital site); *Corynebacterium matruchotii* (species) (e.g., nose site); *Corynebacterium* sp. NML 97-0186 (species) (e.g., nose site); *Cronobacter* (genus) (e.g., gut site); Cyanobacteria (phylum) (e.g., nose site); *Delftia* (genus) (e.g., nose site); *Delftia* sp. BN-SKY3 (species) (e.g., nose site); Deltaproteobacteria (class) (e.g., gut site); Desulfovibrionaceae (family) (e.g., gut site); Desulfovibrionales (order) (e.g., gut site); *Dialister* (genus) (e.g., gut site); *Dialister propionicifaciens* (species) (e.g., gut site); *Dielma* (genus) (e.g., gut site); *Dielma fastidiosa* (species) (e.g., gut site); *Dorea* (genus) (e.g., gut site); *Dorea formicigenerans* (species) (e.g., gut site); *Dorea longicatena* (species) (e.g., gut site); *Eggerthella* (genus) (e.g., gut site); *Eggerthella sinensis* (species) (e.g., gut site); *Eggerthella* sp. HGA1 (species) (e.g., gut site); *Eisenbergiella* (genus) (e.g., gut site); *Eisenbergiella tayi* (species) (e.g., gut site); Enterococcaceae (family) (e.g., gut site); *Enterococcus* (genus) (e.g., gut site); *Enterococcus raffinosus* (species) (e.g., gut site); *Enterococcus* sp. C6I11 (species) (e.g., gut site); *Erysipelatoclostridium* (genus) (e.g., gut site); *Erysipelatoclostridium ramosum* (species) (e.g., gut site); Erysipelotrichaceae (family) (e.g., gut site); Erysipelotrichales (order) (e.g., gut site); Erysipelotrichia (class) (e.g., gut site); Eubacteriaceae (family) (e.g., gut site); *Eubacterium* (genus) (e.g., gut site); *Eubacterium callanderi* (species) (e.g., gut site); *Faecalibacterium* (genus) (e.g., gut site); *Faecalibacterium* (genus) (e.g., mouth site); *Faecalibacterium prausnitzii* (species) (e.g., gut site); *Faecalibacterium prausnitzii* (species) (e.g., mouth site); Fibrobacteraceae (family) (e.g., gut site); Fibrobacterales (order) (e.g., gut site); Fibrobacteres (phylum) (e.g., gut site); Fibrobacteria (class) (e.g., gut site); *Finegoldia* (genus) (e.g., skin site); *Finegoldia* sp. S8 F7 (species) (e.g., gut site); *Finegoldia* sp. S9 AA1-5 (species) (e.g., gut site); Firmicutes (phylum) (e.g., gut site); Flavobacteriaceae (family) (e.g., gut site); Flavobacteriales (order) (e.g., gut site); Flavobacteriia (class) (e.g., gut site); *Flavonifractor* (genus) (e.g., gut site); *Flavonifractor plautii* (species) (e.g., gut site); *Fusicatenibacter* (genus) (e.g., gut site); *Fusicatenibacter saccharivorans* (species) (e.g., gut site); Fusobacteria (phylum) (e.g., gut site); Fusobacteriaceae (family) (e.g., nose site); Fusobacteriales (order) (e.g., nose site); Fusobacteriia (class) (e.g., nose site); *Fusobacterium* (genus) (e.g., nose site); *Fusobacterium* sp. CM21 (species) (e.g., nose site); *Fusobacterium* sp. CM21 (species) (e.g., gut site); *Gelria* (genus) (e.g., gut site); *Gemella* (genus) (e.g., gut site); *Gemella sanguinis* (species) (e.g., mouth site); *Gemella* sp. 933-88 (species) (e.g., gut site); *Gordonibacter* (genus) (e.g., gut site); *Gordonibacter pamelaeae* (species) (e.g., gut site); *Granulicatella* (genus) (e.g., gut site); *Granulicatella adiacens* (species) (e.g., gut site); *Herbaspirillum* (genus) (e.g., nose site); *Herbaspirillum seropedicae* (species) (e.g., nose site); *Hespellia* (genus) (e.g., gut site); *Holdemania* (genus) (e.g., gut site); *Holdemania filiformis* (species) (e.g., gut site); *Howardella* (genus) (e.g., gut site); *Howardella ureilytica* (species) (e.g., gut site); *Intestinibacter* (genus) (e.g., gut site); *Intestinimonas* (genus) (e.g., gut site); *Intestinimonas butyriciproducens* (species) (e.g., gut site); *Klebsiella* (genus) (e.g., gut site); *Klebsiella* sp. SOR89 (species) (e.g., gut site); *Lachnoanaerobaculum saburreum* (species) (e.g., mouth site);

*Lachnospira* (genus) (e.g., gut site); *Lachnospira pectinoschiza* (species) (e.g., gut site); Lachnospiraceae (family) (e.g., genital site); Lactobacillaceae (family) (e.g., gut site); *Lactobacillus* (genus) (e.g., gut site); *Lactobacillus crispatus* (species) (e.g., gut site); *Lactobacillus rhamnosus* (species) (e.g., gut site); *Lactobacillus* sp. BL302 (species) (e.g., genital site); *Lactobacillus* sp. TAB-30 (species) (e.g., gut site); *Lactonifactor* (genus) (e.g., gut site); *Lactonifactor longoviformis* (species) (e.g., gut site); *Leptotrichia* (genus) (e.g., nose site); Leuconostocaceae (family) (e.g., gut site); *Marvinbryantia* (genus) (e.g., gut site); *Megasphaera* (genus) (e.g., gut site); *Megasphaera genomo* sp. C1 (species) (e.g., gut site); Methanobacteria (class) (e.g., gut site); Methanobacteriaceae (family) (e.g., gut site); Methanobacteriales (order) (e.g., gut site); *Methanobrevibacter* (genus) (e.g., gut site); *Methanobrevibacter smithii* (species) (e.g., gut site); Methylobacteriaceae (family) (e.g., nose site); *Methylobacterium* (genus) (e.g., nose site); Micrococcaceae (family) (e.g., nose site); *Micrococcus* (genus) (e.g., nose site); *Micrococcus* sp. WB18-01 (species) (e.g., nose site); Mollicutes (class) (e.g., gut site); *Moraxella* (genus) (e.g., nose site); *Moraxella* sp. WB19-16 (species) (e.g., nose site); Moraxellaceae (family) (e.g., nose site); *Moryella* (genus) (e.g., gut site); *Murdochiella* (genus) (e.g., genital site); *Murdochiella asaccharolytica* (species) (e.g., genital site); Mycobacteriaceae (family) (e.g., nose site); *Mycobacterium* (genus) (e.g., nose site); *Neisseria* (genus) (e.g., nose site); *Neisseria elongata* (species) (e.g., nose site); *Neisseria macacae* (species) (e.g., nose site); *Neisseria mucosa* (species) (e.g., nose site); Neisseriaceae (family) (e.g., nose site); Neisseriales (order) (e.g., nose site); *Odoribacter* (genus) (e.g., gut site); *Odoribacter splanchnicus* (species) (e.g., gut site); *Oscillibacter* (genus) (e.g., gut site); *Oscillospira* (genus) (e.g., gut site); Oscillospiraceae (family) (e.g., gut site); Oxalobacteraceae (family) (e.g., nose site); *Pantoea* (genus) (e.g., gut site); *Parabacteroides* (genus) (e.g., gut site); *Parabacteroides distasonis* (species) (e.g., gut site); *Parabacteroides merdae* (species) (e.g., gut site); *Paraprevotella* (genus) (e.g., gut site); *Paraprevotella clara* (species) (e.g., gut site); *Peptococcus* (genus) (e.g., gut site); *Peptoniphilus* (genus) (e.g., gut site); *Peptoniphilus lacrimalis* (species) (e.g., gut site); *Peptoniphilus* sp. DNF00840 (species) (e.g., gut site); *Phascolarctobacterium* (genus) (e.g., gut site); *Phascolarctobacterium faecium* (species) (e.g., gut site); *Phascolarctobacterium succinatutens* (species) (e.g., gut site); Phyllobacteriaceae (family) (e.g., gut site); *Phyllobacterium* (genus) (e.g., gut site); Porphyromonadaceae (family) (e.g., gut site); *Porphyromonas catoniae* (species) (e.g., nose site); *Prevotella disiens* (species) (e.g., gut site); *Prevotella timonensis* (species) (e.g., genital site); Prevotellaceae (family) (e.g., gut site); Propionibacteriaceae (family) (e.g., mouth site); *Propionibacterium* (genus) (e.g., mouth site); *Propionibacterium acnes* (species) (e.g., nose site); *Propionibacterium* sp. MSP09A (species) (e.g., mouth site); *Pseudoflavonifractor* (genus) (e.g., gut site); *Pseudoflavonifractor capillosus* (species) (e.g., gut site); Pseudomonadaceae (family) (e.g., skin site); Pseudomonadales (order) (e.g., skin site); *Pseudomonas* (genus) (e.g., skin site); *Ralstonia* (genus) (e.g., skin site); Rhizobiaceae (family) (e.g., nose site); Rhizobiales (order) (e.g., gut site); Rhodobacteraceae (family) (e.g., nose site); Rhodobacterales (order) (e.g., nose site); Rhodospirillaceae (family) (e.g., gut site); Rhodospirillales (order) (e.g., gut site); Rikenellaceae (family) (e.g., gut site); *Robinsoniella* (genus) (e.g., gut site); *Roseburia* (genus) (e.g., gut site); *Roseburia intestinalis* (species) (e.g., gut site); *Roseburia inulinivorans* (species) (e.g., gut site); *Roseburia* sp. 11SE39 (species) (e.g., gut site); *Roseburia* sp. 499 (species) (e.g., gut site); *Rothia dentocariosa* (species) (e.g., nose site); *Rothia mucilaginosa* (species) (e.g., nose site); Ruminococcaceae (family) (e.g., gut site); *Sarcina* (genus) (e.g., gut site); Solanales (order) (e.g., nose site); Sphingomonadaceae (family) (e.g., nose site); Sphingomonadales (order) (e.g., nose site); *Sphingomonas* (genus) (e.g., nose site); *Staphylococcus* sp. C-D-MA2 (species) (e.g., skin site); Streptococcaceae (family) (e.g., gut site); *Streptococcus* (genus) (e.g., mouth site); *Streptococcus* sp. BS35a (species) (e.g., gut site); *Streptococcus* sp. oral taxon G59 (species) (e.g., nose site); *Streptococcus* sp. oral taxon G63 (species) (e.g., mouth site); *Streptococcus thermophilus* (species) (e.g., gut site); Streptophyta (phylum) (e.g., nose site); *Subdoligranulum* (genus) (e.g., gut site); *Subdoligranulum variabile* (species) (e.g., gut site); *Sutterella* (genus) (e.g., gut site); *Sutterella wadsworthensis* (species) (e.g., gut site); Sutterellaceae (family) (e.g., gut site); Synergistaceae (family) (e.g., gut site); Synergistales (order) (e.g., gut site); Synergistetes (phylum) (e.g., gut site); Synergistia (class) (e.g., gut site); Tenericutes (phylum) (e.g., gut site); *Terrisporobacter* (genus) (e.g., gut site); *Thalassospira* (genus) (e.g., gut site); Thermoanaerobacteraceae (family) (e.g., gut site); Thermoanaerobacterales (order) (e.g., gut site); *Veillonella* (genus) (e.g., gut site); *Veillonella* sp. 2011_Oral_VSA_D3 (species) (e.g., gut site); *Veillonella* sp. CM60 (species) (e.g., gut site); *Veillonella* sp. MSA12 (species) (e.g., nose site); Veillonellaceae (family) (e.g., gut site); Verrucomicrobia (phylum) (e.g., gut site); Verrucomicrobiaceae (family) (e.g., gut site); Verrucomicrobiae (class) (e.g., gut site); Verrucomicrobiales (order) (e.g., gut site); Xanthomonadales (order) (e.g., gut site).

Additionally or alternatively, performing a egg allergy condition characterization process can be based on microbiome features (e.g., microbiome function features) associated with one or more of (e.g., such as in relation to a corresponding sample site): Metabolism (KEGG2), Translation (KEGG2), Carbohydrate Metabolism (KEGG2), Cellular Processes and Signaling (KEGG2), Transport and Catabolism (KEGG2), Glycan Biosynthesis and Metabolism (KEGG2), Signaling Molecules and Interaction (KEGG2), Biosynthesis of Other Secondary Metabolites (KEGG2), Replication and Repair (KEGG2), Environmental Adaptation (KEGG2), Genetic Information Processing (KEGG2), Nucleotide Metabolism (KEGG2), Lipid Metabolism (KEGG2), Ribosome Biogenesis (KEGG3), D-Alanine metabolism (KEGG3), Ascorbate and aldarate metabolism (KEGG3), Amino acid metabolism (KEGG3), Translation proteins (KEGG3), Pentose and glucuronate interconversions (KEGG3), Peptidoglycan biosynthesis (KEGG3), Phenylalanine metabolism (KEGG3), RNA polymerase (KEGG3), Amino acid related enzymes (KEGG3), Glyoxylate and dicarboxylate metabolism (KEGG3), Biotin metabolism (KEGG3), Inorganic ion transport and metabolism (KEGG3), Others (KEGG3), Aminoacyl-tRNA biosynthesis (KEGG3), Glycosphingolipid biosynthesis—globo series (KEGG3), Bacterial toxins (KEGG3), MAPK signaling pathway—yeast (KEGG3), Penicillin and cephalosporin biosynthesis (KEGG3), Sphingolipid metabolism (KEGG3), Lysosome (KEGG3), Other glycan degradation (KEGG3), Inositol phosphate metabolism (KEGG3), Ribosome (KEGG3), Lipoic acid metabolism (KEGG3), Plant-pathogen interaction (KEGG3), Chromosome (KEGG3), Pores ion channels (KEGG3), Fructose and mannose metabolism (KEGG3), Other transporters (KEGG3), Lipopolysaccharide biosynthesis proteins (KEGG3), Other ion-coupled transporters (KEGG3), Membrane and intracellular structural molecules (KEGG3), Bisphenol degradation (KEGG3), Nitrogen metabolism (KEGG3), Glycosaminoglycan degradation (KEGG3), Signal transduction mechanisms (KEGG3), Huntington's disease (KEGG3), Translation factors (KEGG3), Carbohydrate metabolism (KEGG3), Ion channels (KEGG3), Cell motility and secretion (KEGG3), Lipid metabolism (KEGG3), Geraniol degradation (KEGG3), Terpenoid backbone biosynthesis (KEGG3), DNA repair and recombination proteins (KEGG3), Ribosome biogenesis in eukaryotes (KEGG3), Galactose metabolism (KEGG3), Glycerophospholipid metabolism (KEGG3), Taurine and hypotaurine metabolism (KEGG3), Pyrimidine metabolism (KEGG3), Biosynthesis and biodegradation of secondary metabolites (KEGG3), Nicotinate and nicotinamide metabolism (KEGG3), Phosphonate and phosphinate metabolism (KEGG3), Glycosphingolipid biosynthesis—ganglio series (KEGG3), Amino sugar and nucleotide sugar metabolism (KEGG3), Streptomycin biosynthesis (KEGG3) and Citrate cycle (TCA cycle) (KEGG3), Digestive System (KEGG_Pathways_Level_2) (e.g., mouth site); Xenobiotics Biodegradation and Metabolism (KEGG_Pathways_Level_2) (e.g., mouth site); Butirosin and neomycin biosynthesis (KEGG_Pathways_Level_3) (e.g., mouth site); Carbohydrate digestion and absorption (KEGG_Pathways_Level_3) (e.g., mouth site); Protein export (KEGG_Pathways_Level_3) (e.g., mouth site); Restriction enzyme (KEGG_Pathways_Level_3) (e.g., mouth site); Prion diseases (KEGG_Pathways_Level_3) (e.g., mouth site); Retinol metabolism (KEGG_Pathways_Level_3) (e.g., mouth site); Biosynthesis of vancomycin group antibiotics (KEGG_Pathways_Level_3) (e.g., mouth site); Excretory System (KEGG_Pathways_Level_2) (e.g., gut site); Enzyme Families (KEGG_Pathways_Level_2) (e.g., gut site); Neurodegenerative Diseases (KEGG_Pathways_Level_2) (e.g., gut site); Metabolism (KEGG_Pathways_Level_2) (e.g., gut site); Signaling Molecules and Interaction (KEGG_Pathways_Level_2) (e.g., gut site); Translation (KEGG_Pathways_Level_2) (e.g., gut site); Xenobiotics Biodegradation and Metabolism (KEGG_Pathways_Level_2) (e.g., gut site); Transport and Catabolism (KEGG_Pathways_Level_2) (e.g., gut site); Replication and Repair (KEGG_Pathways_Level_2) (e.g., gut site); Cellular Processes and Signaling (KEGG_Pathways_Level_2) (e.g., gut site); Carbohydrate Metabolism (KEGG_Pathways_Level_2) (e.g., gut site); Genetic Information Processing (KEGG_Pathways_Level_2) (e.g., gut site); Environmental Adaptation (KEGG_Pathways_Level_2) (e.g., gut site); Peptidoglycan biosynthesis (KEGG_Pathways_Level_3) (e.g., gut site); Aminoacyl-tRNA biosynthesis (KEGG_Pathways_Level_3) (e.g., gut site); Ascorbate and aldarate metabolism (KEGG_Pathways_Level_3) (e.g., gut site); Huntington_quote_s disease (KEGG_Pathways_Level_3) (e.g., gut site); MAPK signaling pathway—yeast (KEGG_Pathways_Level_3) (e.g., gut site); Inositol phosphate metabolism (KEGG_Pathways_Level_3) (e.g., gut site); Amino acid metabolism (KEGG_Pathways_Level_3) (e.g., gut site); Others (KEGG_Pathways_Level_3) (e.g., gut site); Biosynthesis and biodegradation of secondary metabolites (KEGG_Pathways_Level_3) (e.g., gut site); Ribosome Biogenesis (KEGG_Pathways_Level_3) (e.g., gut site); Translation proteins (KEGG_Pathways_Level_3) (e.g., gut site); D-Alanine metabolism (KEGG_Pathways_Level_3) (e.g., gut site); Bisphenol degradation (KEGG_Pathways_Level_3) (e.g., gut site); "Valine, leucine and isoleucine degradation" (KEGG_Pathways_Level_3) (e.g., gut site); Oxidative phosphorylation (KEGG_Pathways_Level_3) (e.g., gut site); Linoleic acid metabolism (KEGG_Pathways_Level_3) (e.g., gut site); Other glycan degradation (KEGG_Pathways_Level_3) (e.g., gut site); Fructose and man (e.g., nose site) metabolism (KEGG_Pathways_Level_3) (e.g., gut site); Terpenoid backbone biosynthesis (KEGG_Pathways_Level_3) (e.g., gut site); Polycyclic aromatic hydrocarbon degradation (KEGG_Pathways_Level_3) (e.g., gut site); Ribosome (KEGG_Pathways_Level_3) (e.g., gut site); Aminobenzoate degradation (KEGG_Pathways_Level_3) (e.g., gut site); Glyoxylate and dicarboxylate metabolism (KEGG_Pathways_Level_3) (e.g., gut site); Geraniol degradation (KEGG_Pathways_Level_3) (e.g., gut site); Lipoic acid metabolism (KEGG_Pathways_Level_3) (e.g., gut site); Sphingolipid metabolism (KEGG_Pathways_Level_3) (e.g., gut site); Bacterial toxins (KEGG_Pathways_Level_3) (e.g., gut site); Limonene and pinene degradation (KEGG_Pathways_Level_3) (e.g., gut site); Type II diabetes mellitus (KEGG_Pathways_Level_3) (e.g., gut site); Transcription related proteins (KEGG_Pathways_Level_3) (e.g., gut site); Cysteine and methionine metabolism (KEGG_Pathways_Level_3) (e.g., gut site); Nicotinate and nicotinamide metabolism (KEGG_Pathways_Level_3) (e.g., gut site); Styrene degradation (KEGG_Pathways_Level_3) (e.g., gut site); Amoebiasis (KEGG_Pathways_Level_3) (e.g., gut site); Glycosphingolipid biosynthesis—lacto and neolacto series (KEGG_Pathways_Level_3) (e.g., gut site); alpha-Linolenic acid metabolism (KEGG_Pathways_Level_3) (e.g., gut site); Plant-pathogen interaction (KEGG_Pathways_Level_3) (e.g., gut site); Chromosome (KEGG_Pathways_Level_3) (e.g., gut site); Biosynthesis of Other Secondary Metabolites (KEGG_Pathways_Level_2) (e.g., gut site); Membrane Transport (KEGG_Pathways_Level_2) (e.g., gut site); Infectious Diseases (KEGG_Pathways_Level_2) (e.g., gut site); Cell Motility (KEGG_Pathways_Level_2) (e.g., gut site); Glycan Biosynthesis and Metabolism (KEGG_Pathways_Level_2) (e.g., gut site); Transcription (KEGG_Pathways_Level_2) (e.g., gut site); Poorly Characterized (KEGG_Pathways_Level_2) (e.g., gut site); Lipid Metabolism (KEGG_Pathways_Level_2) (e.g., gut site); Bacterial chemotaxis (KEGG_Pathways_Level_3) (e.g., gut site); Membrane and intracellular structural molecules (KEGG_Pathways_Level_3) (e.g., gut site); Pentose and glucuronate interconversions (KEGG_Pathways_Level_3) (e.g., gut site); RNA polymerase (KEGG_Pathways_Level_3) (e.g., gut site); N-Glycan biosynthesis (KEGG_Pathways_Level_3) (e.g., gut site); Sulfur metabolism (KEGG_Pathways_Level_3) (e.g., gut site); Nucleotide excision repair (KEGG_Pathways_Level_3) (e.g., gut site); Biotin metabolism (KEGG_Pathways_Level_3) (e.g., gut site); Glycosyltransferases (KEGG_Pathways_Level_3) (e.g., gut site); Lipopolysaccharide biosynthesis proteins (KEGG_Pathways_Level_3) (e.g., gut site); Phosphatidylinositol signaling system (KEGG_Pathways_Level_3) (e.g., gut site); Pores ion channels (KEGG_Pathways_Level_3) (e.g., gut site); Phosphonate and phosphinate metabolism (KEGG_Pathways_Level_3) (e.g., gut site); Cell motility and secretion (KEGG_Pathways_Level_3) (e.g., gut site); Protein folding and associated processing (KEGG_Pathways_Level_3) (e.g., gut site); Glycosphingolipid biosynthesis—globo series (KEGG_Pathways_Level_3) (e.g., gut site); Lysosome (KEGG_Pathways_Level_3) (e.g., gut site); Proximal tubule bicarbonate reclamation (KEGG_Pathways_Level_3) (e.g., gut site); Inorganic ion transport and metabolism (KEGG_Pathways_Level_3) (e.g., gut site); Germination (KEGG_Pathways_Level_3) (e.g., gut site); Type I diabetes mellitus (KEGG_Pathways_Level_3) (e.g., gut site); Phenylalanine metabolism (KEGG_Pathways_Level_3) (e.g., gut site); Glycosaminoglycan degradation (KEGG_Pathways_Level_3) (e.g., gut site); Secondary bile acid biosynthesis (KEGG_Pathways_Level_3) (e.g., gut site); Penicillin and cephalosporin biosynthesis (KEGG_Pathways_Level_3) (e.g., gut site); Carbohydrate metabolism (KEGG_Pathways_Level_3) (e.g., gut site); Carbon fixation pathways in prokaryotes (KEGG_Pathways_Level_3) (e.g., gut site); Mismatch repair (KEGG_Pathways_Level_3) (e.g., gut site); Ion channels (KEGG_Pathways_Level_3) (e.g., gut site); Citrate cycle (TCA cycle) (KEGG_Pathways_Level_3) (e.g., gut site); Lipopolysaccharide biosynthesis (KEGG_Pathways_Level_3) (e.g., gut site); Cytoskeleton proteins (KEGG_Pathways_Level_3) (e.g., gut site); Polyketide sugar unit biosynthesis (KEGG_Pathways_Level_3) (e.g., gut site); Cellular antigens (KEGG_Pathways_Level_3) (e.g., gut site); Ribosome biogenesis in eukaryotes (KEGG_Pathways_Level_3) (e.g., gut site); Protein digestion and absorption (KEGG_Pathways_Level_3) (e.g., gut site); Translation factors (KEGG_Pathways_Level_3) (e.g., gut site); Amino sugar and nucleotide sugar metabolism (KEGG_Pathways_Level_3) (e.g., gut site); Steroid biosynthesis (KEGG_Pathways_Level_3) (e.g., gut site); Signal transduction mechanisms (KEGG_Pathways_Level_3) (e.g., gut site); Steroid hormone biosynthesis (KEGG_Pathways_Level_3) (e.g., gut site); Glycerophospholipid metabolism (KEGG_Pathways_Level_3) (e.g., gut site); Transcription factors (KEGG_Pathways_Level_3) (e.g., gut site); Pertussis (KEGG_Pathways_Level_3) (e.g., gut site); Sporulation (KEGG_Pathways_Level_3) (e.g., gut site); Lipid metabolism (KEGG_Pathways_Level_3) (e.g., gut site); Amino acid related enzymes (KEGG_Pathways_Level_3) (e.g., gut site); Streptomycin biosynthesis (KEGG_Pathways_Level_3) (e.g., gut site); Transporters (KEGG_Pathways_Level_3) (e.g., gut site); "1,1,1-Trichloro-2,2-bis(4-chlorophenyl)ethane (DDT) degradation" (KEGG_Pathways_Level_3) (e.g., gut site); Function unknown (KEGG_Pathways_Level_3) (e.g., gut site); Galactose metabolism (KEGG_Pathways_Level_3) (e.g., gut site); Bacterial motility proteins (KEGG_Pathways_Level_3) (e.g., gut site); Flagellar assembly (KEGG_Pathways_Level_3) (e.g., gut site); Pyrimidine metabolism (KEGG_Pathways_Level_3) (e.g., gut site); Taurine and hypotaurine metabolism (KEGG_Pathways_Level_3) (e.g., gut site); Nitrogen metabolism (KEGG_Pathways_Level_3) (e.g., gut site); Homologous recombination (KEGG_Pathways_Level_3) (e.g., gut site); Pantothenate and CoA biosynthesis (KEGG_Pathways_Level_3) (e.g., gut site); Glycosphingolipid biosynthesis—ganglio series (KEGG_Pathways_Level_3) (e.g., gut site); Toluene degradation (KEGG_Pathways_Level_3) (e.g., gut site); DNA repair and recombination proteins (KEGG_Pathways_Level_3) (e.g., gut site); Ubiquinone and other terpenoid-quinone biosynthesis (KEGG_Pathways_Level_3) (e.g., gut site); ABC transporters (KEGG_Pathways_Level_3) (e.g., gut site); Ubiquitin system (KEGG_Pathways_Level_3) (e.g., gut site), and/or other suitable function-related aspects.

Determining an allergy-related characterization of a user can include diagnosing a user with a egg allergy condition based upon one or more of the above microbiome features and/or other suitable features described herein, such as in an additional or alterative manner to typical methods of diagnosis. However, features used in the egg allergy characterization process can include any other suitable features (e.g., features useful for diagnostics), and performing the egg allergy characterization process can be performed in any suitable manner.

3.3.G Dairy Allergy Condition Characterization Process.

In another variation, Block S130 can include performing a dairy allergy condition characterization process (e.g., determining and/or applying a dairy allergy characterization model; etc.) for one or more users. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.)

with a dairy allergy condition. In another example, performing a dairy allergy condition characterization process can facilitate identifications of one or more therapies operable to have a positive effect on the dairy allergy condition (e.g., based upon a random forest predictor algorithm trained with a training dataset derived from a subset of the population of subjects, and validated with a validation dataset derived from a subset of the population of subjects). In particular, a dairy allergy condition can include an immune disorder characterized by an abnormal reaction of the immune system of the subject to any food containing or some of its derivatives, and diagnosis can be associated with laboratory analysis (e.g., skin-prick test, blood-samples analysis, IgE tests, etc.) and/or other suitable diagnostic procedures.

Microbiome features can be associated with one or more of the following taxons in relation to a sample site (e.g., dairy allergy condition correlations with microorganisms observed at a particular sample site): Bacteroidaceae (family) (e.g., genital site); *Bacteroides* (genus) (e.g., genital site); Corynebacteriaceae (family) (e.g., genital site); *Corynebacterium* (genus) (e.g., genital site); Betaproteobacteria (class) (e.g., genital site); Propionibacteriaceae (family) (e.g., genital site); Comamonadaceae (family) (e.g., genital site); Lachnospiraceae (family) (e.g., genital site); *Lactobacillus* sp. BL302 (species) (e.g., genital site); *Corynebacterium mastitidis* (species) (e.g., genital site); *Corynebacterium spheniscorum* (species) (e.g., genital site); *Finegoldia* sp. S8 F7 (species) (e.g., genital site); *Corynebacterium glucuronolyticum* (species) (e.g., genital site); Rhizobiales (order) (e.g., gut site); Neisseriaceae (family) (e.g., gut site); *Neisseria* (genus) (e.g., gut site); Enterobacteriaceae (family) (e.g., gut site); *Actinobacillus* (genus) (e.g., gut site); *Haemophilus influenzae* (species) (e.g., gut site); *Pasteurella* (genus) (e.g., gut site); *Pasteurella pneumotropica* (species) (e.g., gut site); Bacteroidaceae (family) (e.g., gut site); *Bacteroides* (genus) (e.g., gut site); *Bacteroides vulgatus* (species) (e.g., gut site); *Fusobacterium periodonticum* (species) (e.g., gut site); *Megasphaera* (genus) (e.g., gut site); Bacteroidetes (phylum) (e.g., gut site); Micrococcaceae (family) (e.g., gut site); Streptococcaceae (family) (e.g., gut site); *Streptococcus thermophilus* (species) (e.g., gut site); Bacillales (order) (e.g., gut site); *Clostridium* (genus) (e.g., gut site); *Bifidobacterium* (genus) (e.g., gut site); Actinobacteria (class) (e.g., gut site); Actinomycetales (order) (e.g., gut site); Mycoplasmatales (order) (e.g., gut site); Mycoplasmataceae (family) (e.g., gut site); Solanales (order) (e.g., gut site); *Lachnospira* (genus) (e.g., gut site); Bifidobacteriaceae (family) (e.g., gut site); Veillonellaceae (family) (e.g., gut site); *Rothia* (genus) (e.g., gut site); *Parvimonas micra* (species) (e.g., gut site); Streptophyta (phylum) (e.g., gut site); *Dialister* (genus) (e.g., gut site); *Sutterella* (genus)

(e.g., gut site); *Rothia mucilaginosa* (species) (e.g., gut site); *Granulicatella adiacens* (species) (e.g., gut site); *Parabacteroides merdae* (species) (e.g., gut site); *Lactobacillus crispatus* (species) (e.g., gut site); *Actinobacillus porcinus* (species) (e.g., gut site); Pseudomonadales (order) (e.g., gut site); Coriobacteriaceae (family) (e.g., gut site); *Gemella* sp. 933-88 (species) (e.g., gut site); Coriobacteriales (order) (e.g., gut site); Bifidobacteriales (order) (e.g., gut site); *Blautia luti* (species) (e.g., gut site); Enterobacteriales (order) (e.g., gut site); *Bacteroides* sp. AR29 (species) (e.g., gut site); *Collinsella* (genus) (e.g., gut site); *Granulicatella* (genus) (e.g., gut site); *Roseburia intestinalis* (species) (e.g., gut site); Bacteroidales (order) (e.g., gut site); Rikenellaceae (family) (e.g., gut site); Prevotellaceae (family) (e.g., gut site); Carnobacteriaceae (family) (e.g., gut site); *Dorea* (genus) (e.g., gut site); Bacteroidia (class) (e.g., gut site); Actinobacteria (phylum) (e.g., gut site); Neisseriales (order) (e.g., gut site); *Faecalibacterium* (genus) (e.g., gut site); *Alistipes* (genus) (e.g., gut site); *Subdoligranulum* (genus) (e.g., gut site); *Peptostreptococcus stomatis* (species) (e.g., gut site); *Moryella* (genus) (e.g., gut site); Ruminococcaceae (family) (e.g., gut site); *Roseburia* sp. 11SE39 (species) (e.g., gut site); Selenomonadales (order) (e.g., gut site); Acidaminococcaceae (family) (e.g., gut site); Negativicutes (class) (e.g., gut site); *Fusobacterium* sp. CM22 (species) (e.g., gut site); *Fusicatenibacter saccharivorans* (species) (e.g., gut site); *Fusicatenibacter* (genus) (e.g., gut site); *Herbaspirillum* (genus) (e.g., gut site); *Herbaspirillum seropedicae* (species) (e.g., gut site); Oxalobacteraceae (family) (e.g., gut site); *Dorea longicatena* (species) (e.g., gut site); *Intestinibacter* (genus) (e.g., gut site); *Citrobacter* (genus) (e.g., gut site); *Kluyvera* (genus) (e.g., gut site); *Bacteroides fragilis* (species) (e.g., gut site); *Bacteroides thetaiotaomicron* (species) (e.g., gut site); *Bacteroides uniformis* (species) (e.g., gut site); *Desulfovibrio* sp. (species) (e.g., gut site); *Acidaminococcus* (genus) (e.g., gut site); *Lactococcus* (genus) (e.g., gut site); *Erysipelatoclostridium ramosum* (species) (e.g., gut site); *Eubacterium* (genus) (e.g., gut site); *Sutterella wadsworthensis* (species) (e.g., gut site); *Lactobacillus rhamnosus* (species) (e.g., gut site); *Eubacterium callanderi* (species) (e.g., gut site); *Holdemania* (genus) (e.g., gut site); *Holdemania filiformis* (species) (e.g., gut site); Fibrobacteres (phylum) (e.g., gut site); *Kluyvera georgiana* (species) (e.g., gut site); *Collinsella aerofaciens* (species) (e.g., gut site); Rhodocyclaceae (family) (e.g., gut site); *Eggerthella* (genus) (e.g., gut site); *Pseudoflavonifractor capillosus* (species) (e.g., gut site); *Oscillospira* (genus) (e.g., gut site); *Shuttleworthia* (genus) (e.g., gut site); Eubacteriaceae (family) (e.g., gut site); Fibrobacteria (class) (e.g., gut site); Rhodocyclales (order) (e.g., gut site); Oscillospiraceae (family) (e.g., gut site); *Bifidobacterium longum* (species) (e.g., gut site); Fibrobacterales (order) (e.g., gut site); *Bacteroides nordii* (species) (e.g., gut site); *Flavonifractor plautii* (species) (e.g., gut site); *Roseburia hominis* (species) (e.g., gut site); *Lactonifactor longoviformis* (species) (e.g., gut site); *Bacteroides* sp. XB12B (species) (e.g., gut site); *Barnesiella* (genus) (e.g., gut site); *Lactonifactor* (genus) (e.g., gut site); *Adlercreutzia equolifaciens* (species) (e.g., gut site); *Adlercreutzia* (genus) (e.g., gut site); *Oscillibacter* (genus) (e.g., gut site); *Gordonibacter pamelaeae* (species) (e.g., gut site); *Cloacibacillus* (genus) (e.g., gut site); *Cloacibacillus evryensis* (species) (e.g., gut site); *Acidaminococcus* sp. D21 (species) (e.g., gut site); *Parasutterella* (genus) (e.g., gut site); *Bifidobacterium stercoris* (species) (e.g., gut site); *Hydrogenoanaerobacterium* (genus) (e.g., gut site); *Bifidobacterium kashiwanohense* (species) (e.g., gut site); *Gordonibacter* (genus) (e.g., gut site); *Anaerostipes* sp. 3_2_56FAA (species) (e.g., gut site); *Blautia* sp. Ser8 (species) (e.g., gut site); *Lactobacillus* sp. TAB-30 (species) (e.g., gut site); *Eggerthella* sp. HGA1 (species) (e.g., gut site); *Lactococcus* sp. MH5-2 (species) (e.g., gut site); *Flavonifractor* (genus) (e.g., gut site); *Enterococcus* sp. C6I11 (species) (e.g., gut site); *Pseudoflavonifractor* (genus) (e.g., gut site); *Dielma fastidiosa* (species) (e.g., gut site); *Intestinimonas butyriciproducens* (species) (e.g., gut site); *Intestinimonas* (genus) (e.g., gut site); *Eisenbergiella* (genus) (e.g., gut site); *Eisenbergiella tayi* (species) (e.g., gut site); *Candidatus Soleaferrea* (genus) (e.g., gut site); *Dielma* (genus) (e.g., gut site); *Lactobacillus johnsonii* (species) (e.g., gut site); *Citrobacter amalonaticus* (species) (e.g., gut site); *Roseburia* sp. 499 (species) (e.g., gut site); *Lactobacillus salivarius* (species) (e.g., gut site); *Anaerostipes butyraticus* (species) (e.g., gut site); *Cellulosilyticum* (genus) (e.g., gut site); *Anaerostipes* sp. 1y-2 (species) (e.g., gut site); *Bacteroides* sp. C13EG172 (species) (e.g., gut site); *Lactobacillus delbrueckii* (species) (e.g., gut site); *Anaerosporobacter mobilis* (species) (e.g., gut site); *Enterococcus faecalis* (species) (e.g., gut site); *Acinetobacter* (genus) (e.g., mouth site); *Haemophilus influenzae* (species) (e.g., nose site); *Corynebacterium* sp. (species) (e.g., skin site); *Finegoldia* (genus) (e.g., skin site); Aerococcaceae (family) (e.g., skin site); *Finegoldia* sp. S9 AA1-5 (species) (e.g., skin site); *Stenotrophomonas* (genus) (e.g., skin site); *Corynebacterium ulcerans* (species) (e.g., skin site); Rhodospirillales (order) (e.g., skin site); Bacteroidaceae (family) (e.g., gut site); *Bacteroides* (genus) (e.g., gut site); *Bacteroides vulgatus* (species) (e.g., gut site); *Parabacteroides distasonis* (species) (e.g., gut site); *Faecalibacterium prausnitzii* (species) (e.g., gut site); *Megasphaera* (genus) (e.g., gut site); Bacteroidetes (phylum) (e.g., gut site); Gammaproteobacteria (class) (e.g., gut site); Firmicutes (phylum) (e.g., gut site); *Sarcina* (genus) (e.g., gut site); *Lactobacillus* (genus) (e.g., gut site); *Bifidobacterium* (genus) (e.g., gut site); Actinomycetales (order) (e.g., gut site); *Lachnospira* (genus) (e.g., gut site); *Alistipes putredinis* (species) (e.g., gut site); Alphaproteobacteria (class) (e.g., gut site); Deltaproteobacteria (class) (e.g., gut site); Bifidobacteriaceae (family) (e.g., gut site); Mollicutes (class) (e.g., gut site); Clostridiaceae (family) (e.g., gut site); *Phascolarctobacterium* (genus) (e.g., gut site); *Phascolarctobacterium faecium* (species) (e.g., gut site); *Dorea formicigenerans* (species) (e.g., gut site); *Sutterella* (genus) (e.g., gut site); *Parabacteroides merdae* (species) (e.g., gut site); Flavobacteriaceae (family) (e.g., gut site); Verrucomicrobia (phylum) (e.g., gut site); Enterococcaceae (family) (e.g., gut site); Bifidobacteriales (order) (e.g., gut site); *Bacteroides acidifaciens* (species) (e.g., gut site); *Blautia luti* (species) (e.g., gut site); *Bacteroides* sp. AR20 (species) (e.g., gut site); *Bacteroides* sp. AR29 (species) (e.g., gut site); *Collinsella* (genus) (e.g., gut site); Flavobacteriia (class) (e.g., gut site); Erysipelotrichaceae (family) (e.g., gut site); Bacteroidales (order) (e.g., gut site); Rikenellaceae (family) (e.g., gut site); Porphyromonadaceae (family) (e.g., gut site); Clostridia (class) (e.g., gut site); Clostridiales (order) (e.g., gut site); *Dorea* (genus) (e.g., gut site); Desulfovibrionaceae (family) (e.g., gut site); Bacteroidia (class) (e.g., gut site); Flavobacteriales (order) (e.g., gut site); Desulfovibrionales (order) (e.g., gut site); *Subdoligranulum variabile* (species) (e.g., gut site); *Faecalibacterium* (genus) (e.g., gut site); *Alistipes* (genus) (e.g., gut site); *Subdoligranulum* (genus) (e.g., gut site); *Roseburia inulinivorans* (species) (e.g., gut site); *Parabacteroides* (genus) (e.g., gut site); *Moryella* (genus) (e.g., gut site); Erysipelotrichia (class) (e.g., gut site); Erysipelotrichales (order) (e.g., gut site); Ruminococcaceae (family) (e.g., gut site); Tenericutes (phylum) (e.g., gut site); *Blautia* (genus) (e.g., gut site); *Roseburia* sp. 11SE39 (species) (e.g., gut site); *Bacteroides* sp. D22 (species) (e.g., gut site); Acidaminococcaceae (family) (e.g., gut site); *Bacteroides* sp. SLC1-38 (species) (e.g., gut site); *Anaerostipes* sp. 5_1_63FAA (species) (e.g., gut site); *Fusicatenibacter saccharivorans* (species) (e.g., gut site); *Fusicatenibacter* (genus) (e.g., gut site); *Lachnospira pectinoschiza* (species) (e.g., gut site); Verrucomicrobiales (order) (e.g., gut site); *Dorea longicatena* (species) (e.g., gut site); Verrucomicrobiae (class) (e.g., gut site); Verrucomicrobiaceae (family) (e.g., gut site); Rhodospirillales (order) (e.g., gut site); *Akkermansia* (genus) (e.g., gut site); *Corynebacterium freiburgense* (species) (e.g., gut site); *Lactobacillus* sp. 7_1_47FAA (species) (e.g., gut site); *Intestinibacter* (genus) (e.g., gut site); *Bacteroides fragilis* (species) (e.g., gut site); *Bacteroides thetaiotaomicron* (species) (e.g., gut site); *Bacteroides uniformis* (species) (e.g., gut site); *Streptococcus agalactiae* (species) (e.g., gut site); *Enterococcus* (genus) (e.g., gut site); *Lactococcus* (genus) (e.g., gut site); *Erysipelatoclostridium ramosum* (species) (e.g., gut site); *Odoribacter splanchnicus* (species) (e.g., gut site); *Bilophila* (genus) (e.g., gut site); *Sutterella wadsworthensis* (species) (e.g., gut site); Rhodospirillaceae (family) (e.g., gut site); *Butyrivibrio crossotus* (species) (e.g., gut site); *Bacteroides stercoris* (species) (e.g., gut site); *Lactobacillus rhamnosus* (species) (e.g., gut site); *Holdemania* (genus) (e.g., gut site); *Holdemania filiformis* (species) (e.g., gut site); *Collinsella aerofaciens* (species) (e.g., gut site); *Eggerthella* (genus) (e.g., gut site); *Pseudoflavonifractor capillosus* (species) (e.g., gut site); *Thalassospira* (genus) (e.g., gut site); *Bacteroides massiliensis* (species) (e.g., gut site); Oscillospiraceae (family) (e.g., gut site); *Akkermansia muciniphila* (species) (e.g., gut site); *Hespellia* (genus) (e.g., gut site); *Marvinbryantia* (genus) (e.g., gut site); *Odoribacter* (genus) (e.g., gut site); *Flavonifractor plautii* (species) (e.g., gut site); *Lactonifactor longoviformis* (species) (e.g., gut site); *Bacteroides* sp. XB12B (species) (e.g., gut site); *Barnesiella* (genus) (e.g., gut site); *Howardella* (genus) (e.g., gut site); *Howardella ureilytica* (species) (e.g., gut site); *Lactonifactor* (genus) (e.g., gut site); *Adlercreutzia equolifaciens* (species) (e.g., gut site); *Adlercreutzia* (genus) (e.g., gut site); *Alistipes* sp. EBA6-25cl2 (species) (e.g., gut site); *Oscillibacter* (genus) (e.g., gut site); *Gordonibacter pamelaeae* (species) (e.g., gut site); *Alistipes* sp. NML05A004 (species) (e.g., gut site); *Barnesiella intestinihominis* (species) (e.g., gut site); *Blautia glucerasea* (species) (e.g., gut site); *Butyricimonas* (genus) (e.g., gut site); *Enterorhabdus* (genus) (e.g., gut site); *Robinsoniella* (genus) (e.g., gut site); *Bifidobacterium stercoris* (species) (e.g., gut site); *Gordonibacter* (genus) (e.g., gut site); *Slackia* sp. NATTS (species) (e.g., gut site); *Alistipes* sp. RMA 9912 (species) (e.g., gut site); *Anaerosporobacter* (genus) (e.g., gut site); *Anaerostipes* sp. 3_2_56FAA (species) (e.g., gut site); *Blautia* sp. Ser8 (species) (e.g., gut site); *Bilophila* sp. 4_1_30 (species) (e.g., gut site); *Eggerthella* sp. HGA1 (species) (e.g., gut site); *Lactococcus* sp. MH5-2 (species) (e.g., gut site); *Enterococcus* sp. SI-4 (species) (e.g., gut site); *Enterobacter* sp. BS2-1 (species) (e.g., gut site); *Pseudoflavonifractor* (genus) (e.g., gut site); *Dielma fastidiosa* (species) (e.g., gut site); *Blautia* sp. YHC-4 (species) (e.g., gut site); *Intestinimonas* (genus) (e.g., gut site); *Eisenbergiella* (genus) (e.g., gut site); *Eisenbergiella tayi* (species) (e.g., gut site); *Butyricimonas* sp. JCM 18677 (species) (e.g., gut site); *Dielma* (genus) (e.g., gut site); *Terrisporobacter* (genus) (e.g., gut site); *Bifidobacterium adolescentis* (species) (e.g., gut site).

Additionally or alternatively, performing a dairy allergy condition characterization process can be based on microbiome features (e.g., microbiome function features) associated with one or more of (e.g., such as in relation to a corresponding sample site): Nucleotide Metabolism (KEGG_Pathways_Level_2) (e.g., gut site); Biosynthesis of Other Secondary Metabolites (KEGG_Pathways_Level_2) (e.g., gut site); Excretory System (KEGG_Pathways_Level_2) (e.g., gut site); Neurodegenerative Diseases (KEGG_Pathways_Level_2) (e.g., gut site); Metabolism (KEGG_Pathways_Level_2) (e.g., gut site); Signaling Molecules and Interaction (KEGG_Pathways_Level_2) (e.g., gut site); Glycan Biosynthesis and Metabolism (KEGG_Pathways_Level_2) (e.g., gut site); Transcription (KEGG_Pathways_Level_2) (e.g., gut site); Translation (KEGG_Pathways_Level_2) (e.g., gut site); Transport and Catabolism (KEGG_Pathways_Level_2) (e.g., gut site); Replication and Repair (KEGG_Pathways_Level_2) (e.g., gut site); Cellular Processes and Signaling (KEGG_Pathways_Level_2) (e.g., gut site); Carbohydrate Metabolism (KEGG_Pathways_Level_2) (e.g., gut site); Genetic Information Processing (KEGG_Pathways_Level_2) (e.g., gut site); Environmental Adaptation (KEGG_Pathways_Level_2) (e.g., gut site); Bacterial chemotaxis (KEGG_Pathways_Level_3) (e.g., gut site); Cell cycle—*Caulobacter* (KEGG_Pathways_Level_3) (e.g., gut site); Membrane and intracellular structural molecules (KEGG_Pathways_Level_3) (e.g., gut site); Pentose and glucuronate interconversions (KEGG_Pathways_Level_3) (e.g., gut site); RNA polymerase (KEGG_Pathways_Level_3) (e.g., gut site); N-Glycan biosynthesis (KEGG_Pathways_Level_3) (e.g., gut site); Sulfur metabolism (KEGG_Pathways_Level_3) (e.g., gut site); Nucleotide excision repair (KEGG_Pathways_Level_3) (e.g., gut site); Biotin metabolism (KEGG_Pathways_Level_3) (e.g., gut site); Peptidoglycan biosynthesis (KEGG_Pathways_Level_3) (e.g., gut site); Aminoacyl-tRNA biosynthesis (KEGG_Pathways_Level_3) (e.g., gut site); Ascorbate and aldarate metabolism (KEGG_Pathways_Level_3) (e.g., gut site); Huntington_quote_s disease (KEGG_Pathways_Level_3) (e.g., gut site); RNA degradation (KEGG_Pathways_Level_3) (e.g., gut site); Primary bile acid biosynthesis (KEGG_Pathways_Level_3) (e.g., gut site); MAPK signaling pathway—yeast (KEGG_Pathways_Level_3) (e.g., gut site); Inositol phosphate metabolism (KEGG_Pathways_Level_3) (e.g., gut site); Amino acid metabolism (KEGG_Pathways_Level_3) (e.g., gut site); Glycosyltransferases (KEGG_Pathways_Level_3) (e.g., gut site); Others (KEGG_Pathways_Level_3) (e.g., gut site); Lipopolysaccharide biosynthesis proteins (KEGG_Pathways_Level_3) (e.g., gut site); Phosphatidylinositol signaling system (KEGG_Pathways_Level_3) (e.g., gut site); Pores ion channels (KEGG_Pathways_Level_3) (e.g., gut site); Biosynthesis and biodegradation of secondary metabolites (KEGG_Pathways_Level_3) (e.g., gut site); Phosphonate and phosphinate metabolism (KEGG_Pathways_Level_3) (e.g., gut site); Ribosome Biogenesis (KEGG_Pathways_Level_3) (e.g., gut site); Benzoate degradation (KEGG_Pathways_Level_3) (e.g., gut site); Translation proteins (KEGG_Pathways_Level_3) (e.g., gut site); Cell motility and secretion (KEGG_Pathways_Level_3) (e.g., gut site); Other ion-coupled transporters (KEGG_Pathways_Level_3) (e.g., gut site); D-Alanine metabolism (KEGG_Pathways_Level_3) (e.g., gut site); Bisphenol degradation (KEGG_Pathways_Level_3) (e.g., gut site); Glycosphingolipid biosynthesis—globo series (KEGG_Pathways_Level_3) (e.g., gut site); Circadian rhythm—plant (KEGG_Pathways_Level_3) (e.g., gut site); Lysosome (KEGG_Pathways_Level_3) (e.g., gut site); Proximal tubule bicarbonate reclamation (KEGG_Pathways_Level_3) (e.g., gut site); Inorganic ion transport and metabolism (KEGG_Pathways_Level_3) (e.g., gut site); Caffeine metabolism (KEGG_Pathways_Level_3) (e.g., gut site); Linoleic acid metabolism (KEGG_Pathways_Level_3) (e.g., gut site); Fatty acid elongation in mitochondria (KEGG_Pathways_Level_3) (e.g., gut site); Other glycan degradation (KEGG_Pathways_Level_3) (e.g., gut site); Germination (KEGG_Pathways_Level_3) (e.g., gut site); Type I diabetes mellitus (KEGG_Pathways_Level_3) (e.g., gut site); Phenylalanine metabolism (KEGG_Pathways_Level_3) (e.g., gut site); Glycosaminoglycan degradation (KEGG_Pathways_Level_3) (e.g., gut site); Fructose and man (e.g., nose site) metabolism (KEGG_Pathways_Level_3) (e.g., gut site); Terpenoid backbone biosynthesis (KEGG_Pathways_Level_3) (e.g., gut site); Penicillin and cephalosporin biosynthesis (KEGG_Pathways_Level_3) (e.g., gut site); Carbohydrate metabolism (KEGG_Pathways_Level_3) (e.g., gut site); Ribosome (KEGG_Pathways_Level_3) (e.g., gut site); Aminobenzoate degradation (KEGG_Pathways_Level_3) (e.g., gut site); Glyoxylate and dicarboxylate metabolism (KEGG_Pathways_Level_3) (e.g., gut site); Mismatch repair (KEGG_Pathways_Level_3) (e.g., gut site); Ion channels (KEGG_Pathways_Level_3) (e.g., gut site); Lipopolysaccharide biosynthesis (KEGG_Pathways_Level_3) (e.g., gut site); Geraniol degradation (KEGG_Pathways_Level_3) (e.g., gut site); Cytoskeleton proteins (KEGG_Pathways_Level_3) (e.g., gut site); Polyketide sugar unit biosynthesis (KEGG_Pathways_Level_3) (e.g., gut site); Cellular antigens (KEGG_Pathways_Level_3) (e.g., gut site); Ribosome biogenesis in eukaryotes (KEGG_Pathways_Level_3) (e.g., gut site); Protein digestion and absorption (KEGG_Pathways_Level_3) (e.g., gut site); Peroxisome (KEGG_Pathways_Level_3) (e.g., gut site); Lipoic acid metabolism (KEGG_Pathways_Level_3) (e.g., gut site); Sphingolipid metabolism (KEGG_Pathways_Level_3) (e.g., gut site); Amino sugar and nucleotide sugar metabolism (KEGG_Pathways_Level_3) (e.g., gut site); Signal transduction mechanisms (KEGG_Pathways_Level_3) (e.g., gut site); Bacterial toxins (KEGG_Pathways_Level_3) (e.g., gut site); Steroid hormone biosynthesis (KEGG_Pathways_Level_3) (e.g., gut site); Transcription factors (KEGG_Pathways_Level_3) (e.g., gut site); Pertussis (KEGG_Pathways_Level_3) (e.g., gut site); Transcription related proteins (KEGG_Pathways_Level_3) (e.g., gut site); Sporulation (KEGG_Pathways_Level_3) (e.g., gut site); Meiosis—yeast (KEGG_Pathways_Level_3) (e.g., gut site); Amino acid related enzymes (KEGG_Pathways_Level_3) (e.g., gut site); Streptomycin biosynthesis (KEGG_Pathways_Level_3) (e.g., gut site); Function unknown (KEGG_Pathways_Level_3) (e.g., gut site); Galactose metabolism (KEGG_Pathways_Level_3) (e.g., gut site); Systemic lupus erythematosus (KEGG_Pathways_Level_3) (e.g., gut site); Pyrimidine metabolism (KEGG_Pathways_Level_3) (e.g., gut site); Taurine and hypotaurine metabolism (KEGG_Pathways_Level_3) (e.g., gut site); Glycosphingolipid biosynthesis—ganglio series (KEGG_Pathways_Level_3) (e.g., gut site); Toluene degradation (KEGG_Pathways_Level_3) (e.g., gut site); Nicotinate and nicotinamide metabolism (KEGG_Pathways_Level_3) (e.g., gut site); DNA repair and recombination proteins (KEGG_Pathways_Level_3) (e.g., gut site); Glycosphingolipid biosynthesis—lacto and neolacto series (KEGG_Pathways_Level_3) (e.g., gut site); Ubiquinone and other terpenoid-quinone biosynthesis (KEGG_Pathways_Level_3) (e.g., gut site); "Replication recombination and repair proteins" (KEGG_Pathways_Level_3) (e.g., gut site); Plant-pathogen interaction (KEGG_Pathways_Level_3) (e.g., gut site); Ubiquitin system (KEGG_Pathways_Level_3) (e.g., gut site); Chromosome (KEGG_Pathways_Level_3) (e.g., gut site); Enzyme Families (KEGG_Pathways_Level_2) (e.g., gut site); Neurodegenerative Diseases (KEGG_Pathways_Level_2) (e.g., gut site); Metabolism (KEGG_Pathways_Level_2) (e.g., gut site); Metabolism of Cofactors and Vitamins (KEGG_Pathways_Level_2) (e.g., gut site); Translation (KEGG_Pathways_Level_2) (e.g., gut site); Lipid Metabolism (KEGG_Pathways_Level_2) (e.g., gut site); Replication and Repair (KEGG_Pathways_Level_2) (e.g., gut site); Cellular Processes and Signaling (KEGG_Pathways_Level_2) (e.g., gut site); Carbohydrate Metabolism (KEGG_Pathways_Level_2) (e.g., gut site); Genetic Information Processing (KEGG_Pathways_Level_2) (e.g., gut site); Pentose and glucuronate interconversions (KEGG_Pathways_Level_3) (e.g., gut site); RNA polymerase (KEGG_Pathways_Level_3) (e.g., gut site); Sulfur metabolism (KEGG_Pathways_Level_3) (e.g., gut site); Nucleotide excision repair (KEGG_Pathways_Level_3) (e.g., gut site); Peptidoglycan biosynthesis (KEGG_Pathways_Level_3) (e.g., gut site); Aminoacyl-tRNA biosynthesis (KEGG_Pathways_Level_3) (e.g., gut site); Ascorbate and aldarate metabolism (KEGG_Pathways_Level_3) (e.g., gut site); Huntington_quote_s disease (KEGG_Pathways_Level_3) (e.g., gut site); Primary bile acid biosynthesis (KEGG_Pathways_Level_3) (e.g., gut site); MAPK signaling pathway—yeast (KEGG_Pathways_Level_3) (e.g., gut site); Inositol phosphate metabolism (KEGG_Pathways_Level_3) (e.g., gut site); Others (KEGG_Pathways_Level_3) (e.g., gut site); Biosynthesis and biodegradation of secondary metabolites (KEGG_Pathways_Level_3) (e.g., gut site); Caprolactam degradation (KEGG_Pathways_Level_3) (e.g., gut site); Ribosome Biogenesis (KEGG_Pathways_Level_3) (e.g., gut site); Translation proteins (KEGG_Pathways_Level_3) (e.g., gut site); D-Alanine metabolism (KEGG_Pathways_Level_3) (e.g., gut site); Bisphenol degradation (KEGG_Pathways_Level_3) (e.g., gut site); "Valine leucine and isoleucine degradation" (KEGG_Pathways_Level_3) (e.g., gut site); Tryptophan metabolism (KEGG_Pathways_Level_3) (e.g., gut site); Linoleic acid metabolism (KEGG_Pathways_Level_3) (e.g., gut site); Pentose phosphate pathway (KEGG_Pathways_Level_3) (e.g., gut site); Other glycan degradation (KEGG_Pathways_Level_3) (e.g., gut site); Fructose and man (e.g., nose site) metabolism (KEGG_Pathways_Level_3) (e.g., gut site); Terpenoid backbone biosynthesis (KEGG_Pathways_Level_3) (e.g., gut site); Penicillin and cephalosporin biosynthesis (KEGG_Pathways_Level_3) (e.g., gut site); Polycyclic aromatic hydrocarbon degradation (KEGG_Pathways_Level_3) (e.g., gut site); Ribosome (KEGG_Pathways_Level_3) (e.g., gut site); Aminobenzoate degradation (KEGG_Pathways_Level_3) (e.g., gut site); Glyoxylate and dicarboxylate metabolism (KEGG_Pathways_Level_3) (e.g., gut site); Mismatch repair (KEGG_Pathways_Level_3) (e.g., gut site); Ribosome biogenesis in eukaryotes (KEGG_Pathways_Level_3) (e.g., gut site); Epithelial cell signaling in *Helicobacter pylori* infection (KEGG_Pathways_Level_3) (e.g., gut site); Lipoic acid metabolism (KEGG_Pathways_Level_3) (e.g., gut site); Sphingolipid metabolism (KEGG_Pathways_Level_3) (e.g., gut site); Type II diabetes mellitus (KEGG_Pathways_Level_3) (e.g., gut site); Pertussis (KEGG_Pathways_Level_3) (e.g., gut site); Transcription related proteins (KEGG_Pathways_Level_3) (e.g., gut site); Cysteine and methionine metabolism (KEGG_Pathways_Level_3) (e.g., gut site); Galactose metabolism (KEGG_Pathways_Level_3) (e.g., gut site); Nucleotide metabolism (KEGG_Pathways_Level_3) (e.g., gut site); Amyotrophic lateral sclerosis (ALS) (KEGG_Pathways_Level_3) (e.g., gut site); Homologous recombination (KEGG_Pathways_Level_3) (e.g., gut site); Nicotinate and nicotinamide metabolism (KEGG_Pathways_Level_3) (e.g., gut site); DNA repair and recombination proteins (KEGG_Pathways_Level_3) (e.g., gut site); Glycosphingolipid biosynthesis—lacto and neolacto series (KEGG_Pathways_Level_3) (e.g., gut site); "Replication recombination and repair proteins" (KEGG_Pathways_Level_3) (e.g., gut site); Chromosome (KEGG_Pathways_Level_3) (e.g., gut site); Amino Acid Metabolism (KEGG_Pathways_Level_2) (e.g., genital site), and/or other suitable function-related aspects.

Determining an allergy-related characterization of a user can include diagnosing a user with a dairy allergy condition based upon one or more of the above microbiome features and/or other suitable features described herein, such as in an additional or alterative manner to typical methods of diagnosis. However, features used in the dairy allergy characterization process can include any other suitable features (e.g., features useful for diagnostics), and performing the dairy allergy characterization process can be performed in any suitable manner.

3.4 Determining a Therapy Model.

Block S140 recites: generating a therapy model configured to modulate microorganism distributions in subjects characterized according to the characterization process. Block S140 functions to identify or predict therapies (e.g., probiotic-based therapies, phage-based therapies, small molecule-based therapies, etc.) that can shift a subject's microbiome composition and/or functional features toward a desired equilibrium state in promotion of the subject's health. In Block S140, the therapies can be selected from therapies including one or more of: probiotic therapies, phage-based therapies, small molecule-based therapies, cognititive/behavioral therapies, physical rehabilitation therapies, clinical therapies, medication-based therapies, diet-related therapies, and/or any other suitable therapy designed to operate in any other suitable manner in promoting a user's health. In a specific example of a bacteriophage-based therapy, one or more populations (e.g., in terms of colony forming units) of bacteriophages specific to a certain bacteria (or other microorganism) represented in the subject can be used to down-regulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used.

Figure 4:
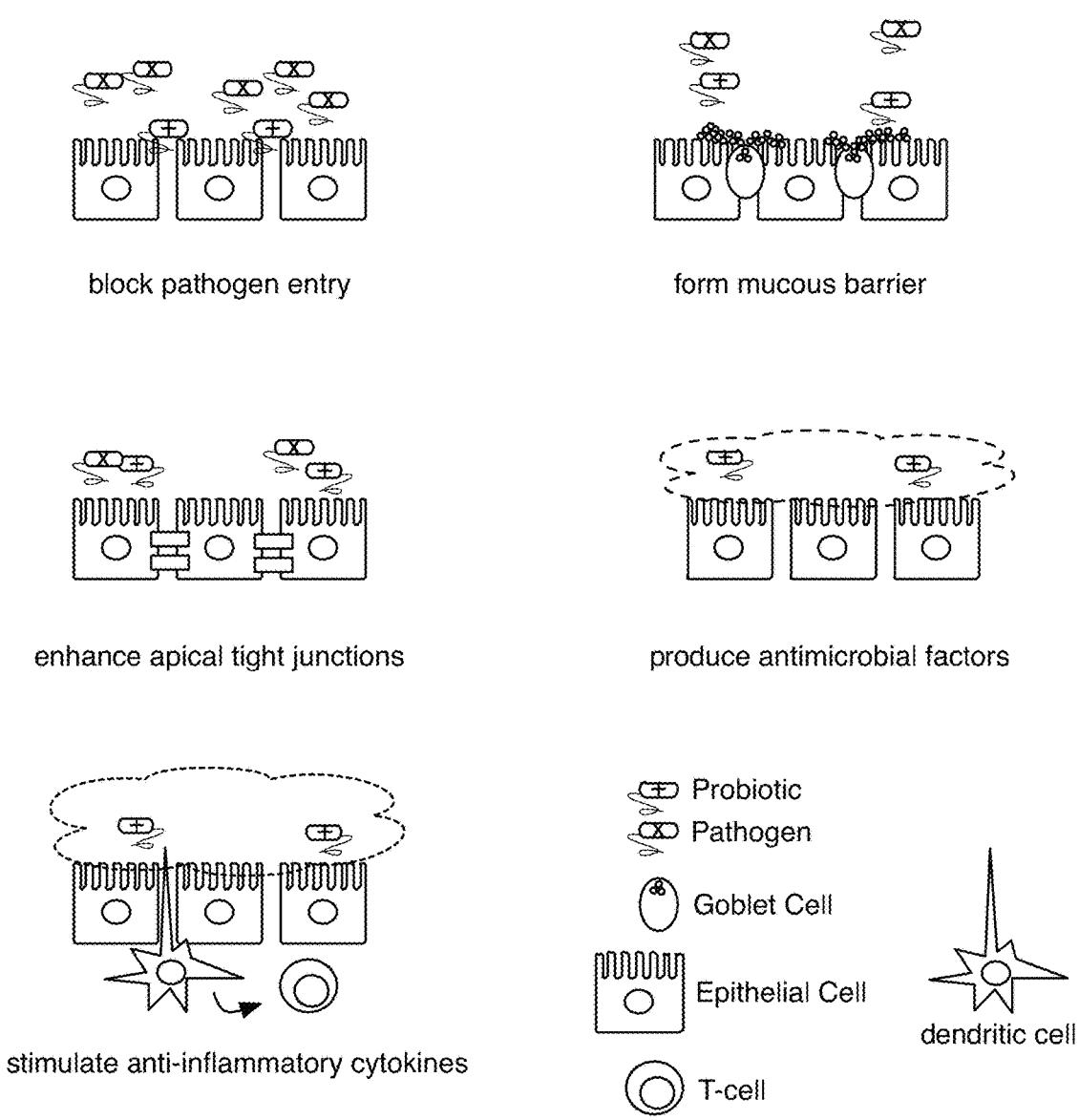
FIG. 4 depicts variations of mechanisms by which probiotic-based therapies operate in an embodiment of a method.

In another specific example of probiotic therapies, as shown in FIG. 4, candidate therapies of the therapy model can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a subject (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a subject's microbiome away from a state of dysbiosis.

In another specific example, therapies can include medical-device based therapies (e.g., allergen detection devices; allergen medication provision devices; etc.).

In variations, the therapy model is preferably based upon data from a large population of subjects, which can include the population of subjects from which the microbiome diversity datasets are derived in Block S110, where microbiome composition and/or functional features or states of health, prior exposure to and post exposure to a variety of therapeutic measures, are well characterized. Such data can be used to train and validate the therapy provision model, in identifying therapeutic measures that provide desired outcomes for subjects based upon different microbiome characterizations. In variations, support vector machines, as a supervised machine learning algorithm, can be used to generate the therapy provision model. However, any other suitable machine learning algorithm described above can facilitate generation of the therapy provision model.

While some methods of statistical analyses and machine learning are described in relation to performance of the Blocks above, variations of the method 100 can additionally or alternatively utilize any other suitable algorithms in performing the characterization process. In variations, the algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the algorithm(s) can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of algorithm.

Additionally or alternatively, the therapy model can be derived in relation to identification of a "normal" or baseline microbiome composition and/or functional features, as assessed from subjects of a population of subjects who are identified to be in good health. Upon identification of a subset of subjects of the population of subjects who are characterized to be in good health (e.g., using features of the characterization process), therapies that modulate microbiome compositions and/or functional features toward those of subjects in good health can be generated in Block S140. Block S140 can thus include identification of one or more baseline microbiome compositions and/or functional features (e.g., one baseline microbiome for each of a set of demographics), and potential therapy formulations and therapy regimens that can shift microbiomes of subjects who are in a state of dysbiosis toward one of the identified baseline microbiome compositions and/or functional features. The therapy model can, however, be generated and/or refined in any other suitable manner.

Microorganism compositions associated with probiotic therapies associated with the therapy model preferably include microorganisms that are culturable (e.g., able to be expanded to provide a scalable therapy) and non-lethal (e.g., non-lethal in their desired therapeutic dosages). Furthermore, microorganism compositions can include a single type of microorganism that has an acute or moderated effect upon a subject's microbiome. Additionally or alternatively, microorganism compositions can include balanced combinations of multiple types of microorganisms that are configured to cooperate with each other in driving a subject's microbiome toward a desired state. For instance, a combination of multiple types of bacteria in a probiotic therapy can include a first bacteria type that generates products that are used by a second bacteria type that has a strong effect in positively affecting a subject's microbiome. Additionally or alternatively, a combination of multiple types of bacteria in a probiotic therapy can include several bacteria types that produce proteins with the same functions that positively affect a subject's microbiome.

Probiotic compositions can be naturally or synthetically derived. For instance, in one application, a probiotic composition can be naturally derived from fecal matter or other biological matter (e.g., of one or more subjects having a baseline microbiome composition and/or functional features, as identified using the characterization process and the therapy model). Additionally or alternatively, probiotic compositions can be synthetically derived (e.g., derived using a benchtop method) based upon a baseline microbiome composition and/or functional features, as identified using the characterization process and the therapy model. In variations, microorganism agents that can be used in probiotic therapies can include one or more of: yeast (e.g., *Saccharomyces boulardii*), gram-negative bacteria (e.g., *E. coli Nissle*), gram-positive bacteria (e.g., *Bifidobacteria bifidum, Bifidobacteria infantis, Lactobacillus rhamnosus, Lactococcus lactis, Lactobacillus plantarum, Lactobacillus acidophilus, Lactobacillus casei, Bacillus polyfermenticus*, etc.), and any other suitable type of microorganism agent.

In a variation, for subjects who exhibit a wheat allergy condition, a probiotic therapy can include a combination of one or more of: *Blautia luti, Collinsella aerofaciens, Flavonifractor plautii, Faecalibacterium prausnitzii, Dorea formicigenerans, Subdoligranulum variabile, Barnesiella intestinihominis, Bacteroides thetaiotaomicron, Roseburia inulinivorans, Parasutterella excrementihominis, Bifidobacterium longum, Erysipelatoclostridium ramosum, Bacteroides fragilis, Bacteroides vulgatus, Bacteroides caccae, Blautia sp. YHC-4, Alistipes putredinis* and/or any other suitable microorganisms (e.g., associated with microbiome features described in relation to the wheat allergy condition) and/or phage vector (e.g., bacteriophage, virus, etc.).

In another variation, for subjects who exhibit a treenut allergy condition, a probiotic therapy can include a combination of one or more of: *Blautia luti, Collinsella aerofaciens, Parabacteroides distasonis, Flavonifractor plautii, Bacteroides fragilis, Dorea formicigenerans, Roseburia inulinivorans*, and/or any other suitable microorganisms (e.g., associated with microbiome features described in relation to the treenut condition) and/or phage vector (e.g., bacteriophage, virus, etc.).

In another variation, for subjects who exhibit a shellfish allergy condition, a probiotic therapy can include a combination of one or more of: *Parabacteroides distasonis* and/or any other suitable microorganisms (e.g., associated with microbiome features described in relation to the shellfish allergy condition) and/or phage vector (e.g., bacteriophage, virus, etc.).

In another variation, for subjects who exhibit a soy allergy condition, a probiotic therapy can include a combination of one or more of: *Blautia luti, Collinsella aerofaciens, Dorea formicigenerans, Flavonifractor plautii, Subdoligranulum variabile, Faecalibacterium prausnitzii, Barnesiella intestinihominis, Roseburia inulinivorans, Blautia sp. YHC-4, Bacteroides caccae, Erysipelatoclostridium ramosum, Bacteroides thetaiotaomicron, Odoribacter splanchnicus, Bacteroides fragilis, Parabacteroides distasonis*, and/or any other suitable microorganisms (e.g., associated with microbiome features described in relation to the soy allergy condition) and/or phage vector (e.g., bacteriophage, virus, etc.).

In another variation, for subjects who exhibit a peanut allergy condition, a probiotic therapy can include a combination of one or more of: *Flavonifractor plautii, Blautia luti, Collinsella aerofaciens, Dorea formicigenerans, Barnesiella intestinihominis*, and/or any other suitable microorganisms (e.g., associated with microbiome features described in relation to the peanut allergy condition) and/or phage vector (e.g., bacteriophage, virus, etc.).

In another variation, for subjects who exhibit an egg allergy condition, a probiotic therapy can include a combination of one or more of: *Blautia luti, Collinsella aerofaciens, Subdoligranulum variabile, Flavonifractor plautii, Faecalibacterium prausnitzii, Alistipes putredinis, Roseburia inulinivorans, Bacteroides caccae, Barnesiella intestinihominis, Parabacteroides distasonis, Odoribacter splanchnicus, Dorea formicigenerans*, and/or any other suitable microorganisms (e.g., associated with microbiome features described in relation to the egg allergy condition) and/or phage vector (e.g., bacteriophage, virus, etc.).

Probiotics and/or other suitable consumables can be provided at dosages of 0.1 million to 10 billion CFUs (and/or other suitable dosages), such as determined from a therapy model that predicts positive adjustment of a patient's microbiome in response to the therapy. In a specific example, a subject can be instructed to ingest capsules including the probiotic formulation according to a regimen tailored to one or more of his/her: physiology (e.g., body mass index, weight, height), demographics (e.g., gender, age), severity of dysbiosis, sensitivity to medications, and any other suitable factor.

For subjects who exhibit an allergy-related condition, associated-microorganisms (e.g., corresponding to correlated microbiome composition features) can provide a dataset based on composition and/or diversity of recognizable patterns of relative abundance in microorganisms that are present in subject microbiome, and can be used as a diagnostic tool using bioinformatics pipelines and characterization describe above.

3.5 Processing a User Biological Sample.

The method 100 can additionally or alternatively include Block S150, which recites: processing one or more biological samples from a user (e.g., subject). Block S150 can function to facilitate generation of a microbiome dataset for the subject that can be used to derive inputs for the characterization process (e.g., for generating an allergy-related characterization for the user, etc.). As such, Block S150 can include receiving, processing, and/or analyzing one or more biological samples from one or more users (e.g., multiple biological samples for the same user over time, different biological samples for different users, etc.). In Block S150, the biological sample is preferably generated from the subject and/or an environment of the subject in a non-invasive manner. In variations, non-invasive manners of sample reception can use any one or more of: a permeable substrate (e.g., a swab configured to wipe a region of a subject's body, toilet paper, a sponge, etc.), a non-permeable substrate (e.g., a slide, tape, etc.) a container (e.g., vial, tube, bag, etc.) configured to receive a sample from a region of a subject's body, and any other suitable sample-reception element. In a specific example, the biological sample can be collected from one or more of the subject's nose, skin, genitals, mouth, and gut in a non-invasive manner (e.g., using a swab and a vial). However, the biological sample can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can include blood samples, plasma/serum samples (e.g., to enable extraction of cell-free DNA), and tissue samples.

In the above variations and examples, the biological sample can be taken from the body of the subject without facilitation by another entity (e.g., a caretaker associated with a subject, a health care professional, an automated or semi-automated sample collection apparatus, etc.), or can alternatively be taken from the body of the subject with the assistance of another entity. In one example, where the biological sample is taken from the subject without facilitation by another entity in the sample extraction process, a sample-provision kit can be provided to the subject. In the example, the kit can include one or more swabs for sample acquisition, one or more containers configured to receive the swab(s) for storage, instructions for sample provision and setup of a user account, elements configured to associate the sample(s) with the subject (e.g., barcode identifiers, tags, etc.), and a receptacle that allows the sample(s) from the subject to be delivered to a sample processing operation (e.g., by a mail delivery system). In another example, where the biological sample is extracted from the subject with the help of another entity, one or more samples can be collected in a clinical or research setting from the subject (e.g., during a clinical appointment). The biological sample can, however, be received from the subject in any other suitable manner.

Furthermore, processing and analyzing the biological sample (e.g., to generate a user microbiome dataset; etc.) from the subject is preferably performed in a manner similar to that of one of the embodiments, variations, and/or examples of sample reception described in relation to Block S110 above, and/or any other suitable portions of the method 100. As such, reception and processing of the biological sample in Block S150 can be performed for the subject using similar processes as those for receiving and processing biological samples used to generate the characterization process and/or the therapy model of the method 100, in order to provide consistency of process. However, biological sample reception and processing in Block S150 can alternatively be performed in any other suitable manner.

3.6 Determining an Allergy-Related Characterization.

The method 100 can additionally or alternatively include Block S160, which recites: determining, with the characterization process, an allergy-related characterization for the user based upon processing a microbiome dataset (e.g., user microorganism sequence dataset, microbiome composition dataset, microbiome functional diversity dataset, etc.) derived from the biological sample of the user. Block S160 can function to characterize one or more allergy-related conditions for a user, such as through extracting features from microbiome-derived data of the subject, and using the features as inputs into an embodiment, variation, or example of the characterization process described in Block S130 above. In an example, Block S160 can include generating an allergy-related characterization for the user based on user microbiome features and an allergy-related condition characterization model (e.g., generated in Block S130). Allergy-related characterizations can be for any number and/or combination of allergy-related conditions (e.g., a combination of allergy-related conditions, a single allergy-related condition, and/or other suitable allergy-related conditions; etc.). Allergy-related characterizations can include one or more of: diagnoses (e.g., presence or absence of an allergy-related condition; etc.); allergy trigger profiles, risk (e.g., risk scores for developing and/or the presence of an allergy-related condition; information regarding allergy-related characterizations (e.g., symptoms, signs, triggers, associated conditions, etc.); comparisons (e.g., comparisons with other subgroups, populations, users, historic health statuses of the user such as historic microbiome compositions and/or functional diversities; comparisons associated with allergy-related conditions; etc.), and/or any other suitable allergy-related data.

Figure 7:
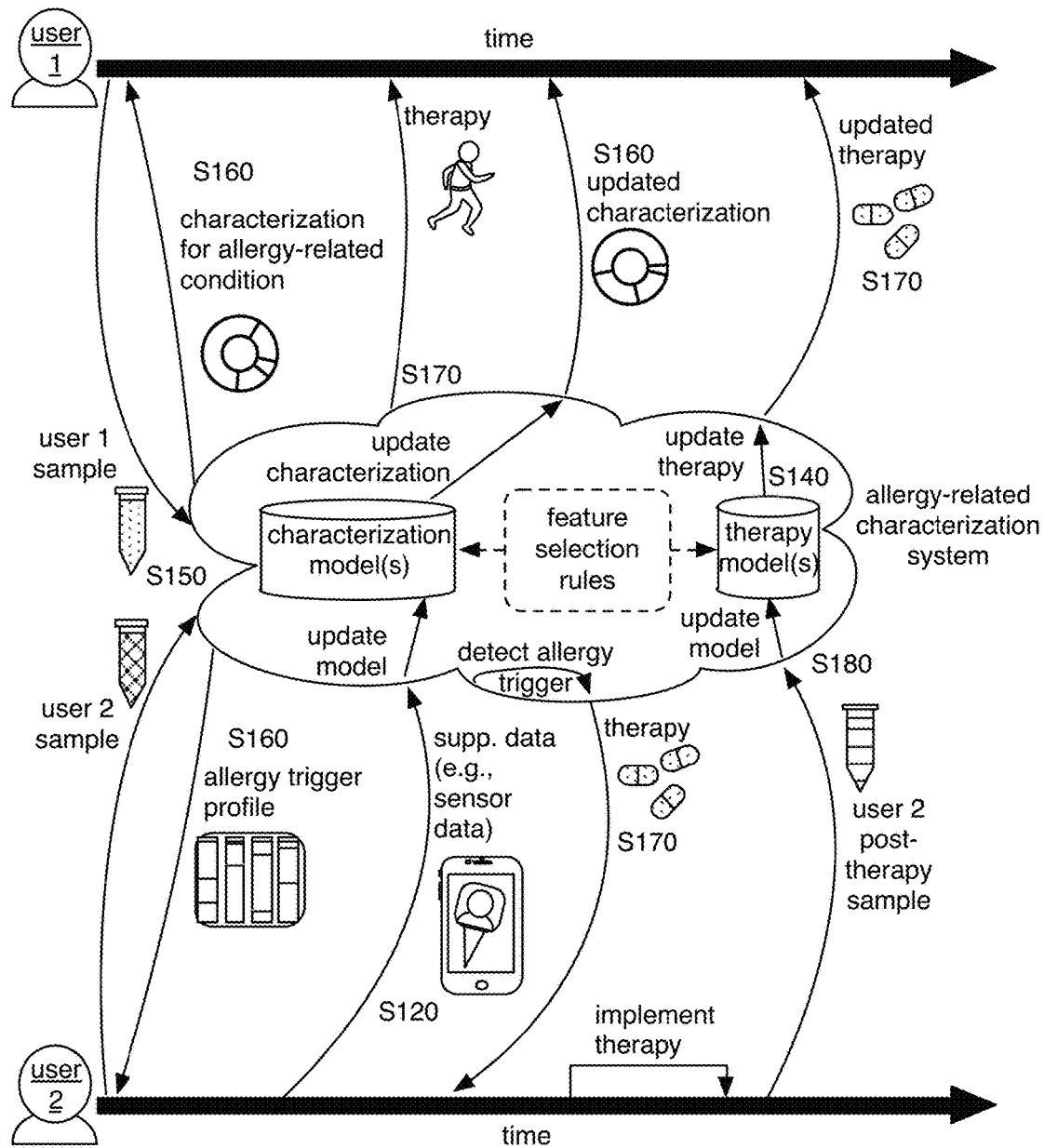
FIG. 7 depicts a schematic representation of variations of an embodiment of the method.

In a variation, as shown in FIG. 7, allergy-related characterization can include one or more allergy-related (e.g., wheat allergy) trigger profiles for the user, where the trigger profile can describe allergy triggers (e.g., conditions correlated with allergy-related symptoms; conditions indicating future allergy-related conditions; causes; presence of allergens; etc.) associated with the user (e.g., known to affect the user; predicted to affect the user, such as based on microbiome features, supplementary data, etc.). Allergy triggers can include any one or more of: dietary triggers (e.g., wheat, egg, treenut, peanut, soy, shellfish, caffeine, alcohol, food additives, salty foods, dietary habits, missing meals, too many meals, etc.); hormonal changes; stress; sensory stimuli (e.g., lights, sounds, smells, etc.); sleep triggers (e.g., sleep deprivation, sleep abundance, etc.); physical activity (e.g., excess physical activity, etc.); environmental triggers (e.g., weather, barometric pressure, etc.); medication-based triggers; animal-based triggers and/or any other suitable triggers. Allergy triggers and/or other allergy-related conditions can be associated with (e.g., correlated with, etc.) one or more of: family history, age, gender, weight, height, other demographic characteristics, and/or any other suitable supplementary data. In a specific example, generating an allergy-related characterization can include generating an allergy trigger profile for the user based on user microbiome features (e.g., and an allergy-related condition characterization model), and promoting (e.g., providing) a therapy operable to reduce allergy triggers indicated by the allergy trigger profile for the user. In examples, the method 100 can include detecting allergy triggers (e.g., allergy triggers) for a user based on a corresponding allergy-related trigger profile (e.g., for the user, for another user, etc.). In a specific example, the method 100 can include: detecting an allergy trigger based on the allergy trigger profile and user supplementary data including at least one of motion sensor data and location sensor data (e.g., indicating physical activity behaviors; user locations; mobility behaviors; other behaviors correlated with allergy triggers; etc.) collected from a mobile computing device (e.g., smartphone, smart watch, tablet, laptop, etc.) associated with the user; and promoting a therapy in response to detecting the allergy trigger (and/or other suitable allergy triggers; etc.). Additionally or alternatively, detecting allergy triggers in relation to an allergy-related trigger profile can be based on any one or more of: microbiome features (e.g., a microbiome composition indicating a high risk of allergy symptoms in response to certain allergy triggers; a microbiome functional diversity indicating a high risk of an allergy-related symptom during a future time period, such as within the next 24 hours, etc.), supplementary features (e.g., historic medical data for the user, sensor data, nutrition supplementary data, sleep data such as derived through sensor data, etc.), and/or any other suitable features.

In another variation, an allergy-related characterization can include a microbiome diversity score (e.g., in relation to microbiome composition, function, etc.) associated with (e.g., correlated with; negatively correlated with; positively correlated with; etc.) a microbiome diversity score correlated with the allergy-related condition. In an example, the method 100 can include promoting a nutrition-related therapy (e.g., probiotics; dietary regimen modifications; etc.) operable to improve the microbiome diversity score for improving a state of the allergy-related condition, such as based on an allergy-related characterization (e.g., including the microbiome diversity score for the user) and/or nutrition-related supplementary data collected from the user. In examples, the allergy-related characterization can include microbiome diversity scores over time (e.g., calculated for a plurality of biological samples of the user collected over time), comparisons to microbiome diversity scores for other users, and/or any other suitable type of microbiome diversity score. However, processing microbiome diversity scores (e.g., determining microbiome diversity scores; using microbiome diversity scores to determine and/or provide therapies; etc.) can be performed in any suitable manner.

Determining an allergy-related characterization in Block S160 preferably includes identifying features and/or combinations of features associated with the microbiome composition and/or functional features of the subject, inputting the features into the characterization process, and receiving an output that characterizes the subject as belonging to one or more of: a behavioral group, a gender group, a dietary group, a disease-state group, and any other suitable group capable of being identified by the characterization process. Block S160 can additionally or alternatively include generation of and/or output of a confidence metric associated with the characterization of the subject. For instance, a confidence metric can be derived from the number of features used to generate the characterization, relative weights or rankings of features used to generate the characterization, measures of bias in the characterization process, and/or any other suitable parameter associated with aspects of the characterization process. However, leveraging user microbiome features can be performed in any suitable manner to generate any suitable allergy-related characterizations.

In some variations, features extracted from the microbiome dataset of the subject can be supplemented with supplementary features (e.g., extracted from supplementary data collected for the user; such as survey-derived features, medical history-derived features, sensor data, etc.), where such data, the user microbiome data, and/or other suitable data can be used to further refine the characterization process of Block S130, Block S160, and/or other suitable portions of the method 100.

Determining an allergy-related characterization preferably includes extracting and applying user microbiome features (e.g., user microbiome composition diversity features; user microbiome functional diversity features; etc.) for the user (e.g., based on a user microbiome dataset), characterization models, and/or other suitable components, such as by employing approaches described in Block S130, and/or by employing any suitable approaches described herein.

Figure 6:
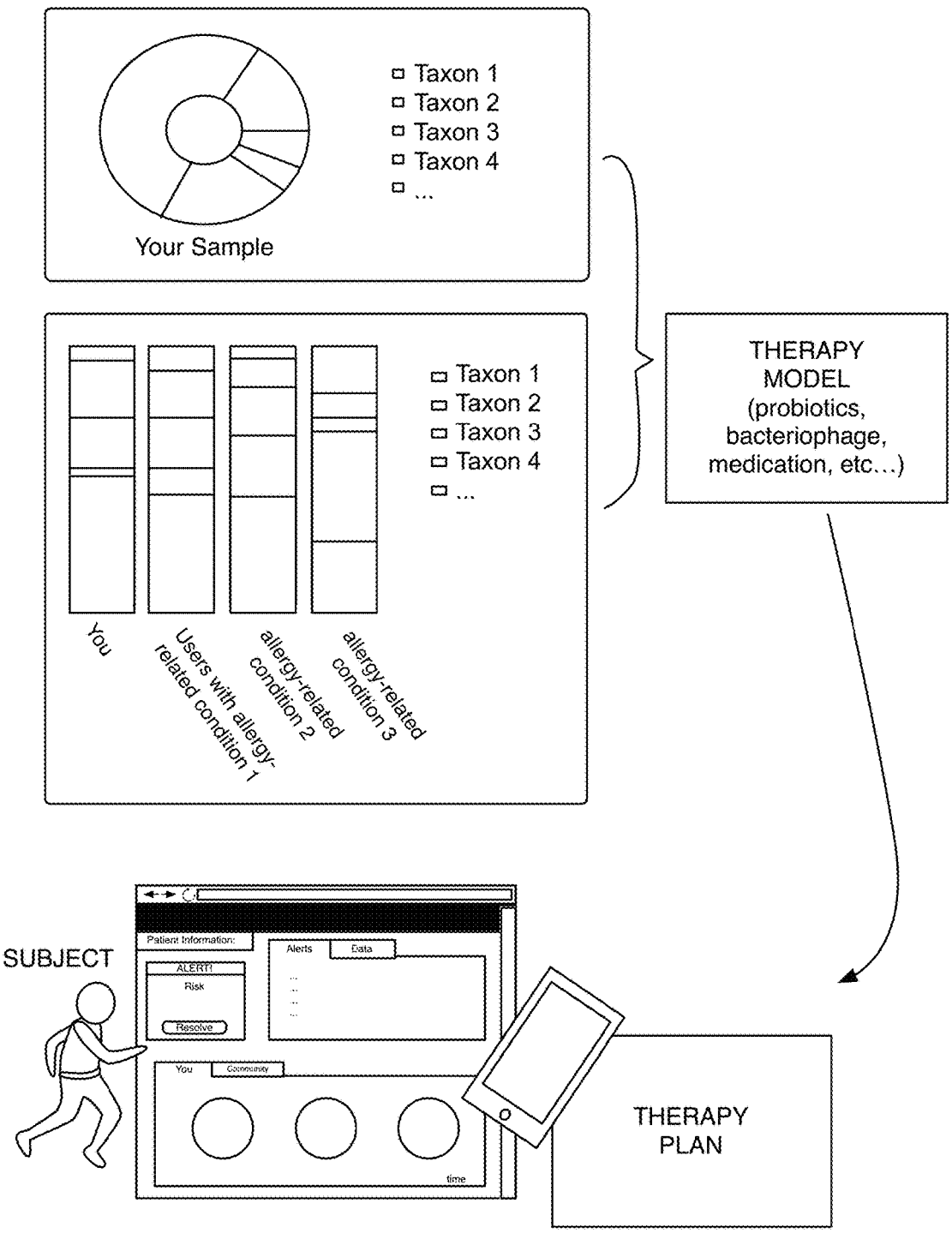
FIG. 6 depicts examples of notification provision.

In variations, as shown in FIG. 6, Block S160 can include presenting allergy-related characterizations (e.g., information extracted from the characterizations, etc.), such as an a web interface, a mobile application, and/or any other suitable interface, but presentation of allergy-related information can be performed in any suitable manner. However, the microbiome dataset of the subject can additionally or alternatively be used in any other suitable manner to enhance the models of the method 100, and Block S160 can be performed in any suitable manner.

3.7 Promoting a Therapy.

Figure 5:
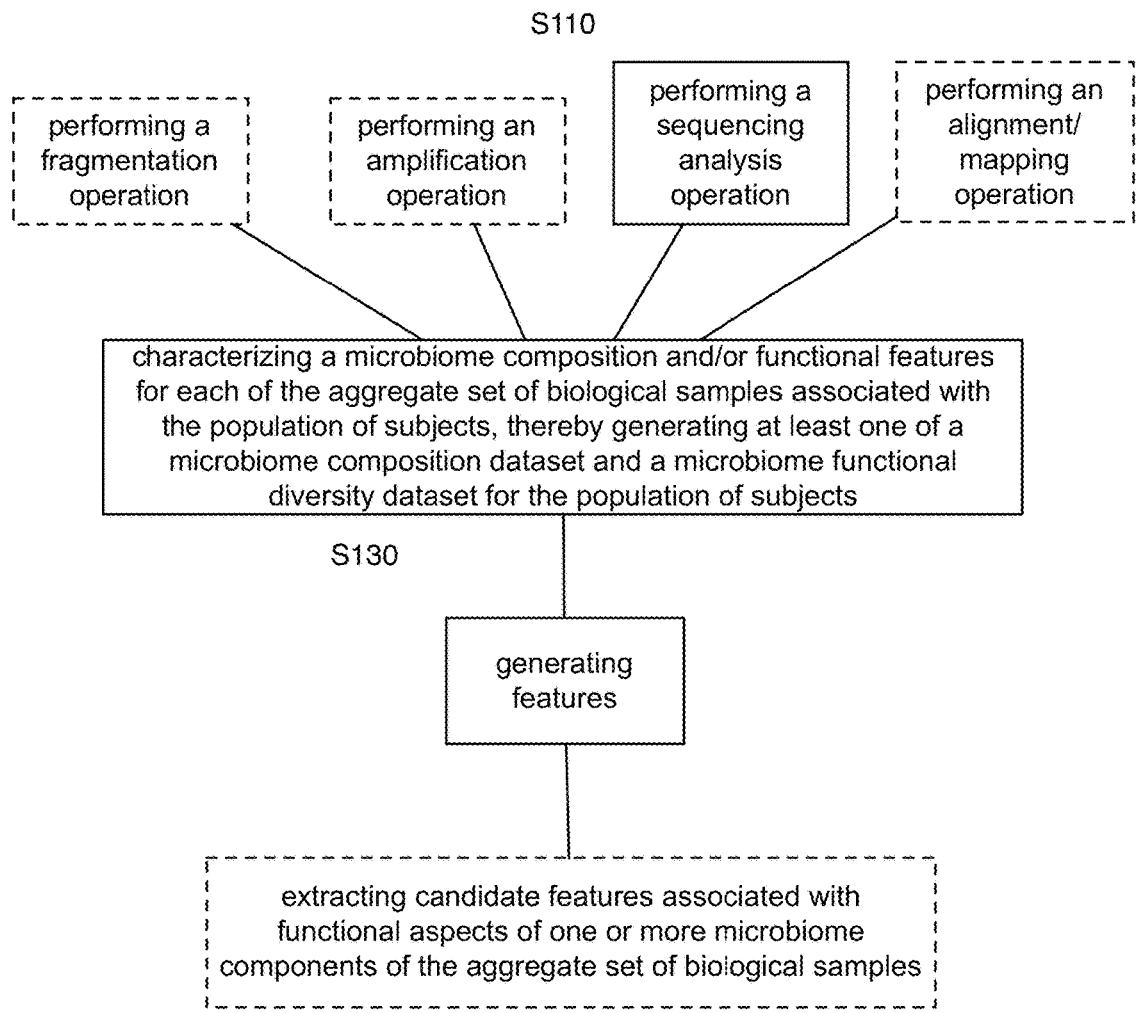
FIG. 5 depicts variations of sample processing in an embodiment of a method.
Figure 9:
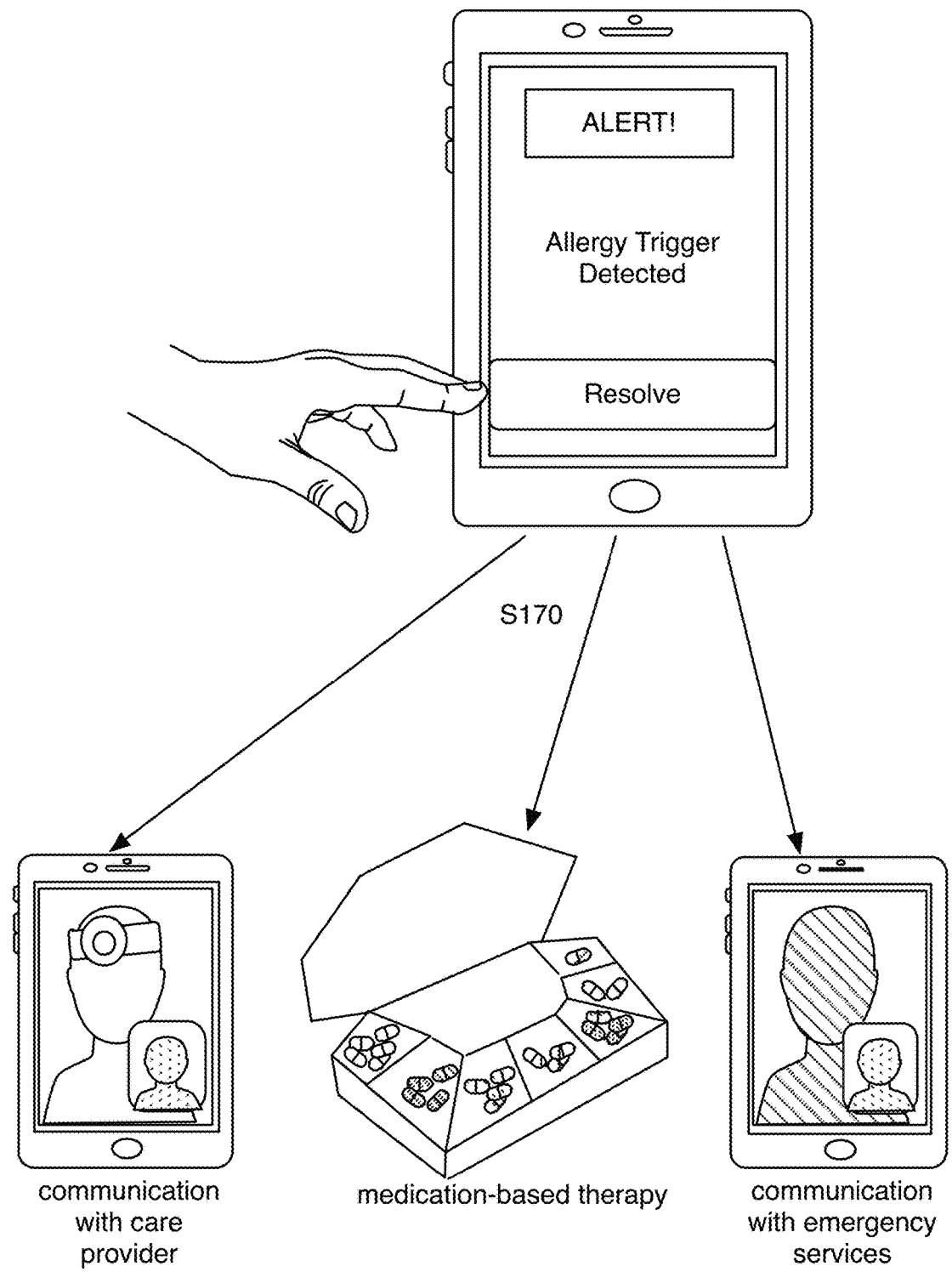
FIG. 9 depicts promoting a therapy in an embodiment of a method.

As shown in FIG. 9, the method 100 can additionally or alternatively include Block S110, which recites: promoting (e.g., providing, facilitating provision of, etc.) a therapy for the allergy-related condition to the user (e.g., based upon the allergy-related characterization and/or a therapy model). Block S110 can function to recommend or provide a personalized therapy to the subject, in order to shift the microbiome composition and/or functional diversity of a user toward a desired equilibrium state. Block S110 can include provision of a customized therapy to the subject according to their microbiome composition and functional features, as shown in FIG. 5, where the customized therapy is a formulation of microorganisms configured to correct dysbiosis characteristic of subjects having the identified characterization. As such, outputs of Block S140 can be used to directly promote a customized therapy formulation and regimen (e.g., dosage, usage instructions) to the subject based upon a trained therapy model. Additionally or alternatively, therapy provision can include recommendation of available therapeutic measures configured to shift microbiome composition and/or functional features toward a desired state. In variations, therapies can include any one or more of: consumables, topical therapies (e.g., lotions, ointments, antiseptics, etc.), medication (e.g., allergy medications, antihistamines, antibiotics, medication sprays such as nasal sprays, anticholinergic medication, steroid medication, eye drops, leukotriene inhibitors, mast cell inhibitors, allergy shots, medications associated with any suitable medication type and/or dosage, etc.), bacteriophages, environmental treatments (e.g., reducing and/or preventing environmental triggers, such as allergy-proofing a living space; dehumidifiers; pillow covers; dust reducers; acupuncture; etc.), behavioral modification (e.g., stress-reduction therapies, physical activity-related therapies, etc.), diagnostic procedures, other medical-related procedures, and/or any other suitable therapies associated with allergy-related conditions. Consumables can include any one or more of: food and/or beverage items (e.g., probiotic and/or prebiotic food and/or beverage items, etc.), nutritional supplements (e.g., vitamins, minerals, fiber, fatty acids, amino acids, prebiotics, probiotics, etc.), consumable medications, and/or any other suitable therapeutic measure. For example, a combination of commercially available probiotic supplements can include a suitable probiotic therapy for the subject according to an output of the therapy model. In another example, promoting a therapy can include providing, based on the food-related allergy characterization, a therapy enabling selective modulation of a microbiome of the user in relation to at least one of a population size of a desired taxon and a desired microbiome function, wherein the therapy is associated with improving a state of an allergy-related condition. In another example, the method 100 can include determining an allergy risk for the user for the allergy-related condition based on a allergy-related characterization model (e.g., and/or user microbiome features); determining an allergy-related trigger for the allergy-related condition based on the allergy risk; and promoting the therapy to the user based on the allergy-related trigger.

In a variation, promoting a therapy can include promoting a diagnostic procedure (e.g., for facilitating detection of allergy-related conditions, which can motivate subsequent promotion of other therapies, such as for modulation of a user microbiome for improving a user health state associated with one or more allergy-related conditions; etc.). Diagnostic procedures can include any one or more of: skin prick testing, patch testing, blood testing, challenge testing, performing portions of the method 100, and/or any other suitable procedures for facilitating the detecting (e.g., observing, predicting, etc.) of allergy-related conditions. Additionally or alternatively, diagnostic device-related information and/or other suitable diagnostic information can be processed as part of a supplementary dataset (e.g., in relation to Block S120, where such data can be used in determining and/or applying characterization models, therapy models, and/or other suitable models; etc.), and/or collected, used, and/or otherwise processed in relation to any suitable portions of the method 100 (e.g., administering diagnostic procedures for users for monitoring therapy efficacy in relation to Block S180; etc.)

In another variation, Block S110 can include promoting a bacteriophage-based therapy. In more detail, one or more populations (e.g., in terms of colony forming units) of bacteriophages specific to a certain bacteria (or other microorganism) represented in the subject can be used to downregulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used.

In another variation, therapy provision in Block S110 can include provision of notifications to a subject regarding the recommended therapy, other forms of therapy, allergy-related characterizations, and/or other suitable allergy-related data. In a specific example, providing a therapy to a user can include providing therapy recommendations (e.g., substantially concurrently with providing information derived from an allergy-related characterization for a user; etc.) and/or other suitable therapy-related information (e.g., therapy efficacy; comparisons to other individual users, subgroups of users, and/or populations of users; therapy comparisons; historic therapies and/or associated therapy-related information; etc.), such as through presenting notifications at a web interface (e.g., through a user account associated with and identifying a user; etc.). Notifications can be provided to a subject by way of an electronic device (e.g., personal computer, mobile device, tablet, wearable, head-mounted wearable computing device, wrist-mounted wearable computing device, etc.) that executes an application, web interface, and/or messaging client configured for notification provision. In one example, a web interface of a personal computer or laptop associated with a subject can provide access, by the subject, to a user account of the subject, where the user account includes information regarding the user's allergy-related characterization, detailed characterization of aspects of the user's microbiome (e.g., in relation to correlations with allergy-related conditions; etc.), and/or notifications regarding suggested therapeutic measures (e.g., generated in Blocks S140 and/or S110, etc.). In another example, an application executing at a personal electronic device (e.g., smart phone, smart watch, head-mounted smart device) can be configured to provide notifications (e.g., at a display, haptically, in an auditory manner, etc.) regarding therapy suggestions generated by the therapy model of Block S110. Notifications and/or probiotic therapies can additionally or alternatively be provided directly through an entity associated with a subject (e.g., a caretaker, a spouse, a significant other, a healthcare professional, etc.). In some further variations, notifications can additionally or alternatively be provided to an entity (e.g., healthcare professional) associated with a subject, such as where the entity is able to facilitate provision of the therapy (e.g., by way of prescription, by way of conducting a therapeutic session, through a digital telemedicine session using optical and/or audio sensors of a computing device, etc.). In examples, providing notifications can be performed in response to and/or in any suitable temporal relation to a trigger condition (e.g., a trigger for an allergy-related condition). In a specific example, the method 100 can include: determining a risk for an allergy-related condition (and/or other suitable allergy-related characterizations; etc.) based on one or more user microbiome datasets; detecting an allergy-related trigger (e.g., predicting the historic, current, and/or future presence of an allergy-related trigger, etc.) based on the risk for the allergy-related condition (and/or supplementary data such as GPS location sensor data indicating a location correlated with the presence of allergy-related triggers, other supplementary sensor data, etc.); and providing an allergy-related notification (e.g., a warning to the user; recommendations; etc.) and/or other suitable therapies (e.g., contacting emergency services; contacting an individual associated with the user; facilitating application of therapeutics by appropriate medical devices; etc.) to the user in response to detecting the allergy-related trigger. Promoting allergy-related notifications and/or other suitable therapies can, however, be performed in any suitable manner.

3.8 Monitoring Therapy Effectiveness.

As shown in FIG. 7, the method can additionally or alternatively include Block S180, which recites: monitoring effectiveness of the therapy for the subject, based upon processing biological samples, to assess microbiome composition and/or functional features for the subject at a set of time points associated with the probiotic therapy. Block S180 can function to gather additional data regarding positive effects, negative effects, and/or lack of effectiveness of a probiotic therapy suggested by the therapy model for subjects of a given characterization. Monitoring of a subject during the course of a therapy promoted by the therapy model (e.g., by receiving and analyzing biological samples from the subject throughout therapy, by receiving survey-derived data from the subject throughout therapy) can thus be used to generate a therapy-effectiveness model for each characterization provided by the characterization process of Block S130, and each recommended therapy measure provided in Blocks S140 and S110.

In Block S180, the subject can be prompted to provide additional biological samples at one or more key time points of a therapy regimen that incorporates the therapy, and the additional biological sample(s) can be processed and analyzed (e.g., in a manner similar to that described in relation to Block S110) to generate metrics characterizing modulation of the subject's microbiome composition and/or functional features. For instance, metrics related to one or more of: a change in relative abundance of one or more taxonomic groups represented in the subject's microbiome at an earlier time point, a change in representation of a specific taxonomic group of the subject's microbiome, a ratio between abundance of a first taxonomic group of bacteria and abundance of a second taxonomic group of bacteria of the subject's microbiome, a change in relative abundance of one or more functional families in a subject's microbiome, and any other suitable metrics can be used to assess therapy effectiveness from changes in microbiome composition and/or functional features. Additionally or alternatively, survey-derived data from the subject, pertaining to experiences of the subject while on the therapy (e.g., experienced side effects, personal assessment of improvement, etc.) can be used to determine effectiveness of the therapy in Block S180. For example, the method 100 can include receiving a post-therapy biological sample from the user; collecting a supplementary dataset from the user, where the supplementary dataset describes user adherence to a therapy (e.g., a determined and promoted therapy); generating a post-therapy microbiome characterization of the first user in relation to the allergy-related condition based on the allergy-related condition characterization model and the post-therapy biological sample; and promoting an updated therapy to the user for the allergy-related condition based on the post-therapy microbiome characterization (e.g., based on a comparison between the post-therapy microbiome characterization and a pre-therapy microbiome characterization; etc.) and the user adherence to the therapy (e.g., modifying the therapy based on positive or negative results for the user microbiome in relation to the allergy-related condition; etc.). Therapy effectiveness, processing of additional biological samples (e.g., to determine additional allergy-related characterizations, therapies, etc.), and/or other suitable aspects associated with continued biological sample collection, processing, and analysis in relation to allergy-related conditions can be performed at any suitable time and frequency for generating, updating, and/or otherwise processing models (e.g., characterization models, therapy models, etc.), and/or for any other suitable purpose (e.g., as inputs associated with other portions of the method 100). However, Block S180 can be performed in any suitable manner.

The method 100 can, however, include any other suitable blocks or steps configured to facilitate reception of biological samples from subjects, processing of biological samples from subjects, analyzing data derived from biological samples, and generating models that can be used to provide customized diagnostics and/or probiotic-based therapeutics according to specific microbiome compositions and/or functional features of subjects.

The method 100 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for characterizing a food-related allergy condition, the method comprising:
   collecting samples from a set of users, wherein the samples comprise microorganism nucleic acids associated with the food-related allergy condition;
   generating a microorganism sequence dataset for the set of users based on the microorganism nucleic acids;
   determining microbiome composition diversity features and microbiome functional diversity features for the set of users based on the microorganism sequence dataset;
   collecting supplementary data associated with the food-related allergy condition for the set of users;
   transforming the supplementary data, the microbiome composition diversity features, and the microbiome functional diversity features into an allergy-related characterization model for the food-related allergy condition;
   generating a food-related allergy characterization for a user based on the allergy-related characterization model; and
   providing a therapy to the user for the food-related allergy condition based on the food-related allergy characterization.

2. The method of claim 1, wherein generating the microorganism sequence dataset comprises:
   identifying a primer type compatible with a genetic target associated with the food-related allergy condition; and
   generating the microorganism sequence dataset based on the primer type and the microorganism nucleic acids.

3. The method of claim 2, wherein generating the microorganism sequence dataset comprises performing experimental methods to generate at least one of metagenomic and metatranscriptomic libraries from the microorganism nucleic acids, and performing metagenomics and metatranscriptomics analysis to identify genetic targets associated with the food-related allergy condition.

4. The method of claim 2, wherein generating the microorganism sequence dataset comprises performing amplification operations including singleplex and multiplex amplifications, directly from the microorganisms nucleic acids using the primer type compatible with the genetic target associated with the food-related allergy condition.

5. The method of claim 4, wherein generating the microorganism sequence dataset comprises:
   fragmenting the microorganism nucleic acids; and
   performing multiplex amplification with the fragmented microorganism nucleic acids based on the primer type compatible with the genetic target associated with the food-related allergy condition.

6. The method of claim 1, wherein the therapy enables selective modulation of a microbiome of the user in relation to at least one of a population size of a desired taxon and a desired microbiome function, wherein the therapy is associated with improving a state of the food-related allergy condition.

7. The method of claim 1, wherein generating the food-related allergy characterization comprises:
   determining an allergy risk for the user for the food-related allergy condition based on the allergy-related characterization model; and
   determining an allergy-related trigger for the allergy-condition based on the allergy risk,
   wherein providing the therapy comprises promoting the therapy to the user based on the allergy-related trigger.

8. The method of claim 1, wherein providing the therapy to the user comprises promoting a diagnostic procedure for the food-related allergy condition based on the food-related allergy condition, wherein the diagnostic procedure comprises at least one of: skin prick testing, patch testing, blood testing, and challenge testing.

9. The method of claim 1, wherein generating the food-related allergy characterization comprises generating the food-related allergy characterization based on the allergy-related characterization model and a set of user microbiome features for the user, wherein the set of user microbiome features are associated with at least one of: presence of a microbiome feature from the set of user microbiome features, absence of the microbiome feature from the set of user microbiome features, relative abundance of different taxonomic groups associated with the food-related allergy condition, a ratio between at least two microbiome features associated with the different taxonomic groups, interactions between the different taxonomic groups, and phylogenetic distance between the different taxonomic groups.

10. The method of claim 1, wherein the food-related allergy condition comprises at least one of a wheat allergy condition and an egg allergy condition, and wherein the microbiome composition diversity features and the microbiome functional diversity features are associated with at least one of: *Blautia luti* (species), *Collinsella aerofaciens* (species), *Flavonifractor plautii* (species), *Faecalibacterium prausnitzii* (species), *Dorea formicigenerans* (species), *Subdoligranulum variabile* (species), *Barnesiella intestinihominis* (species), *Bacteroides thetaiotaomicron* (species), *Roseburia inulinivorans* (species), *Parasutterella excrementihominis* (species), *Bifidobacterium longum* (species), *Erysipelatoclostridium ramosum* (species), *Bacteroides fragilis* (species), *Bacteroides vulgatus* (species), *Bacteroides caccae* (species), *Blautia* sp. YHC-4 (species), *Alistipes putredinis* (species), *Bifidobacterium* (genus), *Subdoligranulum* (genus), *Collinsella* (genus), *Dorea* (genus), *Sarcina* (genus), *Moryella* (genus), *Intestinibacter* (genus), *Faecalibacterium* (genus), *Oscillospira* (genus), *Terrisporobacter* (genus), *Bacteroides* (genus), *Anaerotruncus* (genus), *Marvinbryantia* (genus), *Barnesiella* (genus), *Eggerthella* (genus), *Parabacteroides* (genus), *Dialister* (genus), *Roseburia* (genus), *Akkermansia* (genus), *Sutterella* (genus), Bifidobacteriaceae (family), Ruminococcaceae (family), Coriobacteriaceae (family), Oscillospiraceae (family), Clostridiaceae (family), Bacteroidaceae (family), Peptostreptococcaceae (family), Porphyromonadaceae (family), Streptococcaceae (family), Acidaminococcaceae (family), Veillonellaceae (family), Flavobacteriaceae (family), Verrucomicrobiaceae (family), Sutterellaceae (family), Enterobacteriaceae (family), Prevotellaceae (family), Lactobacillaceae (family), Bifidobacteriales (order), Clostridiales (order), Coriobacteriales (order), Bacteroidales (order), Flavobacteriales (order), Verrucomicrobiales (order), Burkholderiales (order), Enterobacteriales (order), Rhodospirillales (order), Actinobacteria (class), Clostridia (class), Bacteroidia (class), Flavobacteriia (class), Verrucomicrobiae (class), Betaproteobacteria (class), Alphaproteobacteria (class), Actinobacteria (phylum), Firmicutes (phylum), Bacteroidetes (phylum) and Verrucomicrobia (phylum), Xanthomonadaceae (family), Oxalobacteraceae (family), Synergistaceae (family), Eubacteriaceae (family), Microbacteriaceae (family), Enterococcaceae (family), Thermoanaerobacteraceae (family), Bacillaceae (family), Carnobacteriaceae (family), Clostridiales (family) XI. Incertae Sedis (family), Clostridiales (family) XIII. Incertae Sedis (family), Catabacteriaceae (family), Comamonadaceae (family), Methanobacteriaceae (family), Corynebacteriaceae (family), Caldicoprobacteraceae (family), Fibrobacteria (class), Synergistia (class), Gammaproteobacteria (class), Negativicutes (class), Methanobacteria (class), Synergistales (order), Xanthomonadales (order), Thermoanaerobacterales (order), Rhizobiales (order), Bacillales (order), Methanobacteriales (order), Selenomonadales (order), Fibrobacterales (order), Synergistetes (phylum), Bacteroidetes (phylum), Euryarchaeota (phylum), *Finegoldia* (genus), *Oscillibacter* (genus), *Pantoea* (genus), *Dialister* (genus), *Coprobacillus* (genus), *Enterobacter* (genus), *Lactobacillus* (genus), *Cloacibacillus* (genus), *Anaerofilum* (genus), *Klebsiella* (genus), *Kluyvera* (genus), *Anaerobacter* (genus), *Sutterella* (genus), *Faecalibacterium* (genus), *Fusicatenibacter* (genus), *Methanobrevibacter* (genus), *Dielma* (genus), *Catabacter* (genus), *Corynebacterium* (genus), *Odoribacter* (genus), *Eubacterium* (genus), *Actinobacillus* (genus), *Pseudoclavibacter* (genus), *Peptoclostridium* (genus), *Holdemania* (genus), *Erysipelatoclostridium* (genus), *Intestinimonas* (genus), *Adlercreutzia* (genus), *Hydrogenoanaerobacterium* (genus), *Shuttleworthia* (genus), *Enterococcus* (genus), *Roseburia* (genus), *Papillibacter* (genus), *Aerococcus* (genus), *Granulicatella* (genus), *Acidaminococcus* (genus), *Megasphaera* (genus), *Gelria* (genus), *Candidatus Soleaferrea* (genus), *Murdochiella* (genus), *Pseudoflavonifractor* (genus), *Herbaspirillum* (genus),

*Parabacteroides* (genus), *Acetanaerobacterium* (genus), *Gordonibacter* (genus), *Eisenbergiella* (genus), *Lactonifactor* (genus), *Moryella* (genus), *Sutterella* sp. YIT 12072 (species), *Peptoniphilus* sp. gpac018A (species), *Catenibacterium mitsuokai* (species), *Corynebacterium ulcerans* (species), *Granulicatella adiacens* (species), *Blautia glucerasea* (species), *Klebsiella* sp. SOR89 (species), *Roseburia* sp. 499 (species), *Anaerostipes* sp. 494a (species), *Bacteroides finegoldii* (species), *Bifidobacterium stercoris* (species), *Pseudoflavonifractor capillosus* (species), *Bacteroides* sp. DJF_B097 (species), *Sutterella wadsworthensis* (species), *Lactobacillus rhamnosus* (species), *Roseburia* sp. 11SE39 (species), *Dielma fastidiosa* (species), *Robinsoniella peoriensis* (species), *Corynebacterium freiburgense* (species), *Eubacterium* sp. SA11 (species), *Bacteroides chinchillae* (species), *Methanobrevibacter smithii* (species), *Blautia wexlerae* (species), *Enterococcus* sp. C6I11 (species), *Bacteroides* sp. AR20 (species), *Gordonibacter pamelaeae* (species), *Murdochiella asaccharolytica* (species), *Lactobacillus crispatus* (species), *Streptococcus peroris* (species), *Blautia* sp. Ser8 (species), *Enterococcus raffinosus* (species), *Anaerostipes* sp. 5_1_63FAA (species), *Desulfovibrio* sp. (species), *Eubacterium callanderi* (species), *Blautia hydrogenotrophica* (species), *Adlercreutzia equolifaciens* (species), *Bacteroides* sp. EBA5-17 (species), *Peptoniphilus* sp. DNF00840 (species), *Bifidobacterium biavatii* (species), *Anaerotruncus* sp. NML 070203 (species), *Bacteroides massiliensis* (species), *Coprobacillus* sp. D6 (species), *Intestinimonas butyriciproducens* (species), *Cloacibacillus evryensis* (species), *Bifidobacterium* sp. (species), *Holdemania filiformis* (species), *Roseburia hominis* (species), *Dialister propionicifaciens* (species), *Peptoniphilus lacrimalis* (species), *Blautia producta* (species), *Lactobacillus* sp. TAB-26 (species), *Lactobacillus* sp. TAB-30 (species), *Butyrivibrio crossotus* (species), *Alistipes indistinctus* (species), *Anaerococcus* sp. 8404299 (species), *Bacteroides uniformis* (species), *Parabacteroides distasonis* (species), *Bacteroides nordii* (species), *Roseburia cecicola* (species), *Anaerostipes* sp. 3_2_56FAA (species), *Lactonifactor longoviformis* (species), *Fusicatenibacter saccharivorans* (species), *Actinobacillus porcinus* (species), *Finegoldia* sp. S8 F7 (species), *Bifidobacterium kashiwanohense* (species), *Bacteroides* sp. S-17 (species), *Citrobacter amalonaticus* (species), *Corynebacterium epidermidicanis* (species), *Desulfovibrio piger* (species), *Anaerococcus* sp. 9402080 (species), *Lachnospira pectinoschiza* (species), *Corynebacterium canis* (species), *Corynebacterium sphenicorum* (species), *Parabacteroides merdae* (species), *Bacteroides stercoris* (species), *Bifidobacterium choerinum* (species), *Acidaminococcus intestini* (species), *Finegoldia* sp. S9 AA1-5 (species), *Herbaspirillum seropedicae* (species), *Slackia piriformis* (species), *Peptoniphilus* sp. 7-2 (species), *Acidaminococcus* sp. D21 (species), *Dorea longicatena* (species), *Bacteroides ovatus* (species), *Alistipes putredinis* (species), *Odoribacter splanchnicus* (species), *Anaerotruncus colihominis* (species), *Eggerthella* sp. HGA1 (species), *Peptoniphilus* sp. oral taxon 836 (species), *Eisenbergiella tayi* (species), *Aerococcus christensenii* (species), *Streptococcus* sp. oral taxon G59 (species), *Dialister invisus* (species), Propionibacteriaceae (family), Mycobacteriaceae (family), Lactobacillales (order), *Streptococcus* (genus), *Veillonella* (genus), *Comamonas* (genus), *Tessaracoccus* (genus), *Gemella* (genus), *Parvimonas* (genus), *Propionibacterium* (genus), *Granulicatella elegans* (species), *Streptococcus* sp. oral taxon G63 (species), *Tessaracoccus* sp. IPBSL-7 (species), *Actinomyces* sp. ICM41 (species), *Veillonella* sp. CM60 (species), *Gemella sanguinis* (species), *Actinomyces* sp. ZSY-1 (species), *Neisseria sicca* (species), Actinomycetaceae (family), Methylobacteriaceae (family), Rikenellaceae (family), Lachnospiraceae (family), Rhizobiaceae (family), Aerococcaceae (family), Sphingomonadaceae (family), Burkholderiaceae (family), Micrococcaceae (family), Rhodobacteraceae (family), Acidobacteriia (class), Rhodobacterales (order), Sphingomonadales (order), Solanales (order), Acidobacteria (phylum), Cyanobacteria (phylum), *Methylobacterium* (genus), *Centipeda* (genus), *Alistipes* (genus), *Anaerostipes* (genus), *Abiotrophia* (genus), *Brevundimonas* (genus), *Porphyromonas* (genus), *Lautropia* (genus), *Acinetobacter* (genus), *Blautia* (genus), *Mycobacterium* (genus), *Flavobacterium* (genus), *Sarcina* (genus), *Micrococcus* (genus), *Actinomyces* (genus), *Sphingomonas* (genus), *Capnocytophaga* (genus), *Pseudobutyrivibrio* (genus), *Abiotrophia defectiva* (species), *Micrococcus* sp. WB18-01 (species), *Moraxella* sp. WB19-16 (species), *Propionibacterium acnes* (species), *Aggregatibacter aphrophilus* (species), *Capnocytophaga* sp. CM59 (species), *Capnocytophaga sputigena* (species), *Prevotella oris* (species), *Neisseria elongata* (species), Moraxellaceae (family), Caulobacteraceae (family), Neisseriaceae (family), Neisseriales (order), Caulobacterales (order), *Neisseria* (genus), *Lachnospira* (genus), *Shinella* (genus), *Ralstonia* (genus), *Lactobacillus* sp. 7_1_47FAA (species), *Shinella* sp. DR33 (species), *Staphylococcus* sp. C-D-MA2 (species), *Lactobacillus acidophilus* (species), *Corynebacterium mastitidis* (species), *Actinomyces europaeus* (species), *Propionibacterium* sp. MSP09A (species), *Actinomyces neuii* (species), *Staphylococcus* sp. C9I2 (species), Fibrobacteraceae (family), Peptococcaceae (family), Leuconostocaceae (family), Pasteurellaceae (family), Pasteurellales (order), Actinomycetales (order), Streptophyta (phylum), Fibrobacteres (phylum), *Citrobacter* (genus), *Weissella* (genus), *Haemophilus* (genus), *Hespellia* (genus), *Pediococcus* (genus), *Pasteurella* (genus), *Acetitomaculum* (genus), *Cronobacter* (genus), *Fibrobacter* (genus), *Bacillus* (genus), *Intestinibacter* (genus), *Asaccharospora* (genus), *Anaerococcus* (genus), *Anaerotruncus* (genus), *Prevotella* (genus), *Marvinbryantia* (genus), *Howardella* (genus), *Rothia* (genus), *Peptoniphilus* (genus), *Enterobacter* sp. BS2-1 (species), *Veillonella rogosae* (species), *Roseburia intestinalis* (species), *Lactobacillus salivarius* (species), *Blautia stercoris* (species), *Bacteroides plebeius* (species), *Rothia mucilaginosa* (species), *Asaccharospora irregularis* (species), *Weissella hellenica* (species), *Haemophilus parainfluenzae* (species), *Pasteurella pneumotropica* (species), *Bacteroides* sp. SLC1-38 (species), *Bacteroides* sp. AR29 (species), *Streptococcus thermophilus* (species), *Veillonella* sp. MSA12 (species), *Alistipes* sp. HGB5 (species), *Haemophilus influenzae* (species), *Corynebacterium glucuronolyticum* (species), *Kluyvera georgiana* (species), *Howardella ureilytica* (species), *Prevotella bivia* (species), *Prevotella buccalis* (species), *Gemella* sp. 933-88 (species), Cardiobacteriaceae (family), *Cardiobacterium* (genus), *Peptostreptococcus* (genus), *Alloprevotella* (genus), *Cardiobacterium hominis* (species), *Streptococcus* sp. BS35a (species), *Centipeda periodontii* (species), *Streptococcus mitis* (species), *Leptotrichia hongkongensis* (species), Dermabacteraceae (family), Pseudomonadaceae (family), Fusobacteriaceae (family), Deinococci (class), *Kocuria* (genus), *Kingella* (genus), *Aggregatibacter* (genus), *Pseudomonas* (genus), *Rhodobacter* (genus), *Fusobacterium* (genus), *Bergeyella* (genus), *Moraxella* (genus), *Lautropia* sp. TeTO (species), *Prevotella* sp. WAL 2039G (species), *Fusobacterium* sp. CM21 (species), *Streptococcus gordonii* (species), *Corynebacterium* sp. NML97-0186 (species), *Capnocytophaga* sp. oral taxon329 (species), *Neisseria mucosa* (species), *Porphyromonas catoniae* (species), *Rothia dentocariosa* (species), Pseudomonadales (order), *Peptoniphilus* sp. 2002-2300004 (species), *Neisseria macacae* (species), *Terrisporobacter* (Genus), Bacteroidetes (Phylum), Flavobacteriaceae (family), Phyllobacteriaceae (family), *Phascolarctobacterium* (genus), *Paraprevotella* (genus), *Anaerosporobacter* (genus), *Butyricimonas* (genus), *Phyllobacterium* (genus), *Clostridium* (genus), *Paraprevotella clara* (species), *Alistipes* sp. EBA6-25cl2 (species), *Eggerthella sinensis* (species), *Anaerostipes* sp. 1y-2 (species), *Bifidobacterium* sp. MSX5B (species), *Bifidobacterium* sp. 120 (species), *Blautia faecis* (species), *Megasphaera genomo* sp. C1 (species), *Phascolarctobacterium succinatutens* (species), *Phascolarctobacterium faecium* (species), *Bacteroides eggerthii* (species), *Alistipes* sp. NML05A004 (species), *Actinomyces massiliensis* (species), *Cardiobacterium valvarum* (species), Fusobacteriia (class), Fusobacteriales (order), *Leptotrichia* (genus), *Corynebacterium durum* (species), *Actinomyces* sp. oral taxon 175 (species), *Actinomyces* sp. ICM54 (species), *Corynebacterium matruchotii* (species), *Prevotella timonensis* (species), Fusobacteria (phylum), *Prevotella disiens* (species), *Lachnoanaerobaculum saburreum* (species), *Capnocytophaga* sp. AHN9576 (species), Campylobacteraceae (family), Campylobacterales (order), Metabolism (KEGG2), Translation (KEGG2), Carbohydrate Metabolism (KEGG2), Cellular Processes and Signaling (KEGG2), Transport and Catabolism (KEGG2), Glycan Biosynthesis and Metabolism (KEGG2), Signaling Molecules and Interaction (KEGG2), Biosynthesis of Other Secondary Metabolites (KEGG2), Replication and Repair (KEGG2), Environmental Adaptation (KEGG2), Genetic Information Processing (KEGG2), Nucleotide Metabolism (KEGG2), Lipid Metabolism (KEGG2), Ribosome Biogenesis (KEGG3), D-Alanine metabolism (KEGG3), Ascorbate and aldarate metabolism (KEGG3), Amino acid metabolism (KEGG3), Translation proteins (KEGG3), Pentose and glucuronate interconversions (KEGG3), Peptidoglycan biosynthesis (KEGG3), Phenylalanine metabolism (KEGG3), RNA polymerase (KEGG3), Amino acid related enzymes (KEGG3), Glyoxylate and dicarboxylate metabolism (KEGG3), Biotin metabolism (KEGG3), Inorganic ion transport and metabolism (KEGG3), Others (KEGG3), Aminoacyl-tRNA biosynthesis (KEGG3), Glycosphingolipid biosynthesis—globo series (KEGG3), Bacterial toxins (KEGG3), MAPK signaling pathway—yeast (KEGG3), Penicillin and cephalosporin biosynthesis (KEGG3), Sphingolipid metabolism (KEGG3), Lysosome (KEGG3), Other glycan degradation (KEGG3), Inositol phosphate metabolism (KEGG3), Ribosome (KEGG3), Lipoic acid metabolism (KEGG3), Plant-pathogen interaction (KEGG3), Chromosome (KEGG3), Pores ion channels (KEGG3), Fructose and mannose metabolism (KEGG3), Other transporters (KEGG3), Lipopolysaccharide biosynthesis proteins (KEGG3), Other ion-coupled transporters (KEGG3), Membrane and intracellular structural molecules (KEGG3), Bisphenol degradation (KEGG3), Nitrogen metabolism (KEGG3), Glycosaminoglycan degradation (KEGG3), Signal transduction mechanisms (KEGG3), Huntington's disease (KEGG3), Translation factors (KEGG3), Carbohydrate metabolism (KEGG3), Ion channels (KEGG3), Cell motility and secretion (KEGG3), Lipid metabolism (KEGG3), Geraniol degradation (KEGG3), Terpenoid backbone biosynthesis (KEGG3), DNA repair and recombination proteins (KEGG3), Ribosome biogenesis in eukaryotes (KEGG3), Galactose metabolism (KEGG3), Glycerophospholipid metabolism (KEGG3), Taurine and hypotaurine metabolism (KEGG3), Pyrimidine metabolism (KEGG3), Biosynthesis and biodegradation of secondary metabolites (KEGG3), Nicotinate and nicotinamide metabolism (KEGG3), Phosphonate and phosphinate metabolism (KEGG3), Glycosphingolipid biosynthesis—ganglio series (KEGG3), Amino sugar and nucleotide sugar metabolism (KEGG3), Streptomycin biosynthesis (KEGG3), Citrate cycle (TCA cycle) (KEGG3), Enzyme Families (KEGG2), Signal Transduction (KEGG2), Neurodegenerative Diseases (KEGG2), Metabolism of Other Amino Acids (KEGG2), Metabolism of Cofactors and Vitamins (KEGG2), Cell Growth and Death (KEGG2), Poorly Characterized (KEGG2), Cysteine and methionine metabolism (KEGG3), Type II diabetes mellitus (KEGG3), Sulfur metabolism (KEGG3), Phosphatidylinositol signaling system (KEGG3), Peroxisome (KEGG3), Carbohydrate digestion and absorption (KEGG3), Nucleotide excision repair (KEGG3), Pentose phosphate pathway (KEGG3), Cyanoamino acid metabolism (KEGG3), Homologous recombination (KEGG3), Peptidases (KEGG3), Replication, recombination and repair proteins (KEGG3), Nucleotide metabolism (KEGG3), Phenylpropanoid biosynthesis (KEGG3), Purine metabolism (KEGG3), Toluene degradation (KEGG3), Thiamine metabolism (KEGG3), Histidine metabolism (KEGG3), Type I diabetes mellitus (KEGG3), Mismatch repair (KEGG3), Ubiquinone and other terpenoid-quinone biosynthesis (KEGG3), DNA replication proteins (KEGG3), beta-Lactam resistance (KEGG3), Aminobenzoate degradation (KEGG3), Function unknown (KEGG3), Cell cycle—*Caulobacter* (KEGG3), Butanoate metabolism (KEGG3), Caprolactam degradation (KEGG3), Pyruvate metabolism (KEGG3), Valine, leucine and isoleucine degradation (KEGG3), Energy metabolism (KEGG3), Polycyclic aromatic hydrocarbon degradation (KEGG3), Two-component system (KEGG3), Electron transfer carriers (KEGG3), Glycosyltransferases (KEGG3), Oxidative phosphorylation (KEGG3), One carbon pool by folate (KEGG3), Tyrosine metabolism (KEGG3), Drug metabolism—cytochrome P450 (KEGG3), Vitamin metabolism (KEGG3), Transcription factors (KEGG3), Cellular antigens (KEGG3), DNA replication (KEGG3), Drug metabolism—other enzymes (KEGG3), Protein export (KEGG3), Pantothenate and CoA biosynthesis (KEGG3), Limonene and pinene degradation (KEGG3), Carbon fixation pathways in prokaryotes (KEGG3), Epithelial cell signaling in *Helicobacter pylori* infection (KEGG3), Metabolism of xenobiotics by cytochrome P450 (KEGG3), Arginine and proline metabolism (KEGG3), Glutamatergic synapse (KEGG3), and Polyketide sugar unit biosynthesis (KEGG3).

11. The method of claim 1, wherein the food-related allergy condition comprises at least one of a treenut allergy condition and a peanut allergy condition, and wherein the microbiome composition diversity features and the microbiome functional diversity features are associated with at least one of: *Blautia luti* (Species), *Collinsella aerofaciens* (Species), *Parabacteroides distasonis* (Species), *Flavonifractor plautii* (Species), *Bacteroides fragilis* (Species), *Dorea formicigenerans* (Species), *Roseburia inulinivorans* (Species), *Clostridium* (Genus), *Marvinbryantia* (Genus), *Dorea* (Genus), *Eggerthella* (Genus), *Terrisporobacter* (Genus), *Sarcina* (Genus), *Bacteroides* (Genus), *Barnesiella* (Genus), Oscillospiraceae (Family), Clostridiaceae (Family), Bacteroidaceae (Family), Clostridiales (Order), Selenomonadales (Order), Bacteroidales (Order), Flavobacteriales (Order), Clostridia (Class), Negativicutes (Class), Flavobacteriia (Class), Bacteroidia (Class), Firmicutes (Phylum), Bacteroidetes (Phylum), Fusobacteriia (class), Neisseriaceae (family), Cardiobacteriaceae (family), Mycobacteriaceae (family), Actinomycetaceae (family), Aerococcaceae (family), Fusobacteriaceae (family), *Fusobacterium* (genus), *Actinomyces* (genus), *Mycobacterium* (genus), *Cardiobacterium* (genus), *Veillonella* (genus), *Rothia* (genus), Cardiobacteriales (order), Fusobacteriales (order), Neisseriales (order), Fusobacteria (phylum), *Neisseria elongata* (species), *Rothia dentocariosa* (species), *Actinomyces* sp. ICM54 (species), Lachnospiraceae (family), Desulfovibrionaceae (family), Ruminococcaceae (family), *Fusicatenibacter* (genus), *Roseburia* (genus), *Peptococcus* (genus), *Lachnospira* (genus), *Collinsella* (genus), *Anaerostipes* (genus), *Faecalibacterium* (genus), *Moryella* (genus), *Blautia* (genus), *Eisenbergiella* (genus), *Bilophila* (genus), Desulfovibrionales (order), *Parabacteroides merdae* (species), *Eggerthella* sp. HGA1 (species), *Fusicatenibacter saccharivorans* (species), *Erysipelatoclostridium ramosum* (species), *Lachnospira pectinoschiza* (species), *Alistipes putredinis* (species), *Bifidobacterium choerinum* (species), *Enterococcus raffinosus* (species), *Dorea longicatena* (species), *Anaerotruncus colihominis* (species), *Blautia wexlerae* (species), *Roseburia* sp. 11SE39 (species), *Anaerostipes* sp. 5_1_63FAA (species), *Intestinimonas butyriciproducens* (species), *Eisenbergiella tayi* (species), *Bilophila* sp. 4_1_30 (species), Transport and Catabolism (KEGG2), Glycan Biosynthesis and Metabolism (KEGG2), Biosynthesis of Other Secondary Metabolites (KEGG2), Glycosaminoglycan degradation (KEGG3), Lipoic acid metabolism (KEGG3), Lysosome (KEGG3), Inorganic ion transport and metabolism (KEGG3), Cell motility and secretion (KEGG3), Glycosphingolipid biosynthesis—ganglio series (KEGG3), Glycosphingolipid biosynthesis—globo series (KEGG3), Lipopolysaccharide biosynthesis proteins (KEGG3), Ribosome Biogenesis (KEGG3), Other glycan degradation (KEGG3), Phosphatidylinositol signaling system (KEGG3), Membrane and intracellular structural molecules (KEGG3), Sphingolipid metabolism (KEGG3), Huntington's disease (KEGG3), Peroxisome (KEGG3), Signal transduction mechanisms (KEGG3), Pores ion channels (KEGG3), Ubiquinone and other terpenoid-quinone biosynthesis (KEGG3), Metabolism (KEGG2), Signaling Molecules and Interaction (KEGG2), Translation (KEGG2), Cellular Processes and Signalin (KEGG2), Peptidoglycan biosynthesis (KEGG3), Glycosyltransferases (KEGG3), Aminobenzoate degradation (KEGG3), Epithelial cell signaling in *Helicobacter pylori* infection (KEGG3), Valine leucine and isoleucine biosynthesis (KEGG3), *Barnesiella intestinihominis* (Species), *Thalassospira* (Genus), Flavobacteriaceae (Family), Rhodospirillaceae (Family), Rhodospirillales (Order), *Actinomyces* sp. oral strain Hal-1065 (species), Rikenellaceae (family), *Megasphaera* (genus), *Holdemania* (genus), *Alistipes* (genus), *Lactonifactor* (genus), *Gordonibacter* (genus), *Flavonifractor* (genus), *Candidatus Soleaferrea* (genus), *Dielma* (genus), *Lactonifactor longoviformis* (species), *Anaerostipes* sp. 3_2_56FAA (species), *Blautia* sp. Ser8 (species), *Dielma fastidiosa* (species), *Eubacterium callanderi* (species), Carbohydrate Metabolism (KEGG2), Replication and Repair (KEGG2), Nucleotide Metabolism (KEGG2), Lipid Metabolism (KEGG2), Cell Growth and Death (KEGG2), Pentose and glucuronate interconversions (KEGG3), Aminoacyl-tRNA biosynthesis (KEGG3), Ascorbate and aldarate metabolism (KEGG3), Others (KEGG3), Other ion-coupled transporters (KEGG3), Linoleic acid metabolism (KEGG3), Phenylalanine metabolism (KEGG3), Ribosome (KEGG3), Translation factors (KEGG3), Amino acid related enzymes (KEGG3), Prion diseases (KEGG3), and Chromosome (KEGG3).

12. The method of claim 1, wherein the food-related allergy condition comprises at least one of a shellfish allergy condition and a soy allergy condition, and wherein the microbiome composition diversity features and the microbiome functional diversity features are associated with at least one of: *Blautia luti* (Species), *Collinsella aerofaciens* (Species), *Dorea formicigenerans* (Species), *Flavonifractor plautii* (Species), *Subdoligranulum variabile* (Species), *Faecalibacterium prausnitzii* (Species), *Barnesiella intestinihominis* (Species), *Roseburia inulinivorans* (Species), *Blautia* sp. YHC-4 (Species), *Bacteroides caccae* (Species), *Erysipelatoclostridium ramosum* (Species), *Bacteroides thetaiotaomicron* (Species), *Odoribacter splanchnicus* (Species), *Bacteroides fragilis* (Species), *Parabacteroides distasonis* (Species), *Collinsella* (Genus), *Sarcina* (Genus), *Faecalibacterium* (Genus), *Dorea* (Genus), *Eggerthella* (Genus), *Subdoligranulum* (Genus), *Moryella* (Genus), *Marvinbryantia* (Genus), *Barnesiella* (Genus), *Terrisporobacter* (Genus), *Bacteroides* (Genus), *Anaerotruncus* (Genus), *Clostridium* (Genus), *Bifidobacterium* (Genus), *Roseburia* (Genus), *Akkermansia* (Genus), Ruminococcaceae (Family), Flavobacteriaceae (Family), Coriobacteriaceae (Family), Oscillospiraceae (Family), Clostridiaceae (Family), Bacteroidaceae (Family), Lactobacillaceae (Family), Bifidobacteriaceae (Family), Prevotellaceae (Family), Verrucomicrobiaceae (Family), Flavobacteriales (Order), Coriobacteriales (Order), Clostridiales (Order), Bifidobacteriales (Order), Bacteroidales (Order), Verrucomicrobiales (Order), Actinobacteria (Class), Flavobacteriia (Class), Clostridia (Class), Bacteroidia (Class), Verrucomicrobiae (Class), Actinobacteria (Phylum), Firmicutes (Phylum), Bacteroidetes (Phylum) and Verrucomicrobia (Phylum), Mycobacteriaceae (family), Bradyrhizobiaceae (family), Oxalobacteraceae (family), Rhizobiaceae (family), Aerococcaceae (family), *Herbaspirillum* (genus), *Mycobacterium* (genus), *Shinella* (genus), Cyanobacteria (phylum), *Neisseria mucosa* (species), *Herbaspirillum seropedicae* (species), *Shinella* sp. DR33 (species), *Capnocytophaga* sp. CM59 (species), Deltaproteobacteria (class), Rikenellaceae (family), Eubacteriaceae (family), Desulfovibrionaceae (family), *Holdemania* (genus), *Citrobacter* (genus), *Megasphaera* (genus), *Eubacterium* (genus), *Anaerofilum* (genus), *Anaerobacter* (genus), *Oscillospira* (genus), *Alistipes* (genus), *Hespellia* (genus), *Odoribacter* (genus), *Howardella* (genus), *Lactonifactor* (genus), *Enterorhabdus* (genus), *Butyricicoccus* (genus), *Gordonibacter* (genus), *Pseudoflavonifractor* (genus), *Eisenbergiella* (genus), *Candidatus Stoquefichus* (genus), *Candidatus Soleaferrea* (genus), *Dielma* (genus), *Intestinibacter* (genus), *Flavonifractor* (genus), *Fusicatenibacter* (genus), Bacillales (order), Desulfovibrionales (order), Bacteroidetes (phylum), *Dorea longicatena* (species), *Roseburia* sp. 11SE39 (species), *Eggerthella* sp. HGA1 (species), *Fusicatenibacter saccharivorans* (species), *Lachnospira pectinoschiza* (species), *Citrobacter amalonaticus* (species), *Parabacteroides merdae* (species), *Eubacterium callanderi* (species), *Holdemania filiformis* (species), *Enterococcus raffinosus* (species), *Pseudoflavonifractor capillosus* (species), *Roseburia intestinalis* (species), *Megasphaera genomo* sp. C1 (species), *Dialister micraerophilus* (species), *Lactonifactor longoviformis* (species), *Howardella ureilytica* (species), *Blautia wexlerae* (species), *Blautia glucerasea* (species), *Bifidobacterium stercoris* (species), *Bifidobacterium kashiwanohense* (species), *Anaerostipes* sp. 3_2_56FAA (species), *Blautia* sp. Ser8 (species), *Blautia faecis* (species), *Bacteroides* sp. SLC1-38 (species), *Enterococcus* sp. C6I11 (species), *Anaerostipes* sp. 5_1_63FAA (species), *Dielma fastidiosa*

(species), *Roseburia* sp. 499 (species), *Eisenbergiella tayi* (species), *Bacteroides vulgatus* (species), *Bacteroides* sp. AR20 (species), *Bacteroides* sp. AR29 (species), *Alistipes* sp. EBA6-25c12 (species), *Bacteroides* sp. D22 (species), *Lactobacillus* sp. BL302 (species), Metabolism (KEGG2), Translation (KEGG2), Carbohydrate Metabolism (KEGG2), Replication and Repair (KEGG2), Cellular Processes and Signaling (KEGG2), Nucleotide Metabolism (KEGG2), Enzyme Families (KEGG2), Cell Growth and Death (KEGG2), Poorly Characterized (KEGG2), Environmental Adaptation (KEGG2), Glycan Biosynthesis and Metabolism (KEGG2), Signal Transduction (KEGG2), Metabolism of Cofactors and Vitamins (KEGG2), Signaling Molecules and Interaction (KEGG2), Transport and Catabolism (KEGG2), Xenobiotics Biodegradation and Metabolism (KEGG2), Ribosome Biogenesis (KEGG3), Ascorbate and aldarate metabolism (KEGG3), Peptidoglycan biosynthesis (KEGG3), Others (KEGG3), Amino acid related enzymes (KEGG3), RNA polymerase (KEGG3), Ribosome (KEGG3), Glyoxylate and dicarboxylate metabolism (KEGG3), Amino acid metabolism (KEGG3), Other transporters (KEGG3), Aminoacyl-tRNA biosynthesis (KEGG3), D-Alanine metabolism (KEGG3), Chromosome (KEGG3), Pentose and glucuronate interconversions (KEGG3), Translation proteins (KEGG3), Translation factors (KEGG3), Phenylalanine metabolism (KEGG3), DNA repair and recombination proteins (KEGG3), Terpenoid backbone biosynthesis (KEGG3), Pyrimidine metabolism (KEGG3), Protein export (KEGG3), Ribosome biogenesis in eukaryotes (KEGG3), Nicotinate and nicotinamide metabolism (KEGG3), Nucleotide metabolism (KEGG3), Penicillin and cephalosporin biosynthesis (KEGG3), Other ion-coupled transporters (KEGG3), Biosynthesis and biodegradation of secondary metabolites (KEGG3), Inorganic ion transport and metabolism (KEGG3), MAPK signaling pathway—yeast (KEGG3), Carbohydrate metabolism (KEGG3), Plant-pathogen interaction (KEGG3), Phosphonate and phosphinate metabolism (KEGG3), Pores ion channels (KEGG3), Homologous recombination (KEGG3), Lipoic acid metabolism (KEGG3), DNA replication proteins (KEGG3), Cell cycle—*Caulobacter* (KEGG3), Lipopolysaccharide biosynthesis proteins (KEGG3), Nucleotide excision repair (KEGG3), Function unknown (KEGG3), Cell motility and secretion (KEGG3), Glycosaminoglycan degradation (KEGG3), Photosynthesis (KEGG3), Photosynthesis proteins (KEGG3), Huntington's disease (KEGG3), Taurine and hypotaurine metabolism (KEGG3), Ion channels (KEGG3), Geraniol degradation (KEGG3), Caprolactam degradation (KEGG3), Sphingolipid metabolism (KEGG3), Lysosome (KEGG3), Biotin metabolism (KEGG3), Fructose and mannose metabolism (KEGG3), Inositol phosphate metabolism (KEGG3), Glycosphingolipid biosynthesis—globo series (KEGG3), Bacterial toxins (KEGG3), Mismatch repair (KEGG3), Vitamin metabolism (KEGG3), Membrane and intracellular structural molecules (KEGG3), Purine metabolism (KEGG3), Other glycan degradation (KEGG3), Alzheimer's disease (KEGG3), Peptidases (KEGG3), Pantothenate and CoA biosynthesis (KEGG3), Galactose metabolism (KEGG3), Glycosphingolipid biosynthesis—ganglio series (KEGG3), Thiamine metabolism (KEGG3), Glycerophospholipid metabolism (KEGG3), Lysine biosynthesis (KEGG3), Pentose phosphate pathway (KEGG3), Tuberculosis (KEGG3), Polycyclic aromatic hydrocarbon degradation (KEGG3), Sulfur metabolism (KEGG3), Aminobenzoate degradation (KEGG3), Phosphatidylinositol signaling system (KEGG3), DNA replication (KEGG3), One carbon pool by folate (KEGG3), Butanoate metabolism (KEGG3), Bisphenol degradation (KEGG3), Nitrogen metabolism (KEGG3), Amino sugar and nucleotide sugar metabolism (KEGG3), Benzoate degradation (KEGG3), Excretory System (KEGG2), Genetic Information Processing (KEGG2), Proximal tubule bicarbonate reclamation (KEGG3), Linoleic acid metabolism (KEGG3), Epithelial cell signaling in *Helicobacter pylori* infection (KEGG3), Pertussis (KEGG3), Transcription related proteins (KEGG3), Lipid metabolism (KEGG3), Prion diseases (KEGG3), alpha-Linolenic acid metabolism (KEGG3), Digestive System (KEGG2), Butirosin and neomycin biosynthesis (KEGG3), Phenylpropanoid biosynthesis (KEGG3), Carbohydrate digestion and absorption (KEGG3), Naphthalene degradation (KEGG3), Cyano-amino acid metabolism (KEGG3), Restriction enzyme (KEGG3), Biosynthesis of vancomycin group antibiotics (KEGG3), ABC transporters (KEGG3), Acidaminococcaceae (family), *Phascolarctobacterium* (genus), *Bilophila* (genus), *Oscillibacter* (genus), *Alistipes putredinis* (species), *Phascolarctobacterium faecium* (species), *Bilophila* sp. 4_1_30 (species), *Butyricimonas* sp. JCM 18677 (species), Energy Metabolism (KEGG2), Selenocompound metabolism (KEGG3), Two-component system (KEGG3), Protein kinases (KEGG3), Fatty acid biosynthesis (KEGG3), Infectious Diseases (KEGG2), General function prediction only (KEGG3), Polyketide sugar unit biosynthesis (KEGG3), beta-Lactam resistance (KEGG3), *Staphylococcus aureus* infection (KEGG3), Bacterial invasion of epithelial cells (KEGG3), Cellular antigens (KEGG3), D-Glutamine and D-glutamate metabolism (KEGG3), Cell Motility (KEGG2), Bacterial chemotaxis (KEGG3), Alanine aspartate and glutamate metabolism (KEGG3), Basal transcription factors (KEGG3), Oxidative phosphorylation (KEGG3), Secretion system (KEGG3), Carbon fixation pathways in prokaryotes (KEGG3), Protein (e.g., Kinases (KEGG3), Bacterial motility proteins (KEGG3), Flagellar assembly (KEGG3).

13. A method for characterizing an allergy-related condition for a user, the method comprising:
    collecting a sample from the user, the sample comprising microorganism nucleic acids associated with the allergy-condition;
    determining a microorganism sequence dataset from the microorganism nucleic acids of the sample based on sample processing operations associated with the allergy-condition;
    determining at least one of a microbiome composition diversity feature and a microbiome functional diversity feature associated with the allergy-related condition, based on the microorganism sequence dataset;
    generating an allergy-related characterization for the user based on an allergy-related characterization model and the at least one of the microbiome composition diversity feature and the microbiome functional diversity feature; and
    providing a therapy to the user for the allergy-related condition based on the allergy-related characterization.

14. The method of claim 13, wherein providing the therapy comprises promoting a consumable to the user based on the allergy-related characterization for the user, the consumable affecting a microorganism component associated with the allergy-related condition for improving a state of the allergy-related condition.

15. The method of claim 14, wherein promoting the consumable comprises promoting at least one of a probiotic therapy and a prebiotic therapy based on the allergy-related characterization for the user, wherein the at least one of the probiotic therapy and the prebiotic therapy is associated with at least one of: *Blautia luti, Collinsella aerofaciens, Flavonifractor plautii, Faecalibacterium prausnitzii, Dorea formicigenerans, Subdoligranulum variabile, Barnesiella intestinihominis, Bacteroides thetaiotaomicron, Roseburia inulinivorans, Parasutterella excrementihominis, Bifidobacterium longum, Erysipelatoclostridium ramosum, Bacteroides fragilis, Bacteroides vulgatus, Bacteroides caccae, Blautia* sp. YHC-4, *Alistipes putredinis, Parabacteroides distasonis*, and *Odoribacter splanchnicus*.

16. The method of claim 13, further comprising after providing the therapy:
   collecting a post-therapy sample from the user;
   collecting a supplementary dataset from the user, wherein the supplementary dataset describes user adherence to the therapy;
   generating a post-therapy allergy-related characterization of the user in relation to the allergy-related condition based on post-therapy microbiome features derived from the post-therapy sample; and
   promoting an updated therapy to the user for the allergy-related condition based on the post-therapy allergy-related characterization and the supplementary dataset.

17. The method of claim 13, wherein the at least one of the microbiome composition diversity feature and the microbiome functional diversity feature is associated with microorganisms collected at a gut site, and wherein the at least one of the microbiome composition diversity feature and the microbiome functional diversity feature is associated with at least one of: Ruminococcaceae (family), Flavobacteriaceae (family), Enterobacteriaceae (family), Prevotellaceae (family), Xanthomonadaceae (family), Oxalobacteraceae (family), Verrucomicrobiaceae (family), Lactobacillaceae (family), Synergistaceae (family), Bacteroidaceae (family), Eubacteriaceae (family), Microbacteriaceae (family), Enterococcaceae (family), Thermoanaerobacteraceae (family), Bacillaceae (family), Coriobacteriaceae (family), Carnobacteriaceae (family), Clostridiales (family) XI. Incertae Sedis (family), Bifidobacteriaceae (family), Clostridiales (family) XIII. Incertae Sedis (family), Catabacteriaceae (family), Comamonadaceae (family), Clostridiaceae (family), Methanobacteriaceae (family), Corynebacteriaceae (family), Oscillospiraceae (family), Caldicoprobacteraceae (family), Fibrobacteria (class), Synergistia (class), Clostridia (class), Betaproteobacteria (class), Bacteroidia (class), Gammaproteobacteria (class), Actinobacteria (class), Verrucomicrobiae (class), Negativicutes (class), Flavobacteriia (class), Methanobacteria (class), Coriobacteriales (order), Bifidobacteriales (order), Bacteroidales (order), Synergistales (order), Clostridiales (order), Xanthomonadales (order), Thermoanaerobacterales (order), Verrucomicrobiales (order), Enterobacteriales (order), Rhizobiales (order), Bacillales (order), Methanobacteriales (order), Selenomonadales (order), Fibrobacterales (order), Synergistetes (phylum), Bacteroidetes (phylum), Firmicutes (phylum), Euryarchaeota (phylum), *Finegoldia* (genus), *Oscillibacter* (genus), *Pantoea* (genus), *Dialister* (genus), *Coprobacillus* (genus), *Enterobacter* (genus), *Barnesiella* (genus), *Lactobacillus* (genus), *Cloacibacillus* (genus), *Oscillospira* (genus), *Anaerofilum* (genus), *Klebsiella* (genus), *Kluyvera* (genus), *Anaerobacter* (genus), *Sutterella* (genus), *Faecalibacterium* (genus), *Fusicatenibacter* (genus), *Methanobrevibacter* (genus), *Dielma* (genus), *Bifidobacterium* (genus), *Eggerthella* (genus), *Catabacter* (genus), *Corynebacterium* (genus), *Odoribacter* (genus), *Eubacterium* (genus), *Actinobacillus* (genus), *Collinsella* (genus), *Pseudoclavibacter* (genus), *Peptoclostridium* (genus), *Holdemania* (genus), *Erysipelatoclostridium* (genus), *Intestinimonas* (genus), *Adlercreutzia* (genus), *Subdoligranulum* (genus), *Hydrogenoanaerobacterium* (genus), *Bacteroides* (genus), *Shuttleworthia* (genus), *Enterococcus* (genus), *Roseburia* (genus), *Papillibacter* (genus), *Aerococcus* (genus), *Granulicatella* (genus), *Dorea* (genus), *Akkermansia* (genus), *Acidaminococcus* (genus), *Megasphaera* (genus), *Gelria* (genus), *Candidatus Soleaferrea* (genus), *Murdochiella* (genus), *Pseudoflavonifractor* (genus), *Herbaspirillum* (genus), *Parabacteroides* (genus), *Acetanaerobacterium* (genus), *Gordonibacter* (genus), *Eisenbergiella* (genus), *Lactonifactor* (genus), *Moryella* (genus), *Blautia* sp. YHC-4 (species), *Erysipelatoclostridium ramosum* (species), *Sutterella* sp. YIT 12072 (species), *Peptoniphilus* sp. gpacoi8A (species), *Catenibacterium mitsuokai* (species), *Corynebacterium ulcerans* (species), *Granulicatella adiacens* (species), *Blautia glucerasea* (species), *Klebsiella* sp. SOR89 (species), *Roseburia* sp. 499 (species), *Anaerostipes* sp. 494a (species), *Bacteroides finegoldii* (species), *Bifidobacterium stercoris* (species), *Pseudoflavonifractor capillosus* (species), *Bacteroides* sp. DJF_B097 (species), *Sutterella wadsworthensis* (species), *Lactobacillus rhamnosus* (species), *Roseburia* sp. 11SE39 (species), *Dielma fastidiosa* (species), *Robinsoniella peoriensis* (species), *Corynebacterium freiburgense* (species), *Eubacterium* sp. SA11 (species), *Bacteroides chinchillae* (species), *Methanobrevibacter smithii* (species), *Blautia wexlerae* (species), *Enterococcus* sp. C6I11 (species), *Bacteroides* sp. AR20 (species), *Gordonibacter pamelaeae* (species), *Murdochiella asaccharolytica* (species), *Lactobacillus crispatus* (species), *Bifidobacterium longum* (species), *Streptococcus peroris* (species), *Blautia* sp. Ser8 (species), *Enterococcus raffinosus* (species), *Anaerostipes* sp. 5_1_63FAA (species), *Collinsella aerofaciens* (species), *Desulfovibrio* sp. (species), *Eubacterium callanderi* (species), *Blautia hydrogenotrophica* (species), *Adlercreutzia equolifaciens* (species), *Bacteroides* sp. EBA5-17 (species), *Peptoniphilus* sp. DNF00840 (species), *Bifidobacterium biavatii* (species), *Anaerotruncus* sp. NML 070203 (species), *Bacteroides massiliensis* (species), *Coprobacillus* sp. D6 (species), *Intestinimonas butyriciproducens* (species), *Cloacibacillus evryensis* (species), *Bifidobacterium* sp. (species), *Holdemania filiformis* (species), *Roseburia hominis* (species), *Dialister propionicifaciens* (species), *Barnesiella intestinihominis* (species), *Peptoniphilus lacrimalis* (species), *Blautia producta* (species), *Lactobacillus* sp. TAB-26 (species), *Lactobacillus* sp. TAB-30 (species), *Butyrivibrio crossotus* (species), *Alistipes indistinctus* (species), *Anaerococcus* sp. 8404299 (species), *Bacteroides thetaiotaomicron* (species), *Bacteroides uniformis* (species), *Parabacteroides distasonis* (species), *Bacteroides nordii* (species), *Subdoligranulum variabile* (species), *Roseburia cecicola* (species), *Anaerostipes* sp. 3_2_56FAA (species), *Faecalibacterium prausnitzii* (species), *Lactonifactor longoviformis* (species), *Fusicatenibacter saccharivorans* (species), *Roseburia inulinivorans* (species), *Actinobacillus porcinus* (species), *Finegoldia* sp. S8 F7 (species), *Bifidobacterium kashiwanohense* (species), *Bacteroides* sp. S-17 (species), *Dorea formicigenerans* (species), *Citrobacter amalonaticus* (species), *Corynebacterium epidermidicanis* (species), *Desulfovibrio piger* (species), *Anaerococcus* sp. 9402080 (species), *Lachnospira pectinoschiza* (species), *Corynebacterium canis* (species), *Corynebacterium spheniscorum* (species), *Parabacteroides merdae* (species), *Bacteroides stercoris* (species), *Bifidobacterium choerinum* (species), *Blautia luti* (species), *Acidaminococcus intestini* (species), *Flavonifractor plautii* (species), *Finegoldia* sp. S9 AA1-5 (species), *Herbaspirillum seropedicae* (species), *Slackia piriformis*

(species), *Peptoniphilus* sp. 7-2 (species), *Acidaminococcus* sp. D21 (species), *Dorea longicatena* (species), *Bacteroides ovatus* (species), *Alistipes putredinis* (species), *Odoribacter splanchnicus* (species), *Anaerotruncus colihominis* (species), *Eggerthella* sp. HGA1 (species), *Peptoniphilus* sp. oral taxon 836 (species), *Eisenbergiella tayi* (species), *Aerococcus christensenii* (species), *Streptococcus* sp. oral taxon G59 (species), *Dialister invisus* (species), Lachnospiraceae (family), Desulfovibrionaceae (family), *Clostridium* (genus), *Peptococcus* (genus), *Lachnospira* (genus), *Anaerostipes* (genus), *Blautia* (genus), *Terrisporobacter* (genus), *Bilophila* (genus), Desulfovibrionales (order), *Bilophila* sp. 4_1_30 (species), Metabolism (KEGG2), Signaling Molecules and Interaction (KEGG2), Glycan Biosynthesis and Metabolism (KEGG2), Translation (KEGG2), Transport and Catabolism (KEGG2), Cellular Processes and Signaling (KEGG2), Peptidoglycan biosynthesis (KEGG3), Glycosyltransferases (KEGG3), Ribosome Biogenesis (KEGG3), Glycosphingolipid biosynthesis—globo series (KEGG3), Lysosome (KEGG3), Inorganic ion transport and metabolism (KEGG3), Aminobenzoate degradation (KEGG3), Epithelial cell signaling in *Helicobacter pylori* infection (KEGG3), Valine leucine and isoleucine biosynthesis (KEGG3), Sphingolipid metabolism (KEGG3), Cell Growth and Death (KEGG2), Cell Motility (KEGG2), Signal Transduction (KEGG2), Energy Metabolism (KEGG2), Bacterial chemotaxis (KEGG3), Cell cycle—*Caulobacter*(KEGG3), Alanine aspartate and glutamate metabolism (KEGG3), Basal transcription factors (KEGG3), Oxidative phosphorylation (KEGG3), Secretion system (KEGG3), Fatty acid biosynthesis (KEGG3), Selenocompound metabolism (KEGG3), Carbon fixation pathways in prokaryotes (KEGG3), Amino acid related enzymes (KEGG3), Two-component system (KEGG3), Kinases (KEGG3), Bacterial motility proteins (KEGG3), Flagellar assembly (KEGG3), Deltaproteobacteria (class), Rikenellaceae (family), *Citrobacter* (genus), *Sarcina* (genus), *Alistipes* (genus), *Hespellia* (genus), *Howardella* (genus), *Enterorhabdus* (genus), *Butyricicoccus* (genus), *Candidatus Stoquefichus* (genus), *Intestinibacter* (genus), *Flavonifractor* (genus), Actinobacteria (phylum), *Roseburia intestinalis* (species), *Megasphaera genomo* sp. C1 (species), *Dialister micraerophilus* (species), *Howardella ureilytica* (species), *Blautia faecis* (species), *Bacteroides* sp. SLC1-38 (species), *Bacteroides fragilis* (species), *Bacteroides vulgatus* (species), *Bacteroides* sp. AR29 (species), *Alistipes* sp. EBA6-25c12 (species), *Bacteroides* sp. D22 (species), Excretory System (KEGG2), Enzyme Families (KEGG2), Xenobiotics Biodegradation and Metabolism (KEGG2), Carbohydrate Metabolism (KEGG2), Genetic Information Processing (KEGG2), Pentose and glucuronate interconversions (KEGG3), RNA polymerase (KEGG3), Sulfur metabolism (KEGG3), Aminoacyl-tRNA biosynthesis (KEGG3), Ascorbate and aldarate metabolism (KEGG3), MAPK signaling pathway—yeast (KEGG3), Inositol phosphate metabolism (KEGG3), Others (KEGG3), Biosynthesis and biodegradation of secondary metabolites (KEGG3), Phosphonate and phosphinate metabolism (KEGG3), Caprolactam degradation (KEGG3), Translation proteins (KEGG3), Other ion-coupled transporters (KEGG3), Bisphenol degradation (KEGG3), Proximal tubule bicarbonate reclamation (KEGG3), Linoleic acid metabolism (KEGG3), Other glycan degradation (KEGG3), Phenylalanine metabolism (KEGG3), Terpenoid backbone biosynthesis (KEGG3), Polycyclic aromatic hydrocarbon degradation (KEGG3), Other transporters (KEGG3), Glyoxylate and dicarboxylate metabolism (KEGG3), Ion channels (KEGG3), Lipoic acid metabolism (KEGG3), Pertussis (KEGG3), Transcription related proteins (KEGG3), Lipid metabolism (KEGG3), Tuberculosis (KEGG3), Prion diseases (KEGG3), Nicotinate and nicotinamide metabolism (KEGG3), alpha-Linolenic acid metabolism (KEGG3), Chromosome (KEGG3), Actinomycetaceae (family), Ribosome (KEGG3), Translation factors (KEGG3), Phyllobacteriaceae (family), Sutterellaceae (family), Acidaminococcaceae (family), Flavobacteriales (order), Burkholderiales (order), *Phascolarctobacterium* (genus), *Veillonella* (genus), *Paraprevotella* (genus), *Cronobacter* (genus), *Anaerosporobacter* (genus), *Butyricimonas* (genus), *Phyllobacterium* (genus), *Paraprevotella clara* (species), *Bacteroides plebeius* (species), *Eggerthella sinensis* (species), *Bacteroides caccae* (species), *Anaerostipes* sp. 1y-2 (species), *Bifidobacterium* sp. MSX5B (species), *Streptococcus* sp. BS35a (species), *Bifidobacterium* sp. 120 (species), *Phascolarctobacterium succinatutens* (species), *Phascolarctobacterium faecium* (species), *Streptococcus thermophilus* (species), *Bacteroides eggerthii* (species), *Alistipes* sp. NML05A004 (species), Fibrobacteraceae (family), Streptococcaceae (family), Porphyromonadaceae (family), Leuconostocaceae (family), Veillonellaceae (family), Actinomycetales (order), Fusobacteria (phylum), Fibrobacteres (phylum), *Gemella* (genus), *Peptoniphilus* (genus), *Gemella* sp. 933-88 (species), *Veillonella* sp. CM60 (species), and *Prevotella disiens* (species).

18. The method of claim 17, wherein the at least one of the microbiome composition diversity feature and the microbiome functional diversity feature is associated with a healthy gut site, and wherein the at least one of the microbiome composition diversity feature and the microbiome functional diversity feature is associated with at least one of: Biosynthesis of Other Secondary Metabolites (KEGG2), Excretory System (KEGG2), Membrane Transport (KEGG2), Infectious Diseases (KEGG2), Cell Motility (KEGG2), Metabolism (KEGG2), Signaling Molecules and Interaction (KEGG2), Glycan Biosynthesis and Metabolism (KEGG2), Transcription (KEGG2), Translation (KEGG2), Metabolism of Other Amino Acids (KEGG2), Poorly Characterized (KEGG2), Lipid Metabolism (KEGG2), Transport and Catabolism (KEGG2), Metabolism of Terpenoids and Polyketides (KEGG2), Cellular Processes and Signaling (KEGG2), Carbohydrate Metabolism (KEGG2), Environmental Adaptation (KEGG2), Bacterial chemotaxis (KEGG3), Membrane and intracellular structural molecules (KEGG3), Pentose and glucuronate interconversions (KEGG3), RNA polymerase (KEGG3), N-Glycan biosynthesis (KEGG3), Sulfur metabolism (KEGG3), Peptidoglycan biosynthesis (KEGG3), Xylene degradation (KEGG3), Aminoacyl-tRNA biosynthesis (KEGG3), Huntingtons disease (KEGG3), RNA degradation (KEGG3), Glycosyltransferases (KEGG3), Others (KEGG3), Lipopolysaccharide biosynthesis proteins (KEGG3), Phosphatidylinositol signaling system (KEGG3), Pores ion channels (KEGG3), Biosynthesis and biodegradation of secondary metabolites (KEGG3), Phosphonate and phosphinate metabolism (KEGG3), Dioxin degradation (KEGG3), Ribosome Biogenesis (KEGG3), Benzoate degradation (KEGG3), Translation proteins (KEGG3), Cell motility and secretion (KEGG3), Other ion-coupled transporters (KEGG3), Photosynthesis (KEGG3), D-Alanine metabolism (KEGG3), Bisphenol degradation (KEGG3), Glycosphingolipid biosynthesis—globo series (KEGG3), Circadian rhythm—plant (KEGG3), Lysosome (KEGG3), Proximal tubule bicarbonate reclamation (KEGG3), Inorganic ion transport and metabolism (KEGG3), Caffeine metabolism (KEGG3), Linoleic acid metabolism (KEGG3), Methane metabolism (KEGG3), Other glycan degradation (KEGG3), Germination (KEGG3), Phenylalanine metabolism (KEGG3), Glycosaminoglycan degradation (KEGG3), Penicillin and cephalosporin biosynthesis (KEGG3), Ribosome (KEGG3), Aminobenzoate degradation (KEGG3), Lysine biosynthesis (KEGG3), Ion channels (KEGG3), Citrate cycle (TCA cycle) (KEGG3), Lipopolysaccharide biosynthesis (KEGG3), Geraniol degradation (KEGG3), Cytoskeleton proteins (KEGG3), Cellular antigens (KEGG3), Ribosome biogenesis in eukaryotes (KEGG3), Protein digestion and absorption (KEGG3), Peroxisome (KEGG3), RNA transport (KEGG3), Biosynthesis of siderophore group nonribosomal peptides (KEGG3), Lipoic acid metabolism (KEGG3), Valine leucine and isoleucine biosynthesis (KEGG3), Sphingolipid metabolism (KEGG3), Amino sugar and nucleotide sugar metabolism (KEGG3), Steroid biosynthesis (KEGG3), Signal transduction mechanisms (KEGG3), Bacterial toxins (KEGG3), Steroid hormone biosynthesis (KEGG3), Transcription factors (KEGG3), Pertussis (KEGG3), Sporulation (KEGG3), Amino acid related enzymes (KEGG3), Streptomycin biosynthesis (KEGG3), Transporters (KEGG3), Isoquinoline alkaloid biosynthesis (KEGG3), Function unknown (KEGG3), Galactose metabolism (KEGG3), Cyanoamino acid metabolism (KEGG3), Taurine and hypotaurine metabolism (KEGG3), Pantothenate and CoA biosynthesis (KEGG3), Glycosphingolipid biosynthesis—ganglio series (KEGG3), Toluene degradation (KEGG3), Photosynthesis proteins (KEGG3), Ubiquinone and other terpenoid-quinone biosynthesis (KEGG3), ABC transporters (KEGG3), Plant-pathogen interaction (KEGG3), Ubiquitin system (KEGG3), Chromosome (KEGG3), Oscillospiraceae (family), Acidaminococcaceae (family), *Clostridium* (genus), *Phascolarctobacterium* (genus), *Bilophila* (genus), *Odoribacter* (genus), *Oscillibacter* (genus), *Parabacteroides distasonis* (species), *Alistipes putredinis* (species), *Odoribacter splanchnicus* (species), *Phascolarctobacterium faecium* (species), *Flavonifractor plautii* (species), *Alistipes* sp. EBA6-25c12 (species), *Bilophila* sp. 4_1_30 (species), *Butyricimonas* sp. JCM 18677 (species), Cell Growth and Death (KEGG2), Signal Transduction (KEGG2), Energy Metabolism (KEGG2), Cell cycle —Caulobacter (KEGG3), Basal transcription factors (KEGG3), Oxidative phosphorylation (KEGG3), Secretion system (KEGG3), Fatty acid biosynthesis (KEGG3), Selenocompound metabolism (KEGG3), Two-component system (KEGG3), Protein kinases (KEGG3), Bacterial motility proteins (KEGG3), Flagellar assembly (KEGG3), Betaproteobacteria (class), Clostridia (class), Bacteroidia (class), Negativicutes (class), Gammaproteobacteria (class), Actinobacteria (class), Alphaproteobacteria (class), Mollicutes (class), Flavobacteriia (class), Erysipelotrichia (class), Deltaproteobacteria (class), Verrucomicrobiae (class), Bacteroidaceae (family), Clostridiaceae (family), Porphyromonadaceae (family), Ruminococcaceae (family), Sutterellaceae (family), Bifidobacteriaceae (family), Rhodospirillaceae (family), Flavobacteriaceae (family), Coriobacteriaceae (family), Anaeroplasmataceae (family), Eubacteriaceae (family), Peptococcaceae (family), Erysipelotrichaceae (family), Rikenellaceae (family), Desulfovibrionaceae (family), Verrucomicrobiaceae (family), *Bacteroides* (genus), *Roseburia* (genus), *Megasphaera* (genus), *Sarcina* (genus), *Holdemania* (genus), *Eggerthella* (genus), *Collinsella* (genus), *Dorea* (genus), *Faecalibacterium* (genus), *Hespellia* (genus), *Marvinbryantia* (genus), *Subdoligranulum* (genus), *Parabacteroides* (genus), *Moryella* (genus), *Fusicatenibacter* (genus), *Eisenbergiella* (genus), *Terrisporobacter* (genus), *Lactococcus* (genus), *Bifidobacterium* (genus), *Peptococcus* (genus), *Lachnospira* (genus), *Acetitomaculum* (genus), *Thalassospira* (genus), *Shuttleworthia* (genus), *Barnesiella* (genus), *Howardella* (genus), *Lactonifactor* (genus), *Butyricimonas* (genus), *Enterorhabdus* (genus), *Butyricicoccus* (genus), *Gordonibacter* (genus), *Anaerosporobacter* (genus), *Pseudoflavonifractor* (genus), *Candidatus Stoquefichus* (genus), *Candidatus Soleaferrea* (genus), *Dielma* (genus), *Intestinibacter* (genus), *Enterobacter* (genus), *Gemella* (genus), *Actinomyces* (genus), *Veillonella* (genus), *Oscillospira* (genus), *Alistipes* (genus), *Akkermansia* (genus), *Adlercreutzia* (genus), *Parasutterella* (genus), *Flavonifractor* (genus), *Intestinimonas* (genus), Burkholderiales (order), Bacteroidales (order), Clostridiales (order), Rhodospirillales (order), Selenomonadales (order), Coriobacteriales (order), Bifidobacteriales (order), Flavobacteriales (order), Bacillales (order), Actinomycetales (order), Verrucomicrobiales (order), Desulfovibrionales (order), Erysipelotrichales (order), Bacteroidetes (phylum), Firmicutes (phylum), Actinobacteria (phylum), Tenericutes (phylum), Verrucomicrobia (phylum), *Faecalibacterium prausnitzii* (species), *Erysipelatoclostridium ramosum* (species), *Lachnospira pectinoschiza* (species), *Dorea formicigenerans* (species), *Collinsella aerofaciens* (species), *Dorea longicatena* (species), *Blautia luti* (species), *Subdoligranulum variabile* (species), *Roseburia inulinivorans* (species), *Barnesiella intestinihominis* (species), *Roseburia* sp. 11SE39 (species), *Blautia* sp. Ser8 (species), *Eggerthella* sp. HGA1 (species), *Fusicatenibacter saccharivorans* (species), *Eisenbergiella tayi* (species), *Bacteroides* thetaiotaomicron (species), *Campylobacter ureolyticus* (species), *Desulfovibrio piger* (species), *Holdemania filiformis* (species), *Bacteroides* sp. AR20 (species), *Pseudoflavonifractor capillosus* (species), *Collinsella intestinalis* (species), *Bacteroides plebeius* (species), *Lactonifactor longoviformis* (species), *Howardella ureilytica* (species), *Blautia wexlerae* (species), *Gordonibacter pamelaeae* (species), *Parasutterella excrementihominis* (species), *Butyricicoccus pullicaecorum* (species), *Blautia glucerasea* (species), *Butyricimonas virosa* (species), *Bifidobacterium stercoris* (species), *Bacteroides clarus* (species), *Anaerostipes* sp. 3_2_56FAA (species), *Bacteroides* sp. SLC1-38 (species), *Lactococcus* sp. MH5-2 (species), *Anaerostipes* sp. 5_1_63FAA (species), *Dielma fastidiosa* (species), *Blautia* sp. YHC-4 (species), *Intestinimonas butyriciproducens* (species), *Bacteroides fragilis* (species), *Bacteroides vulgatus* (species), *Sutterella wadsworthensis* (species), *Butyrivibrio crossotus* (species), *Parabacteroides merdae* (species), *Gemella* sp. 933-88 (species), *Bacteroides* sp. AR29 (species), *Sutterella stercoricanis* (species), *Akkermansia muciniphila* (species), *Bacteroides nordii* (species), *Bacteroides* sp. XB12B (species), *Adlercreutzia equolifaciens* (species), *Bacteroides* sp. DJF_B097 (species), *Bacteroides* sp. D22 (species), *Alistipes* sp. RMA9912 (species), *Lactobacillus* sp. BL302 (species), *Enterococcus* sp. C6I11 (species), *Enterobacter* sp. BS2-1 (species), Neurodegenerative Diseases (KEGG2), Replication and Repair (KEGG2), Genetic Information Processing (KEGG2), Biosynthesis of unsaturated fatty acids (KEGG3), Biotin metabolism (KEGG3), Ascorbate and aldarate metabolism (KEGG3), MAPK signaling pathway—yeast (KEGG3), Inositol phosphate metabolism (KEGG3), Amino acid metabolism (KEGG3), Caprolactam degradation (KEGG3), Type I diabetes mellitus (KEGG3), Fructose and mannose metabolism (KEGG3), Terpenoid backbone biosynthesis (KEGG3), Carbohydrate metabolism (KEGG3), Polycyclic aromatic hydrocarbon degradation (KEGG3), Other transporters (KEGG3), Glyoxylate and dicarboxylate metabolism (KEGG3), Carbon fixation pathways in prokaryotes (KEGG3), Mismatch repair (KEGG3), Epithelial cell signaling in *Helicobacter pylori* infection (KEGG3), Translation factors (KEGG3), Glycerophospholipid metabolism (KEGG3), Transcription related proteins (KEGG3), Lipid metabolism (KEGG3), Meiosis—yeast (KEGG3), 1 1 1-Trichloro-2 2-bis(4-chlorophenyl)ethane (DDT) degradation (KEGG3), Amyotrophic lateral sclerosis (ALS) (KEGG3), Pyrimidine metabolism (KEGG3), Nicotinate and nicotinamide metabolism (KEGG3), DNA repair and recombination proteins (KEGG3), Glycosphingolipid biosynthesis—lacto and neolacto series (KEGG3), Epsilonproteobacteria (class), Actinomycetaceae (family), Enterobacteriaceae (family), Campylobacteraceae (family), *Kluyvera* (genus), *Lactobacillus* (genus), Anaeroplasmatales (order), Enterobacteriales (order), Campylobacterales (order), *Anaerotruncus colihominis* (species), *Lactobacillus crispatus* (species), and *Kluyvera georgiana* (species).

19. The method of claim 13, wherein the at least one of the microbiome composition diversity feature and the microbiome functional diversity feature is associated with microorganisms collected at a mouth site, and wherein the at least one of the microbiome composition diversity feature and the microbiome functional diversity feature is associated with at least one of: Streptococcaceae (family), Propionibacteriaceae (family), Mycobacteriaceae (family), Lactobacillales (order), *Streptococcus* (genus), *Veillonella* (genus), *Comamonas* (genus), *Tessaracoccus* (genus), *Gemella* (genus), *Parvimonas* (genus), *Propionibacterium* (genus), *Granulicatella elegans* (species), *Streptococcus* sp. oral taxon G63 (species), *Tessaracoccus* sp. IPBSL-7 (species), *Actinomyces* sp. ICM41 (species), *Veillonella* sp. CM60 (species), *Gemella sanguinis* (species), *Actinomyces* sp. ZSY-1 (species), *Neisseria sicca* (species), Cardiobacteriaceae (family), *Cardiobacterium* (genus), *Peptostreptococcus* (genus), *Alloprevotella* (genus), *Cardiobacterium hominis* (species), *Streptococcus* sp. BS35a (species), *Centipeda periodontii* (species), *Streptococcus mitis* (species), *Leptotrichia hongkongensis* (species), Cell Growth and Death (KEGG2), Metabolism (KEGG2), Signal Transduction (KEGG2), Digestive System (KEGG2), Replication and Repair (KEGG2), Cell cycle—*Caulobacter*(KEGG3), Nucleotide excision repair (KEGG3), Bacterial invasion of epithelial cells (KEGG3), Pentose phosphate pathway (KEGG3), Ribosome (KEGG3), General function prediction only (KEGG3), Cellular antigens (KEGG3), Carbohydrate digestion and absorption (KEGG3), D-Glutamine and D-glutamate metabolism (KEGG3), Amino acid related enzymes (KEGG3), Two-component system (KEGG3), Protein export (KEGG3), Restriction enzyme (KEGG3), DNA repair and recombination proteins (KEGG3), Biosynthesis of vancomycin group antibiotics (KEGG3), ABC transporters (KEGG3), Xenobiotics Biodegradation and Metabolism (KEGG2), Carbohydrate Metabolism (KEGG2), Genetic Information Processing (KEGG2), Environmental Adaptation (KEGG2), Butirosin and neomycin biosynthesis (KEGG3), Phenylpropanoid biosynthesis (KEGG3), Naphthalene degradation (KEGG3), Cyanoamino acid metabolism (KEGG3), *Actinomyces* sp. oral strain Hal-1065 (species), Comamonadaceae (family), *Actinomyces massiliensis* (species), *Cardiobacterium valvarum* (species), *Propionibacterium* sp. MSP09A (species), *Lachnoanaerobaculum saburreum* (species), and *Capnocytophaga* sp. AHN9576 (species).

20. The method of claim 13, wherein the at least one of the microbiome composition diversity feature and the microbiome functional diversity feature is associated with microorganisms collected at a nose site, and wherein the at least one of the microbiome composition diversity feature and the microbiome functional diversity feature is associated with at least one of: Actinomycetaceae (family), Methylobacteriaceae (family), Rikenellaceae (family), Lachnospiraceae (family), Rhizobiaceae (family), Sutterellaceae (family), Aerococcaceae (family), Sphingomonadaceae (family), Burkholderiaceae (family), Micrococcaceae (family), Rhodobacteraceae (family), Acidobacteriia (class), Alphaproteobacteria (class), Rhodobacterales (order), Sphingomonadales (order), Solanales (order), Acidobacteria (phylum), Cyanobacteria (phylum), *Methylobacterium* (genus), *Centipeda* (genus), *Alistipes* (genus), *Anaerostipes* (genus), *Abiotrophia* (genus), *Brevundimonas* (genus), *Porphyromonas* (genus), *Lautropia* (genus), *Acinetobacter* (genus), *Blautia* (genus), *Mycobacterium* (genus), *Flavobacterium* (genus), *Sarcina* (genus), *Micrococcus* (genus), *Actinomyces* (genus), *Sphingomonas* (genus), *Capnocytophaga* (genus), *Pseudobutyrivibrio* (genus), *Abiotrophia defectiva* (species), *Micrococcus* sp. WB18-01 (species), *Moraxella* sp. WB19-16 (species), *Propionibacterium acnes* (species), *Aggregatibacter aphrophilus* (species), *Bacteroides vulgatus* (species), *Capnocytophaga* sp. CM59 (species), *Capnocytophaga sputigena* (species), *Prevotella oris* (species), *Neisseria elongata* (species), Dermabacteraceae (family), Pseudomonadaceae (family), Fusobacteriaceae (family), Deinococci (class), Rhodospirillales (order), *Kocuria* (genus), *Kingella* (genus), *Aggregatibacter* (genus), *Pseudomonas* (genus), *Rhodobacter* (genus), *Fusobacterium* (genus), *Bergeyella* (genus), *Moraxella* (genus), *Lautropia* sp. TeTO (species), *Prevotella* sp. WAL 2039G (species), *Fusobacterium* sp. CM21 (species), *Streptococcus gordonii* (species), *Corynebacterium* sp. NML97-0186 (species), *Capnocytophaga* sp. oral taxon329 (species), *Neisseria mucosa* (species), *Porphyromonas catoniae* (species), *Rothia dentocariosa* (species), Fusobacteriia (class), Neisseriaceae (family), Cardiobacteriaceae (family), Mycobacteriaceae (family), *Cardiobacterium* (genus), *Veillonella* (genus), *Rothia* (genus), Cardiobacteriales (order), Fusobacteriales (order), Neisseriales (order), Fusobacteria (phylum), *Actinomyces* sp. ICM54 (species), Infectious Diseases (KEGG2), Metabolism of Cofactors and Vitamins (KEGG2), Poorly Characterized (KEGG2), General function prediction only (KEGG3), Polyketide sugar unit biosynthesis (KEGG3), beta-Lactam resistance (KEGG3), *Staphylococcus aureus* infection (KEGG3), Taurine and hypotaurine metabolism (KEGG3), Bradyrhizobiaceae (family), Oxalobacteraceae (family), *Herbaspirillum* (genus), *Shinella* (genus), *Herbaspirillum seropedicae* (species), *Shinella* sp. DR33 (species), Moraxellaceae (family), Streptophyta (phylum), *Leptotrichia* (genus), *Neisseria* (genus), *Veillonella* sp. MSA12 (species), *Corynebacterium durum* (species), *Actinomyces* sp. oral taxon 175 (species), *Neisseria macacae* (species), *Corynebacterium matruchotii* (species), *Streptococcus* sp. oral taxon G59 (species), Campylobacteraceae (family), Campylobacterales (order), and *Rothia mucilaginosa* (species).

21. The method of claim 13, wherein the at least one of the microbiome composition diversity feature and the microbiome functional diversity feature is associated with microorganisms collected at a genital site, and wherein the at least one of the microbiome composition diversity feature and the microbiome functional diversity feature is associated with at least one of: Burkholderiales (order), *Lactobacillus acidophilus* (species), *Corynebacterium mastitidis* (species), *Actinomyces europaeus* (species), *Propionibacterium* sp.

MSP09A (species), *Actinomyces neuii* (species), *Staphylococcus* sp. C912 (species), *Lactobacillus* sp. BL302 (species), Benzoate degradation (KEGG3), Lachnospiraceae (family), *Murdochiella* (genus), *Blautia* (genus), *Murdochiella asaccharolytica* (species), and *Prevotella timonensis* (species).

22. The method of claim 13, wherein the at least one of the microbiome composition diversity feature and the microbiome functional diversity feature is associated with microorganisms collected at a skin site, and wherein the at least one of the microbiome composition diversity feature and the microbiome functional diversity feature is associated with at least one of: Moraxellaceae (family), Caulobacteraceae (family), Neisseriaceae (family), Neisseriales (order), Caulobacterales (order), Flavobacteriales (order), *Neisseria* (genus), *Lachnospira* (genus), *Shinella* (genus), *Lactobacillus* sp. 7_1_47FAA (species), *Shinella* sp. DR33 (species), *Staphylococcus* sp. C-D-MA2 (species), Pseudomonadales (order), *Peptoniphilus* sp. 2002-2300004 (species), *Neisseria macacae* (species), *Ralstonia* (genus), *Staphylococcus* sp. C-D-MA2 (species), Pseudomonadaceae (family), *Finegoldia* (genus), and *Pseudomonas* (genus).

\* \* \* \* \*